US007109243B2

(12) United States Patent
Liu et al.

(10) Patent No.: US 7,109,243 B2
(45) Date of Patent: Sep. 19, 2006

(54) INHIBITORS OF CATHEPSIN S

(75) Inventors: Hong Liu, San Diego, CA (US); David Tully, San Diego, CA (US); Robert Epple, San Diego, CA (US); Badry Bursulaya, San Diego, CA (US); Jennifer Williams, La Jolla, CA (US); Arnab Chatterjee, Encinitas, CA (US); Jennifer Leslie Harris, San Diego, CA (US); Jun Li, San Diego, CA (US)

(73) Assignee: IRM LLC, Hamilton (BM)

( * ) Notice: Subject to any disclaimer, the term of this patent is extended or adjusted under 35 U.S.C. 154(b) by 38 days.

(21) Appl. No.: 10/807,612

(22) Filed: Mar. 23, 2004

(65) Prior Publication Data
US 2004/0198780 A1 Oct. 7, 2004

Related U.S. Application Data

(60) Provisional application No. 60/457,595, filed on Mar. 24, 2003.

(51) Int. Cl.
*A01N 47/28* (2006.01)

(52) U.S. Cl. .................. 514/595; 514/237.5; 514/249; 514/275; 514/279; 514/255.01; 514/330; 514/355; 514/364; 514/359; 514/406; 514/394; 514/422; 514/416; 514/448; 514/459; 514/471; 514/472; 514/602; 514/603; 514/604; 514/522; 514/596; 514/598; 544/165; 544/231; 544/332; 544/312; 544/391; 546/226; 546/316; 548/131; 548/255; 548/269.4; 548/304.4; 548/374.1; 548/492; 548/517; 548/560

(58) Field of Classification Search ................ 514/471, 514/472, 602, 603, 604, 237.5, 249, 275, 514/274, 255.01, 330, 355, 364, 359, 406, 514/394, 422, 416, 448, 459, 522, 595, 596, 514/598; 549/424, 425, 72, 414; 564/154, 564/155, 157, 158, 47, 48, 52, 53, 54, 56; 544/165, 281, 332, 312, 391; 546/226, 316; 548/131, 255, 269.4, 304.4, 374.1, 492, 517, 548/560; 558/415
See application file for complete search history.

(56) References Cited

U.S. PATENT DOCUMENTS

| 4,499,295 | A | 2/1985 | Mueller et al. |
|---|---|---|---|
| 5,374,623 | A | 12/1994 | Zimmerman et al. |
| 5,574,064 | A | 11/1996 | Shibata et al. |
| 5,691,368 | A | 11/1997 | Peet et al. |
| 5,723,469 | A | 3/1998 | Shibata et al. |
| 5,849,711 | A | 12/1998 | Tung et al. |
| 5,858,982 | A | 1/1999 | Tung et al. |
| 5,916,887 | A | 6/1999 | Singh et al. |
| 5,998,470 | A | 12/1999 | Halbert et al. |
| 6,004,933 | A | 12/1999 | Spruce et al. |
| 6,030,946 | A | 2/2000 | Klaus et al. |
| 6,057,362 | A | 5/2000 | Yamashita |
| 6,232,342 | B1 | 5/2001 | Carr et al. |
| 6,274,336 | B1 | 8/2001 | Abdel-Meguid et al. |
| 6,331,542 | B1 | 12/2001 | Carr et al. |
| 6,353,017 | B1 | 3/2002 | Altmann et al. |
| 6,369,077 | B1 | 4/2002 | Marquis et al. |
| 6,395,897 | B1 | 5/2002 | Cywin et al. |
| 6,420,364 | B1 | 7/2002 | Emmanuel et al. |
| 6,455,502 | B1 | 9/2002 | Bryant et al. |

FOREIGN PATENT DOCUMENTS

| WO | WO 98/00171 A2 | 1/1998 |
|---|---|---|
| WO | WO 98/50534 A1 | 11/1998 |
| WO | WO 00/48993 A1 | 8/2000 |
| WO | WO 00/51998 A1 | 9/2000 |
| WO | WO 01/09110 A1 | 2/2001 |
| WO | WO 01/19816 A1 | 3/2001 |
| WO | WO 02/14314 A2 | 2/2002 |
| WO | WO 02/14317 A2 | 2/2002 |
| WO | WO 02/14315 A2 | 3/2002 |
| WO | WO 02/051983 A2 | 7/2002 |
| WO | WO 02/069901 A2 | 9/2002 |
| WO | WO 02/070517 A2 | 9/2002 |
| WO | WO 02/070519 A1 | 9/2002 |
| WO | WO 03/013518 A1 | 2/2003 |
| WO | WO 03/020287 A2 | 3/2003 |

OTHER PUBLICATIONS

Bania, J. et al.: "Human cathepsin S, but not cathepsin L, degrades efficiently MHC class II-associated invariant chain in nonprofessional APCs" PNAS; vol. 100, No. 11; pp. 6664-6669 (May 27, 2003).

*Primary Examiner*—Peter O'Sullivan
(74) *Attorney, Agent, or Firm*—Townsend and Townsend and Crew LLP

(57) ABSTRACT

The present invention provides compounds, compositions and methods for the selective inhibition of cathepsin S. In a preferred aspect, cathepsin S is selectively inhibited in the presence of at least one other cathepsin isozyme (e.g., cathespin K). The present invention also provides methods for treating a disease state in a subject by selectively inhibiting cathepsin S.

19 Claims, 1 Drawing Sheet

INHIBITORS OF CATHEPSIN S

CROSS-REFERENCE TO RELATED APPLICATIONS

The present application claims priority to U.S. Pat. No. 60/457,595, filed Mar. 24, 2003, the teachings of which are hereby incorporated by reference in their entirety.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, *J Biol Chem* 1997, 272(13), 8109–12; Saftig, P., E. Hunziker, et al., *Adv Exp Med Biol* 2000+*ADs* 2000, 477, 293–303; Saftig, P., E. Hunziker, et al., *Proc Natl Acad Sci USA* 1998, 95(23), 13453–8), periodontal diseases, Paget's disease, atherosclerosis (Jormsjo, S., D. M. Wuttge, et al., *Am J Pathol* 2002 161(3), 939–45), multiple sclerosis (Beck, H., G. Schwarz, et al., *Eur J Immunol* 2001, 31(12), 3726–36), rheumatoid arthritis (Nakagawa, T. Y., W. H. Brissette, et al., *Immunity* 1999, 10(2), 207–17; Hou, W. S., Z. Li, et al., *Am J Pathol* 2001, 159(6), 2167–77), juvenile onset diabetes, lupus, asthma (Cimerman, N., P. M. Brguljan, et al., *Pflugers Arch* 2001, 442(6 Suppl 1), R204–6), tissue rejection, Alzheimer's disease (Lemere, C. A., J. S. Munger, et al., *Am J Pathol* 1995, 146(4), 848–60), Parkinson's disease (Liu, Y., L. Fallon, et al., *Cell* 2002, 111(2), 209–18), neuronal degeneration, shock (Jaeschke, H., M. A. Fisher, et al., *J Immunol* 1998, 160(7), 3480–6), cancer (Fernandez, P. L., X. Farre, et al., *Int J Cancer* 2001, 95(1), 51–5), malaria (Malhotra, P., P. V. Dasaradhi, et al., *Mol Microbiol* 2002, 45(5), 1245–54), Chagas (Eakin, A. E., A. A. Mills, et al., *J Biol Chem* 1992, 267(11), 7411–20), leishmaniasis, shistosomiasis, and African trypanosomiasis (Caffrey, C. R., S. Scory, et al., *Curr Drug Targets* 2000, 1(2), 155–62; Lalmanach, G., A. Boulange, et al., *Biol Chem* 2002, 383(5), 739–49).

Cathepsins are a subclass of cysteine protease that belong to the enzyme classification EC 3.4.22 (Barrett, A. J., N. D. Rawlings, et al., *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281–94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al., *Immunity* 1999, 10(2) 197–206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al., *J Biol Chem* 1996, 271(4), 2126–32). There is a need in the art for compounds and methods that selectively inhibit specific cysteine proteases for treating several pathogenic disorders in mammals. The present invention satisfies these and other needs.

SUMMARY OF THE INVENTION

The present invention provides compounds, compositions and methods for the selective inhibition of cathepsin S. The compounds of the present invention are selective for cathepsin S in the presence of other cathepsin isozymes (e.g., cathespin K). In a preferred embodiment, the compounds of the present invention are selective for cathepsin S in the presence of cathepsin K. The present invention also provides methods for treating a disease state in a subject by selectively inhibiting cathepsin S in the presence of other cathepsin isozymes. In a preferred aspect, cathepsin S is selectively inhibited in the presence of cathepsin K.

As such, the present invention provides a compound of Formula I:

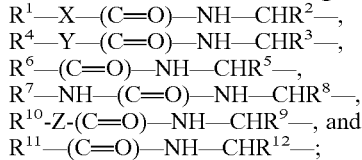

or a pharmaceutically acceptable salt or prodrug thereof, wherein:
W is a member selected from the group of:
$R^1$—X—(C=O)—NH—CHR$^2$—,
$R^4$—Y—(C=O)—NH—CHR$^3$—,
$R^6$—(C=O)—NH—CHR$^5$—,
$R^7$—NH—(C=O)—NH—CHR$^8$—,
$R^{10}$-Z-(C=O)—NH—CHR$^9$—, and
$R^{11}$—(C=O)—NH—CHR$^{12}$—;
$R^1$ is a member selected from the group of phenyl substituted with 0–2 $R^{1a}$, pyridyl substituted with 0–2 $R^{1a}$, and pyridinium N-oxide substituted with 0–2 $R^{1a}$;
each $R^{1a}$ is independently a member selected from the group of Cl, F, OCF$_3$, OCH$_3$, CH$_3$ and CF$_3$;
X is a member selected from the group of furanylene substituted with 0–1 $R^x$, thienylene substituted with 0–1 $R^x$, pyrazolylene substituted with 0–1 $R^x$, thiazolylene substituted with 0–1 $R^x$, and oxazolylene substituted with 0–1 $R^X$;
$R^x$ is a member selected from the group of F, Cl, CH$_3$ and CF$_3$;
$R^2$ is a member selected from the group of phenyl substituted with 0–2 $R^{2a}$, and (CH$_2$)$_n$R$^{2b}$;
each $R^{2a}$ is independently a member selected from the group of Cl, F, OCF$_3$, OCH$_3$, CH$_3$ and CF$_3$;
$R^{2b}$ is independently a member selected from the group of phenyl substituted with 0–2 $R^{2a}$; cyclopentyl, cyclohexyl and tetrahydropyranyl;
n is the integer 1 or 2;
$R^3$ is (CH$_2$)$_m$R$^{3b}$;
$R^{3b}$ is selected from the group of phenyl substituted with 0–2 $R^{2a}$, cyclopentyl and cyclohexyl;
m is the integer 1 or 2;
$R^4$ is a member selected from the group of phenyl substituted with 0–3 $R^{4a}$, thienyl, tetrazolyl, cyclopentenyl and indolyl;
each $R^{4a}$ is a member selected from the group of phenyl, OH, C$_1$–C$_4$ alkyl, C$_1$–C$_4$ alkoxy, CF$_3$, OCF$_3$, F, Cl, CH$_3$S(=O)$_2$—, morpholinyl, pyrrolidinyl, piperidinyl and 4-acetylpiperazinyl;

Y is a member selected from the group of —CR$^{17}$R$^{18}$, —NH—CH$_2$— and —O—CH$_2$—;

R$^5$ is a member selected from the group of phenyl substituted with 0–2 R$^{5a}$, thiophene, naphthyl, and CH$_2$R$^{5b}$, CH$_2$CH$_2$(cyclohexyl), CH$_2$CH$_2$CH$_2$(cyclohexyl), CH$_2$CH$_2$Ph, CH(CH$_3$)R$^{5e}$, CH$_2$CH=CHPh, —CH$_2$OCH$_2$Ph, —CH(CH$_3$)OCH$_2$Ph;

each R$^{5a}$ is independently a member selected from the group of F, Cl, NO$_2$, OCH$_3$, OCH$_2$Ph, OPh, CH$_3$, OCF$_3$ and CF$_3$;

R$^{5b}$ is independently a member selected from the group of phenyl substituted with 0–2 R$^{5c}$; cyclopentyl, cyclohexyl, naphthyl, indolyl and pyridyl;

R$^{5c}$ is independently a member selected from the group of OH, Cl, F, Br, I, CN, NO$_2$, CH$_3$, OCH$_3$, $^t$Bu, O-$^t$Bu, —NHC(=O)CH$_3$, CF$_3$, OCF$_3$; phenyl substituted with 0–2 R$^{5d}$; phenoxy substituted with 0–2 R$^{5d}$; benzyloxy substituted with 0–2 R$^{5d}$; pyridyl substituted with 0–2 R$^{5d}$; pyrimidinyl substituted with 0–2 R$^{5d}$; thienyl substituted with 0–2 R$^{5d}$;

R$^{5d}$ is independently a member selected from the group of CH$_3$, Cl, F, OCH$_3$, CF$_3$, OCF$_3$, N(CH$_3$)$_2$, acetyl, OH, CH$_2$OH, NH$_2$, CN and NO$_2$;

R$^{5e}$ is phenyl substituted with 0–2 R$^{5a}$;

R$^6$ is a member selected from the group of phenyl substituted with 0–3 R$^{6a}$, furanyl substituted with 0–2 R$^{6b}$, thienyl substituted with 0–2 R$^{6b}$, oxazolyl substituted with 0–2 R$^{6b}$, thiazolyl substituted with 0–2 R$^{6b}$, pyridyl, pyridazinyl and cyclopropyl;

each R$^{6a}$ is independently a member selected from the group of Cl, F, Br, OCF$_3$, CF$_3$, C$_1$–C$_4$ alkyl, C$_1$–C$_4$ alkoxy, —S(=O)$_2$CH$_3$, CN, —N(CH$_3$)$_2$, OCF$_2$H, —CH$_2$-benzimidazole, —NH—S(=O)$_2$CH$_3$, —NR$^{13}$R$^{14}$, OR$^{14}$, CH$_2$-morpholine, CH$_2$NH$_2$, OCH$_2$Ph, and OPh;

alternatively, two R$^{6a}$ substituents on adjacent atoms may be combined to form a 5 to 6 membered heterocyclic fused radical, wherein said 5 to 6 membered heterocyclic fused radical has 1 or 2 oxygen atom(s);

each R$^{6b}$ is independently a member selected from the group of NH$_2$, F, Cl, Br, —S(=O)$_2$R$^{15}$, CH$_3$, and CF$_3$;

R$^7$ is a member selected from the group of (CH$_2$)$_p$R$^{7a}$, and naphthyl substituted with 0–2 R$^{7b}$;

p is the integer 0, 1, or 2;

R$^{7a}$ is phenyl substituted with 0–2 R$^{7b}$;

R$^{7b}$ is a member selected from the group of F, Cl, CF$_3$, C$_1$–C$_4$ alkyl, C$_1$–C$_4$ alkoxy, OCF$_3$, phenoxy and acetyl;

alternatively, two R$^{7b}$ substituents on adjacent atoms may be combined to form a 5 to 6 membered heterocyclic fused radical, wherein said 5 to 6 membered heterocyclic fused radical has 1 or 2 oxygen atom(s);

R$^8$ is —CH$_2$—R$^{3b}$;

R$^9$ is (CH$_2$)$_q$R$^{9a}$;

R$^{9a}$ is a member selected from the group of cyclopentyl, phenyl and cyclohexyl;

q is the integer 1 or 2;

R$^{10}$ is a member selected from the group of phenyl substituted with 0–2 R$^{10a}$, 5 membered heteroaryl containing 1 to 4 heteroatoms each independently a member selected from the group of N, O and S, wherein said heteroaryl is substituted with 0–2 R$^{10a}$, 6 membered heteroaryl containing 1 to 2 N, wherein said heteroaryl is substituted with 0–2 R$^{10a}$, morpholinyl substituted with 0–2 R$^{10a}$, piperazinyl substituted with 0–2 R$^{10a}$ and piperidinyl substituted with 0–2 R$^{10a}$;

each R$^{10a}$ is independently a member selected from the group of Cl, F, C$_1$–C$_4$ alkyl, C$_1$–C$_4$ alkoxy, OCF$_3$, and CF$_3$;

alternatively, two R$^{10a}$ substituents on adjacent atoms may be combined to form a 5 to 6 membered heterocyclic fused radical, wherein said 5 to 6 membered heterocyclic fused radical comprises 1 or 2 heteroatom(s);

Z is phenylene;

R$^{11}$ is a member selected from the group of indolyl substituted with 0–2 R$^{11a}$, benzofuranyl substituted with 0–2 R$^{11a}$, benzothienyl substituted with 0–2 R$^{11a}$, benzothiazole substituted with 0–2 R$^{11a}$, benzisoxazolyl substituted with 0–2 R$^{11a}$, benzoxazolyl substituted with 0–2 R$^{11a}$, and pyrazolo[1,5-a]pyrimidinyl substituted with 0–2 R$^{11a}$, piperidinyl N-substituted with 0–1 R$^{11b}$, morpholinyl N-substituted with 0–1 R$^{11b}$; and 2-oxo-pyrrolidinyl with 0–1 R$^{11b}$;

each R$^{11a}$ is independently a member selected from the group of Cl, F, NH$_2$, CH$_3$, OCH$_3$, —C(=O)OCH$_3$, OCF$_3$, and CF$_3$;

each R$^{11b}$ is independently a member selected from the group of pyrimidinyl substituted with 0–2 R$^{11c}$; benzyl, acetyl, CH$_2$-furanyl, and CH$_2$-thienyl;

each R$^{11c}$ is independently a member selected from the group of Br and CH$_3$;

R$^{12a}$ is (CH$_2$)$_s$R$^{12a}$;

R$^{12a}$ is a member selected from the group of cyclopentyl and cyclohexyl;

s is the integer 1 or 2;

R$^{13}$ is a member selected from the group of H and C$_1$–C$_4$ alkyl;

R$^{14}$ is pyrimidinyl substituted with 0–2 R$^{16}$;

R$^{15}$ is a member selected from the group of C$_1$–C$_4$ alkyl, morpholinyl, pyrrolidinyl and piperidinyl;

R$^{16}$ is a member selected from the group of CH$_3$ and OCH$_3$;

each of R$^{17}$ and R$^{18}$ is independently a member of H, OH, F, phenyl and C$_1$–C$_3$ alkyl;

alternatively, R$^{17}$ and R$^{18}$ may be taken together to form a C$_3$–C$_6$ cycloalkyl;

Ar is a phenyl substituted with 0–2 R$^{19}$; and each R$^{19}$ is independently a member selected from the group consisting of F, Cl, COOH, C$_1$–C$_4$ alkoxy, OCHF$_2$ and OCF$_3$.

In a second aspect, the present invention provides a pharmaceutical composition comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

These and other aspects, objects and embodiments will become more apparent when read with the accompanying FIGURE and detailed description which follows.

DETAILED DESCRIPTION OF THE INVENTION

I. Definitions

Figure 1:
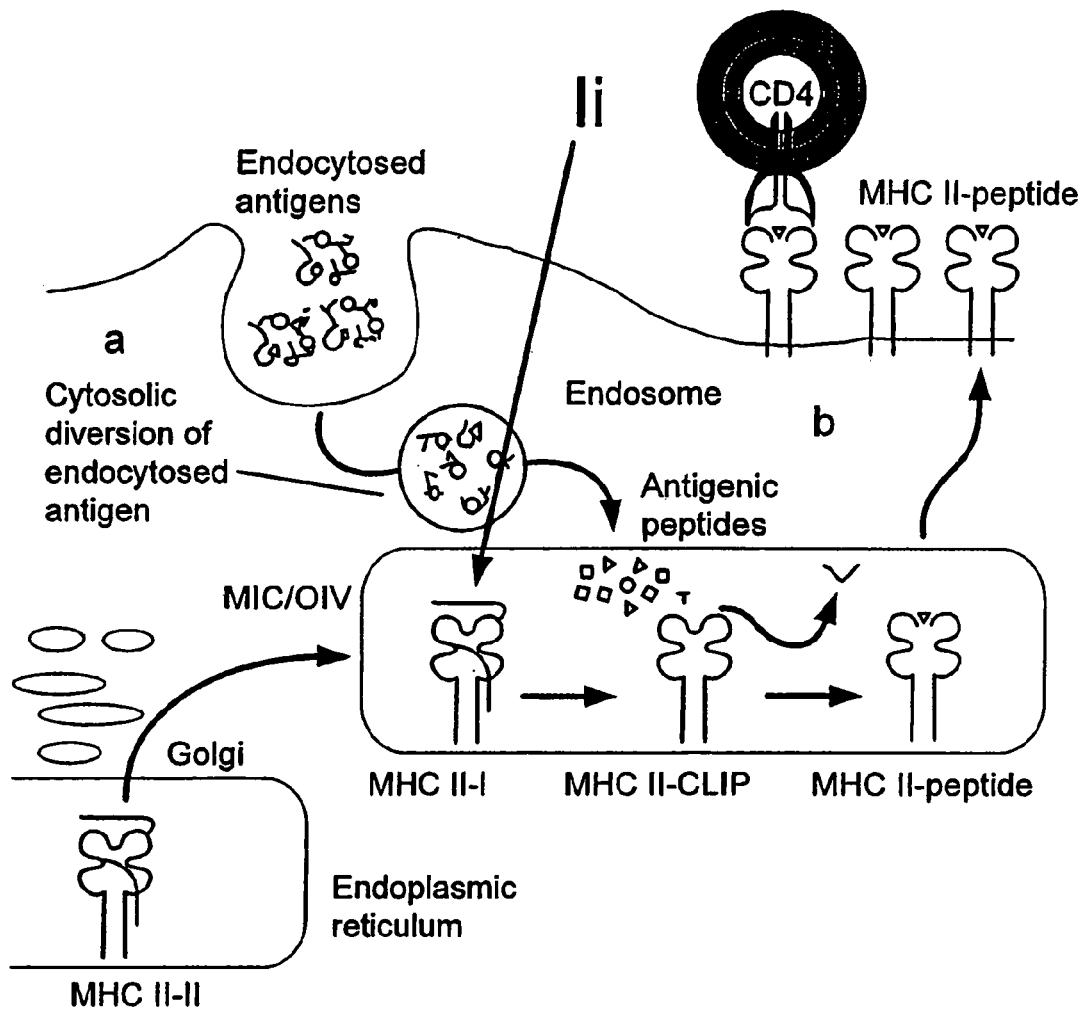
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

| | |
|---|---|
| Ac | acetyl |
| Bn | benzyl |
| Boc | t-butoxycarbonyl |
| Cbz or Z | benzyloxycarbonyl |
| DCC | N,N'-dicyclohexylcarbodiimide |
| DCM | dichoromethane |
| DIBAL | diisobutylaluminum hydride |
| DIC | N,N'-diisopropylcarbodiimide |
| DIEA or DIPEA | diisopropylethylamine |
| DMAP | 4-(dimethylamino)pyridine |
| DMF | dimethylformamide |
| DMSO | dimethyl sulfoxide |
| EDC or EDCI | 1-ethyl-3-(dimethylaminopropyl)-carbodiimide |
| Fmoc | 9-fluorenylmethoxycarbonyl |
| HATU | O-(7-azabenzoatriazol-1-yl)-N,N,N',N'-tetramethyluronium hexafluorophosphate |
| HOBt | 1-hydroxybenzotriazole |
| KHMDS | potassium hexamethyldisilazide |
| LAH | lithium aluminum hydride |
| LDA | lithium diisopropylamide |
| LHMDS | lithium hexamethyldisilazide |
| m-CPBA | m-chloroperbenzoic acid |
| MW | microwave |
| NaHMDS | sodium hexamethyldisilazide |
| PCC | pyridinium chlorochromate |
| PDC | pyridinium dichromate |
| PG | protecting group |
| PTSA | p-toluenesulfonic acid |
| Py | pyridine |
| RT or rt | room temperature |
| TEA | triethylamine |
| Tf | trifluoromethanesulfonyl |
| TFA | trifluoroacetic acid |
| THF | tetrahydrofuran |
| Tol | p-tolyl |
| TPAP | tetrapropylammonium perruthenate |

The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

An alkyl group is branched or unbranched and contains 1 to 7 carbon atoms, preferably 1–4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2–4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2–4 carbon atoms, e.g. as acetylenyl, propynyl, isoprpropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, or optionally substituted amino-oxy or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by $C_1$–$C_3$-alkyl (preferably methyl) or disubstituted on the same or different carbon atoms by $C_1$–$C_3$-alkyl (preferably methyl), the total number of carbon atoms being up to and including 7.

An alkoxy (or alkyloxy) group preferably contains 1–7 carbon atoms, more preferably 1–6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$–$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, pyridyl N-oxide, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, pyridyl N-oxide, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl.

Bicycloalkyl represents a saturated bicyclic ring group of 7–15 carbon atoms. Exemplary bicycloalkyl rings include [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth, optionally substituted by alkyl.

Amino can be optionally substituted by, e.g., alkyl.

Carbocyclic represents a saturated or partially unsaturated cyclic hydrocarbon with 5 to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2 heteroatoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W.H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{app}$ using described methods (Kuzmic, P., K. C. Elrod, et al., *Anal Biochem* 2000, 286(1), 45–50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$, for competitive inhibitors by using the following relationship:

$$K_i = \frac{K_i^{app}}{1 + [S]/K_m}.$$

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

"Prodrug" refers to the compounds of this invention which may be modified by appending appropriate functionalities to enhance selective biological properties. Such modifications are known in the art and include those which increase penetration into a given biological compartment (e.g. central nervous system), increase oral bioavailability, increase solubility to allow administration by injection, alter metabolism and alter rate and/or route of excretion. In addition, the compounds may be altered to prodrug form such that the desired compound is created in the body of the patient as the result of the action of metabolic or other biochemical processes on the prodrug.

It will be apparent to one skilled in the art that certain compounds of this invention may exist in tautomeric forms or hydrated forms, all such forms of the compounds being within the scope of the invention.

Structures depicted herein are also meant to include compounds that differ only in the presence of isotopically enriched atoms. For example, compounds having the present structures except for the replacement of a hydrogen by a deuterium are expressly included in the present invention.

II. General

Cathepsin S is a cysteine protease that has been associated with several normal and disease processes in mammals. Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme.

III. Compounds

A. Preparation of Compounds

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

Compounds of the present invention wherein W is not $R^7$—NH—(C=O)—NH—$CHR^8$—, can be made via the route shown in Scheme 1.

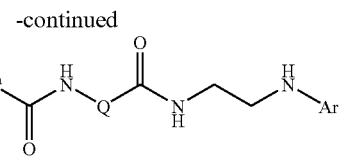

a) i) $NH_2CH_2CH_2NHAr$, AcOH, DMF, rt;
   ii) $NaHB(OAc)_3$, DMF;
b) i) $FmocHNQCO_2H$, HOBt, DIC, DMF, rt;
   ii) 20% piperidine in DMF;
c) i) $R^aCO_2H$, HOBt, DIC, DMF, rt;
   ii) TFA/DCM/$H_2O$.

As shown therein, polystyrene aldehyde (PAL) resin is reductively aminated with a monoaryl diamine ($NH_2CH_2CH_2NHAr$) to obtain the resin 1-A (Scheme 1). This material is acylated with an N-protected amino acid (e.g. $FmocHNQCO_2H$) using standard conditions (as described in A. R. Chamberlin, *Chem. Rev.* 1997, 97, 2243–2266; M. Bodanszky et al. The Practice of Peptide Synthesis $2^{nd}$, Springer-Verlag, 1984) and the product is then deprotected with piperidine to furnish 1-B. After acylation with $R^aCO_2H$ under standard amide coupling condition, cleavage from resin using TFA furnishes 1-C. In scheme 1, $R^a$ can be $R^1$, $R^4$, $R^6$, $R^{10}$ or $R^{11}$; Q can be —$CHR^2$—, —$CHR^3$—, —$CHR^5$—, —$CHR^9$—, or —$CHR^{12}$—.

The arylaminoethylamines 2-A (Scheme 2) used in the present invention are prepared by a decarboxylative ring opening of oxazolidin-2-one with an aromatic amine as described in G. S. Poindexter et al. *J. Org. Chem.* 1992, 57, 6257–65; E. Altman et al. *J. Med Chem.* 2002, 45, 2352–54 and references cited therein.

Scheme 2

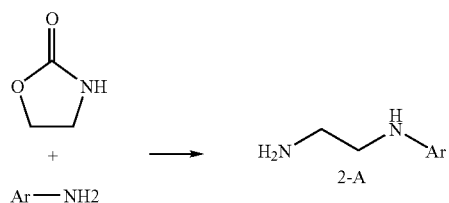

In an alternate aspect, compounds of the present invention wherein W is not $R^7$—NH—(C=O)—NH—$CHR^8$— can also be prepared according to Scheme 3. In scheme 3, $R^a$ can be $R^1$, $R^4$, $R^6$, $R^{10}$, or $R^{11}$; $R^b$ can be $R^2$, $R^3$, $R^5$, $R^9$, or $R^{12}$.

Scheme 1

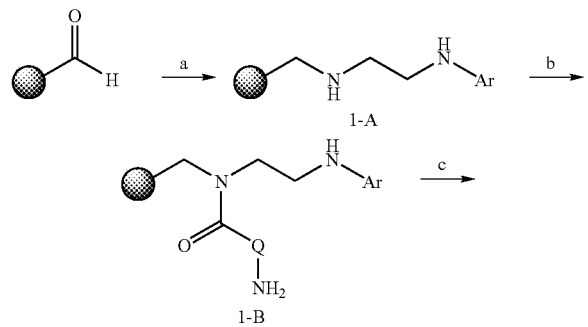

Scheme 3

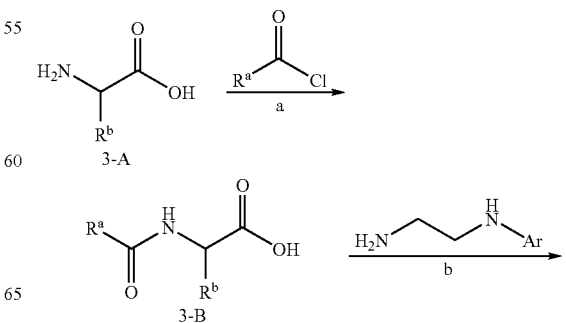

-continued

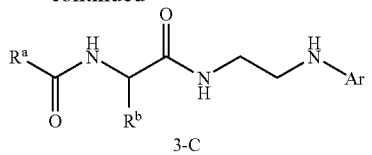
3-C a) NaOH, H₂O;
b) HOBt, DIC.

Compounds of the present invention wherein W is R⁷—NH—(C=O)—NH—CHR⁸—, can be made via the route shown in Scheme 4. In scheme 4, R$^a$ can be R⁷; Q can be —CHR⁸—.

Scheme 4

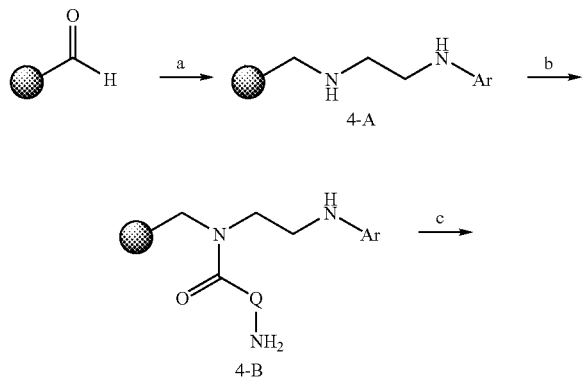

a) i) NH₂CH₂CH₂NHAr, AcOH, DMF, rt;
   ii) NaHB(OAc)₃, DMF;
b) i) FmocHNQCO₂H, HOBt, DIC, DMF, rt;
   ii) 20% piperidine in DMF;
c) i) R$^a$NCO, base, DMF, rt;
   ii) TFA/DCM/H₂O.

Compounds of the present invention in which $R^2$, $R^3$, $R^5$, $R^8$, $R^9$ or $R^{12}$ consists of, for example, a biaryl moiety, can be prepared by transition metal catalyzed cross coupling reactions, according to Scheme 5 (Ar¹ and Ar² are aryls and/or heteroaryls, X is OTf, I, Br, Cl and the like). For typical methods, see: a) A. Suzuki et al. *Chem Rev.* 1995, 95, 2457–2483; b) A. Suzuki, *J. Organomet. Chem.* 1999, 576, 147–168; c) R. D. Larsen *Current opinion in drug discovery and development* 1999, 2, 651–667; d) S. P. Stanforth *Tetrahedron* 1998, 54, 263–303; e) S. L. Buchwald et al. *J. Am. Chem. Soc.* 1999, 121, 9550; f) G. C. Fu et al. *Angew. Chem. Int. Ed.* 1998, 38, 3387 and references cited therein. Typically, the cross coupling reactions can be performed under microwave assistance. See: A. P. Combs et al. in *Annual reports in medicinal chemistry* Vol. 37, 2002; A. M. Doherty ed. pp. 247–256. In scheme 5, R$^a$ can be $R^1$, $R^4$, $R^6$, $R^{10}$ or $R^{11}$.

Scheme 5

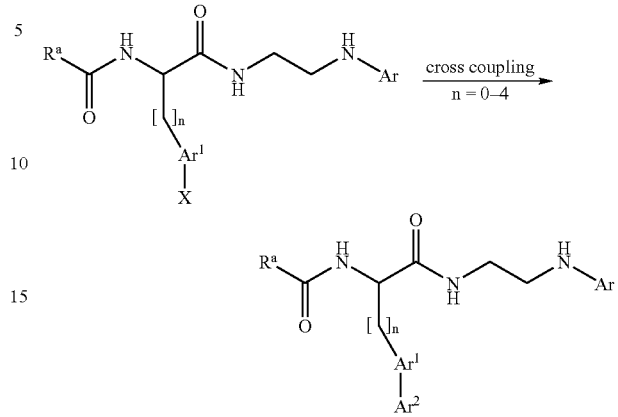

Compounds of the present invention, wherein $R^2$, $R^3$, $R^5$, $R^8$, $R^9$ or $R^{12}$ consists of, for example, an aryloxy-aryl moiety, can be prepared via copper-promoted arylation of phenols with arylboronic acids (Scheme 6) according to (a) D. A. Evans et al. *Tetrahedron Lett.* 1998, 39, 2937–40; (b) D. M. Chan et al. *Tetrahedron Lett.* 1998, 39, 2933–36; and (c) S. V. Ley et al. *Angew. Chem. Int. Ed. Engl.* 2003, 42, 5400–5449; or Ullman ether synthesis, see (a) S. L. Buchwald et al. *J. Am. Chem. Soc.* 1999, 121, 4369–4378; (b) J. F. Hartwig et al. *J. Am. Chem. Soc.* 1999, 121, 3224–3225 and references cited therein. In scheme 6, R$^a$ can be $R^1$, $R^4$, $R^6$, $R^{10}$ or $R^{11}$.

Scheme 6

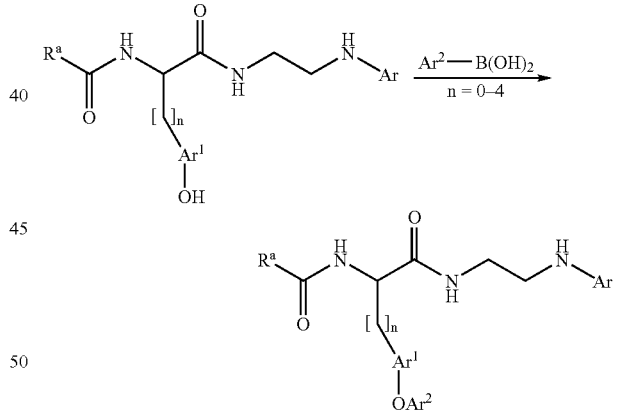

Synthetic approaches to non-commercially available α- and β-amino acids used in the present invention are widely described in the literature. The typical methods are illustrated in the following references. See: (a) D. J. Ager et al. *Current opinion in drug discovery & development* 2001, 4, 800–807; (b) R. O. Duthaler *Tetrahedron* 1994, 50, 1539–1650; (c) M. J. O'Donnell *Aldrichimica Acta* 2001, 34, 3–15; (d) K. B. Sharpless et al. *J. Am. Chem. Soc.* 1998, 120, 1207–17; (e) E. Juaristi et al. *Aldrichimica Acta* 1994, 27, 3–11; (f) D. C. Cole *Tetrahedron* 1994, 50, 9517–9582, and references cited therein.

Compounds of the present invention in which W is, for example, $R^1$—X—(C=O)—NH—CHR²—, are prepared (a) by Suzuki coupling (N. Miyaura et al. *Synth. Commun.*

1981, 11(7), 513–19; A. Suzuki et al. *Chem Rev.* 1995, 95, 2457–2483) of appropriate phenylboronic acid with bromofurancarboxylic acid or bromothiophenecarboxylic acid, when X is furanyl or thienyl; (b) according to Bartoli, J. et. al. *J. Med. Chem.* 1998, 41, 1855–1868; Holzer, W. et al. *J. Hetcycl. Chem.* 1993, 30(4), 865–872; Molteni, G. et al. *New J. Chem.* 2002, 26(10), 1340–1345; Seigo I. et al. *Bioorg. Med. Chem.* 2001, 11(7), 879–882, when X is pyrazolyl; (c) according to Evans, D. L. et. al. *J. Org. Chem.* 1979, 44, 497; Takeuchi, K. et. al. *J. Med. Chem.* 1998, 41, 5362–5374; Dondoni, A. et al. *J. Org. Chem.* 1987, 52(15), 3413–3420; Millan, D. S. et al. *Tetrahedron* 2000, 56(5), 811–816; Duarte, M. P. et al. *Tetrahedron Lett.* 2000, 41(39), 7433–7435, when X is oxazolyl; and (d) according to Bartroli, J. et al. *J. Med. Chem.* 1998, 41(11), 1855–1868; Wright, S. W. et al *J. Med. Chem.* 2002, 45(18), 3865–3877; Janusz, J. M. et al. *J. Med. Chem.* 1998, 41(18), 3515–3529; Tanaka, C. et al. *Chem. Pharm. Bulletin* 1982, 30(11), 4195–8, when X is thiazolyl.

B. Preferred Compounds

In one aspect, preferred compounds of the present invention have the following structural formula:

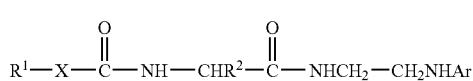

Ia wherein:
- $R^1$ is a member selected from the group consisting of phenyl substituted with 0–2 $R^{1a}$, pyridyl substituted with 0–2 $R^{1a}$, and pyridinium N-oxide substituted with 0–2 $R^{1a}$;
- each $R^{1a}$ is independently a member selected from the group consisting of Cl, F, $OCF_3$, $OCH_3$, $CH_3$ and $CF_3$;
- X is a member selected from the group consisting of furanylene substituted with 0–1 $R^x$, thienylene substituted with 0–1 $R^x$, pyrazolylene substituted with 0–1 $R^x$, thiazolylene substituted with 0–1 $R^x$, and oxazolylene substituted with 0–1 $R^x$;
- $R^x$ is a member selected from the group consisting of F, Cl, $CH_3$ and $CF_3$;
- $R^2$ is a member selected from the group consisting of phenyl substituted with 0–2 $R^{2a}$, and $(CH_2)_n R^{2b}$;
- each $R^{2a}$ is independently a member selected from the group consisting of Cl, F, $OCF_3$, $OCH_3$, $CH_3$ and $CF_3$;
- $R^{2b}$ is independently a member selected from the group consisting of phenyl substituted with 0–2 $R^{2a}$, cyclopentyl, cyclohexyl and tetrahydropyranyl;
- n is the integer 1 or 2;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

In another aspect, preferred compounds of the present invention have the following structural formula:

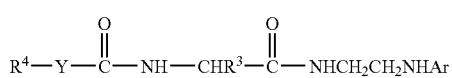

Ib wherein:
- $R^4$ is a member selected from the group consisting of phenyl substituted with 0–3 $R^{4a}$, thienyl, tetrazolyl, cyclopentenyl and indolyl;
- each $R^{4a}$ is a member selected from the group consisting of phenyl, OH, $C_1$–$C_4$ alkyl, $C_1$–$C_4$ alkoxy, $CF_3$, $OCF_3$, F, Cl, $CH_3S(=O)_2$—, morpholinyl, pyrrolidinyl, piperidinyl and 4-acetylpiperazinyl;
- Y is a member selected from the group consisting of —$CR^{17}R^{18}$, —NH—$CH_2$— and —O—$CH_2$—;
- $R^3$ is $(CH_2)_m R^{3b}$;
- $R^{3b}$ is selected from the group consisting of phenyl substituted with 0–2 $R^{2a}$, cyclopentyl and cyclohexyl;
- each $R^{2a}$ is independently a member selected from the group consisting of Cl, F, $OCF_3$, $OCH_3$, $CH_3$ and $CF_3$;
- m is the integer 1 or 2;
- each of $R^{17}$ and $R^{18}$ is independently a member of H, OH, F, phenyl and $C_1$–$C_3$ alkyl;
- alternatively, $R^{17}$ and $R^{18}$ may be taken together to form a $C_3$–$C_6$ cycloalkyl;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

In still another aspect, preferred compounds of the present invention have the following structural formula:

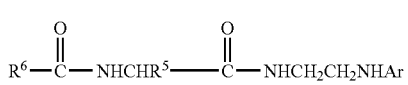

Ic wherein:
- $R^5$ is a member selected from the group consisting of phenyl substituted with 0–2 $R^{5a}$, thiophene, naphthyl, and $CH_2 R^{5b}$, $CH_2CH_2$(cyclohexyl), $CH_2CH_2CH_2$(cyclohexyl), $CH_2CH_2Ph$, $CH(CH_3)R^{5e}$, $CH_2CH=CHPh$, —$CH_2OCH_2Ph$, and —$CH(CH_3)OCH_2Ph$;
- each $R^{5a}$ is independently a member selected from the group consisting of F, Cl, $NO_2$, $OCH_3$, $OCH_2Ph$, OPh, $CH_3$, $OCF_3$ and $CF_3$;
- $R^{5b}$ is independently a member selected from the group consisting of phenyl substituted with 0–2 $R^{5c}$; cyclopentyl, cyclohexyl, naphthyl, indolyl and pyridyl;
- $R^{5c}$ is independently a member selected from the group consisting of OH, Cl, F, Br, I, CN, $NO_2$, $CH_3$, $OCH_3$, $^tBu$, O-$^tBu$, —NHC(=O)$CH_3$, $CF_3$, $OCF_3$, phenyl substituted with 0–2 $R^{5d}$, phenoxy substituted with 0–2 $R^{5d}$, benzyloxy substituted with 0–2 $R^{5d}$, pyridyl substituted with 0–2 $R^{5d}$, pyrimidinyl substituted with 0–2 $R^{5d}$, and thienyl substituted with 0–2 $R^{5d}$;
- $R^{5d}$ is independently a member selected from the group consisting of $CH_3$, Cl, F, $OCH_3$, $CF_3$, $OCF_3$, $N(CH_3)_2$, acetyl, OH, $CH_2OH$, $NH_2$, CN and $NO_2$;
- $R^{5e}$ is phenyl substituted with 0–2 $R^{5a}$;
- $R^6$ is a member selected from the group consisting of phenyl substituted with 0–3 $R^{6a}$, furanyl substituted with 0–2 $R^{6b}$; thienyl substituted with 0–2 $R^{6b}$; oxazolyl substituted with 0–2 $R^{6b}$; thiazolyl substituted with 0–2 $R^{6b}$; pyridyl, pyridazinyl and cyclopropyl;
- each $R^{6a}$ is independently a member selected from the group consisting of Cl, F, Br, $OCF_3$, $CF_3$, $C_1$–$C_4$ alkyl, $C_1$–$C_4$ alkoxy, —$S(=O)_2CH_3$, CN, —$N(CH_3)_2$, $OCF_2H$, —$CH_2$-benzimidazole, —NH—$S(=O)_2CH_3$, —$NR^{13}R^{14}$, $OR^{14}$, $CH_2$-morpholine, $CH_2NH_2$, $OCH_2Ph$, and OPh;
- alternatively, two $R^{6a}$ substituents on adjacent atoms may be combined to form a 5 to 6 membered heterocyclic fused radical, wherein said 5 to 6 membered heterocyclic fused radical has 1 or 2 oxygen atom(s);

each $R^{6b}$ is independently a member selected from the group consisting of $NH_2$, F, Cl, Br, $—S(=O)_2R^{15}$, $CH_3$, and $CF_3$;

$R^{13}$ is a member selected from the group consisting of H and $C_1$–$C_4$ alkyl;

$R^{14}$ is pyrimidinyl substituted with 0–2 $R^{16}$;

$R^{15}$ is a member selected from the group consisting of $C_1$–$C_4$ alkyl, morpholinyl, pyrrolidinyl and piperidinyl;

$R^{16}$ is a member selected from the group consisting of $CH_3$ and $OCH_3$;

Ar is a phenyl substituted with 0–2 $R^{19}$; and each $R^{19}$ is independently a member selected from the group consisting of F, Cl, COOH, $C_1$–$C_4$ alkoxy, $OCHF_2$ and $OCF_3$.

In still yet another aspect, preferred compounds of the present invention have the following structural formula:

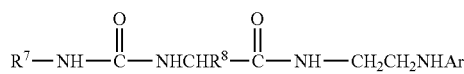

Id wherein:

$R^7$ is a member selected from the group consisting of $(CH_2)_pR^{7a}$; and naphthyl substituted with 0–2 $R^{7b}$;

p is the integer 0, 1, or 2;

$R^{7a}$ is a member selected from the group consisting of phenyl substituted with 0–2 $R^{7b}$;

$R^{7b}$ is a member selected from the group consisting of F, Cl, $CF_3$, $C_1$–$C_4$ alkyl, $C_1$–$C_4$ alkoxy, $OCF_3$, phenoxy and acetyl;

alternatively, two $R^{7b}$ substituents on adjacent atoms may be combined to form a 5 to 6 membered heterocyclic fused radical, wherein said 5 to 6 membered heterocyclic fused radical has 1 or 2 oxygen atom(s);

$R^8$ is $—CH_2—R^{3b}$;

$R^{3b}$ is selected from the group consisting of phenyl substituted with 0–2 $R^{2a}$, cyclopentyl and cyclohexyl;

each $R^{2a}$ is independently a member selected from the group consisting of Cl, F, $OCF_3$, $OCH_3$, $CH_3$ and $CF_3$;

Ar is a phenyl substituted with 0–2 $R^{19}$; and each $R^{19}$ is independently a member selected from the group consisting of F, Cl, COOH, $C_1$–$C_4$ alkoxy, $OCHF_2$ and $OCF_3$.

In another aspect, preferred compounds of the present invention have the following structural formula:

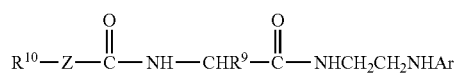

Ie wherein:

$R^{10}$ is a member selected from the group consisting of phenyl substituted with 0–2 $R^{10a}$, 5 membered heteroaryl containing 1 to 4 heteroatoms each independently a member selected from the group consisting of N, O and S, wherein said heteroaryl is substituted with 0–2 $R^{10a}$, 6 membered heteroaryl containing 1 to 2 N, wherein said heteroaryl is substituted with 0–2 $R^{10a}$, morpholinyl substituted with 0–2 $R^{10a}$, piperazinyl substituted with 0–2 $R^{10a}$ and piperidinyl substituted with 0–2 $R^{10a}$;

each $R^{10a}$ is independently a member selected from the group consisting of Cl, F, $C_1$–$C_4$ alkyl, $C_1$–$C_4$ alkoxy, $OCF_3$, and $CF_3$;

alternatively, two $R^{10a}$ substituents on adjacent atoms may be combined to form a 5 to 6 membered heterocyclic fused radical, wherein said 5 to 6 membered heterocyclic fused radical comprises 1 or 2 heteroatom(s);

Z is phenylene;

$R^9$ is $(CH_2)_qR^{9a}$;

$R^{9a}$ is a member selected from the group consisting of cyclopentyl, phenyl and cyclohexyl;

q is the integer 1 or 2;

Ar is a phenyl substituted with 0–2 $R^{19}$; and each $R^{19}$ is independently a member selected from the group consisting of F, Cl, COOH, $C_1$–$C_4$ alkoxy, $OCHF_2$ and $OCF_3$.

In still another aspect, preferred compounds of the present invention have the following structural formula:

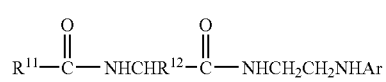

If wherein:

$R^{11}$ is a member selected from the group consisting of indolyl substituted with 0–2 $R^{11a}$; benzofuranyl substituted with 0–2 $R^{11a}$; benzothienyl substituted with 0–2 $R^{11a}$; benzothiazole substituted with 0–2 $R^{11a}$; benzisoxazolyl substituted with 0–2 $R^{11a}$; benzoxazolyl substituted with 0–2 $R^{11a}$; and pyrazolo[1,5-a]pyrimidinyl substituted with 0–2 $R^{11a}$; piperidinyl N-substituted with 0–1 $R^{11b}$; morpholinyl N-substituted with 0–1 $R^{11b}$; and 2-oxo-pyrrolidinyl with 0–1 $R^{11b}$;

each $R^{11a}$ is independently a member selected from the group consisting of Cl, F, $NH_2$, $CH_3$, $OCH_3$, $—C(=O)OCH_3$, $OCF_3$, and $CF_3$;

each $R^{11b}$ is independently a member selected from the group consisting of pyrimidinyl substituted with 0–2 $R^{11c}$; benzyl, acetyl, $CH_2$-furanyl, and $CH_2$-thienyl;

each $R^{11c}$ is independently a member selected from the group consisting of Br and $CH_3$;

$R^{12}$ is $(CH_2)_sR^{12a}$;

$R^{12a}$ is a member selected from the group consisting of cyclopentyl and cyclohexyl;

s is the integer 1 or 2;

Ar is a phenyl substituted with 0–2 $R^{19}$; and each $R^{19}$ is independently a member selected from the group consisting of F, Cl, COOH, $C_1$–$C_4$ alkoxy, $OCHF_2$ and $OCF_3$.

Preferred compounds of Formula I are set forth below in Table I:

TABLE I

1. N-((S)-1-(2-(4-methoxyphenylamino)ethylcarbamoyl)-3-phenylpropyl)-5-(3-(trifluoromethyl)phenyl)furan-2-carboxamide;
2. N-((S)-1-(2-(4-methoxyphenylamino)ethylcarbamoyl)-2-(2-chlorophenyl)ethyl)-5-(3-(trifluoromethyl)phenyl)furan-2-carboxamide;
3. N-((S)-1-(2-(4-methoxyphenylamino)ethylcarbamoyl)-2-(3-chlorophenyl)ethyl)-5-(3-(trifluoromethyl)phenyl)furan-2-carboxamide;
4. N-((S)-1-(2-(4-methoxyphenylamino)ethylcarbamoyl)-2-(4-chlorophenyl)ethyl)-5-(3-(trifluoromethyl)phenyl)furan-2-carboxamide;
5. N-((S)-1-(2-(4-methoxyphenylamino)ethylcarbamoyl)-2-(tetrahydro-2H-Pyran-4-yl)ethyl)-5-(3-(trifluoromethyl)phenyl)furan-2-carboxamide;
6. N-((S)-1-(2-(4-methoxyphenylamino)ethylcarbamoyl)-2-cyclopentylethyl)-5-(3-(trifluoromethyl)phenyl)furan-2-carboxamide;
7. (S)-N-{2-[4-(2,3-Dimethyl-phenoxy)-phenyl]-1-[2-(4-methoxy-phenylamino)-ethylcarbamoyl]-ethyl}-3-methyl-benzamide;
8. (±)-N-((2-(4-methoxyphenylamino)ethylcarbamoyl)(4-chlorophenyl)methyl)-3-methylbenzamide;
9. (±)-N-((2-(4-methoxyphenylamino)ethylcarbamoyl)(phenyl)-methyl)-5-(3-(trifluoromethyl)phenyl)furan-2-carboxamide;
10. N-((S)-1-(2-(4-(difluoromethoxy)phenylamino)ethylcarbamoyl)-2-cyclohexylethyl)-5-(3-(trifluoromethyl)phenyl)furan-2-carboxamide;
11. 4-[2-(3-Cyclohexyl-2-(S)-{[5-(3-trifluoromethyl-phenyl)-furan-2-carbonyl]-amino}-propionylamino)-ethylamino]-benzoic acid;
12. 2-[2-(3-Cyclohexyl-2-(S)-{[5-(3-trifluoromethyl-phenyl)-furan-2-carbonyl]-amino}-propionylamino)-ethylamino]-benzoic acid;
13. 4-Cyclohexyl-2-(S)-(2-(R)-phenyl-propionylamino)-N-[2-(4-trifluoromethoxy-phenylamino)-ethyl]-butyramide;
14. Acetyl-piperidine-4-carboxylic acid (S)-{2-cyclohexyl-1-[2-(4-trifluoromethoxy-phenylamino)-ethylcarbamoyl]-ethyl}-amide;
15. (S)-2-{2-[4-(4-Acetyl-piperazin-1-yl)-phenoxy]-acetylamino}-3-cyclohexyl-N-[2-(4-trifluoromethoxy-phenylamino)-ethyl]-propionamide;
16. (S)-2-Chloro-N-{1-[2-(4-methoxy-phenylamino)-ethylcarbamoyl]-2-phenyl-ethyl}-3-methyl-benzamide;
17. Cyclohexyl-2-[2-(4-methoxy-phenyl)-acetylamino]-N-[2-(4-trifluoromethoxy-phenylamino)-ethyl]-propionamide;
18. (S)-N-{2-[4-(3,5-Dichloro-phenoxy)-phenyl]-1-[2-(4-methoxy-phenylamino)-ethylcarbamoyl]-ethyl}-3-methyl-benzamide;
19. N-(S)-{2-cyclohexyl-1-[2-(4-trifluoromethoxy-phenylamino)-ethylcarbamoyl]-ethyl}-4-methanesulfonyl-benzamide;
20. (S)-4-Benzyloxy-N-{1-[2-(4-methoxy-phenylamino)-ethylcarbamoyl]-2-phenyl-ethyl}-3,5-dimethyl-benzamide;
21. (S)-4-Methoxy-N-{1-[2-(4-methoxy-phenylamino)-ethylcarbamoyl]-2-phenyl-ethyl}-3,5-dimethyl-benzamide;
22. 5-Methoxy-1H-indole-2-carboxylic acid (S)-{2-cyclohexyl-1-[2-(4-trifluoromethoxy-phenylamino)-ethylcarbamoyl]-ethyl}-amide;
23. (S)-3-Bromo-N-{1-[2-(4-methoxy-phenylamino)-ethylcarbamoyl]-2-phenyl-ethyl}-4-methyl-benzamide;
24. Furan-2-carboxylic acid (S)-{2-cyclohexyl-1-[2-(4-trifluoromethoxy-phenylamino)-ethylcarbamoyl]-ethyl}-amide;
25. Thiophene-2-carboxylic acid (S)-{2-cyclohexyl-1-[2-(4-trifluoromethoxy-phenylamino)-ethylcarbamoyl]-ethyl}-amide;
26. Furan-3-carboxylic acid (S)-{2-cyclohexyl-1-[2-(4-trifluoromethoxy-phenylamino)-ethylcarbamoyl]-ethyl}-amide;
27. N-(S)-{2-cyclohexyl-1-[2-(4-trifluoromethoxy-phenylamino)-ethylcarbamoyl]-ethyl}-4-(5-methyl-[1,2,4]oxadiazol-3-yl)-benzamide;
28. 5-(4-Fluoro-phenyl)-thiophene-2-carboxylic acid (S)-{2-cyclohexyl-1-[2-(4-trifluoromethoxy-phenylamino)-ethylcarbamoyl]-ethyl}-amide;
29. (S)-N-{1-[2-(4-Methoxy-phenylamino)-ethylcarbamoyl]-2-phenyl-ethyl}-2,4,5-trimethyl-benzamide;
30. (S)-N-{1-[2-(4-Methoxy-phenylamino)-ethylcarbamoyl]-2-phenyl-ethyl}-2,4,5-trimethyl-benzamide;
31. 5-(3-Fluoro-phenyl)-furan-2-carboxylic acid (S)-{2-cyclohexyl-1-[2-(4-trifluoromethoxy-phenylamino)-ethylcarbamoyl]-ethyl}-amide;
32. Benzyl-morpholine-2-carboxylic acid (S)-{2-cyclohexyl-1-[2-(4-trifluoromethoxy-phenylamino)-ethylcarbamoyl]-ethyl}-amide;
33. (S)-N-{2-[4-(4-Dimethylamino-phenoxy)-phenyl]-1-[2-(4-methoxy-phenylamino)-ethylcarbamoyl]-ethyl}-3-methyl-benzamide;
34. 2'-Chloro-biphenyl-3-carboxylic acid (S)-{2-cyclohexyl-1-[2-(4-trifluoromethoxy-phenylamino)-ethylcarbamoyl]-ethyl}-amide;
35. 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
36. 5-(3-Fluoro-phenyl)-thiophene-2-carboxylic acid (S)-{2-cyclohexyl-1-[2-(4-trifluoromethoxy-phenylamino)-ethylcarbamoyl]-ethyl}-amide;
37. Thiophene-3-carboxylic acid (S)-{2-cyclohexyl-1-[2-(4-trifluoromethoxy-phenylamino)-ethylcarbamoyl]-ethyl}-amide;
38. Oxo-1-thiophen-2-ylmethyl-pyrrolidine-3-carboxylic acid (S)-{2-cyclohexyl-1-[2-(4-trifluoromethoxy-phenylamino)-ethylcarbamoyl]-ethyl}-amide;
39. Furan-2-ylmethyl-5-oxo-pyrrolidine-3-carboxylic acid (S)-{2-cyclohexyl-1-[2-(4-trifluoromethoxy-phenylamino)-ethylcarbamoyl]-ethyl}-amide;

TABLE I-continued

40. Methyl-5-(pyrrolidine-1-sulfonyl)-furan-3-carboxylic acid (S)-{2-cyclohexyl-1-[2-(4-trifluoromethoxy-phenylamino)-ethylcarbamoyl]-ethyl}-amide;
41. (S)-1-Phenyl-5-trifluoromethyl-1H-pyrazole-4-carboxylic acid {1-[2-(4-methoxy-phenylamino)-ethylcarbamoyl]-2-phenyl-ethyl}-amide;
42. 5-p-Tolyl-thiophene-2-carboxylic acid (S)-{2-cyclohexyl-1-[2-(4-trifluoromethoxy-phenylamino)-ethylcarbamoyl]-ethyl}-amide;
43. Benzoimidazol-1-ylmethyl-N-{2-cyclohexyl-1-(S)-[2-(4-trifluoromethoxy-phenylamino)-ethyl]}-benzamide;
44. (S)-1-(4-Chloro-phenyl)-5-trifluoromethyl-1H-pyrazole-4-carboxylic acid {1-[2-(4-methoxy-phenylamino)-ethylcarbamoyl]-2-phenyl-ethyl}-amide;
45. (S)-N-[1-[2-(4-Methoxy-phenylamino)-ethylcarbamoyl]-2-(4-p-tolyloxy-phenyl)-ethyl]-3-methyl-benzamide;
46. Cyclohexyl-2-(S)-(2-tetrazol-1-yl-acetylamino)-N-[2-(4-trifluoromethoxy-phenylamino)-ethyl]-propionamide;
47. 5-m-Tolyl-thiophene-2-carboxylic acid (S)-{2-cyclohexyl-1-[2-(4-trifluoromethoxy-phenylamino)-ethylcarbamoyl]-ethyl}-amide;
48. 2,7-Dimethyl-pyrazolo[1,5-a]pyrimidine-6-carboxylic acid (S)-{2-cyclohexyl-1-[2-(4-trifluoromethoxy-phenylamino)-ethylcarbamoyl]-ethyl}-amide;
49. 2-Methyl-5-(morpholine-4-sulfonyl)-furan-3-carboxylic acid (S)-{2-cyclohexyl-1-[2-(4-trifluoromethoxy-phenylamino)-ethylcarbamoyl]-ethyl}-amide;
50. 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
51. 5-m-Tolyl-furan-2-carboxylic acid (S)-{2-cyclohexyl-1-[2-(4-trifluoromethoxy-phenylamino)-ethylcarbamoyl]-ethyl}-amide;
52. (S)-2,3-Dihydro-benzofuran-7-carboxylic acid {1-[2-(4-methoxy-phenylamino)-ethylcarbamoyl]-2-phenyl-ethyl}-amide;
53. Methanesulfonyl-thiophene-2-carboxylic acid (S)-{2-cyclohexyl-1-[2-(4-trifluoromethoxy-phenylamino)-ethylcarbamoyl]-ethyl}-amide;
54. 2-Phenyl-thiazole-4-carboxylic acid (S)-{2-cyclohexyl-1-[2-(4-trifluoromethoxy-phenylamino)-ethylcarbamoyl]-ethyl}-amide;
55. (S)-3-Cyano-N-{1-[2-(4-methoxy-phenylamino)-ethylcarbamoyl]-2-phenyl-ethyl}-benzamide;
56. (S)-N-{1-[2-(4-Methoxy-phenylamino)-ethylcarbamoyl]-2-phenyl-ethyl}-3-(2-methyl-thiazol-4-yl)-benzamide;
57. (S)-N-[2-(4-Methoxy-phenylamino)-ethyl]-3-phenyl-2-(3-phenyl-ureido)-propionamide;
58. 3-Cyclohexyl-2-(S)-(2-(S)-hydroxy-2-phenyl-acetylamino)-N-[2-(4-trifluoromethoxy-phenylamino)-ethyl]-propionamide;
59. Benzo[c]isoxazole-3-carboxylic acid (S)-{2-cyclohexyl-1-[2-(4-trifluoromethoxy-phenylamino)-ethylcarbamoyl]-ethyl}-amide;
60. N-(S)-{2-cyclohexyl-1-[2-(4-trifluoromethoxy-phenylamino)-ethylcarbamoyl]-ethyl}-4-difluoromethoxy-benzamide;
61. N-(S)-{2-cyclohexyl-1-[2-(4-trifluoromethoxy-phenylamino)-ethylcarbamoyl]-ethyl}-4-isopropoxy-benzamide;
62. Phenyl-thiophene-2-carboxylic acid (S)-{2-cyclohexyl-1-[2-(4-trifluoromethoxy-phenylamino)-ethylcarbamoyl]-ethyl}-amide;
63. (S)-N-{1-[2-(4-Methoxy-phenylamino)-ethylcarbamoyl]-2-phenyl-ethyl}-nicotinamide;
64. (S)-N-{1-[2-(4-Methoxy-phenylamino)-ethylcarbamoyl]-2-phenyl-ethyl}-isonicotinamide;
65. Phenyl-furan-2-carboxylic acid (S)-{2-cyclohexyl-1-[2-(4-trifluoromethoxy-phenylamino)-ethylcarbamoyl]-ethyl}-amide;
66. (S)-N-[1-[2-(4-Methoxy-phenylamino)-ethylcarbamoyl]-2-(4-o-tolyloxy-phenyl)-ethyl]-3-methyl-benzamide;
67. N-(S)-{2-cyclohexyl-1-[2-(4-trifluoromethoxy-phenylamino)-ethylcarbamoyl]-ethyl}-4-oxazol-5-yl-benzamide;
68. 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
69. 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
70. 5-p-Tolyl-furan-2-carboxylic acid (S)-{2-cyclohexyl-1-[2-(4-trifluoromethoxy-phenylamino)-ethylcarbamoyl]-ethy}-amide;
71. N-(S)-{2-cyclohexyl-1-[2-(4-trifluoromethoxy-phenylamino)-ethylcarbamoyl]-ethyl}-3-[(4,6-dimethyl-pyrimidin-2-yl)-methyl-amino]-benzamide;
72. 1-(4,6-Dimethyl-pyrimidin-2-yl)-piperidine-4-carboxylic acid (S)-{2-cyclohexyl-1-[2-(4-trifluoromethoxy-phenylamino)-ethylcarbamoyl]-ethyl}-amide;
73. N-(S)-{2-cyclohexyl-1-[2-(4-trifluoromethoxy-phenylamino)-ethylcarbamoyl]-ethyl}-3-(4,6-dimethoxy-pyrimidin-2-yloxy)-benzamide;
74. 3'-Methoxy-biphenyl-3-carboxylic acid (S)-{2-cyclohexyl-1-[2-(4-trifluoromethoxy-phenylamino)-ethylcarbamoyl]-ethyl}-amide;
75. N-{3-Cyclohexyl-1-(S)-[2-(4-methoxy-phenylamino)-ethylcarbamoyl]-propyl}-2-(R)-phenyl-butyramide;
76. 3-Cyclohexyl-N-[2-(4-fluoro-phenylamino)-ethyl]-2-(S)-(2-thiophen-2-yl-acetylamino)-propionamide;
77. 3-Cyclohexyl-N-[2-(4-fluoro-phenylamino)-ethyl]-2-(S)-(2-thiophen-3-yl-acetylamino)-propionamide;
78. (S)-3-Bromo-N-{1-[2-(4-methoxy-phenylamino)-ethylcarbamoyl]-2-phenyl-ethyl}-benzamide;

TABLE I-continued

79. Acetyl-piperidine-4-carboxylic acid (S)-{2-cyclohexyl-1-[2-(4-fluoro-phenylamino)-ethylcarbamoyl]-ethyl}-amide;
80. N-(S)-{2-cyclohexyl-1-[2-(4-trifluoromethoxy-phenylamino)-ethylcarbamoyl]-ethyl}-4-(4,6-dimethoxy-pyrimidin-2-yl)-benzamide;
81. 1-(5-Bromo-pyrimidin-2-yl)-piperidine-4-carboxylic acid (S)-{2-cyclohexyl-1-[2-(4-trifluoromethoxy-phenylamino)-ethylcarbamoyl]-ethyl}-amide;
82. (S)-2-(2-Cyclopent-2-enyl-acetylamino)-N-[2-(4-methoxy-phenylamino)-ethyl]-3-phenyl-propionamide;
83. Cyclohexyl-N-[2-(4-fluoro-phenylamino)-ethyl]-2-(2-1H-indol-3-yl-acetylamino)-propionamide;
84. N-(S)-{2-cyclohexyl-1-[2-(4-fluoro-phenylamino)-ethylcarbamoyl]-ethyl}-3-methanesulfonylamino-benzamide;
85. 5-(3-Trifluoromethyl-phenyl)-furan-2-carboxylic acid (S)-{2-cyclohexyl-1-[2-(4-fluoro-phenylamino)-ethylcarbamoyl]-ethyl}-amide;
86. Cyclohexyl-2-(S)-(2-(R,S)-fluoro-2-phenyl-acetylamino)-N-[2-(4-fluoro-phenylamino)-ethyl]-propionamide;
87. Cyclohexyl-N-(S)-[2-(4-fluoro-phenylamino)-ethyl]-2-[2-(4-trifluoromethoxy-phenyl)-acetylamino]-propionamide;
88. (S)-2-[3-(4-Chloro-phenyl)-ureido]-N-[2-(4-methoxy-phenylamino)-ethyl]-3-phenyl-propionamide;
89. (S)-N-[2-(4-Methoxy-phenylamino)-ethyl]-2-[3-(4-phenoxy-phenyl)-ureido]-3-phenyl-propionamide;
90. (S)-N-[2-(4-Methoxy-phenylamino)-ethyl]-2-(3-phenethyl-ureido)-3-phenyl-propionamide;
91. (S)-2-[3-(4-Fluoro-benzyl)-ureido]-N-[2-(4-methoxy-phenylamino)-ethyl]-3-phenyl-propionamide;
92. N-(S)-{2-cyclohexyl-1-[2-(4-trifluoromethoxy-phenylamino)-ethylcarbamoyl]-ethyl}-4-(4,6-dimethyl-pyrimidin-2-ylamino)-benzamide;
93. 1-(5-Bromo-pyrimidin-2-yl)-piperidine-3-carboxylic acid (S)-{2-cyclohexyl-1-[2-(4-trifluoromethoxy-phenylamino)-ethylcarbamoyl]-ethyl}-amide;
94. (S)-2-(3-Benzo[1,3] dioxol-5-yl-ureido)-N-[2-(4-methoxy-phenylamino)-ethyl]-3-phenyl-propionamide;
95. 3-Cyclohexyl-2-(S)-[2-(2,5-difluorophenyl)-acetylamino]-N-[2-(4-fluoro-phenylamino)-ethyl]-propionamide;
96. (S)-2-[3-(3-Fluoro-benzyl)-ureido]-N-[2-(4-methoxy-phenylamino)-ethyl]-3-phenyl-propionamide;
97. (S)-N-[2-(4-Methoxy-phenylamino)-ethyl]-3-phenyl-2-(3-o-tolyl-ureido)-propionamide;
98. (S)-N-{2-[4-(3,4-Dichloro-phenoxy)-phenyl]-1-[2-(4-methoxy-phenylamino)-ethylcarbamoyl]-ethyl}-3-methyl-benzamide;
99. 3-Cyclohexyl-2-(S)-[2-(3,4-difluoro-phenyl)-acetylamino]-N-[2-(4-fluoro-phenylamino)-ethyl]-propionamide;
100. 3-Cyclohexyl-2-(S)-[2-(2,4-difluoro-phenyl)-acetylamino]-N-[2-(4-fluoro-phenylamino)-ethyl]-propionamide;
101. (S)-N-[2-(4-Methoxy-phenylamino)-ethyl]-2-(3-naphthalen-1-yl-ureido)-3-phenyl-propionamide;
102. (S)-2-[3-(2-tert-Butyl-6-methyl-phenyl)-ureido]-N-[2-(4-methoxy-phenylamino)-ethyl]-3-phenyl-propionamide;
103. (S)-2-[3-(4-Acetyl-phenyl)-ureido]-N-[2-(4-methoxy-phenylamino)-ethyl]-3-phenyl-propionamide;
104. (S)-N-[2-(4-Methoxy-phenylamino)-ethyl]-2-[3-(3-methoxy-phenyl)-ureido]-3-phenyl-propionamide;
105. (S)-Biphenyl-4-carboxylic acid {2-cyclohexyl-1-[2-(4-methoxy-phenylamino)-ethylcarbamoyl]-ethyl}-amide;
106. (S)-N-{2-Cyclohexyl-1-[2-(4-methoxy-phenylamino)-ethylcarbamoyl]-ethyl}-3-trifluoromethyl-benzamide;
107. 2-(S)-[2-(2-Chloro-4-fluoro-phenyl)-acetylamino]-3-cyclohexyl-N-[2-(4-fluoro-phenylamino)-ethyl]-propionamide;
108. (S)-2-Chloro-N-{2-cyclohexyl-1-[2-(4-methoxy-phenylamino)-ethylcarbamoyl]-ethyl}-3-methyl-benzamide;
109. (S)-4-Benzyloxy-N-{2-cyclohexyl-1-[2-(4-methoxy-phenylamino)-ethylcarbamoyl]-ethyl}-benzamide;
110. (S)-4-Benzyloxy-N-{2-cyclohexyl-1-[2-(4-methoxy-phenylamino)-ethylcarbamoyl]-ethyl}-3,5-dimethyl-benzamide;
111. (S)-N-{2-Cyclohexyl-1-[2-(4-methoxy-phenylamino)-ethylcarbamoyl]-ethyl}-4-methoxy-3,5-dimethyl-benzamide;
112. (S)-3-Bromo-N-{2-cyclohexyl-1-[2-(4-methoxy-phenylamino)-ethylcarbamoyl]-ethyl}-4-methyl-benzamide;
113. (S)-5-Fluoro-1H-indole-2-carboxylic acid {2-cyclohexyl-1-[2-(4-methoxy-phenylamino)-ethylcarbamoyl]-ethyl}-amide;
114. (S)-2-Amino-4-methyl-thiazole-5-carboxylic acid {2-cyclohexyl-1-[2-(4-methoxy-phenylamino)-ethylcarbamoyl]-ethyl}-amide;
115. (S)-1-Phenyl-5-trifluoromethyl-1H-pyrazole-4-carboxylic acid {2-cyclohexyl-1-[2-(4-methoxy-phenylamino)-ethylcarbamoyl]-ethyl}-amide;
116. (S)-1-(4-Chloro-phenyl)-5-trifluoromethyl-1H-pyrazole-4-carboxylic acid {2-cyclohexyl-1-[2-(4-methoxy-phenylamino)-ethylcarbamoyl]-ethyl}-amide;
117. (S)-5-(3-Trifluoromethyl-phenyl)-furan-2-carboxylic acid {2-cyclohexyl-1-[2-(4-methoxy-phenylamino)-ethylcarbamoyl]-ethyl}-amide;

TABLE I-continued 118. (S)-3-Chloro-N-{2-cyclohexyl-1-[2-(4-methoxy-phenylamino)-ethylcarbamoyl]-ethyl}-benzamide;
119. (S)-N-{2-Cyclohexyl-1-[2-(4-methoxy-phenylamino)-ethylcarbamoyl]-ethyl}-3-dimethylamino-benzamide;
120. (S)-3-Cyano-N-{2-cyclohexyl-1-[2-(4-methoxy-phenylamino)-ethylcarbamoyl]-ethyl}-benzamide;
121. (S)-4-Cyano-N-{2-cyclohexyl-1-[2-(4-methoxy-phenylamino)-ethylcarbamoyl]-ethyl}-benzamide;
122. N-{2-cyclohexyl-1-(S)-[2-(4-trifluoromethoxy-phenylamino)-ethylcarbamoyl]-ethyl}-2-(R)-phenyl-propionamide;
123. (S)-N-{2-Cyclohexyl-1-[2-(4-methoxy-phenylamino)-ethylcarbamoyl]-ethyl}-3-(2-methyl-thiazol-4-yl)-benzamide;
124. (S)-N-{2-Cyclohexyl-1-[2-(4-methoxy-phenylamino)-ethylcarbamoyl]-ethyl}-4-[1,2,4]triazol-1-yl-benzamide;
125. 3-Cyclohexyl-2-(S)-[2-(3,5-difluoro-phenyl)-acetylamino]-N-[2-(4-fluoro-phenylamino)-ethyl]-propionamide;
126. (S)-N-{3-Cyclohexyl-1-[2-(4-methoxy-phenylamino)-ethylcarbamoyl]-propyl}-3-trifluoromethyl-benzamide;
127. (S)-N-{3-Cyclohexyl-1-[2-(4-methoxy-phenylamino)-ethylcarbamoyl]-propyl}-4-morpholin-4-yl-benzamide;
128. (4-Cyclohexyl-N-[2-(4-methoxy-phenylamino)-ethyl-2-(S)-(2-(S)-phenyl-propionylamino)-butyramide;
129. (S)-4-Benzyloxy-N-{3-cyclohexyl-1-[2-(4-methoxy-phenylamino)-ethylcarbamoyl]-propyl}-benzamide;
130. (S)-Biphenyl-4-carboxylic acid {3-cyclohexyl-1-[2-(4-methoxy-phenylamino)-ethylcarbamoyl]-propyl}-amide;
131. (S)-5-Chloro-1H-indole-2-carboxylic acid {3-cyclohexyl-1-[2-(4-methoxy-phenylamino)-ethylcarbamoyl]-propyl}-amide;
132. (S)-5-Fluoro-1H-indole-2-carboxylic acid {3-cyclohexyl-1-[2-(4-methoxy-phenylamino)-ethylcarbamoyl]-propyl}-amide;
133. (S)-2-Amino-4-methyl-thiazole-5-carboxylic acid {3-cyclohexyl-1-[2-(4-methoxy-phenylamino)-ethylcarbamoyl]-propyl}-amide;
134. (S)-5-Chloro-benzofuran-2-carboxylic acid {3-cyclohexyl-1-[2-(4-methoxy-phenylamino)-ethylcarbamoyl]-propyl}-amide;
135. N-{2-cyclohexyl-1-(S)-[2-(4-trifluoromethoxy-phenylamino)-ethylcarbamoyl]-ethyl}-2-(R)-phenyl-butyramide;
136. (S)-5-(3-Trifluoromethyl-phenyl)-furan-2-carboxylic acid {3-cyclohexyl-1-[2-(4-methoxy-phenylamino)-ethylcarbamoyl]-propyl}-amide;
137. (S)-Benzothiazole-6-carboxylic acid {3-cyclohexyl-1-[2-(4-methoxy-phenylamino)-ethylcarbamoyl]-propyl}-amide;
138. (S)-N-{3-Cyclohexyl-1-[2-(4-methoxy-phenylamino)-ethylcarbamoyl]-propyl}-3-trifluoromethoxy-benzamide;
139. (S)-3-Cyano-N-{3-cyclohexyl-1-[2-(4-methoxy-phenylamino)-ethylcarbamoyl]-propyl}-benzamide;
140. (S)-4-Cyano-N-{3-cyclohexyl-1-[2-(4-methoxy-phenylamino)-ethylcarbamoyl]-propyl}-benzamide;
141. N-{2-cyclohexyl-1-(S)-[2-(4-trifluoromethoxy-phenylamino)-ethylcarbamoyl]-ethyl}-4-phenoxy-benzamide;
142. (S)-N-{3-Cyclohexyl-1-[2-(4-methoxy-phenylamino)-ethylcarbamoyl]-propyl}-3-(2-methyl-thiazol-4-yl)-benzamide;
143. (S)-N-{3-Cyclohexyl-1-[2-(4-methoxy-phenylamino)-ethylcarbamoyl]-propyl}-4-[1,2,4]triazol-1-yl-benzamide;
144. (S)-Biphenyl-3-carboxylic acid {3-cyclohexyl-1-[2-(4-methoxy-phenylamino)-ethylcarbamoyl]-propyl}-amide;
145. (S)-N-{2-Cyclohexyl-1-[2-(4-methoxy-phenylamino)-ethylcarbamoyl]-ethyl}-2-fluoro-benzamide;
146. (S)-N-{2-Cyclohexyl-1-[2-(4-methoxy-phenylamino)-ethylcarbamoyl]-ethyl}-3,4-difluoro-benzamide;
147. (S)-N-{2-Cyclohexyl-1-[2-(4-methoxy-phenylamino)-ethylcarbamoyl]-ethyl}-3-fluoro-2-methyl-benzamide;
148. (S)-2-Chloro-N-{2-cyclohexyl-1-[2-(4-methoxy-phenylamino)-ethylcarbamoyl]-ethyl}-5-methyl-benzamide;
149. (S)-N-{2-Cyclohexyl-1-[2-(4-methoxy-phenylamino)-ethylcarbamoyl]-ethyl}-4-fluoro-3-trifluoromethyl-benzamide;
150. (S)-5-Methyl-1-phenyl-1H-pyrazole-4-carboxylic acid {2-cyclohexyl-1-[2-(4-methoxy-phenylamino)-ethylcarbamoyl]-ethyl}-amide;
151. (S)-N-{2-Cyclohexyl-1-[2-(4-methoxy-phenylamino)-ethylcarbamoyl]-ethyl}-4-propyl-benzamide;
152. 3-Cyclohexyl-2-(S)-[2-(4-fluoro-phenyl)-acetylamino]-N-[2-(4-fluoro-phenylamino)-ethyl]-propionamide;
153. (S)-N-{2-Cyclohexyl-1-[2-(4-methoxy-phenylamino)-ethylcarbamoyl]-ethyl}-4-methoxy-benzamide;
154. (S)-N-{2-Cyclohexyl-1-[2-(4-methoxy-phenylamino)-ethylcarbamoyl]-ethyl}-2-fluoro-5-trifluoromethyl-benzamide;
155. (S)-3-Chloro-N-{2-cyclohexyl-1-[2-(4-methoxy-phenylamino)-ethylcarbamoyl]-ethyl}-2-fluoro-benzamide;
156. (S)-5-Chloro-N-{2-cyclohexyl-1-[2-(4-methoxy-phenylamino)-ethylcarbamoyl]-ethyl}-2-fluoro-benzamide;

TABLE I-continued 157. (S)-N-{2-Cyclohexyl-1-[2-(4-methoxy-phenylamino)-ethylcarbamoyl]-ethyl}-5-fluoro-2-methyl-benzamide;
158. (S)-1-Phenyl-cyclopropanecarboxylic acid {2-cyclohexyl-1-[2-(4-methoxy-phenylamino)-ethylcarbamoyl]-ethyl}-amide;
159. (S)-3-Cyclohexyl-N-[2-(4-methoxy-phenylamino)-ethyl-2-(2-phenylamino-acetylamino)-propionamide;
160. 3-Cyclohexyl-2-(S)-(2-(R)-hydroxy-2-phenyl-acetylamino)-N-[2-(4-methoxy-phenylamino)-ethyl]-propionamide;
161. (S)-1-(4-Fluoro-phenyl)-5-methyl-1H-pyrazole-4-carboxylic acid {2-cyclohexyl-1-[2-(4-methoxy-phenylamino)-ethylcarbamoyl]-ethyl}-amide;
162. (S)-1-(4-Methoxy-phenyl)-5-methyl-1H-pyrazole-4-carboxylic acid {2-cyclohexyl-1-[2-(4-methoxy-phenylamino)-ethylcarbamoyl]-ethyl}-amide;
163. (S)-1-(4-Chloro-phenyl)-5-methyl-1H-pyrazole-4-carboxylic acid {2-cyclohexyl-1-[2-(4-methoxy-phenylamino)-ethylcarbamoyl]-ethyl}-amide;
164. N-{2-Cyclohexyl-1-(S)-[2-(4-methoxy-phenylamino)-ethylcarbamoyl]-ethyl}-2-(S)-phenyl-butyramide;
165. (S)-N-{2-Cyclohexyl-1-[2-(4-methoxy-phenylamino)-ethylcarbamoyl]-ethyl}-3-fluoro-5-trifluoromethyl-benzamide;
166. (S)-N-{2-Cyclohexyl-1-[2-(4-methoxy-phenylamino)-ethylcarbamoyl]-ethyl}-2-fluoro-3-trifluoromethyl-benzamide;
167. (S)-N-{2-Cyclohexyl-1-[2-(4-methoxy-phenylamino)-ethylcarbamoyl]-ethyl}-4-fluoro-3-methyl-benzamide;
168. (S)-5-(4-Chloro-phenyl)-furan-2-carboxylic acid {2-cyclohexyl-1-[2-(4-methoxy-phenylamino)-ethylcarbamoyl]-ethyl}-amide;
169. (S)-N-{2-Cyclohexyl-1-[2-(4-methoxy-phenylamino)-ethylcarbamoyl]-ethyl}-2-fluoro-4-trifluoromethyl-benzamide;
170. (S)-4'-Chloro-biphenyl-4-carboxylic acid {2-cyclohexyl-1-[2-(4-methoxy-phenylamino)-ethylcarbamoyl]-ethyl}-amide;
171. (S)-3',5'-Dichloro-biphenyl-4-carboxylic acid {2-cyclohexyl-1-[2-(4-methoxy-phenylamino)-ethylcarbamoyl]-ethyl}-amide;
172. (S)-3'-Methoxy-biphenyl-4-carboxylic acid {2-cyclohexyl-1-[2-(4-methoxy-phenylamino)-ethylcarbamoyl]-ethyl}-amide;
173. (S)-3'-Chloro-biphenyl-4-carboxylic acid {2-cyclohexyl-1-[2-(4-methoxy-phenylamino)-ethylcarbamoyl]-ethyl}-amide;
174. (S)-2'-Methoxy-biphenyl-4-carboxylic acid {2-cyclohexyl-1-[2-(4-methoxy-phenylamino)-ethylcarbamoyl]-ethyl}-amide;
175. (S)-4'-Chloro-biphenyl-3-carboxylic acid {2-cyclohexyl-1-[2-(4-methoxy-phenylamino)-ethylcarbamoyl]-ethyl}-amide;
176. (S)-4-Benzo[1,3]dioxol-5-yl-N-{2-cyclohexyl-1-[2-(4-methoxy-phenylamino)-ethylcarbamoyl]-ethyl}-benzamide;
177. (S)-5-Bromo-furan-2-carboxylic acid {2-cyclohexyl-1-[2-(4-methoxy-phenylamino)-ethylcarbamoyl]-ethyl}-amide;
178. (S)-3,5-Dibromo-N-{2-cyclohexyl-1-[2-(4-methoxy-phenylamino)-ethylcarbamoyl]-ethyl}-benzamide;
179. (S)-3,5-Dichloro-N-{2-cyclohexyl-1-[2-(4-methoxy-phenylamino)-ethylcarbamoyl]-ethyl}-benzamide;
180. (S)-N-{2-Cyclohexyl-1-[2-(4-methoxy-phenylamino)-ethylcarbamoyl]-ethyl}-3,5-dimethoxy-benzamide;
181. (S)-Biphenyl-3-carboxylic acid {2-cyclohexyl-1-[2-(4-methoxy-phenylamino)-ethylcarbamoyl]-ethyl}-amide;
182. (S)-5-Bromo-thiophene-2-carboxylic acid {2-cyclohexyl-1-[2-(4-methoxy-phenylamino)-ethylcarbamoyl]-ethyl}-amide;
183. (S)-N-{2-Cyclohexyl-1-[2-(4-methoxy-phenylamino)-ethylcarbamoyl]-ethyl}-4-phenoxy-benzamide;
184. (S)-N-{2-Cyclohexyl-1-[2-(4-methoxy-phenylamino)-ethylcarbamoyl]-ethyl}-3-phenoxy-benzamide;
185. (S)-1H-Indole-3-carboxylic acid {2-cyclohexyl-1-[2-(4-methoxy-phenylamino)-ethylcarbamoyl]-ethyl}-amide;
186. (S)-Benzothiazole-6-carboxylic acid {2-cyclohexyl-1-[2-(4-methoxy-phenylamino)-ethylcarbamoyl]-ethyl}-amide;
187. (S)-2-Amino-benzothiazole-6-carboxylic acid {2-cyclohexyl-1-[2-(4-methoxy-phenylamino)-ethylcarbamoyl]-ethyl}-amide;
188. (S)-4-Methyl-2-(4-trifluoromethyl-phenyl)-thiazole-5-carboxylic acid {2-cyclohexyl-1-[2-(4-methoxy-phenylamino)-ethylcarbamoyl]-ethyl}-amide;
189. (S)-4-(4-Chloro-phenyl)-thiophene-2-carboxylic acid {2-cyclohexyl-1-[2-(4-methoxy-phenylamino)-ethylcarbamoyl]-ethyl}-amide;
190. (S)-2-Methyl-5-trifluoromethyl-oxazole-4-carboxylic acid {2-cyclohexyl-1-[2-(4-methoxy-phenylamino)-ethylcarbamoyl]-ethyl}-amide;
191. (S)-4-(4-Methoxy-phenyl)-thiophene-2-carboxylic acid {2-cyclohexyl-1-[2-(4-methoxy-phenylamino)-ethylcarbamoyl]-ethyl}-amide;
192. N-{2-Cyclohexyl-1-(S)-[2-(4-methoxy-phenylamino)-ethylcarbamoyl]-ethyl}-2-(S)-phenyl-propionamide;
193. (S)-5-(2-Chloro-5-trifluoromethyl-phenyl)-furan-2-carboxylic acid {2-cyclohexyl-1-[2-(4-methoxy-phenylamino)-ethylcarbamoyl]-ethyl}-amide;
194. (S)-2'-Chloro-biphenyl-4-carboxylic acid {2-cyclohexyl-1-[2-(4-trifluoromethoxy-phenylamino)-ethylcarbamoyl]-ethyl}-amide;
195. (S)-1-(5-Bromo-pyrimidin-2-yl)-piperidine-4-carboxylic acid {2-cyclohexyl-1-[2-(4-methoxy-phenylamino)-ethylcarbamoyl]-ethyl}-amide;

TABLE I-continued 196. (S)-N-{2-Cyclohexyl-1-[2-(4-methoxy-phenylamino)-ethylcarbamoyl]-ethyl}-4-(4,6-dimethyl-pyrimidin-2-ylamino)-benzamide;
197. (S)-1-(5-Bromo-pyrimidin-2-yl)-piperidine-3-carboxylic acid {2-cyclohexyl-1-[2-(4-methoxy-phenylamino)-ethylcarbamoyl]-ethyl}-amide;
198. (S)-3'-Fluoro-biphenyl-4-carboxylic acid {2-cyclohexyl-1-[2-(4-trifluoromethoxy-phenylamino)-ethylcarbamoyl]-ethyl}-amide;
199. (S)-3-Aminomethyl-N-{2-cyclohexyl-1-[2-(4-methoxy-phenylamino)-ethylcarbamoyl]-ethyl}-benzamide;
200. (S)-N-{2-Cyclohexyl-1-[2-(4-trifluoromethoxy-phenylamino)-ethylcarbamoyl]-ethyl}-3-morpholin-4-ylmethyl-benzamide;
201. (S)-5-(2-Fluoro-phenyl)-thiophene-2-carboxylic acid {2-cyclohexyl-1-[2-(4-trifluoromethoxy-phenylamino)-ethylcarbamoyl]-ethyl}-amide;
202. (S)-N-{3-Cyclohexyl-1-[2-(4-methoxy-phenylamino)-ethylcarbamoyl]-propyl}-3-methyl-benzamide;
203. (S)-N-{4-Cyclohexyl-1-[2-(4-methoxy-phenylamino)-ethylcarbamoyl]-butyl}-3-methyl-benzamide;
204. (S)-N-{[2-(4-Methoxy-phenylamino)-ethylcarbamoyl]-phenyl-methyl}-3-methyl-benzamide;
205. (S)-5-(4-Trifluoromethyl-phenyl)-thiophene-2-carboxylic acid {2-cyclohexyl-1-[2-(4-trifluoromethoxy-phenylamino)-ethylcarbamoyl]-ethyl}-amide;
206. (S)-N-{1-[2-(4-Methoxy-phenylamino)-ethylcarbamoyl]-3-phenyl-propyl}-3-methyl-benzamide;
207. (S)-5-(4-Trifluoromethoxy-phenyl)-thiophene-2-carboxylic acid {2-cyclohexyl-1-[2-(4-trifluoromethoxy-phenylamino)-ethylcarbamoyl]-ethyl}-amide;
208. (S)-N-{1-[2-(4-Methoxy-phenylamino)-ethylcarbamoyl]-4-phenyl-but-3-enyl}-3-methyl-benzamide;
209. (S)-5-(3-Trifluoromethoxy-phenyl)-thiophene-2-carboxylic acid {2-cyclohexyl-1-[2-(4-trifluoromethoxy-phenylamino)-ethylcarbamoyl]-ethyl}-amide;
210. (S)-5-(2-Methoxy-phenyl)-furan-2-carboxylic acid {2-cyclohexyl-1-[2-(4-trifluoromethoxy-phenylamino)-ethylcarbamoyl]-ethyl}-amide;
211. N-{(4-Methoxy-phenyl)-[2-(4-methoxy-phenylamino)-ethylcarbamoyl]-methyl}-3-methyl-benzamide;
212. (S)-5-(2-Fluoro-phenyl)-furan-2-carboxylic acid {2-cyclohexyl-1-[2-(4-trifluoromethoxy-phenylamino)-ethylcarbamoyl]-ethyl}-amide;
213. (S)-5-(4-Trifluoromethyl-phenyl)-furan-2-carboxylic acid {2-cyclohexyl-1-[2-(4-trifluoromethoxy-phenylamino)-ethylcarbamoyl]-ethyl}-amide;
214. N-{(2-Benzyloxy-phenyl)-[2-(4-methoxy-phenylamino)-ethylcarbamoyl]-methyl}-3-methyl-benzamide;
215. (S)-5-(4-Trifluoromethoxy-phenyl)-furan-2-carboxylic acid {2-cyclohexyl-1-[2-(4-trifluoromethoxy-phenylamino)-ethylcarbamoyl]-ethyl}-amide;
216. N-{(2-Chloro-phenyl)-[2-(4-methoxy-phenylamino)-ethylcarbamoyl]-methyl}-3-methyl-benzamide;
217. N-{(4-Benzyloxy-phenyl)-[2-(4-methoxy-phenylamino)-ethylcarbamoyl]-methyl}-3-methyl-benzamide;
218. N-{[2-(4-Methoxy-phenylamino)-ethylcarbamoyl]-naphthalen-1-yl-methyl}-3-methyl-benzamide;
219. (S)-5-(2-Trifluoromethyl-phenyl)-furan-2-carboxylic acid {2-cyclohexyl-1-[2-(4-trifluoromethoxy-phenylamino)-ethylcarbamoyl]-ethyl}-amide;
220. N-{[2-(4-Methoxy-phenylamino)-ethylcarbamoyl]-o-tolyl-methyl}-3-methyl-benzamide;
221. (S)-N-{2-Cyclohexyl-1-[2-(4-trifluoromethoxy-phenylamino)-ethylcarbamoyl]-ethyl}-4-[1,2,4]triazol-1-yl-benzamide;
222. N-{(2,4-Dichloro-phenyl)-[2-(4-methoxy-phenylamino)-ethylcarbamoyl]-methyl}-3-methyl-benzamide;
223. N-{(2,3-Dichloro-phenyl)-[2-(4-methoxy-phenylamino)-ethylcarbamoyl]-methyl}-3-methyl-benzamide;
224. N-{(2,4-Dimethyl-phenyl)-[2-(4-methoxy-phenylamino)-ethylcarbamoyl]-methyl}-3-methyl-benzamide;
225. N-{(2,4-Dimethoxy-phenyl)-[2-(4-methoxy-phenylamino)-ethylcarbamoyl]-methyl}-3-methyl-benzamide;
226. N-{[2-(4-Methoxy-phenylamino)-ethylcarbamoyl]-thiophen-2-yl-methyl}-3-methyl-benzamide;
227. N-{(4-Fluoro-phenyl)-[2-(4-methoxy-phenylamino)-ethylcarbamoyl]-methyl}-3-methyl-benzamide;
228. (S)-N-{2-(4-Hydroxy-phenyl)-1-[2-(4-methoxy-phenylamino)-ethylcarbamoyl]-ethyl}-3-methyl-benzamide;
229. (S)-N-{2-(2,4-Dichloro-phenyl)-1-[2-(4-methoxy-phenylamino)-ethylcarbamoyl]-ethyl}-3-methyl-benzamide;
230. (S)-N-{2-(3,5-Difluoro-phenyl)-1-[2-(4-methoxy-phenylamino)-ethylcarbamoyl]-ethyl}-3-methyl-benzamide;
231. (S)-N-{2-(3,4-Dichloro-phenyl)-1-[2-(4-methoxy-phenylamino)-ethylcarbamoyl]-ethyl}-3-methyl-benzamide;
232. (S)-4-Benzyloxy-N-{2-cyclohexyl-1-[2-(4-trifluoromethoxy-phenylamino)-ethylcarbamoyl]-ethyl}-benzamide;
233. (S)-N-{2-(4-Acetylamino-phenyl)-1-[2-(4-methoxy-phenylamino)-ethylcarbamoyl]-ethyl}-3-methyl-benzamide;
234. (S)-Biphenyl-4-carboxylic acid {2-cyclohexyl-1-[2-(4-trifluoromethoxy-phenylamino)-ethylcarbamoyl]-ethyl}-amide;

TABLE I-continued 235. (S)-N-{1-[2-(4-Methoxy-phenylamino)-ethylcarbamoyl]-2-p-tolyl-ethyl}-3-methyl-benzamide;
236. (S)-N-{2-(3-Fluoro-phenyl)-1-[2-(4-methoxy-phenylamino)-ethylcarbamoyl]-ethyl}-3-methyl-benzamide;
237. (S)-N-{2-(3,4-Difluoro-phenyl)-1-[2-(4-methoxy-phenylamino)-ethylcarbamoyl]-ethyl}-3-methyl-benzamide;
238. (S)-N-{1-[2-(4-Methoxy-phenylamino)-ethylcarbamoyl]-2-m-tolyl-ethyl}-3-methyl-benzamide;
239. (S)-N-[1-[2-(4-Methoxy-phenylamino)-ethylcarbamoyl]-2-(2-trifluoromethyl-phenyl)-ethyl]-3-methyl-benzamide;
240. (S)-N-{2-(4-Cyano-phenyl)-1-[2-(4-methoxy-phenylamino)-ethylcarbamoyl]-ethyl}-3-methyl-benzamide;
241. (S)-N-{2-(4-Bromo-phenyl)-1-[2-(4-methoxy-phenylamino)-ethylcarbamoyl]-ethyl}-3-methyl-benzamide;
242. (S)-N-{2-(4-Iodo-phenyl)-1-[2-(4-methoxy-phenylamino)-ethylcarbamoyl]-ethyl}-3-methyl-benzamide;
243. (S)-N-{2-(4-Chloro-phenyl)-1-[2-(4-methoxy-phenylamino)-ethylcarbamoyl]-ethyl}-3-methyl-benzamide;
244. (S)-N-[1-[2-(4-Methoxy-phenylamino)-ethylcarbamoyl]-2-(4-nitro-phenyl)-ethyl]-3-methyl-benzamide;
245. (S)-N-{2-(4-Fluoro-phenyl)-1-[2-(4-methoxy-phenylamino)-ethylcarbamoyl]-ethyl}-3-methyl-benzamide;
246. (S)-5-(3-Trifluoromethyl-phenyl)-furan-2-carboxylic acid {2-cyclohexyl-1-[2-(4-trifluoromethoxy-phenylamino)-ethylcarbamoyl]-ethyl}-amide;
247. (S)-N-{2-(4-Benzyloxy-phenyl)-1-[2-(4-methoxy-phenylamino)-ethylcarbamoyl]-ethyl}-3-methyl-benzamide;
248. (S)-N-{2-[4-(2,6-Dichloro-benzyloxy)-phenyl]-1-[2-(4-methoxy-phenylamino)-ethylcarbamoyl]-ethyl}-3-methyl-benzamide;
249. (S)-N-{2-(4-Methoxy-phenyl)-1-[2-(4-methoxy-phenylamino)-ethylcarbamoyl]-ethyl}-3-methyl-benzamide;
250. 2-Amino-4-methyl-thiazole-5-carboxylic acid (S)-{2-cyclohexyl-1-[2-(4-trifluoromethoxy-phenylamino)-ethylcarbamoyl]-ethyl}-amide;
251. (S)-5-(2-Chloro-5-trifluoromethyl-phenyl)-furan-2-carboxylic acid {2-cyclohexyl-1-[2-(4-trifluoromethoxy-phenylamino)-ethylcarbamoyl]-ethyl}-amide;
252. (S)-N-[1-[2-(4-Methoxy-phenylamino)-ethylcarbamoyl]-2-(3-trifluoromethyl-phenyl)-ethyl]-3-methyl-benzamide;
253. (S)-N-[1-[2-(4-Methoxy-phenylamino)-ethylcarbamoyl]-2-(4-trifluoromethyl-phenyl)-ethyl]-3-methyl-benzamide;
254. (S)-N-{2-Benzyloxy-1-[2-(4-methoxy-phenylamino)-ethylcarbamoyl]-ethyl}-3-methyl-benzamide;
255. (S)-N-{2-(4-tert-Butyl-phenyl)-1-[2-(4-methoxy-phenylamino)-ethylcarbamoyl]-ethyl}-3-methyl-benzamide;
256. Cyclohexyl-N-[2-(4-methoxy-phenylamino)-ethyl]-2-(S)-(2-(S)-phenyl-propionylamino)-butyramide;
257. (S)-N-{2-(1H-Indol-3-yl)-1-[2-(4-methoxy-phenylamino)-ethylcarbamoyl]-ethyl}-3-methyl-benzamide;
258. (S)-N-{1-[2-(4-Methoxy-phenylamino)-ethylcarbamoyl]-2-naphthalen-1-yl-ethyl}-3-methyl-benzamide;
259. (S)-N-{2-Benzyloxy-1-[2-(4-methoxy-phenylamino)-ethylcarbamoyl]-propyl}-3-methyl-benzamide;
260. 3-Cyclohexyl-2-(S)-[2-(3-fluoro-phenyl)-acetylamino]-N-[2-(4-fluoro-phenylamino)-ethyl]-propionamide;
261. (S)-N-{1-[2-(4-Methoxy-phenylamino)-ethylcarbamoyl]-2-naphthalen-2-yl-ethyl}-3-methyl-benzamide;
262. (S)-N-{1-[2-(4-Methoxy-phenylamino)-ethylcarbamoyl]-2-pyridin-3-yl-ethyl}-3-methyl-benzamide;
263. (S)-N-{1-[2-(4-Methoxy-phenylamino)-ethylcarbamoyl]-2-pyridin-4-yl-ethyl}-3-methyl-benzamide;
264. Furan-2-carboxylic acid (S)-{2-cyclohexyl-1-[2-(4-fluoro-phenylamino)-ethylcarbamoyl]-ethyl}-amide;
265. 3-Cyclohexyl-N-[2-(4-fluoro-phenylamino)-ethyl]-2-(S)-(2-tetrazol-1-yl-acetylamino)-propionamide;
266. N-[1-[2-(4-Methoxy-phenylamino)-ethylcarbamoyl]-2-(4-nitro-phenyl)-propyl]-3-methyl-benzamide;
267. (S)-N-[1-[2-(4-Methoxy-phenylamino)-ethylcarbamoyl]-2-(4-m-tolyloxy-phenyl)-ethyl]-3-methyl-benzamide;
268. threo-N-{1-[2-(4-Methoxy-phenylamino)-ethylcarbamoyl]-2-phenyl-propyl}-3-methyl-benzamide;
269. erythro-N-{1-[2-(4-Methoxy-phenylamino)-ethylcarbamoyl]-2-phenyl-propyl}-3-methyl-benzamide;
270. (S)-N-{2-Biphenyl-4-yl-1-[2-(4-methoxy-phenylamino)-ethylcarbamoyl]-ethyl}-3-methyl-benzamide;
271. (S)-N-[1-[2-(4-Methoxy-phenylamino)-ethylcarbamoyl]-2-(3'-nitro-biphenyl-4-yl)-ethyl]-3-methyl-benzamide;
272. Furan-3-carboxylic acid (S)-{2-cyclohexyl-1-[2-(4-fluoro-phenylamino)-ethylcarbamoyl]-ethyl}-amide;
273. (S)-N-[1-[2-(4-Methoxy-phenylamino)-ethylcarbamoyl]-2-(2'-nitro-biphenyl-4-yl)-ethyl]-3-methyl-benzamide;

TABLE I-continued 274. (S)-N-[1-[2-(4-Methoxy-phenylamino)-ethylcarbamoyl]-2-(4-pyridin-3-yl-phenyl)-ethyl]-3-methyl-benzamide;
275. (S)-N-[1-[2-(4-Methoxy-phenylamino)-ethylcarbamoyl]-2-(4-thiophen-3-yl-phenyl)-ethyl]-3-methyl-benzamide;
276. (S)-N-{2-(4'-Cyano-biphenyl-4-yl)-1-[2-(4-methoxy-phenylamino)-ethylcarbamoyl]-ethyl}-3-methyl-benzamide;
277. (S)-N-[1-[2-(4-Methoxy-phenylamino)-ethylcarbamoyl]-2-(4-pyridin-4-yl-phenyl)-ethyl]-3-methyl-benzamide;
278. (S)-N-{2-(4'-Chloro-biphenyl-4-yl)-1-[2-(4-methoxy-phenylamino)-ethylcarbamoyl]-ethyl}-3-methyl-benzamide;
279. (S)-N-{2-(2',3'-Dimethoxy-biphenyl-4-yl)-1-[2-(4-methoxy-phenylamino)-ethylcarbamoyl]-ethyl}-3-methyl-benzamide;
280. (S)-N-{2-(3'-Amino-biphenyl-4-yl)-1-[2-(4-methoxy-phenylamino)-ethylcarbamoyl]-ethyl}-3-methyl-benzamide;
281. (S)-N-{2-(3',4'-Dimethoxy-biphenyl-4-yl)-1-[2-(4-methoxy-phenylamino)-ethylcarbamoyl]-ethyl}-3-methyl-benzamide;
282. (S)-N-{2-(4'-Hydroxymethyl-biphenyl-4-yl)-1-[2-(4-methoxy-phenylamino)-ethylcarbamoyl]-ethyl}-3-methyl-benzamide;
283. (S)-N-{2-(5'-Fluoro-2'-methoxy-biphenyl-4-yl)-1-[2-(4-methoxy-phenylamino)-ethylcarbamoyl]-ethyl}-3-methyl-benzamide;
284. (S)-N-{2-(3'-Hydroxymethyl-biphenyl-4-yl)-1-[2-(4-methoxy-phenylamino)-ethylcarbamoyl]-ethyl}-3-methyl-benzamide;
285. (S)-N-{2-(2',5'-Dimethoxy-biphenyl-4-yl)-1-[2-(4-methoxy-phenylamino)-ethylcarbamoyl]-ethyl}-3-methyl-benzamide;
286. (S)-N-{2-(2',5'-Dichloro-biphenyl-4-yl)-1-[2-(4-methoxy-phenylamino)-ethylcarbamoyl]-ethyl}-3-methyl-benzamide;
287. (S)-N-{2-(4'-Dimethylamino-biphenyl-4-yl)-1-[2-(4-methoxy-phenylamino)-ethylcarbamoyl]-ethyl}-3-methyl-benzamide;
288. (S)-N-{2-(2'-Acetyl-biphenyl-4-yl)-1-[2-(4-methoxy-phenylamino)-ethylcarbamoyl]-ethyl}-3-methyl-benzamide;
289. (S)-N-{2-(4'-Hydroxy-biphenyl-4-yl)-1-[2-(4-methoxy-phenylamino)-ethylcarbamoyl]-ethyl}-3-methyl-benzamide;
290. (S)-N-{2-(3'-Acetyl-biphenyl-4-yl)-1-[2-(4-methoxy-phenylamino)-ethylcarbamoyl]-ethyl}-3-methyl-benzamide;
291. (S)-N-{2-[4-(2,4-Dimethoxy-pyrimidin-5-yl)-phenyl]-1-[2-(4-methoxy-phenylamino)-ethylcarbamoyl]-ethyl}-3-methyl-benzamide;
292. (S)-N-{1-[2-(4-Methoxy-phenylamino)-ethylcarbamoyl]-2-[4-(6-methoxy-pyridin-3-yl)-phenyl]-ethyl}-3-methyl-benzamide;
293. Methanesulfonyl-thiophene-2-carboxylic acid (S)-{2-cyclohexyl-1-[2-(4-fluoro-phenylamino)-ethylcarbamoyl]-ethyl}-amide;
294. N-(S)-{2-cyclohexyl-1-[2-(4-fluoro-phenylamino)-ethylcarbamoyl]-ethyl}-2-(S)-phenyl-propionamide;
295. Pyridazine-4-carboxylic acid (S)-{2-cyclohexyl-1-[2-(4-fluoro-phenylamino)-ethylcarbamoyl]-ethyl}-amide;
296. N-(S)-{2-cyclohexyl-1-[2-(4-fluoro-phenylamino)-ethylcarbamoyl]-ethyl}-3-methanesulfonyl-benzamide;
297. 3-Cyclohexyl-N-[2-(4-fluoro-phenylamino)-ethyl]-2-(S)-(2-1H-tetrazol-5-yl-acetylamino)-propionamide;
298. Cyclopropanecarboxylic acid (S)-{2-cyclohexyl-1-[2-(4-fluoro-phenylamino)-ethylcarbamoyl]-ethyl}-amide;
299. N-(S)-{2-cyclohexyl-1-[2-(4-fluoro-phenylamino)-ethylcarbamoyl]-ethyl}-4-methanesulfonylamino-benzamide;
300. (S)-N-{2-[4-(4-Chloro-phenoxy)-phenyl]-1-[2-(4-methoxy-phenylamino)-ethylcarbamoyl]-ethyl}-3-methyl-benzamide;
301. 3-Cyclohexyl-N-[2-(4-fluoro-phenylamino)-ethyl]-2-(S)-[2-(4-methoxy-phenyl)-acetylamino]-propionamide;
302. 2-(S)-[2-(3-Chloro-phenyl)-acetylamino]-3-cyclohexyl-N-[2-(4-fluoro-phenylamino)-ethyl]-propionamide;
303. 3-Cyclohexyl-N-[2-(4-fluoro-phenylamino)-ethyl]-2-(S)-phenylacetylamino-propionamide;
304. 3-Cyclohexyl-N-[2-(4-fluoro-phenylamino)-ethyl]-2-(S)-(2-o-tolyl-acetylamino)-propionamide;
305. 2-(S)-[2-(4-Chloro-phenyl)-acetylamino]-3-cyclohexyl-N-[2-(4-fluoro-phenylamino)-ethyl]-propionamide;
306. 3-Cyclohexyl-2-(S)-[2-(2-fluoro-phenyl)-acetylamino]-N-[2-(4-fluoro-phenylamino)-ethyl]-propionamide;
307. 3-Cyclohexyl-2-(S)-diphenylacetylamino-N-[2-(4-fluoro-phenylamino)-ethyl]-propionamide;
308. N-(S)-{2-cyclohexyl-1-[2-(4-fluoro-phenylamino)-ethylcarbamoyl]-ethyl}-2-(2-fluoro-biphenyl-4-yl)-propionamide;
309. N-{2-cyclohexyl-1-(S)-[2-(4-fluoro-phenylamino)-ethylcarbamoyl]-ethyl}-2-p-tolyl-propionamide;
310. N-{2-cyclohexyl-1-(S)-[2-(4-fluoro-phenylamino)-ethylcarbamoyl]-ethyl}-2-(4-fluoro-phenyl)-propionamide;
311. N-{2-cyclohexyl-1-(S)-[2-(4-fluoro-phenylamino)-ethylcarbamoyl]-ethyl}-2-(4-hydroxy-phenyl)-propionamide;
312. 2-(4-Chloro-phenyl)-N-{2-cyclohexyl-1-(S)-[2-(4-fluoro-phenylamino)-ethylcarbamoyl]-ethyl}-propionamide;

TABLE I-continued

313. N-(S)-{2-cyclohexyl-1-[2-(4-fluoro-phenylamino)-ethylcarbamoyl]-ethyl}-4-methanesulfonyl-benzamide;
314. Thiazole-4-carboxylic acid (S)-{2-cyclohexyl-1-[2-(4-fluoro-phenylamino)-ethylcarbamoyl]-ethyl}-amide;
315. N-{2-cyclohexyl-1-(S)-[2-(4-fluoro-phenylamino)-ethylcarbamoyl]-ethyl}-2-(R)-phenyl-propionamide;
316. 4-Cyano-N-(S)-{2-cyclohexyl-1-[2-(4-fluoro-phenylamino)-ethylcarbamoyl]-ethyl}-benzamide;
317. 3-Cyclohexyl-N-[2-(4-fluoro-phenylamino)-ethyl]-2-(S)-(2-(R)-hydroxy-2-phenyl-acetylamino)-propionamide;
318. N-{2-cyclohexyl-1-(S)-[2-(4-fluoro-phenylamino)-ethylcarbamoyl]-ethyl}-2-(R)-phenyl-butyramide;
319. Phenyl-cyclopropanecarboxylic acid (S)-{2-cyclohexyl-1-[2-(4-fluoro-phenylamino)-ethylcarbamoyl]-ethyl}-amide;
320. N-(S)-{2-cyclohexyl-1-[2-(4-fluoro-phenylamino)-ethylcarbamoyl]-ethyl}-2-(R,S)-(4-fluoro-phenyl)-propionamide;
321. Cyano-N-(S)-{2-cyclohexyl-1-[2-(4-fluoro-phenylamino)-ethylcarbamoyl]-ethyl}-benzamide;
322. 5-(4-Fluoro-phenyl)-furan-2-carboxylic acid (S)-{2-cyclohexyl-1-[2-(4-fluoro-phenylamino)-ethylcarbamoyl]-ethyl}-amide;
323. Cyclohexyl-N-[2-(4-fluoro-phenylamino)-ethyl]-2-(S)-[2-(3-trifluoromethyl-phenyl)-acetylamino]-propionamide;
324. Cyano-N-(S)-{2-cyclohexyl-1-[2-(4-fluoro-phenylamino)-ethylcarbamoyl]-ethyl}-benzamide;
325. 3-Cyclohexyl-N-[2-(4-fluoro-phenylamino)-ethyl]-2-(S)-[2-(4-trifluoromethyl-phenyl)-acetylamino]-propionamide;
326. 3-Cyclohexyl-N-[2-(4-fluoro-phenylamino)-ethyl]-2-(S)-[2-(4-methanesulfonyl-phenyl)-acetylamino]-propionamide;
327. (S)-N-[1-[2-(4-Methoxy-phenylamino)-ethylcarbamoyl]-2-(4-phenoxy-phenyl)-ethyl]-3-methyl-benzamide;
328. (S)-N-{2-[4-(4-Methoxy-phenoxy)-phenyl]-1-[2-(4-methoxy-phenylamino)-ethylcarbamoyl]-ethyl}-3-methyl-benzamide;
329. (S)-N-{2-[4-(3-Chloro-phenoxy)-phenyl]-1-[2-(4-methoxy-phenylamino)-ethylcarbamoyl]-ethyl}-3-methyl-benzamide;
330. (S)-N-{2-[4-(3,5-Dimethyl-phenoxy)-phenyl]-1-[2-(4-methoxy-phenylamino)-ethylcarbamoyl]-ethyl}-3-methyl-benzamide.

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$–$C_4$) alkane carboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example, glycolic, lactic, malic, tartaric or citric acid, such as amino acids, for example, aspartic or glutamic acid, or with organic sulfonic acids, such as ($C_1$–$C_4$)-alkylsulfonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W, X and combinations thereof. In a more preferred aspect, the present invention provides compounds which selectively inhibit cathepsin S in the presence of cathepsin K.

Compounds of the present invention useful for treating cathepsin S dependent conditions, preferably have cathepsin S inhibition constants less than 10 µM. More preferably, compounds of the present invention useful for treating cathepsin S dependent conditions have cathepsin S inhibition constants of less than 1.0 µM. Most preferably, compounds of the present invention useful for treating cathepsin S dependent conditions have cathepsin S inhibition constants of less than 0.1 µM.

In a preferred aspect, compounds of the present invention that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of a cathepsin isozyme, have a cathepsin isozyme inhibition constant at least 100 times greater than their cathepsin S inhibition constant. In a most preferred aspect, compounds of the present invention that selectively inhibit cathepsin S in the presence of a cathepsin isozyme, have a cathepsin isozyme inhibition constant at least 1000 times greater than their cathepsin S inhibition constant.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular chronic neuropathic pain (see, WO 03/020287), Alzheimer's disease and certain autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In a preferred aspect, the pharmaceutical composition of the present invention provides a compound according to Formula I.

In one aspect of the present invention, compositions of the present invention that comprise compounds of the present invention and pharmaceutically acceptable excipients, selectively inhibit cathepsin S in the presence of other cathepsin isozymes. In a more preferred aspect, the present invention provides compositions which selectively inhibit cathepsin S in the presence of cathepsin K.

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in vitro and in vivo pharmacological tests generally known in the art, and as illustrated herein.

The above cited properties are demonstrable in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et al., *J. Rheumatology* 1993, 20, 1176). The efficacy of the compounds of the present invention for the treatment of osteoarthritis can be determined using models such as, or similar to, the rabbit partial lateral meniscectomy model, as described previously (Colombo et al., *Arth. Rheum.* 1993, 26, 875–886). The efficacy of the compounds in the model can be quantified using histological scoring methods, as described previously (O'Byrne et al., *Inflamm. Res.* 1995, 44, S 177–S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I.

Methods of the present invention useful for treating cathepsin S dependent conditions, preferably use compounds that have cathepsin S inhibition constants less than 10 µM. More preferably, methods of the present invention useful for treating cathepsin S dependent conditions use compounds that have cathepsin S inhibition constants of less than 1.0 µM. Most preferably, methods of the present invention useful for treating cathepsin S dependent conditions use compounds that have cathepsin S inhibition constants of less than 0.1 µM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W and X. In a more preferred aspect, methods of the present invention use compounds that selectively inhibit cathepsin S in the presence of cathepsin K.

In a preferred aspect, methods of the present invention use compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

VI. EXAMPLES

A. Compounds

General Procedure. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard.

Preparation 1. Solid phase synthesis (S)-3-methoxy-N-{1-[2-(4-methoxy-phenylamino)-ethylcarbamoyl]-2-phenyl-ethyl}-benzamide.

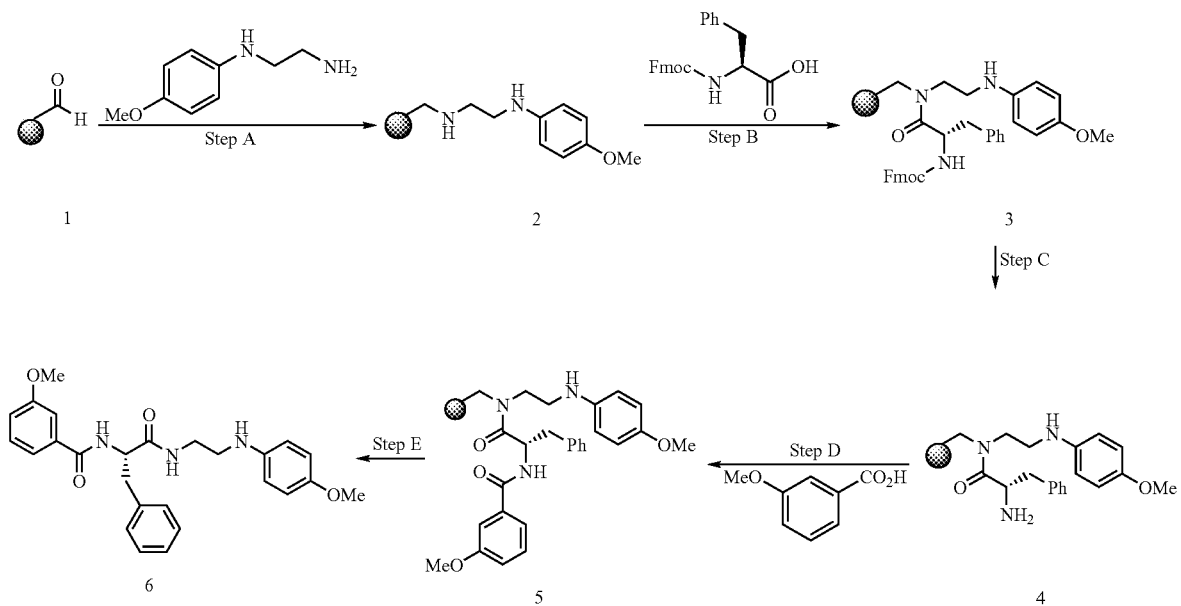

Step A: An aldehyde-functionalized polystyrene resin 1 ("Pal-Resin", 16.76 g @1.05 mmol/g, 17.6 mmol) was swelled in DMF (50 mL) for 10 min. N1-(4-methoxy-phenyl)-ethane-1,2-diamine (5.85 g, 35 mmol) in DMF (150 mL) was added followed by acetic acid (8.1 mL, 8 eq), and the mixture was agitated for 1 h at room temperature. Sodium triacetoxyborohydride (11.2 g, 52.8 mmol eq.) was then added and the mixture was shaken for 16 hours at room temperature. The reductively aminated resin 2 was then filtered and washed (DMF×3, equal mixture of methanol/dichloromethane×4, Acetonitrile×3).

Step B: The resin 2 (17.6 mmol) was swelled in DMF (50 mL) and a solution of Fmoc-Phe-OH (20.45 g, 3 eq), HOBt (8.08 g, 3 eq) and DIC (4.58 mL, 3 eq) was added. The mixture was shaken for 3 h, then washed (DMF×3, equal mixture of methanol/dichloromethane×4, Acetonitrile×3).

Step C: The resin 3 (117 mg, 0.077 mmol) was weighed into reaction vessels followed by a stirrer bar then treated with piperidine in DMF (4 mL of a 20% solution) and the mixture agitated for 1 h. The resin is then washed (3×DMF, 3×dichloromethane) to yield resin 4.

Step D: Resin 4 (0.077 mmol) was swelled in DMF (1 mL) and a premixed solution of hydroxybenzotriazole (35 mg, 0.23 mmol), 3-methoxybenzoic acid (35 mg, 0.23 mmol) and diisopropylcarbodiimide (20 μL, 0.231 mmol) in DMF (3.0 mL) is added. The reaction is agitated for three hours and then washed (DMF×4, then dichloromethane×3) and dried under nitrogen to yield resin 5.

Step E: The resin 5 (0.077 mmol) was treated with a mixture of trifluoroacetic acid, dichloromethane and water (45:45:10, v/v, 4 mL). The resin was agitated for one hour then retreated, agitated again for 5 min, then washed with the above cleavage mixture and filtered into vials. The solvent was evaporated in vacuo and the title compound purified using a Waters mass-directed reverse phase LCMS system (flow 7.5 min method, gradient 10–90% acetonitrile/water with 0.35% trifluoroacetic acid). Solvent was removed by lyophilization to afford the title compound as a white solid. (9 mg, 0.02 mmol, 26%). $^1$H NMR (CD$_3$OD) δ(ppm) 7.38(d, J=9.0 Hz, 2H), 7.31(m, 2H), 7.28(m, 5H), 7.21(m, 1H), 7.10(m, 1H), 7.50(d, J=9.0 Hz, 2H), 4.64(dd, J=7.1 Hz, J=8.4 Hz, 1H), 3.82(s, 3H), 3.81(s, 3H), 3.60(m, 1H), 3.44(m, 1H), 3.37(m, 2H), 3.22(dd, J=8.6 Hz, J=13.6 Hz, 1H), 3.12(dd, J=7.0 Hz, J=13.6 Hz, 1H); C$_{26}$H$_{29}$N$_3$O$_4$; LCMS: 448.2 (M+H)$^+$.

Preparation 2. (S)-N-{1-[2-(4-Methoxy-phenylamino)-ethylcarbamoyl]-4-phenyl-butyl}-3-methyl-benzamide.

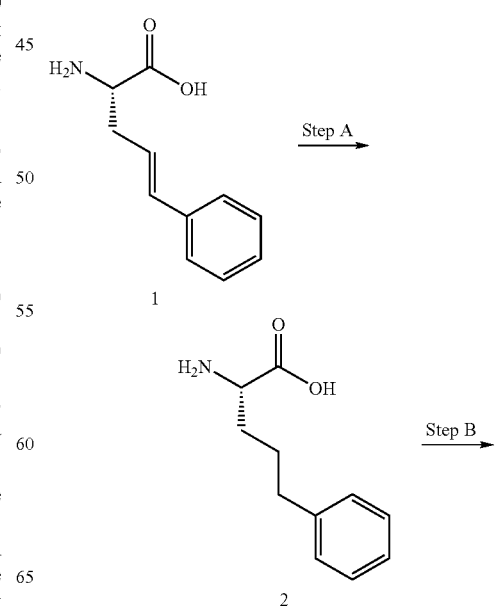

-continued

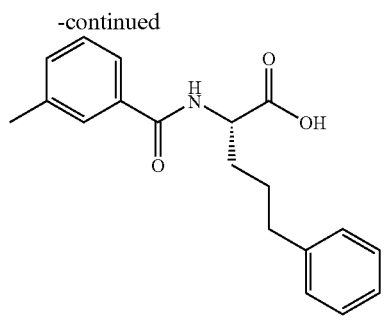

3

↓ Step C

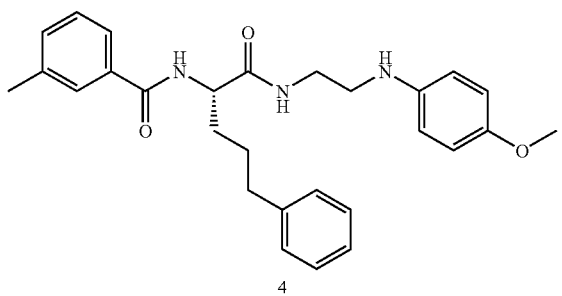

4

Step A: L-Styryl alanine 1 (50 mg, 0.26 mmol) was dissolved in MeOH (5 mL) and the reaction vessel was flushed with nitrogen. Catalytic amount of palladium (10% on carbon) was added and the reaction vessel was placed under a hydrogen atmosphere. The mixture was stirred for 2 h at room temperature, then filtered over celite. The organic solvent was removed in vacuo to yield (S)-2-amino-5-phenyl-pentanoic acid 2 (51 mg, quant.) as a white powder: $^1$H-NMR (400 MHz, CD$_3$OD) δ=7.42–7.25 (m, 5H), 3.71 (t, J=6.0, 1H), 2.69 (t, J=6.4, 2H), 1.85 (m, 2H), 1.70 (m, 2H). MS calcd. for $C_{11}H_{16}NO_2$ (M+H$^+$) 194.12. found 194.4.

Step B: (S)-2-Amino-5-phenyl-pentanoic acid 2 (23 mg, 0.12 mmol) was dissolved in H$_2$O (1 mL) containing equimolar amounts of NaOH (5 mg, 0.12 mmol). The solution was cooled to 0° C., then m-Toluic acid chloride (16 μL, 0.12 mmol) was added dropwise under vigorous stirring. The mixture was allowed to warm to room temperature and stirred for approx. 12 h. After acidification with 1 M HCl (1 mL), the product was extracted from the reaction mixture with DCM (4 mL). The organic layer was separated and the solvent was removed in vacuo to yield (S)-2-(3-methyl-benzoylamino)-5-phenyl-pentanoic acid 3 (21 mg, 56%) as a white solid: $^1$H-NMR (400 MHz, CD$_3$OD) δ=7.83–7.09 (m, 9H), 4.62 (dd, J=5.0, J=9.1, 1H), 2.65 (m, 2H), 2.37 (s, 3H), 2.01–1.67 (m, 4H). MS calcd. for $C_{19}H_{22}NO_3$ (M+H$^+$) 312.16. found 312.4.

Step C: (S)-2-(3-Methyl-benzoylamino)-5-phenyl-pentanoic acid 3 (21 mg, 0.07 mmol) was dissolved in DCM (2 mL), HOBt (20 mg, 0.14 mmol) and DIC (23 μL, 0.14 mmol) were added and the solution was stirred for 10 min at room temperature. N-(4-Methoxyphenyl)-ethane-1,2-diamine (24 mg, 0.14 mmol) was added and the solution was stirred for 3 h at room temperature. The solvent was removed in vacuo, and the remainder was purified by reverse HPLC to afford the title compound (S)-N-{1-[2-(4-Methoxy-phenylamino)-ethylcarbamoyl]-4-phenyl-butyl}-3-methyl-benzamide 4 (18 mg, 0.04 mmol, 56%) as a white solid: $^1$H-NMR (400 MHz, CD$_3$OD) δ=7.56–7.48 (m, 2H), 7.36–7.16 (m, 7H), 6.96–6.87 (m, 4H), 4.48 (dd, J=6.2, J=13.7, 1H), 3.82 (s, 3H), 3.78–3.64 (m, 2H), 3.58–3.50 (m, 2H), 2.71–2.64 (m, 2H), 2.35 (s, 3H), 2.06–1.70 (m, 4H). MS calcd. for $C_{28}H_{34}N_3O_3$ (M+H$^+$) 460.26. found 460.5.

Example 1

N-((S)-1-(2-(4-methoxyphenylamino)ethylcarbamoyl)-3-phenylpropyl)-5-(3-(trifluoromethyl)phenyl)furan-2-carboxamide*

$C_{31}H_{30}F_3N_3O_4$; LCMS: 566.5 (M+H)$^+$.

Example 2

N-((S)-1-(2-(4-methoxyphenylamino)ethylcarbamoyl)-2-(2-chlorophenyl)ethyl)-5-(3-(trifluoromethyl)phenyl)furan-2-carboxamide*

$C_{30}H_{27}ClF_3N_3O_4$; LCMS: 586.4 (M+H)$^+$.

Example 3

N-((S)-1-(2-(4-methoxyphenylamino)ethylcarbamoyl)-2-(3-chlorophenyl)ethyl)-5-(3-(trifluoromethyl)phenyl)furan-2-carboxamide*

$C_{30}H_{27}ClF_3N_3O_4$; LCMS: 586.4 (M+H)$^+$.

Example 4

N-((S)-1-(2-(4-methoxyphenylamino)ethylcarbamoyl)-2-(4-chlorophenyl)ethyl)-5-(3-(trifluoromethyl)phenyl)furan-2-carboxamide*

$C_{30}H_{27}ClF_3N_3O_4$; LCMS: 586.4 (M+H)$^+$.

Example 5

N-((S)-1-(2-(4-methoxyphenylamino)ethylcarbamoyl)-2-(tetrahydro-2H-pyran-4-yl)ethyl)-5-(3-(trifluoromethyl)phenyl)furan-2-carboxamide*

$C_{29}H_{32}F_3N_3O_5$; LCMS: 560.4 (M+H)$^+$.

Example 6

N-((S)-1-(2-(4-methoxyphenylamino)ethylcarbamoyl)-2-cyclopentylethyl)-5-(3-(trifluoromethyl)phenyl)furan-2-carboxamide*

$C_{29}H_{32}F_3N_3O_4$; LCMS: 544.5 (M+H)$^+$.

Example 7

(S)-N-{2-[4-(2,3-Dimethyl-phenoxy)-phenyl]-1-[2-(4-methoxy-phenylamino)-ethylcarbamoyl]-ethyl}-3-methyl-benzamide.$^{\$\$}$ Following the procedure of Example 327, except substituting phenyl-boronic acid for 2,3-dimethylphenyl-boronic acid in Step D, the title compound was prepared as a white solid (5 mg, 18%): $^1$HNMR (400 MHz, CD$_3$OD) δ=7.59–6.64 (m, 15H), 4.62 (dd, J=7.2, J=8.3, 1H), 3.81 (s, 3H), 3.61–3.04 (m, 6H), 2.37 (s, 3H), 2.29 (s, 3H), 2.05 (s, 3H). MS calcd. for $C_{34}H_{38}N_3O_4$ (M+H$^+$) 552.29. found 552.4.

Example 8

(±)-N-((2-(4-methoxyphenylamino)ethylcarbamoyl)(4-chlorophenyl)methyl)-3-methylbenzamide**

$C_{25}H_{26}ClN_3O_3$; LCMS: 452.4 (M+H)$^+$.

Example 9

(±)-N-((2-(4-methoxyphenylamino)ethylcarbamoyl)(phenyl)-methyl)-5-(3-(trifluoromethyl)phenyl)furan-2-carboxamide** $C_{29}H_{26}F_3N_3O_4$; LCMS: 538.4 (M+H)$^+$.

Example 10

N-((S)-1-(2-(4-(difluoromethoxy)phenylamino)ethylcarbamoyl)-2-cyclohexylethyl)-5-(3-(trifluoromethyl)phenyl)furan-2-carboxamide 3.51–3.69 (m, 3H), 4.24 (dt, 1H, J=8.8 Hz, 5.6 Hz), 4.94 (d, 1H, J=12.0 Hz), 5.07 (d, 1H, J=12.0 Hz), 5.93 (1H, J=12.0 Hz), 7.24–7.30 (m, 5H).

Step B: (S)-[2-Cyclohexyl-1-(2-hydroxy-ethylcarbamoyl)-ethyl]-carbamic acid benzyl ester 2 (630 mg, 1.81 mmol) was dissolved in dry MeOH (15 mL) and Pd/C (15 mg, catalytic) was added under N$_2$. The nitrogen atmosphere was replaced with a H$_2$ balloon and allowed to stir at room temperature. The reaction was judged to be complete by LC/MS and the reaction was purged with nitrogen and filtered through celite. The solvent was removed in vacuo to yield (S)-2-Amino-3-cyclohexyl-N-(2-hydroxy-ethyl)-propionamide 3 (380 mg, 1.77 mmol, 98%) as a clear oil: MS calcd. for $C_{11}H_{22}N_2O_2$ (M+H$^+$) 215.2. found 215.4.

Step C: (S)-2-Amino-3-cyclohexyl-N-(2-hydroxy-ethyl)-propionamide 3 (216 mg, 1.0 mmol, 1.0 eq.), O-(7-Azabenzotrizol-1-yl)-N,N,N',N'-tetramethyluronium hexafluorophosphate (HATU, 364 mg, 1.11 mmol, 1.1 eq.), and 5-(3-Trifluoromethyl-phenyl)-furan-2-carboxylic acid (284 mg, 1.11 mmol, 1.1 eq.) was dissolved in CH$_2$Cl$_2$ (10 mL, 0.1 M) and the solution was stirred for 10 min at room temperature.

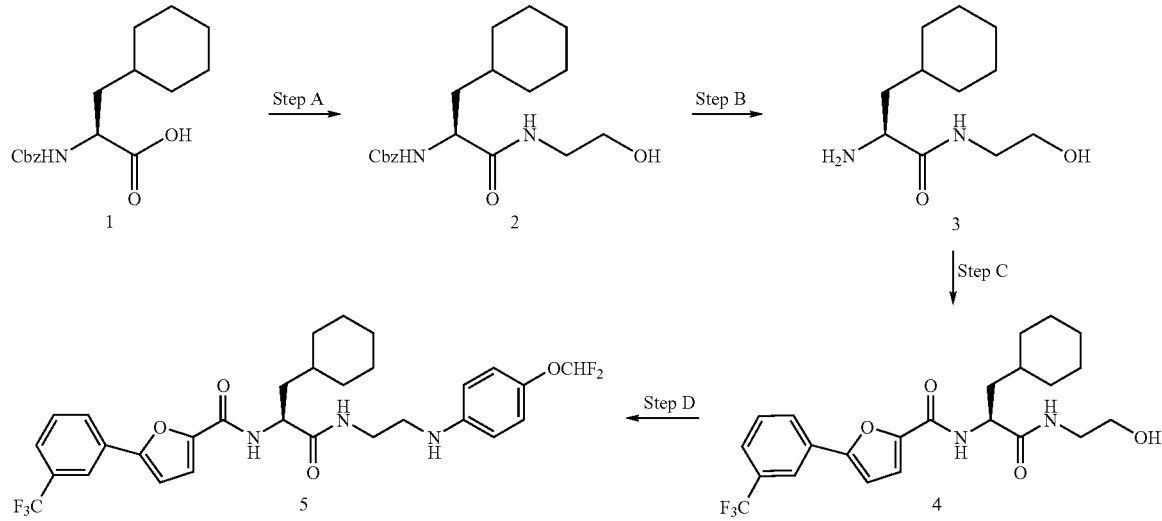

Step A: (S)-2-Benzyloxycarbonylamino-3-cyclohexyl-propionic acid 1 (2.065 g, 6.77 mmol, 1.0 eq.) was dissolved in CH$_2$Cl$_2$ (50 mL). N-(3-Dimethylaminopropyl)-N'-ethyl-carbodiimide hydrochloride (EDC, 1.56 g, 8.11 mmol, 1.2 eq.) and 1-Hydroxybenzotriazole hydrate (HOBT, 1.10 g, 8.16 mmol, 1.2 eq.) were added to the reaction slurry. After 20 minutes, ethanolamine (1.6 mL, 26.58 mmol, 3.9 eq.) was added via syringe and the reaction was allowed to stir at room temperature and monitored by LC/MS. After the reaction was allowed to proceed to completion, the reaction mixture was extracted with water (40 mL), 1M HCl (30 mL), followed by saturated NaHCO$_3$ and saturated NaCl. The organic layer was dried over MgSO$_4$ and filtered. The organic solvent was removed in vacuo and purified by silica gel chromatography to yield (S)-[2-Cyclohexyl-1-(2-hydroxy-ethylcarbamoyl)-ethyl]-carbamic acid benzyl ester 2 (780 mg, 2.24 mmol, 28%) as a white solid: $^1$H-NMR (400 MHz, CDCl$_3$) δ 0.76–0.92 (m, 2H), 1.02–1.35 (m, 4H), 1.44–1.73 (m, 7H), 3.17–3.25 (m, 1H), 3.34–3.40 (m, 1H), N,N-Diisopropylethylamine (DIPEA, 500 μL, 2.88 mmol, 2.9 eq.) was added and the solution was stirred at room temperature until all stating materials were consumed by LC/MS. The solvent was removed in vacuo and the residue purified by silica gel chromatography (0% to 40% EtOAc gradient in hexanes) to provide (S)-5-(3-Trifluoromethyl-phenyl)-furan-2-carboxylic acid [2-cyclohexyl-1-(2-hydroxy-ethylcarbamoyl)-ethyl]-amide 4 (293 mg, 0.65 mmol, 64%) as a white solid: MS calcd. for $C_{23}H_{27}F_3N_2O_4$ (M+H$^+$) 453.2. found 453.4.

Step D: (S)-5-(3-Trifluoromethyl-phenyl)-furan-2-carboxylic acid [2-cyclohexyl-1-(2-hydroxy-ethylcarbamoyl)-ethyl]-amide 4 (170 mg, 0.38 mmol) was dissolved in CH$_2$Cl$_2$ (5 mL, 0.07M) under a N$_2$ atmosphere. Dess-Martin Periodinane (210 mg, 0.49 mmol, 1.3 eq.) was added in one portion and allowed the reaction to stir at room temperature for 3 hours. After the reaction was judged to be complete by TLC, the reaction was diluted with EtOAc (50 mL) and extracted with 1M sodium thiosulfate (30 mL). The organic layer was extracted with saturated NaHCO$_3$ and saturated NaCl. The organic layer was dried over MgSO$_4$ and filtered. The organic solvent was removed in vacuo and the resulting aldehyde (158 mg, 0.35 mmol, 93%) was used directly without storage: R$_f$=0.67 (1:1 hexanes:EtOAc). The aldehyde (43 mg, 0.10 mmol) was dissolved in MeOH (2.5 mL, 0.04M) and brought to 0° C. in an ice bath. 4-Difluoromethoxyaniline (50 µL, 0.31 mol, 3.3 eq.) and acetic acid (20 mL, 0.34 mmol, 3.6 eq.) were added via syringe followed by sodium cyanoborohydride (20 mg, 0.32 mmol) in one portion. The clear reaction mixture was allowed to slowly warm to room temperature and monitored to completion by LC/MS. The reaction was worked up by rotary evaporation of MeOH, dilution with EtOAc (20 mL) and water (20 mL). The organic phase was separated and washed with 1M NaOH (15 mL) and saturated NaCl (15 mL). The organic layer was dried over MgSO4, filtered, and concentrated by rotary evaporation. Purification by mass-directed HPLC, evaporation and lyophilization provided (S)-5-(3-Trifluoromethyl-phenyl)-furan-2-carboxylic acid {2-cyclohexyl-1-[2-(4-difluoromethoxy-phenylamino)-ethylcarbamoyl]-ethyl}-amide 5 as a white amorphous solid (15 mg, 0.02 mmol, 22%): $^1$H NMR (CD$_3$OD, 400 MHz) δ 0.95–1.06 (m, 2H), 1.19–1.29 (m, 3H), 1.40–1.44 (m, 1H), 1.66–1.86 (m, 7H), 3.26–3.29 (m, 2H), 3.43–3.46 (m, 2H), 4.64 (dd, 1H, J=9.2, 6.0 Hz), 6.59 (t, 1H, J=74.8 Hz), 6.76 (d, 2H, J=8.8 Hz), 6.95 (d, 2H, J=8.8 Hz), 7.11 (s, 1H), 7.29 (d, 1H, J=3.6 Hz), 7.66 (s, 2H), 8.13 (s, 1H), 8.25 (s, 1H); HPLC-MS calcd. for C$_{30}$H$_{32}$F$_5$N$_3$O$_4$ (M+H$^+$) 594.2. found 594.5.

Example 11

4-[2-(3-Cyclohexyl-2-(S)-{[5-(3-trifluoromethyl-phenyl)-furan-2-carbonyl]-amino}-propionylamino)-ethylamino]-benzoic acid#

H NMR (CD$_3$OD, 400 MHz) δ 0.95–1.06 (m, 2H), 1.19–1.29 (m, 3H), 1.40–1.44 (m, 1H), 1.63–1.85 (m, 7H), 3.31–3.35 (m, 2H), 3.39–3.48 (m, 2H), 4.64 (dd, 1H, J=9.6, 5.6 Hz), 6.62 (d, 2H, J=8.8 Hz), 7.10 (d, 1H, J=8.0 Hz), 7.28 (d, 1H, J=7.2 Hz), 7.62–7.66(m, 2H), 7.75 (d, 2H, J=8.8 Hz), 8.12–8.14 (m, 1H), 8.29 (s, 1H); HPLC-MS calcd. for C$_{30}$H$_{32}$F$_3$N$_3$O$_5$ (M+H$^+$) 572.2. found 572.5.

Example 12

2-[2-(3-Cyclohexyl-2-(S)-{[5-(3-trifluoromethyl-phenyl)-furan-2-carbonyl]-amino}-propionylamino)-ethylamino]-benzoic acid#

H NMR (CD$_3$OD, 400 MHz) δ 0.93–1.02 (m, 2H), 1.17–1.29 (m, 3H), 1.32–1.48 (m, 1H), 1.64–1.86 (m, 7H), 3.31–3.44 (m, 3H), 3.49–3.53 (m, 1H), 4.68 (t, 1H, J=7.6 Hz), 6.57 (t, 1H, J=15.2 Hz), 6.83 (d, 1H, J=8.4 Hz), 7.09 (d, 1H, J=3.6 Hz), 7.27 (d, 1H, J=3.6 Hz), 7.32–7.36 (m, 1H), 7.61–7.65 (m, 2H), 7.86 (dd, 1H, J=8.0, 1.6 Hz), 8.11–8.13 (m, 1H), 8.23 (s, 1H); HPLC-MS calcd. for C$_{30}$H$_{32}$F$_3$N$_3$O$_5$ (M+H$^+$) 572.2. found 572.5.

Example 13

4-Cyclohexyl-2-(S)-(2-(R)-phenyl-propionylamino)-N-[2-(4-trifluoromethoxy-phenylamino)-ethyl]-butyramide C$_{28}$H$_{36}$F$_3$N$_3$O$_3$; $^1$H NMR (CDCl$_3$) δ(ppm) 6.97(m, 5H), 6.74(m, 2H), 6.42(m, 1H), 6.27(m, 2H), 5.85(d, J=8.4 Hz, 1H), 3.95(m, 1H), 3.32(m, 1H), 3.11(m, 2H), 2.86(m, 2H), 1.52(m, 1H), 1.35(m, 5H), 1.21(m, 4H), 0.83(m, 6H), 0.49 (m, 2H); LCMS: 520.6 (M+H)$^+$.

Example 14

1-Acetyl-piperidine-4-carboxylic acid (S)-{2-cyclohexyl-1-[2-(4-trifluoromethoxy-phenylamino)-ethyl-carbamoyl]-ethyl}-amide*

C$_{26}$H$_{37}$F$_3$N$_4$O$_4$; $^1$H NMR (CDCl$_3$) δ(ppm) 7.29(m, 1H), 7.08(d, J=8.4 Hz, 2H), 6.91(d, J=8.4 Hz, 2H), 6.17(m, 1H), 4.50(m, 1H), 4.22(m, 1H), 3.72(m, 1H), 3.48(m, 2H), 3.30 (m, 2H), 2.97(m, 1H), 2.53(m, 1H), 2.31(m, 1H), 2.00(m, 3H), 1.72(m, 3H), 1.50(m, 8H), 1.10(m, 4H), 0.83(m, 2H); LCMS: 527.5 (M+H)$^+$.

Example 15

(S)-2-{2-[4-(4-Acetyl-piperazin-1-yl)-phenoxy]-acetylamino}-3-cyclohexyl-N-[2-(4-trifluoromethoxy-phenylamino)-ethyl]-propionamide*

C$_{32}$H$_{42}$F$_3$N$_5$O$_5$; $^1$H NMR (CDCl$_3$) δ(ppm) 7.84(m, 1H), 7.26(m, 2H), 7.15(m, 2H), 7.11(m, 2H), 6.84(m, 2H), 4.38 (m, 1H), 4.19(m, 1H), 3.85(m, 2H), 3.72(m, 2H), 3.51(m, 2H), 3.34(m, 1H), 3.20(m, 4H), 2.06(s, 3H), 1.54(m, 7H), 1.04(m, 6H), 0.80(m, 2H); LCMS: 634.5(M+H)$^+$.

Example 16

(S)-2-Chloro-N-{1-[2-(4-methoxy-phenylamino)-ethylcarbamoyl]-2-phenyl-ethyl}-3-methyl-benzamide*

C$_{26}$H$_{28}$ClN$_3$O$_3$; LCMS: 466.2(M+H)$^+$.

Example 17

3-Cyclohexyl-2-[2-(4-methoxy-phenyl)-acetylamino]-N-[2-(4-trifluoromethoxy-phenylamino)-ethyl]-propionamide*

C$_{27}$H$_{34}$F$_3$N$_3$O$_4$; $^1$H NMR (CDCl$_3$) δ(ppm)7.12((m, 1H), 7.04(m, 4H), 6.77(m, 4H), 5.81(m, 1H), 4.18(m, 1H), 3.71(s, 3H), 3.43(m, 4H), 3.23(m, 2H), 1.58(m, 7H), 1.35(m, 1H), 1.04(m, 3H), 1.35(m, 2H), LCMS: 522.5 (M+H)$^+$.

Example 18

(S)-N-{2-[4-(3,5-Dichloro-phenoxy)-phenyl]-1-[2-(4-methoxy-phenylamino)-ethylcarbamoyl]-ethyl}-3-methyl-benzamide$$

Following the procedure of Example 327, except substituting phenyl-boronic acid for 3,5-dichlorophenyl-boronic acid in Step D, the title compound was prepared as a white solid (2 mg, 7%): $^1$H-NMR (400 MHz, CD$_3$OD) δ=7.61–6.68 (m, 15H), 4.68 (dd, J=7.1, J=8.5, 1H), 3.79 (s, 3H), 3.57-3.10 (m, 6H), 2.38 (s, 3H). MS calcd. for C$_{32}$H$_{32}$Cl$_2$N$_3$O$_4$ (M+H$^+$) 592.18. found 592.4.

Example 19

N-(S)-{2-cyclohexyl-1-[2-(4-trifluoromethoxy-phenylamino)-ethylcarbamoyl]-ethyl}-4-methanesulfonyl-benzamide*

$C_{26}H_{32}F_3N_3O_5S$; $^1$H NMR (CDCl$_3$) δ(ppm)7.87(m, 7H), 7.23(m, 3H), 4.41(m, 1H), 3.52(m, 3H), 3.34(m, 1H), 2.97(s, 3H), 1.68(m, 7H), 1.35(m, 1H), 1.11(m, 3H), 0.91(m, 2H); LCMS: 556.4 (M+H)$^+$.

Example 20

(S)-4-Benzyloxy-N-{1-[2-(4-methoxy-phenylamino)-ethylcarbamoyl]-2-phenyl-ethyl}-3,5-dimethyl-benzamide*

$C_{34}H_{37}N_3O_4$; LCMS: 552.25(M+H)$^+$.

Example 21

(S)-4-Methoxy-N-{1-[2-(4-methoxy-phenylamino)-ethylcarbamoyl]-2-phenyl-ethyl}-3,5-dimethyl-benzamide*

$C_{28}H_{33}N_3O_4$; LCMS: 476.2(M+H)$^+$.

Example 22

5-Methoxy-1H-indole-2-carboxylic acid (S)-{2-cyclohexyl-1-[2-(4-trifluoromethoxy-phenylamino)-ethylcarbamoyl]-ethyl}-amide*

$C_{28}H_{33}F_3N_4O_4$; LCMS: 547.5(M+H)$^+$.

Example 23

5-(3-Fluoro-phenyl)-furan-2-carboxylic acid (S)-{2-cyclohexyl-1-[2-(4-fluoro-phenylamino)-ethylcarbamoyl]-ethyl}-amide*

$C_{28}H_{31}F_2N_3O_3$; 496.5 (M+H)$^+$.

Example 24

(S)-3-Bromo-N-{1-[2-(4-methoxy-phenylamino)-ethylcarbamoyl]-2-phenyl-ethyl}-4-methyl-benzamide*

$C_{26}H_{28}BrN_3O_3$; LCMS: 510.1($^{79}$BrM+H)$^+$, 512.1 ($^{80}$BrM+H)$^+$.

Example 25

Furan-2-carboxylic acid (S)-{2-cyclohexyl-1-[2-(4-trifluoromethoxy-phenylamino)-ethylcarbamoyl]-ethyl}-amide*

$C_{23}H_{28}F_3N_3O_4$; $^1$H NMR (CDCl$_3$) δ(ppm)7.86(m, 1H), 7.65(m, 1H), 7.34(m, 2H), 7.25(m, 2H), 7.20(m, 1H), 7.04(m, 1H), 6.66(m, 1H), 4.60(m, 1H), 3.75(m, 2H), 3.60(m, 2H), 1.90(m, 7H), 1.55(m, 1H), 1.35(m, 3H), 1.11(m, 2H); LCMS: 468.4(M+H)$^+$.

Example 26

Thiophene-2-carboxylic acid (S)-{2-cyclohexyl-1-[2-(4-trifluoromethoxy-phenylamino)-ethylcarbamoyl]-amide*

$C_{23}H_{28}F_3N_3O_3S$; $^1$H NMR (CDCl$_3$) δ(ppm) 7.64(m, 1H), 7.44(m, 2H), 7.07(m, 2H), 6.99(m, 3H), 6.78(m, 1H), 4.40(m, 1H), 3.50(m, 2H), 3.32(m, 2H), 1.62(m, 7H), 1.29(m, 1H), 1.09(m, 3H), 0.85(m, 2H); LCMS: 484.4(M+H)$^+$.

Example 27

Furan-3-carboxylic acid (S)-{2-cyclohexyl-1-[2-(4-trifluoromethoxy-phenylamino)-ethylcarbamoyl]-ethyl}-amide*

$C_{23}H_{28}F_3N_3O_4$; $^1$H NMR (CDCl$_3$) δ(ppm) 7.84(m, 1H), 7.35(m, 2H), 7.04(d, J=8.0 Hz, 2H), 6.83(m, 2H), 6.54(m, 2H), 4.40(m, 1H), 3.47(m, 2H), 3.28(m, 2H), 1.61(m, 7H), 1.26(m, 1H), 1.08(m, 3H), 0.85(m, 2H); LCMS: 468.4(M+H)$^+$.

Example 28

N-(S)-{2-cyclohexyl-1-[2-(4-trifluoromethoxy-phenylamino)-ethylcarbamoyl]-ethyl}-4-(5-methyl-[1,2,4]oxadiazol-3-yl)-benzamide*

$C_{28}H_{32}F_3N_5O_4$; LCMS: 560.5(M+H)$^+$.

Example 29

5-(4-Fluoro-phenyl)-thiophene-2-carboxylic acid (S)-{2-cyclohexyl-1-[2-(4-trifluoromethoxy-phenylamino)-ethylcarbamoyl]-ethyl}-amide*

$C_{29}H_{31}F_4N_3O_3S$; $^1$H NMR (CDCl$_3$) δ(ppm) 7.55(m, 1H), 7.43(m, 3H), 7.05(m, 7H), 6.76(d, J=6.4 Hz, 1H), 4.41(m, 1H), 3.51(m, 2H), 3.33(m, 2H), 1.61(m, 7H), 1.31(m, 1H), 1.13(m, 3H), 0.89(m, 2H); LCMS: 577.4 (M+H)$^+$.

Example 30

(S)-N-{1-[2-(4-Methoxy-phenylamino)-ethylcarbamoyl]-2-phenyl-ethyl}-2,4,5-trimethyl-benzamide*

$C_{28}H_{33}N_3O_3$; LCMS: 460.2(M+H)$^+$.

Example 31

5-(3-Fluoro-phenyl)-furan-2-carboxylic acid (S)-{2-cyclohexyl-1-[2-(4-trifluoromethoxy-phenylamino)-ethylcarbamoyl]-ethyl}-amide*

$C_{29}H_{31}F_4N_3O_4$; LCMS: 562.4 (M+H)$^+$.

Example 32

4-Benzyl-morpholine-2-carboxylic acid (S)-{2-cyclohexyl-1-[2-(4-trifluoromethoxy-phenylamino)-ethylcarbamoyl]-ethyl}-amide*

$C_{30}H_{91}F_3N_4O_4$; $^1$H NMR (CDCl$_3$) δ(ppm) 7.42(m, 4H), 7.35(m, 2H), 7.19(m, 2H), 7.04(m, 3H), 4.57(m, 1H), 4.33(m, 1H), 4.21(m, 1H), 4.11(m, 3H), 3.86(m, 1H), 3.59(m, 2H), 3.44(m, 2H), 3.34(m, 1H), 2.79(m, 2H), 1.73(m, 7H), 1.17(m, 4H), 0.93(m, 2H); LCMS: 577.5 (M+H)$^+$.

Example 33

(S)-N-{2-[4-(4-Dimethylamino-phenoxy)-phenyl]-1-[2-(4-methoxy-phenylamino)-ethylcarbamoyl]-ethyl}-3-methyl-benzamide$^{\$\$}$ Following the procedure of Example 327, except substituting phenyl-boronic acid for 4-dimethylaminophenyl-boronic acid in Step D, the title compound was prepared as a white solid (2 mg, 7%): MS calcd. for $C_{34}H_{39}N_4O_4$ (M+H$^+$) 567.30. found 567.5.

Example 34

2'-Chloro-biphenyl-3-carboxylic acid (S)-{2-cyclohexyl-1-[2-(4-trifluoromethoxy-phenylamino)-ethylcarbamoyl]-ethyl}-amide*

$C_{31}H_{33}ClF_3N_3O_3$; $^1$H NMR (CD$_3$OD) δ(ppm) 7.93(m, 2H), 7.56(m, 3H), 7.41(m, 3H), 7.02(m, 2H), 6.76(m, 2H), 5.40(m, 1H), 3.44(m, 2H), 3.29(m, 2H), 1.74(m, 7H), 1.42(m, 1H), 1.19(m, 3H), 0.97(m, 2H); LCMS: 588.4(M+H)$^+$.

Example 35

5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide*

$C_{30}H_{31}F_6N_3O_3S$; $^1$H NMR (CDCl$_3$) δ(ppm) 7.83(m, 1H), 7.69(d, J=7.6 Hz, 1H), 7.41(m, 4H), 7.10(s, 4H), 6.99(m, 1H), 6.82(m, 1H), 4.38(m, 1H), 3.55(m, 2H), 3.39(m, 2H), 1.65(m, 7H), 1.34(m, 1H), 1.12(m, 3H), 0.89(m, 2H); LCMS: 628.4 (M+H)$^+$.

Example 36

5-(3-Fluoro-phenyl)-thiophene-2-carboxylic acid (S)-{2-cyclohexyl-1-[2-(4-trifluoromethoxy-phenylamino)-ethylcarbamoyl]-ethyl}-amide*

$C_{29}H_{31}F_4N_3O_3S$; $^1$H NMR (CDCl$_3$) δ(ppm) 7.41(m, 1H), 7.28(m, 3H), 7.19(m, 2H), 7.04(d, J=8.0 Hz, 2H), 7.11(m, 1H), 6.85(d, J=12.0 Hz, 2H), 6.64(m, 1H), 4.43(m, 1H), 3.49(m, 2H), 3.30(m, 2H), 1.16(m, 7H), 1.32(m, 1H), 1.13(m, 3H), 0.88(m, 2H); LCMS: 578.3 (M+H)$^+$.

Example 37

Thiophene-3-carboxylic acid (S)-{2-cyclohexyl-1-[2-(4-trifluoromethoxy-phenylamino)-ethylcarbamoyl]-ethyl}-amide*

$C_{23}H_{28}F_3N_3O_3S$; $^1$H NMR (CDCl$_3$) δ(ppm) 7.82(m, 1H), 7.41(m, 1H), 7.26(m, 2H), 7.01(m, 2H), 6.78(m, 3H), 4.46(m, 1H), 3.45(m, 2H), 3.27(m, 2H), 1.63(m, 7H), 1.29(m, 1H), 1.08(m, 3H), 0.87(m, 2H); LCMS: 484.4 (M+H)$^+$.

Example 38

5-Oxo-1-thiophen-2-ylmethyl-pyrrolidine-3-carboxylic acid (S)-{2-cyclohexyl-1-[2-(4-trifluoromethoxy-phenylamino)-ethylcarbamoyl]-ethyl}-amide*

$C_{28}H_{35}F_3N_4O_4S$; $^1$H NMR (CDCl$_3$) δ(ppm)7.61(m, 1H), 7.11(m, 5H), 6.83(m, 2H), 6.51(m, 1H), 4.47(m, 2H), 4.18(m, 1H), 3.52(m, 6H), 3.06(m, 1H), 2.60(m, 2H), 1.60(m, 6H), 1.46(m, 1H), 1.09(m, 4H), 0.83(m, 2H); LCMS: 581.4 (M+H)$^+$.

Example 39

1-Furan-2-ylmethyl-5-oxo-pyrrolidine-3-carboxylic acid (S)-{2-cyclohexyl-1-[2-(4-trifluoromethoxy-phenylamino)-ethylcarbamoyl]-ethyl}-amide*

$C_{28}H_{35}F_3N_4O_5$; $^1$H NMR (CDCl$_3$) δ(ppm) 7.76(m, 1H), 7.18(m, 5H), 6.62(m, 1H), 6.16(m, 2H), 4.29(m, 3H), 3.41(m, 6H), 3.07(m, 1H), 2.61(m, 2H), 1.60(m, 7H), 1.08(m, 4H), 0.81(m, 2H); LCMS: 565.5 (M+H)$^+$.

Example 40

2-Methyl-5-(pyrrolidine-1-sulfonyl)-furan-3-carboxylic acid (S)-{2-cyclohexyl-1-[2-(4-trifluoromethoxy-phenylamino)-ethylcarbamoyl]-ethyl}-amide*

$C_{28}H_{37}F_3N_4O_6S$; $^1$H NMR (CDCl$_3$) δ(ppm)7.37(m, 1H), 7.09(m, 3H), 6.97(m, 2H), 6.61(m, 1H), 4.33(m, 1H), 3.50(m, 3H), 3.27(m, 5H), 2.41(s, 3H), 1.77(m, 4H), 1.66(m, 7H), 1.29(m, 1H), 1.08(m, 3H), 0.86(m, 2H); LCMS: 615.4 (M+H)$^+$.

Example 41

(S)-1-Phenyl-5-trifluoromethyl-1H-pyrazole-4-carboxylic acid {1-[2-(4-methoxy-phenylamino)-ethylcarbamoyl]-2-phenyl-ethyl}-amide*

$C_{29}H_{28}F_3N_5O_3$; $^1$H NMR (CD$_3$Cl) δ(ppm) 8.38(bs, 1H), 7.99(s, 1H), 7.71(m, 3H), 7.58(m, 4H), 7.52(m, 5H), 7.13(m, 3H), 4.84(dd, J=5.4 Hz, J=13.9 Hz, 1H), 4.03(s, 3H), 3.87(m, 3H), 3.66(m, 3H), 3.56(m, 1H), 3.37(m, 1H); LCMS: 552.2(M+H)$^+$.

Example 42

5-p-Tolyl-thiophene-2-carboxylic acid (S)-{2-cyclohexyl-1-[2-(4-trifluoromethoxy-phenylamino)-ethylcarbamoyl]-ethyl}-amide*

$C_{30}H_{34}F_3N_3O_3S$; $^1$H NMR (CDCl$_3$) δ(ppm) 7.40(m, 3H), 7.14(m, 3H), 6.94(d, J=8.4 Hz, 2H), 6.79(m, 1H), 6.59(d, J=8.8 Hz, 2H), 6.37(d, J=7.6 Hz, 1H), 4.48(m, 1H), 3.45(m, 2H), 3.23(m, 2H), 2.30(s, 3H), 1.63(m, 7H), 1.29(m, 1H), 1.08(m, 3H), 0.88(m, 2H); LCMS: 574.5 (M+H)$^+$.

Example 43

4-Benzoimidazol-1-ylmethyl-N-{2-cyclohexyl-1-(S)-[2-(4-trifluoromethoxy-phenylamino)-ethylcarbamoyl]-ethyl}-benzamide*

$C_{33}H_{36}F_3N_5O_3S$; $^1$H NMR (CDCl$_3$) δ(ppm) 9.41(s, 1H), 8.14(m, 1H), 7.82(d, J=8.0 Hz, 1H), 7.45(m, 6H), 7.05(d, J=8.0 Hz, 2H), 6.98(d, J=12 Hz, 2H), 6.87(d, J=8.0 Hz, 2H), 5.43(m, 2H), 4.53(m, 1H), 3.43(m, 2H), 3.26(m, 2H), 1.55 (m, 7H), 1.29(m, 1H), 1.04(m, 3H), 0.84(m, 2H); LCMS: 608.5 (M+H)$^+$.

Example 44

(S)-1-(4-Chloro-phenyl)-5-trifluoromethyl-1H-pyrazole-4-carboxylic acid {1-[2-(4-methoxy-phenylamino)-ethylcarbamoyl]-2-phenyl-ethyl}-amide*

$C_{29}H_{27}ClF_3N_5O_3$; LCMS: 586.2(M+H)$^+$.

Example 45

(S)-N-[1-[2-(4-Methoxy-phenylamino)-ethylcarbamoyl]-2-(4-p-tolyloxy-phenyl)-ethyl]-3-methyl-benzamide$^{\$\$}$ Following the procedure of Example 327, except substituting phenyl-boronic acid for 4-methylphenyl-boronic acid in Step D, the title compound was prepared as a white solid (6 mg, 22%): $^1$H-NMR (400 MHz, CD$_3$OD) δ=7.60–6.79 (m, 16H), 4.63 (dd, J=7.2, J=8.3, 1H), 3.81 (s, 3H), 3.61–3.06 (m, 6H), 2.38 (s, 3H), 2.30 (s, 3H). MS calcd. for $C_{33}H_{36}N_3O_4$ (M+H$^+$) 538.27. found 538.4.

Example 46

3-Cyclohexyl-2-(S)-(2-tetrazol-1-yl-acetylamino)-N-[2-(4-trifluoromethoxy-phenylamino)-ethyl]-propionamide*

$C_{21}H_{28}F_3N_7O_3$; $^1$H NMR (CDCl$_3$) δ(ppm) 8.81(s, 1H), 7.85(m, 1H), 7.56(m, 1H), 7.17(m, 4H), 5.16(m, 2H), 4.27 (m, 1H), 3.50(m, 2H), 3.41(m, 1H), 3.33(m, 1H), 1.51(m, 7H), 1.09(m, 4H), 0.83(m, 2H); LCMS: 484.5 (M+H)$^+$.

Example 47

5-m-Tolyl-thiophene-2-carboxylic acid (S)-{2-cyclohexyl-1-[2-(4-trifluoromethoxy-phenylamino)-ethylcarbamoyl]-ethyl}-amide*

$C_{30}H_{34}F_3N_3O_3S$; $^1$H NMR (CDCl$_3$) δ(ppm) 7.40(d, J=4.0 Hz, 1H), 7.31(m, 2H), 7.20(m, 1H), 7.14(d, J=4 Hz, 1H), 7.09(m, 1H), 7.02(m, 1H), 6.95(d, J=8 Hz, 2H), 6.62(m, 2H), 6.54(d, J=7.2 Hz), 1H), 4.49(m, 1H), 3.44(m, 2H), 3.22(m, 2H), 2.31(s, 3H), 1.63(m, 7H), 1.31(m, 1H), 1.11(m, 3H), 0.87(m, 2H); LCMS: 574.5 (M+H)$^+$.

Example 48

2,7-Dimethyl-pyrazolo[1,5-a]pyrimidine-6-carboxylic acid (S)-{2-cyclohexyl-1-[2-(4-trifluoromethoxy-phenylamino)-ethylcarbamoyl]-ethyl}-amide*

$C_{27}H_{33}F_3N_6O_3$; $^1$H NMR (CDCl$_3$) δ(ppm) 8.42(s, 1H), 7.38(m, 1H), 7.07(m, 2H), 6.93(m, 3H), 6.44(m, 1H), 4.48(m, 1H), 3.55(m, 2H), 3.37(m, 2H), 2.83(s, 3H), 2.45(s, 3H), 1.63(m, 7H), 1.31(m, 1H), 1.10(m, 3H), 0.90(m, 2H); LCMS: 547.5 (M+H)$^+$.

Example 49

2-Methyl-5-(morpholine-4-sulfonyl)-furan-3carboxylic acid (S)-{2-cyclohexyl-1-[2-(4-trifluoromethoxy-phenylamino)-ethylcarbamoyl]-ethyl}-amide*

$C_{28}H_{37}F_3N_4O_7S$; $^1$H NMR (CDCl$_3$) δ(ppm) 7.61(m, 1H), 7.17(m, 3H), 7.07(m, 2H), 6.78(d, J=6.0 Hz, 1H), 4.33(m, 1H), 3.67(m, 4H), 3.48(m, 3H), 3.33(m, 1H), 3.10(m, 4H), 2.42(s, 3H), 1.63(m, 7H), 1.29(m, 1H), 1.19(m, 3H), 0.89(m, 2H); LMCS: 631.5(M+H)$^+$.

Example 50

5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide*

$C_{30}H_{31}F_6N_3O_3S$; $^1$H NMR (CDCl$_3$) δ(ppm) 7.75(s, 1H), 7.67(d, J=7.6 Hz, 1H), 7.53(d, J=8.0 Hz, 1H), 7.45(m, 2H), 7.23(m, 1H), 7.05(m, 1H), 6.99(d, J=8.0 Hz, 2H), 6.71(m, 2H), 6.65(d, J=7.2 Hz, 1H), 4.48(m, 1H), 3.48(m, 2H), 3.27(m, 2H), 1.63(m, 7H), 1.32(m, 1H), 1.10(m, 3H), 0.90 (m, 2H); LCMS: 628.4(M+H)$^+$.

Example 51

5-m-Tolyl-furan-2-carboxylic acid (S)-{2-cyclohexyl-1-[2-(4-trifluoromethoxy-phenylamino)-ethylcarbamoyl]-ethyl}-amide*

$C_{30}H_{34}F_3N_3O_4$; $^1$H NMR (CDCl$_3$) δ(ppm) 7.82(m, 1H), 7.43(m, 2H), 7.24(m, 1H), 7.12(m, 5H), 7.02(d, J=3.6 Hz, 1H), 6.96(d, J=6.0 Hz, 1H), 6.62(d, J=3.6 Hz, 1H), 4.41(m, 1H), 3.56(m, 2H), 3.40(m, 2H), 2.33(s, 3H), 1.67(m, 7H), 1.34(m, 1H), 1.13(m, 3H), 0.90(m, 2H); LCMS: 558.5 (M+H)$^+$.

Example 52

(S)-2,3-Dihydro-benzofuran-7-carboxylic acid {1-[2-(4-methoxy-phenylamino)-ethylcarbamoyl]-2-phenyl-ethyl}-amide*

$C_{27}H_{29}N_3O_4$; LCMS: 460.2(M+H)$^+$.

Example 53

5-Methanesulfonyl-thiophene-2-carboxylic acid (S)-{2-cyclohexyl-1-[2-(4-trifluoromethoxy-phenylamino)-ethylcarbamoyl]-ethyl}-amide*

$C_{24}H_{30}F_3N_3O_5S_2$; $^1$H NMR (CDCl$_3$) δ(ppm) 7.65(m, 1H), 7.55(m, 1H), 7.44(m, 1H), 7.23(m, 1H), 7.16(m, 2H), 7.06(m, 2H), 4.38(m, 1H), 3.51(m, 2H), 3.43(m, 1H), 3.33 (m, 1H), 3.10(s, 3H), 1.61(m, 7H), 1.18(m, 3H), 0.89(m, 3H), 0.86(m, 2H); LCMS: 562.4 (M+H)$^+$.

Example 54

2-Phenyl-thiazole-4-carboxylic acid (S)-{2-cyclohexyl-1-[2-(4-trifluoromethoxy-phenylamino)-ethyl-carbamoyl]-ethyl}-amide*

$C_{28}H_{31}F_3N_4O_3S$; $^1$H NMR (CDCl$_3$) δ(ppm)7.91(s, 1H), 7.86(m, 2H), 7.78(d, J=4 Hz, 1H), 7.51(m, 1H), 7.40(m, 3H), 7.06(m, 2H), 6.97(m, 2H), 4.44(m, 1H), 3.53(m, 2H), 3.35(m, 2H), 1.81(m, 1H), 1.67(m, 6H), 1.35(m, 1H), 1.14 (m, 3H), 0.91(m, 2H); LCMS: 561.4 (M+H)$^+$.

Example 55

(S)-3-Cyano-N-{1-[2-(4-methoxy-phenylamino)-ethylcarbamoyl]-2-phenyl-ethyl}-benzamide*

$C_{26}H_{26}N_4O_3$; LCMS: 443.2(M+H)$^+$.

Example 56

(S)-N-{1-[2-(4-Methoxy-phenylamino)-ethylcarbamoyl]-2-phenyl-ethyl}-3-(2-methyl-thiazol-4-yl)-benzamide*

$C_{29}H_{30}N_4O_3S$; LCMS: 515.2(M+H)$^+$.

Example 57

(S)-N-[2-(4-Methoxy-phenylamino)-ethyl]-3-phenyl-2-(3-phenyl-ureido)-propionamide

Example 58

3-Cyclohexyl-2-(S)-(2-(S)-hydroxy-2-phenyl-acetylamino)-N-[2-(4-trifluoromethoxy-phenylamino)-ethyl]-propionamide*

$C_{26}H_{32}F_3N_3O_4$; LCMS: 508.5 (M+H)$^+$.

Example 59

Benzo[c]isoxazole-3-carboxylic acid (S)-{2-cyclohexyl-1-[2-(4-trifluoromethoxy-phenylamino)-ethyl-carbamoyl]-ethyl}-amide*

$C_{26}H_{29}F_3N_4O_4$; $^1$H NMR (CDCl$_3$) δ(ppm) 8.12(m, 1H), 7.50(m, 3H), 7.39(m, 2H), 7.17(m, 3H), 6.97(m, 1H), 4.46 (m, 1H), 3.59(m, 4H), 1.65(m, 7H), 1.39(m, 1H), 1.16(m, 3H), 0.92(m, 2H); LCMS: 519.5 (M+H)$^+$.

Example 60

N-(S)-{2-cyclohexyl-1-[2-(4-trifluoromethoxy-phenylamino)-ethylcarbamoyl]-ethyl}-4-difluoromethoxy-benzamide*

$C_{26}H_{30}F_3N_3O_4$; $^1$H NMR (CDCl$_3$) δ(ppm) 7.74(m, 3H), 7.11(m, 6H), 6.96(d, J=6 Hz, 1H), 6.55(t, J=72.8 Hz, 1H) 4.49(m, 1H), 3.59(m, 2H), 3.47(m, 1H), 3.39(m, 1H), 1.70 (m, 7H), 1.37(m, 1H), 1.19(m, 3H), 0.97(m, 2H); LCMS: 544.4(M+H)$^+$.

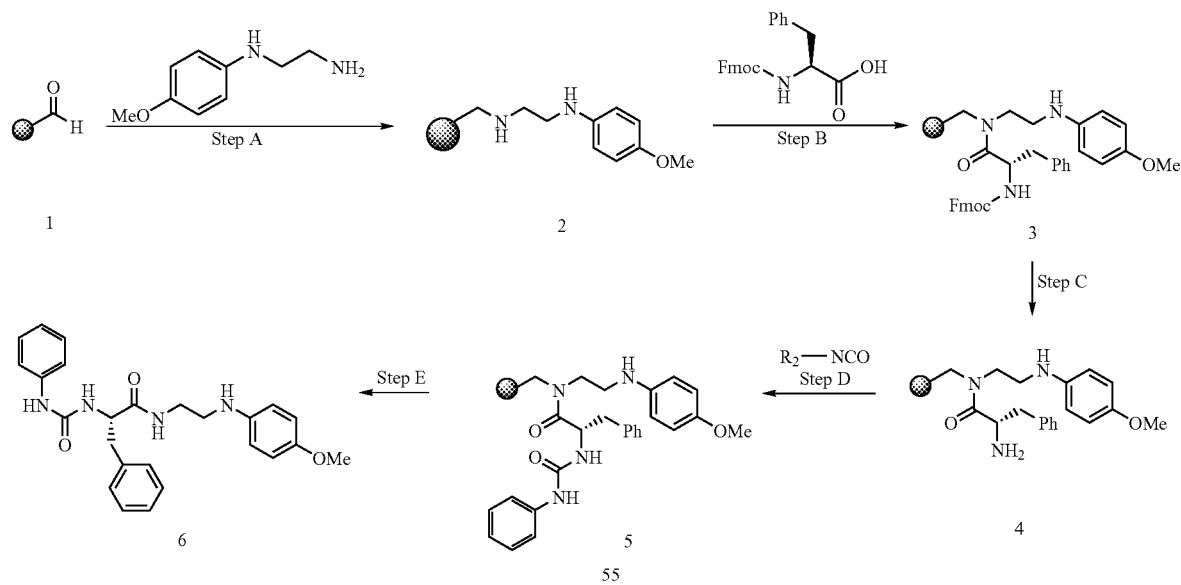

Solid phase synthesis: Steps A, B, C and E were described in Preparation 1.

Step D: Resin 4 (0.077 mmol) was swelled in DMF (1 mL) and phenyl isocyanate (18 mg, 0.154 mmol, 2 eq) was added in 1 mL DMF followed by pyridine (0.012 mL, 0.154 mmol, 2 eq). The reaction was agitated for 3 h and then washed (DMF×4, then dichloromethane×3) and dried under nitrogen to yield resin 5. $C_{25}H_{28}N_4O_3$; $^1$H NMR (CD$_3$OD) δ(ppm) 7.27(m, 11H); 7.00(m, 3H); 4.38(m, 1H); 3.80(s, 3H); 3.61(m, 1H); 3.47(m, 1H); 3.38(m, 2H); 3.09(m, 1H); 2.99 (m, 1H); LCMS: 433.2(M+H)$^+$. (14 mg, 0.032 mmol, 42%).

Example 61

N-(S)-{2-cyclohexyl-1-[2-(4-trifluoromethoxy-phenylamino)-ethylcarbamoyl]-ethyl}-4-isopropoxy-benzamide*

$C_{28}H_{36}F_3N_3O_4$; $^1$H NMR (CDCl$_3$) δ(ppm) 7.66(m, 3H), 7.14(d, J=8.4 Hz, 2H), 7.02(d, J=8.8 Hz, 2H), 6.87(d, J=9.2 Hz, 2H), 6.70(d, J=6 Hz, 1H), 4.61(m, 1H), 4.49(m, 1H), 3.58(m, 2H), 3.38(m, 2H), 1.70(m, 7H), 1.35(m, 7H), 1.19 (m, 3H), 0.98(m, 2H); LCMS: 536.5(M+H)$^+$.

Example 62

5-Phenyl-thiophene-2-carboxylic acid (S)-{2-cyclohexyl-1-[2-(4-trifluoromethoxy-phenylamino)-ethylcarbamoyl]-ethyl}-amide*

$C_{29}H_{32}F_3N_3O_3S$; $^1H$ NMR (CDCl$_3$) δ(ppm) 7.50(m, 2H), 7.42(m, 1H), 7.32(m, 4H), 7.17(m, 1H), 7.02(m, 2H), 6.84 (m, 2H), 6.64(m, 1H), 4.43(m, 1H), 3.48(m, 2H), 3.29(m, 2H), 1.61(m, 7H), 1.29(m, 1H), 1.09(m, 3H), 0.89(m, 2H); LCMS: 560.3 (M+H)$^+$.

Example 63

(S)-N-{1-[2-(4-Methoxy-phenylamino)-ethylcarbamoyl]-2-phenyl-ethyl}-nicotinamide*

$C_{24}H_{26}N_4O_3$; LCMS: 419.2(M+H)$^+$.

Example 64

(S)-N-{1-[2-(4-Methoxy-phenylamino)-ethylcarbamoyl]-2-phenyl-ethyl}-isonicotinamide*

$C_{24}H_{26}N_4O_3$; LCMS: 419.2(M+H)$^+$.

Example 65

5-Phenyl-furan-2-carboxylic acid (S)-{2-cyclohexyl-1-[2-(4-trifluoromethoxy-phenylamino)-ethylcarbamoyl]-ethyl}-amide*

$C_{29}H_{32}F_3N_3O_4$; $^1H$ NMR (CDCl$_3$) δ(ppm) 7.75(m, 1H), 7.64(m, 2H), 7.35(m, 3H), 7.12(s, 3H), 7.02(d, J=3.6 Hz, 1H), 6.93(m, 1H), 6.65(m, 2H), 4.39(m, 1H), 3.56(m, 2H), 3.39(m, 2H), 1.66(m, 7H), 1.35(m, 1H), 1.13(m, 3H), 0.92 (m, 2H); LCMS: 544.4 (M+H)$^+$.

Example 66

(S)-N-[1-[2-(4-Methoxy-phenylamino)-ethylcarbamoyl]-2-(4-o-tolyloxy-phenyl)-ethyl]-3-methyl-benzamide$^{\$\$}$ Following the procedure of Example 327, except substituting phenyl-boronic acid for 2-methylphenyl-boronic acid in Step D, the title compound was prepared as a white solid (6 mg, 22%): $^1$H-NMR (400 MHz, CD$_3$OD) δ=7.59–6.77 (m, 16H), 4.63 (dd, J=7.1, J=8.4, 1H), 3.81 (s, 3H), 3.61–3.05 (m, 6H), 2.37 (s, 3H), 2.14 (s, 3H). MS calcd. for $C_{33}H_{36}N_3O_4$ (M+H$^+$) 538.27. found 538.4.

Example 67

N-(S)-{2-cyclohexyl-1-[2-(4-trifluoromethoxy-phenylamino)-ethylcarbamoyl]-ethyl}-4-oxazol-5-yl-benzamide*

$C_{28}H_{31}F_3N_4O_4$; $^1H$ NMR (CDCl$_3$) δ(ppm)7.93(m, 1H), 7.73(d, J=8.0 Hz, 2H), 7.63(d, J=8.0 Hz, 2H), 7.39(s, 1H), 7.11(m, 1H), 7.01(d, J=8.0 Hz, 2H), 6.76(m, 2H), 6.70(d, J=8.0 Hz, 1H), 4.49(m, 1H), 3.49(m, 2H), 3.29(m, 2H), 1.65(m, 7H), 1.31(m, 1H), 1.10(m, 3H), 0.88(m, 2H); LCMS: 545.5(M+H)$^+$.

Example 68

5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide*

$C_{30}H_{31}F_6N_3O_3S$; $^1H$ NMR (CDCl$_3$) δ(ppm) 7.92(m, 1H), 7.71(m, 1H), 7.64(d, J=8.0 Hz, 1H), 7.52(m, 1H), 7.46(m, 2H), 7.22(m, 1H), 7.17(m, 4H), 6.99(d, J=6 Hz, 1H), 4.39 (m, 1H), 3.56(m, 2H), 3.40(m, 2H), 1.64(m, 7H), 1.34(m, 1H), 1.11(m, 3H), 0.89(m, 2H); LCMS: 628.4(M+H)$^+$.

Example 69

5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide*

$C_{30}H_{31}F_6N_3O_3S$; $^1H$ NMR (CDCl$_3$) δ(ppm) 8.14(m, 1H), 7.69(m, 1H), 7.45(m, 3H), 7.36(m, 1H), 7.26(m, 2H), 7.17 (m, 2H), 7.00(m, 2H), 4.36(m, 1H), 3.57(m, 2H), 3.44(m, 2H), 1.64(m, 7H), 1.35(m, 1H), 1.13(m, 3H), 0.89(m, 2H); LCMS:628.3 (M+H)$^+$.

Example 70

5-p-Tolyl-furan-2-carboxylic acid (S)-{2-cyclohexyl-1-[2-(4-trifluoromethoxy-phenylamino)-ethylcarbamoyl]-ethyl}-amide*

$C_{30}H_{34}F_3N_3O_4$; $^1H$ NMR (CDCl$_3$) δ(ppm)7.94(m, 1H), 7.40(m, 2H), 7.16(m, 2H), 7.06(m, 4H), 6.93(m, 1H), 6.89 (m, 1H), 6.47(m, 1H), 4.27(m, 1H), 3.48(m, 2H), 3.34(m, 2H), 2.21(s, 3H), 1.61(m, 7H), 1.26(m, 1H), 1.03(m, 3H), 0.82(m, 2H); LCMS: 558.4 (M+H)$^+$.

Example 71

N-(S)-{2-cyclohexyl-1-[2-(4-trifluoromethoxy-phenylamino)-ethylcarbamoyl]-ethyl}-3-[(4,6-dimethyl-pyrimidin-2-yl)-methyl-amino]-benzamide*

$C_{32}H_{39}F_3N_6O_3$; LCMS:613.5(M+H)$^+$.

Example 72

1-(4,6-Dimethyl-pyrimidin-2-yl)-piperidine-4-carboxylic acid (S)-{2-cyclohexyl-1-[2-(4-trifluoromethoxy-phenylamino)-ethylcarbamoyl]-ethyl}-amide*

$C_{30}H_{41}F_3N_6O_3$; $^1H$ NMR (CDCl$_3$) δ(ppm) 7.33(m, 1H), 6.96(m, 1H), 6.91(d, j=8.8 Hz, 2H), 6.82(d, J=8.8 Hz, 2H), 6.18(s, 1H), 4.45(m, 2H), 4.09(m, 1H), 3.31(m, 2H), 3.10(m, 2H), 2.94(m, 2H), 2.36(m, 1H), 2.22(s, 6H), 1.72(m, 2H), 1.56(m, 2H), 1.41(m, 7H), 1.07(m, 1H), 1.01(m, 3H), 0.64 (m, 2H); LCMS: 591.5 (M+H)$^+$.

Example 73

N-(S)-{2-cyclohexyl-1-[2-(4-trifluoromethoxy-phenylamino)-ethylcarbamoyl]-ethyl}-3-(4,6-dimethoxy-pyrimidin-2-yloxy)-benzamide*

$C_{31}H_{36}F_3N_5O_6$; $^1H$ NMR (CDCl$_3$) δ(ppm) 7.69(m, 1H), 7.50(m, 2H), 7.33(m, 2H), 7.07(m, 4H), 6.86(d, J=6 Hz, 1H), 5.72(s, 1H), 4.39(m, 1H), 3.73(m, 6H), 3.52(m, 2H),

Example 74

3'-Methoxy-biphenyl-3-carboxylic acid (S)-{2-cyclohexyl-1-[2-(4-trifluoromethoxy-phenylamino)-ethylcarbamoyl]-ethyl}-amide*

$C_{32}H_{36}F_3N_3O_4$; $^1H$ NMR (CDCl$_3$) δ(ppm) 7.98(m, 1H), 7.86(m, 1H), 7.66(m, 1H), 7.60(m, 1H), 7.41(m, 1H), 7.29(m, 1H), 7.13(m, 4H), 7.06(m, 1H), 7.03(m, 2H), 6.80(m, 1H), 4.43(m, 1H), 3.78(s, 3H), 3.54(m, 2H), 3.39(m, 2H), 1.68(m, 7H), 1.60(m, 1H), 1.10(m, 3H), 0.91(m, 2H); LCMS: 584.4 (M+H)$^+$.

Example 75

N-{3-Cyclohexyl-1-(S)-[2-(4-methoxy-phenylamino)-ethylcarbamoyl]-propyl}-2-(R)-phenyl-butyramide*

$C_{29}H_{41}N_3O_3$; $^1H$ NMR (CDCl$_3$) δ(ppm) 7.89(m, 1H), 7.19(m, 3H), 7.13(m, 2H), 7.07(d, J=9.2 Hz, 2H), 6.79(m, 2H), 6.25(m, 1H), 3.92(m, (m, 1H), 3.73(s, 3H), 3.28(m, 5H), 1.96(m, 1H), 1.75(m, 2H), 1.53(m, 6H), 1.06(m, 6H), 0.75(m, 5H); LCMS: 480.6(M+H)$^+$.

Example 76

3-Cyclohexyl-N-[2-(4-fluoro-phenylamino)-ethyl]-2-(S)-(2-thiophen-2-yl-acetylamino)-propionamide*

$C_{23}H_{30}FN_3O_2S$; $^1H$ NMR (CDCl$_3$) δ(ppm) 8.35(m, 1H), 7.35(m, 2H), 7.13(m, 1H), 7.07(m, 2H), 6.89(m, 2H), 6.39(d, J=4.0 Hz, 1H), 4.03(m, 1H), 3.69(m, 5H), 3.33(m, 1H), 1.58(m, 7H), 1.10(m, 4H), 0.82(m, 2H); LCMS: 432.5(M+H)$^+$.

Example 77

3-Cyclohexyl-N-[2-(4-fluoro-phenylamino)-ethyl]-2-(S)-(2-thiophen-3-yl-acetylamino)-propionamide*

$C_{23}H_{30}FN_3O_2S$; $^1H$ NMR (CDCl$_3$) δ(ppm) 8.36(m, 1H), 7.33(m, 2H), 7.22(m, 1H), 7.07(m, 3H), 6.92(m, 1H), 6.24(d, J=4.0 Hz, 1H), 4.01(m, 1H), 3.54(m, 5H), 3.32(m, 1H), 1.58(m, 7H), 1.07(m, 4H), 0.80(m, 2H); LCMS: 432.5(M+H)$^+$.

Example 78

(S)-3-Bromo-N-{1-[2-(4-methoxy-phenylamino)-ethylcarbamoyl]-2-phenyl-ethyl}-benzamide*

$C_{25}H_{26}BrN_3O_3$; LCMS: 496.1($^{79}$BrM+H)$^+$, 498.1 ($^{80}$BrM+H)$^+$.

Example 79

1-Acetyl-piperidine-4-carboxylic acid (S)-{2-cyclohexyl-1-[2-(4-fluoro-phenylamino)-ethylcarbamoyl]-ethyl}-amide $C_{25}H_{37}FN_4O_3$; $^1H$ NMR (CDCl$_3$) δ(ppm) 8.33(m, 1H), 7.42(m, 2H), 7.12(m, 2H), 6.40(m, 1H), 4.51(m, 3H), 4.09 (m, 1H), 3.58(m, 3H), 3.35(m, 1H), 2.98(m, 1H), 2.42(m, 2H), 2.03(m, 3H), 1.51(m, 10H), 1.13(m, 4H), 0.88(m, 2H); LCMS: 461.6(M+H)$^+$.

Example 80

N-(S)-{2-cyclohexyl-1-[2-(4-trifluoromethoxy-phenylamino)-ethylcarbamoyl]-ethyl}-4-(4,6-dimethoxy-pyrimidin-2-yl)-benzamide*

$C_{31}H_{36}F_3N_5O_5$; $^1H$ NMR (CDCl$_3$) δ(ppm) 8.40(d, J=8.0 Hz, 2H), 7.91(m, 1H), 7.71(d, J=8.0 Hz, 2H), 7.13(m, 4H), 7.01(d, J=5.6 Hz, 1H), 5.93(s, 1H), 3.96(s, 6H), 3.56(m, 2H), 3.40(m, 2H), 1.68(m, 7H), 1.35(m, 1H), 1.14(m, 3H), 0.89(m, 2H); LCMS: 616.5(M+H)$^+$.

Example 81

1-(5-Bromo-pyrimidin-2-yl)-piperidine-4-carboxylic acid (S)-{2-cyclohexyl-1-[2-(4-trifluoromethoxy-phenylamino)-ethylcarbamoyl]-ethyl}-amide*

$C_{28}H_{36}BrF_3N_6O_3$; LCMS: 641.4($^{79}$BrM+H)$^+$, 643.4 ($^{80}$BrM+H)$^+$.

Example 82

(S)-2-(2-Cyclopent-2-enyl-acetylamino)-N-[2-(4-methoxy-phenylamino)-ethyl]-3-phenyl-propionamide*

$C_{25}H_{31}N_3O_3$; LCMS: 422.2(M+H)$^+$

Example 83

3-Cyclohexyl-N-[2-(4-fluoro-phenylamino)-ethyl]-2-(2-1H-indol-3-yl-acetylamino)-propionamide*

$C_{27}H_{33}FN_4O_2$; $^1H$ NMR (CDCl$_3$) δ(ppm) 8.19(m, 2H), 7.45(d, J=7.6 Hz, 1H), 7.32(m, 3H), 7.16(m, 2H), 7.01(m, 3H), 6.30(d, J=4.0 Hz, 1H), 3.99(m, 1H), 3.53(m, 5H), 3.27(m, 1H), 1.50(m, 5H), 1.30(m, 2H), 0.91(m, 3H), 0.65(m, 3H); LCMS: 465.5(M+H)$^+$.

Example 84

N-(S)-{2-cyclohexyl-1-[2-(4-fluoro-phenylamino)-ethylcarbamoyl]-ethyl}-3-methanesulfonylamino-benzamide*

$C_{25}H_{25}FN_4O_4S$; $^1H$ NMR (CDCl$_3$) δ(ppm) 8.63(m, 1H), 8.36(m, 1H), 7.53(s, 1H), 7.40(m, 3H), 7.27(m, 1H), 7.22(m, 1H), 7.02(m, 2H), 4.48(m, 1H), 3.50(m, 4H), 2.86(s, 3H), 1.63(m, 7H), 1.32(m, 1H), 1.09(m, 3H), 0.89(m, 2H); LCMS: 505.5(M+H)$^+$.

Example 85

5-(3-Trifluoromethyl-phenyl)-furan-2-carboxylic acid (S)-{2-cyclohexyl-1-[2-(4-fluoro-phenylamino)-ethylcarbamoyl]-ethyl}-amide*

$C_{29}H_{31}F_4N_3O_3$; $^1H$ NMR (CDCl$_3$) δ(ppm) 8.59(m, 1H), 7.88(m, 2H), 7.55(m, 4H), 7.34(m, 1H), 7.18(m, 2H), 7.08(d, J=3.6 Hz, 1H), 6.79(d, J=3.6 Hz, 1H), 4.42(m, 1H), 3.64(m, 4H), 1.77(m, 7H), 1.46(m, 1H), 1.22(m, 3H), 1.01(m, 2H); LCMS: 546.5(M+H)$^+$.

Example 86

3-Cyclohexyl-2-(S)-(2-(R,S)-fluoro-2-phenyl-acetylamino)-N-[2-(4-fluoro-phenylamino)-ethyl]-propionamide*

$C_{25}H_{31}F_2N_3O_2$; LCMS: 444.5(M+H)$^+$.

Example 87

3-Cyclohexyl-N-(S)-[2-(4-fluoro-phenylamino)-ethyl]-2-[2-(4-trifluoromethoxy-phenyl)-acetylamino]-propionamide*

$C_{26}H_{31}F_4N_3O_3$; $^1$H NMR (CDCl$_3$) δ(ppm) 8.44(m, 1H), 7.35(m, 2H), 7.24(m, 2H), 7.10(m, 4H), 6.43(d, J=4.0 Hz, 1H), 4.11(m, 1H), 3.61(m, 5H), 3.37(m, 1H), 1.65(m, 7H), 1.20(m, 4H), 0.89(m, 2H); LCMS: 510.5(M+H)$^+$.

Example 88

(S)-2-[3-(4-Chloro-phenyl)-ureido]-N-[2-(4-methoxy-phenylamino)-ethyl]-3-phenyl-propionamide$^\$$

$C_{25}H_{27}ClN_4O_3$; 467.2($^{35}$ClM+H)$^+$, 469.2($^{37}$ClM+H)$^+$.

Example 89

(S)-N-[2-(4-Methoxy-phenylamino)-ethyl]-2-[3-(4-phenoxy-phenyl)-ureido]-3-phenyl-propionamide$^\$$

$C_{31}H_{32}N_4O_4$; $^1$H NMR (CD$_3$Cl) δ(ppm) 8.56(bs, 1H), 7.71(bs, 1H), 7.28(m, 7H), 7.19(m, 3H), 7.03(m, 3H), 6.88(m, 4H), 6.73(d, J=8.8 Hz, 2H), 6.15(bs, 1H), 4.25(m, 1H), 3.77(s, 3H), 3.57(m, 2H), 3.33(m, 1H), 3.21(m, 2H), 2.95(m, 1H); LCMS: 525.2(M+H)$^+$.

Example 90

(S)-N-[2-(4-Methoxy-phenylamino)-ethyl]-2-(3-phenethyl-ureido)-3-phenyl-propionamide$^\$$

$C_{27}H_{32}N_4O_3$; LCMS: 461.2(M+H)$^+$.

Example 91

(S)-2-[3-(4-Fluoro-benzyl)-ureido]-N-[2-(4-methoxy-phenylamino)-ethyl]-3-phenyl-propionamide$^\$$

$C_{26}H_{29}FN_4O_3$; LCMS: 465.2(M+H)$^+$.

Example 92

N-(S)-{2-cyclohexyl-1-[2-(4-trifluoromethoxy-phenylamino)-ethylcarbamoyl]-ethyl}-4-(4,6-dimethyl-pyrimidin-2-ylamino)-benzamide*

$C_{31}H_{37}F_3N_6O_3$; $^1$H NMR (CDCl$_3$) δ(ppm) 12.30(s, 1H), 7.76(m, 2H), 7.64(m, 2H), 7.34(m, 1H), 7.01(m, 2H), 6.78(m, 3H), 6.58(s, 1H), 4.46(m, 1H), 3.48(m, 2H), 3.27(m, 2H), 2.50(s, 6H), 1.62(m, 7H), 1.31(m, 3H), 1.08(m, 3H), 0.86(m, 2H); LCMS: 599.5(M+H)$^+$.

Example 93

1-(5-Bromo-pyrimidin-2-yl)-piperidine-3-carboxylic acid (S)-{2-cyclohexyl-1-[2-(4-trifluoromethoxy-phenylamino)-ethylcarbamoyl]-ethyl}-amide*

$C_{28}H_{36}BrF_3N_6O_3$; $^1$H NMR (CDCl$_3$) δ(ppm) 8.24(m, 2H), 7.89(m, 1H), 7.26(m, 2H), 7.18(m, 2H), 7.05(m, 1H), 4.15(m, 1H), 4.01(m, 1H), 3.79(m, 1H), 3.50(m, 3H), 3.34(m, 1H), 2.46(m, 1H), 1.84(m, 3H), 1.57(m, 9H), 1.18(m, 1H), 1.02(m, 3H), 0.87(m, 2H), LCMS: 641.4($^{79}$BrM+H)$^+$, 643.4($^{80}$BrM+H)$^+$.

Example 94

(S)-2-(3-Benzo[1,3]dioxol-5-yl-ureido)-N-[2-(4-methoxy-phenylamino)-ethyl]-3-phenyl-propionamide$^\$$

$C_{26}H_{28}N_4O_5$; LCMS: 477.2(M+H)$^+$.

Example 95

3-Cyclohexyl-2-(S)-[2-(2,5-difluorophenyl)-acetylamino]-N-[2-(4-fluoro-phenylamino)-ethyl]-propionamide*

$C_{25}H_{30}F_3N_3O_2$; $^1$H NMR (CDCl$_3$) δ(ppm) 8.27(m, 1H), 7.26(m, 2H), 7.02(m, 2H), 6.85(m, 3H), 6.44(m, 1H), 4.08(m, 1H), 3.50(m, 5H), 3.32(m, 1H), 1.59(m, 7H), 1.13(m, 4H), 0.83(m, 2H); LCMS: 462.5(M+H)$^+$.

Example 96

(S)-2-[3-(3-Fluoro-benzyl)-ureido]-N-[2-(4-methoxy-phenylamino)-ethyl]-3-phenyl-propionamide$^\$$

$C_{26}H_{29}FN_4O_3$; LCMS: 465.2(M+H)$^+$.

Example 97

(S)-N-[2-(4-Methoxy-phenylamino)-ethyl]-3-phenyl-2-(3-o-tolyl-ureido)-propionamide$^\$$

$C_{26}H_{30}N_4O_3$; LCMS: 447.2(M+H)$^+$.

Example 98

(S)-N-{2-[4-(3,4-Dichloro-phenoxy)-phenyl]-1-[2-(4-methoxy-phenylamino)-ethylcarbamoyl]-ethyl}-3-methyl-benzamide$^{\$\$}$ Following the procedure of Example 327, except substituting phenyl-boronic acid for 3,4-dichlorophenyl-boronic acid in Step D, the title compound was prepared as a white solid (5 mg, 17%): $^1$H-NMR (400 MHz, CD$_3$OD) δ=7.61–6.83 (m, 15H), 4.67 (dd, J=7.0, J=8.6, 1H), 3.81 (s, 3H), 3.62–3.09 (m, 6H), 2.38 (s, 3H). MS calcd. for $C_{32}H_{32}Cl_2N_3O_4$ (M+H$^+$) 592.18. found 592.4.

Example 99

3-Cyclohexyl-2-(S)-[2-(3,4-difluoro-phenyl)-acetylamino]-N-[2-(4-fluoro-phenylamino)-ethyl]-propionamide*

$C_{25}H_{30}F_3N_3O_2$; $^1$H NMR (CDCl$_3$) δ(ppm) 8.30(m, 1H), 7.25(m, 2H), 7.02(m, 5H), 6.35(m, 1H), 4.04(m, 1H), 3.51(m, 5H), 3.26(m, 1H), 1.63(m, 6H), 1.48(m, 1H), 1.13(m, 4H), 0.83(m, 2H); LCMS: 462.5 (M+H)$^+$.

Example 100

3-Cyclohexyl-2-(S)-[2-(2,4-difluoro-phenyl)-acetylamino]-N-[2-(4-fluoro-phenylamino)-ethyl]-propionamide*

$C_{25}H_{30}F_3N_3O_2$; $^1$H NMR (CDCl$_3$) δ(ppm) 8.18(m, 1H), 7.12(m, 2H), 6.90(m, 3H), 6.50(m, 2H), 6.35(m, 1H), 3.90 (m, 1H), 3.35(m, 5H), 3.17(m, 1H), 1.35(m, 7H), 0.96(m, 4H), 0.66(m, 2H); LCMS: 462.5(M+H)$^+$.

Example 101

(S)-N-[2-(4-Methoxy-phenylamino)-ethyl]-2-(3-naphthalen-1-yl-ureido)-3-phenyl-propionamide$^\$$

$C_{29}H_{30}N_4O_3$; LCMS: 483.2(M+H)$^+$.

Example 102

(S)-2-[3-(2-tert-Butyl-6-methyl-phenyl)-ureido]-N-[2-(4-methoxy-phenylamino)-ethyl]-3-phenyl-propionamide$^\$$

$C_{30}H_{38}N_4O_3$; LCMS: 503.3(M+H)$^+$.

Example 103

(S)-2-[3-(4-Acetyl-phenyl)-ureido]-N-[2-(4-methoxy-phenylamino)-ethyl]-3-phenyl-propionamide$^\$$

$C_{27}H_{30}N_4O_4$; $^1$H NMR (CD$_3$Cl) δ(ppm) 8.75(bs, 1H), 8.56(bs, 1H), 7.67(d, J=8.3 Hz, 2H), 7.25(m, 10H), 6.88(d, J=8.6, 2H), 6.82(m, 1H), 4.37(m, 1H), 3.82(s, 3H), 3.64(m, 1H), 3.33(m, 3H), 3.15(m, 1H), 3.00(m, 1H), 2.47(s, 3H); LCMS: 475.2(M+H)$^+$.

Example 104

(S)-N-[2-(4-Methoxy-phenylamino)-ethyl]-2-[3-(3-methoxy-phenyl)-ureido]-3-phenyl-propionamide$^\$$

$C_{26}H_{30}N_4O_4$; LCMS: 463.2(M+H)$^+$.

Example 105

(S)-Biphenyl-4-carboxylic acid {2-cyclohexyl-1-[2-(4-methoxy-phenylamino)-ethylcarbamoyl]-ethyl}-amide*

$C_{31}H_{37}N_3O_3$; $^1$H NMR (CD$_3$Cl) δ(ppm) 8.72(m, 1H); 7.77(d, J=8.3 Hz, 2H); 7.60(m, 2H), 7.58(m, 2H); 7.47(m, 5H); 7.16(m, 1H); 6.96(d, J=9.0 Hz, 2H); 4.41(m, 1H); 3.82(s, 3H); 3.67(m, 3H); 3.50(m, 1H) 1.78(m, 7H); 1.49(m, 1H); 1.22(m, 3H); 1.00(m, 2H); LCMS: 500.25(M+H)$^+$.

Example 106

(S)-N-{2-Cyclohexyl-1-[2-(4-methoxy-phenylamino)-ethylcarbamoyl]-ethyl}-3-trifluoromethyl-benzamide*

$C_{26}H_{32}F_3N_3O_3$; LCMS: 492.4(M+H)$^+$.

Example 107

2-(S)-[2-(2-Chloro-4-fluoro-phenyl)-acetylamino]-3-cyclohexyl-N-[2-(4-fluoro-phenylamino)-ethyl]-propionamide*

$C_{25}H_{30}F_2N_3O_2$; $^1$H NMR (CDCl$_3$) δ(ppm) 8.31(m, 1H), 7.29(m, 2H), 7.22(m, 1H), 7.01(m, 3H), 6.85(m, 1H), 6.25 (m, 1H), 4.06(m, 1H), 3.55(m, 5H), 3.32(m, 1H), 1.62(m, 6H), 1.46(m, 1H), 1.11(m, 4H), 0.83(m, 2H); LCMS: 478.5 (M+H)$^+$.

Example 108

(S)-2-Chloro-N-{2-cyclohexyl-1-[2-(4-methoxy-phenylamino)-ethylcarbamoyl]-ethyl}-3-methyl-benzamide*

$C_{26}H_{34}ClN_3O_3$; LCMS: 472.2(M+H)$^+$.

Example 109

(S)-4-Benzyloxy-N-{2-cyclohexyl-1-[2-(4-methoxy-phenylamino)-ethylcarbamoyl]-ethyl}-benzamide*

$C_{32}H_{39}N_3O_4$; $^1$H NMR (CD$_3$Cl) δ(ppm) 8.70(m, 1H), 7.64(d, J=8.9 Hz, 2H), 7.45(d, J=8.9 Hz, 2H), 7.38(m, 4H), 6.95(m, 5H), 6.84(m, 1H), 5.09(s, 2H), 4.33(m, 1H), 3.83(s, 3H), 3.64(m, 3H), 3.45(m, 1H), 1.75(m, 7H), 1.46(m, 1H), 1.25(m, 3H), 1.01(m, 2H); LCMS: 530.3(M+H)$^+$.

Example 110

(S)-4-Benzyloxy-N-{2-cyclohexyl-1-[2-(4-methoxy-phenylamino)-ethylcarbamoyl]-ethyl}-3,5-dimethyl-benzamide*

$C_{34}H_{43}N_3O_4$; LCMS: 558.3(M+H)$^+$.

Example 111

(S)-N-{2-Cyclohexyl-1-[2-(4-methoxy-phenylamino)-ethylcarbamoyl]-ethyl}-4-methoxy-3,5-dimethyl-benzamide*

$C_{28}H_{39}N_3O_4$; LCMS: 482.3(M+H)$^+$.

Example 112

(S)-3-Bromo-N-{2-cyclohexyl-1-[2-(4-methoxy-phenylamino)-ethylcarbamoyl]-ethyl}-4-methyl-benzamide*

$C_{26}H_{34}BrN_3O_3$; LCMS: 516.4($^{79}$BrM+H)$^+$, 518.4 ($^{80}$BrM+H)$^+$.

Example 113

(S)-5-Fluoro-1H-indole-2-carboxylic acid {2-cyclohexyl-1-[2-(4-methoxy-phenylamino)-ethylcarbamoyl]-ethyl}-amide*

$C_{27}H_{33}FN_4O_3$; LCMS: 481.3(M+H)$^+$.

Example 114

(S)-2-Amino-4-methyl-thiazole-5-carboxylic acid {2-cyclohexyl-1-[2-(4-methoxy-phenylamino)-ethylcarbamoyl]-ethyl}-amide*

$C_{23}H_{33}N_5O_3S$; LCMS: 460.2(M+H)$^+$.

Example 115

(S)-1-Phenyl-5-trifluoromethyl-1H-pyrazole-4-carboxylic acid {2-cyclohexyl-1-[2-(4-methoxy-phenylamino)-ethylcarbamoyl]-ethyl}-amide*

$C_{29}H_{34}F_3N_5O_3$; LCMS: 558.2(M+H)$^+$.

Example 116

(S)-1-(4-Chloro-phenyl)-5-trifluoromethyl-1H-pyrazole-4-carboxylic acid {2-cyclohexyl-1-[2-(4-methoxy-phenylamino)-ethylcarbamoyl]-ethyl}-amide*

$C_{29}H_{33}ClF_3N_5O_3$; LCMS: 592.2(M+H)$^+$.

Example 117

(S)-5-(3-Trifluoromethyl-phenyl)-furan-2-carboxylic acid {2-cyclohexyl-1-[2-(4-methoxy-phenylamino)-ethylcarbamoyl]-ethyl}-amide*

$C_{30}H_{34}F_3N_3O_4$; $^1$H NMR (CD$_3$Cl) δ(ppm) 8.68(bs, 1H), 7.86(m, 2H), 7.56(m, 2H), 7.45(d, J=8.8 Hz, 2H), 7.29(m, 1H), 7.06(d, J=3.3 Hz, 1H), 6.95(d, J=8.7 Hz, 2H), 6.77(d, J=3.5 Hz, 1H), 4.40(m, 1H), 3.82(s, 3H), 3.69(m, 2H), 3.59(m, 1H), 3.52(m, 1H), 1.77(m, 7H), 1.47(m, 1H), 1.24 (m, 3H), 1.00(m, 2H); LCMS: 558.2(M+H)$^+$.

Example 118

(S)-3-Chloro-N-{2-cyclohexyl-1-[2-(4-methoxy-phenylamino)-ethylcarbamoyl]-ethyl}-benzamide*

$C_{25}H_{32}ClN_3O_3$; LCMS: 458.2($^{35}$ClM+H)$^+$, 460.2 ($^{37}$ClM+H)$^+$.

Example 119

(S)-N-{2-Cyclohexyl-1-[2-(4-methoxy-phenylamino)-ethylcarbamoyl]-ethyl}-3-dimethylamino-benzamide*

$C_{27}H_{38}N_4O_3$; LCMS: 467.3(M+H)$^+$.

Example 120

(S)-3-Cyano-N-{2-cyclohexyl-1-[2-(4-methoxy-phenylamino)-ethylcarbamoyl]-ethyl}-benzamide*

$C_{26}H_{32}N_4O_3$; LCMS: 449.2(M+H)$^+$.

Example 121

(S)-4-Cyano-N-{2-cyclohexyl-1-[2-(4-methoxy-phenylamino)-ethylcarbamoyl]-ethyl}-benzamide*

$C_{26}H_{32}N_4O_3$; LCMS: 449.2(M+H)$^+$.

Example 122

N-{2-cyclohexyl-1-(S)-[2-(4-trifluoromethoxy-phenylamino)-ethylcarbamoyl]-ethyl}-2-(R)-phenyl-propionamide*

$C_{27}H_{34}F_3N_3O_3S$ Error! Objects cannot be created from editing field codes.; $^1$H NMR (CDCl$_3$) δ(ppm) 7.18(m, 5H), 6.98(m, 2H), 6.79(m, 1H), 6.61(m, 2H), 5.73(d, J=7.2 Hz. 1H), 4.20(m, 1H), 3.52(m, 1H), 3.31(m, 5H), 3.10(m, 2H), 1.58(m, 4H), 1.41(d, J=7.2 Hz, 3H), 1.34(m, 1H), 1.04(m, 3H), 0.78(m, 2H); LCMS: 506.5 (M+H)$^+$.

Example 123

(S)-N-{2-Cyclohexyl-1-[2-(4-methoxy-phenylamino)-ethylcarbamoyl]-ethyl}-3-(2-methyl-thiazol-4-yl)-benzamide*

$C_{29}H_{36}N_4O_3S$; LCMS: 521.2(M+H)$^+$.

Example 124

(S)-N-{2-Cyclohexyl-1-[2-(4-methoxy-phenylamino)-ethylcarbamoyl]-ethyl}-4-[1,2,4]triazol-1-yl-benzamide*

$C_{27}H_{34}N_6O_3$; LCMS: 491.3(M+H)$^+$.

Example 125

3-Cyclohexyl-2-(S)-[2-(3,5-difluoro-phenyl)-acetylamino]-N-[2-(4-fluoro-phenylamino)-ethyl]-propionamide*

$C_{25}H_{30}F_3N_3O_2$; $^1$H NMR (CDCl$_3$) δ(ppm) 8.40(m, 1H), 7.36(m, 2H), 7.12(m, 2H), 6.77(m, 2H), 6.66(m, 1H), 6.50 (m, 1H), 4.13(m, 1H), 3.58(m, 5H), 3.36(m, 1H), 1.65(m, 7H), 1.18(m, 4H), 0.92(m, 2H); LCMS: 462.5(M+H)$^+$.

Example 126

(S)-N-{3-Cyclohexyl-1-[2-(4-methoxy-phenylamino)-ethylcarbamoyl]-propyl}-3-trifluoromethyl-benzamide*

$C_{27}H_{34}F_3N_3O_3$; $^1$H NMR (CD$_3$Cl) δ(ppm) 8.75(bs, 1H), 8.06(bs, 1H), 7.97(d, J=7.6 Hz, 1H), 7.78(d, J=7.8 Hz, 1H), 7.58(m, 1H), 7.44(m, 3H), 6.95(d, J=8.5 Hz, 2H), 4.34(m, 1H), 3.84(s, 3H), 3.71(m, 1H), 3.58(m, 3H), 1.99(m, 1H), 1.87(m, 1H), 1.69(m, 5H), 1.32(m, 6H), 0.89(m, 2H); LCMS: 506.4(M+H)$^+$.

Example 127

(S)-N-{3-Cyclohexyl-1-[2-(4-methoxy-phenylamino)-ethylcarbamoyl]-propyl}-4-morpholin-4-yl-benzamide*

$C_{30}H_{42}N_4O_4$; $^1$H NMR (CD$_3$Cl) δ(ppm) 8.70(bs, 1H), 7.65(d, J=8.6 Hz, 2H), 7.49(d, J=8.6 Hz, 2H), 7.07(m, 1H), 6.97(d, J=8.6 Hz, 2H), 6.84(d, J=8.6 Hz, 2H), 4.24(m, 1H), 3.85(m, 7H), 3.58(m, 2H), 3.54(m, 2H), 3.25(m, 4H), 1.96 (m, 1H), 1.83(m, 1H), 1.69(m, 5H), 1.27(m, 6H), 0.89(m, 2H); LCMS: 523.5(M+H)$^+$.

Example 128

(4-Cyclohexyl-N-[2-(4-methoxy-phenylamino)-ethyl]-2-(S)-(2-(S)-phenyl-propionylamino)-butyramide*

$C_{28}H_{39}N_3O_3$; $^1$H NMR (CD$_3$Cl) δ(ppm) 8.46(bs, 1H), 7.31(m, 7H), 6.90(m, 2H), 6.43(m, 1H), 3.95(m, 1H), 3.84(s, 3H), 3.68(m, 2H), 3.50(m, 2H), 3.34(m, 1H), 1.82(m, 1H), 1.66(m, 6H), 1.49(d, J=7.2 Hz, 3H), 1.14(m, 6H), 0.82(m, 2H); LCMS: 466.5(M+H)$^+$.

Example 129

(S)-4-Benzyloxy-N-{3-cyclohexyl-1-[2-(4-methoxy-phenylamino)-ethylcarbamoyl]-propyl}-benzamide*

$C_{33}H_{41}N_3O_4$; $^1$H NMR (CD$_3$Cl) δ(ppm) 8.71(bs, 1H), 7.71(d, J=8.5 Hz, 2H), 7.39(m, 7H), 7.17(m, 1H), 6.95(m, 4H), 5.10(s, 2H), 4.27(m, 1H),m 3.83(s, 3H), 3.66(m, 2H), 3.53(m, 2H), 1.93(m, 1H), 1.82(m, 1H), 1.68(m, 5H), 1.25 (m, 6H), 0.87(m, 2H); LCMS: 544.5(M+H)$^+$.

Example 130

(S)-Biphenyl-4-carboxylic acid {3-cyclohexyl-1-[2-(4-methoxy-phenylamino)-ethylcarbamoyl]-propyl}-amide*

$C_{32}H_{39}N_3O_3$; $^1$H NMR (CD$_3$Cl) δ(ppm) 8.80(bs, 1H), 7.81(d, J=7.9 Hz, 2H), 7.60(m, 4H), 7.47(m, 5H), 7.19(m, 1H), 6.96(d, J=8.7 Hz, 2H), 4.32(m, 1H), 3.84(s, 3H), 3.70(m, 2H), 3.57(m, 2H), 1.56(m, 1H), 1.43(m, 1H), 1.70 (m, 5H), 1.22(m, 6H), 0.90(m, 2H); LCMS: 514.5(M+H)$^+$.

Example 131

(S)-5-Chloro-1H-indole-2-carboxylic acid {3-cyclohexyl-1-[2-(4-methoxy-phenylamino)-ethylcarbamoyl]-propyl}-amide*

$C_{28}H_{35}ClN_4O_3$; $^1$H NMR (CD$_3$Cl) δ(ppm) 10.19(bs, 1H), 8.69(bs, 1H), 7.37(m, 4H), 7.18(m, 2H), 6.90(m, 2H), 6.65 (bs, 1H), 4.40(m, 1H), 3.80(s, 3H), 3.56(m, 4H), 1.84(m, 1H), 1.63(m, 6H), 1.19(m, 6H), 0.81(m, 2H); LCMS: 511.5 (M+H)$^+$.

Example 132

(S)-5-Fluoro-1H-indole-2-carboxylic acid {3-cyclohexyl-1-[2-(4-methoxy-phenylamino)-ethylcarbamoyl]-propyl}-amide*

$C_{28}H_{35}FN_4O_3$; $^1$H NMR (CD$_3$Cl) δ(ppm) 10.03(bs, 1H), 8.66(bs, 1H), 7.42(d, J=8.5 Hz, 2H), 7.26(m, 1H), 7.04(m, 2H), 6.90(m, 2H), 6.72(m, 1H), 4.39(m, 1H), 3.80(s, 3H), 3.52(m, 4H), 1.87(m, 1H), 1.72(m, 6H), 1.17(m, 6H), 0.81 (m, 2H); LCMS: 495.5(M+H)$^+$.

Example 133

(S)-2-Amino-4-methyl-thiazole-5-carboxylic acid {3-cyclohexyl-1-[2-(4-methoxy-phenylamino)-ethylcarbamoyl]-propyl}-amide*

$C_{24}H_{35}N_5O_3S$; $^1$H NMR (CD$_3$Cl) δ(ppm) 9.61(bs, 2H), 8.30(bs, 1H), 7.55(m, 1H), 7.39(d, J=8.6 Hz, 2H), 6.95(d, J=8.6 Hz, 2H), 4.27(m, 1H), 3.83(s, 3H), 3.71(m, 1H), 3.51(m, 3H), 2.44(s, 3H), 1.93(m, 1H), 1.82(m, 1H), 1.68(m, 5H), 1.22(m, 6H), 0.87(m, 2H); LCMS: 474.5(M+H)$^+$.

Example 134

(S)-5-Chloro-benzofuran-2-carboxylic acid {3-cyclohexyl-1-[2-(4-methoxy-phenylamino)-ethylcarbamoyl]-propyl}-amide*

$C_{28}H_{34}ClN_3O_4$; $^1$H NMR (CD$_3$Cl) δ(ppm) 8.69(bs, 1H), 7.55(s, 1H), 7.40(m, 6H), 6.95(d, J=8.6 Hz, 2H), 4.39(m, 1H), 3.83(s, 3H), 3.62(m, 4H), 1.99(m, 1H), 1.85(m, 1H), 1.69(m, 5H), 1.28(m, 6H), 0.89(m, 2H); LCMS: 512.4(M+H)$^+$.

Example 135

N-{2-cyclohexyl-1-(S)-[2-(4-trifluoromethoxy-phenylamino)-ethylcarbamoyl]-ethyl}-2-(R)-phenyl-butyramide*

$C_{28}H_{36}F_3N_3O_3$; $^1$H NMR (CDCl$_3$) δ(ppm) 7.65(m, 1H), 7.08(m, 7H), 7.00(m, 2H), 6.37(d, J=5.6 Hz, 1H), 4.14(m, 1H), 3.40(m, 2H), 3.21(m, 3H), 1.95(m, 1H), 1.74(m, 1H), 1.55(m, 7H), 1.44(m, 1H), 1.03(m, 3H), 0.79(m, 5H); LCMS: 520.5(M+H)$^+$.

Example 136

(S)-5-(3-Trifluoromethyl-phenyl)-furan-2-carboxylic acid {3-cyclohexyl-1-[2-(4-methoxy-phenylamino)-ethylcarbamoyl]-propyl}-amide*

$C_{31}H_{36}F_3N_3O_4$; $^1$H NMR (CD$_3$Cl) δ(ppm) 8.77(bs, 1H), 7.89(m, 2H), 7.59(m, 2H), 7.48(m, 2H), 7.25(m, 1H), 7.11 (d, J=3.5 Hz, 1H), 6.97(d, J=8.7 Hz, 2H), 6.97(d, J=3.4 Hz, 1H), 4.29(m, 1H), 3.84(s, 3H), 3.73(m, 2H), 3.59(m, 2H), 2.01(m, 1H), 1.88(m, 1H), 1.74(m, 5H), 1.23(m, 6H), 0.91 (m, 2H); LCMS: 572.5(M+H)$^+$.

Example 137

(S)-Benzothiazole-6-carboxylic acid {3-cyclohexyl-1-[2-(4-methoxy-phenylamino)-ethylcarbamoyl]-propyl}-amide*

$C_{27}H_{34}N_4O_3S$; $^1$H NMR (CD$_3$Cl) δ(ppm) 9.15(s, 1H), 8.74(bs, 1H), 8.43(s, 1H), 8.12(d, J=8.5, 1H), 7.90(d, J=8.7, 1H), 7.60(m, 1H), 7.45(d, J=8.2, 2H), 6.94(d, J=8.2, 2H), 4.40(m, 1H), 3.83(s, 3H), 3.71(m, 1H), 3.65(m, 1H), 3.57(m, 2H), 1.96(m, 1H), 1.85(m, 1H), 1.68(m, 5H), 1.18(m, 6H), 0.88(m, 2H); LCMS: 495.5(M+H)$^+$.

Example 138

(S)-N-{3-Cyclohexyl-1-[2-(4-methoxy-phenylamino)-ethylcarbamoyl]-propyl}-3-trifluoromethoxy-benzamide*

$C_{27}H_{34}F_3N_3O_4$; $^1$H NMR (CD$_3$Cl) δ(ppm) 8.73(bs, 1H), 7.72(d, J=7.5 Hz, 1H), 7.65(s, 1H), 7.43(m, 5H), 6.94(d, J=8.2 Hz, 2H), 4.34(m, 1H), 3.83(s, 3H), 3.62(m, 4H), 1.94(m, 1H), 1.83(m, 1H), 1.68(m, 5H), 1.27(m, 6H), 0.88 (m, 2H); LCMS: 522.5(M+H)$^+$.

Example 139

(S)-3-Cyano-N-{3-cyclohexyl-1-[2-(4-methoxy-phenylamino)-ethylcarbamoyl]-propyl}-benzamide*

$C_{27}H_{34}N_4O_3$; $^1$H NMR (CD$_3$Cl) δ(ppm) 8.71(m, 1H), 8.07(s, 1H), 8.00(d, J=7.7 Hz, 1H), 7.80(d, J=7.8 Hz, 1H), 7.56(m, 1H), 7.43(d, J=8.7 Hz, 2H), 7.35(d, J=4.3 Hz, 1H), 6.98(d, J=8.7 Hz, 2H), 4.33(m, 1H), 3.85(s, 3H), 3.62(m, 4H), 2.00(m, 1H), 1.86(m, 1H), 1.70(m, 5H), 1.26(m, 6H), 0.92(m, 2H); LCMS: 463.5(M+H)$^+$.

Example 140

(S)-4-Cyano-N-{3-cyclohexyl-1-[2-(4-methoxy-phenylamino)-ethylcarbamoyl]-propyl}-benzamide*

$C_{27}H_{34}N_4O_3$; $^1$H NMR (CD$_3$Cl) δ(ppm) 8.67(bs, 1H), 7.88(d, J=8.1 Hz, 2H), 7.71(d, J=8.1 Hz, 2H), 7.45(m, 1H), 7.42(d, J=8.6 Hz, 2H), 6.96(d, J=8.6 Hz, 2H), 4.34(m, 1H), 3.85(s, 3H), 3.58(m, 4H), 1.98(m, 1H), 1.84(m, 1H), 1.70(m, 5H), 1.27(m, 6H), 0.89(m, 2H); LCMS: 463.5(M+H)$^+$.

Example 141

N-{2-cyclohexyl-1-(S)-[2-(4-trifluoromethoxy-phenylamino)-ethylcarbamoyl]-ethyl}-4-phenoxy-benzamide*

$C_{31}H_{34}F_3N_3O_4$; LCMS: 570.5 (M+H)$^+$.

Example 142

(S)-N-{3-Cyclohexyl-1-[2-(4-methoxy-phenylamino)-ethylcarbamoyl]-propyl}-3-(2-methyl-thiazol-4-yl)-benzamide*

$C_{30}H_{38}N_4O_3S$; $^1$H NMR (CD$_3$Cl) δ(ppm) 8.69((bs, 1H), 8.30(bs, 1H), 7.95(d, J=7.7 Hz, 1H), 7.75(m, 2H), 7.46(m, 3H) 6.94(d, J=8.6 Hz, 2H), 7.38(m, 1H), 4.35(m, 1H), 3.82(s, 3H), 3.59(m, 4H), 2.82(s, 3H), 1.92(m, 2H), 1.68(m, 5H), 1.22(m, 6H), 0.88(m, 2H); LCMS: 535.5(M+H)$^+$.

Example 143

(S)-N-{3-Cyclohexyl-1-[2-(4-methoxy-phenylamino)-ethylcarbamoyl]-propyl}-4-[1,2,4]triazol-1-yl-benzamide*

$C_{28}H_{36}N_6O_3$; $^1$H NMR (CD$_3$CD) δ(ppm) 8.72(bs, 2H), 8.16(bs, 1H), 7.92(d, J=8.3 Hz, 2H), 7.74(d, J=8.3 Hz, 2H), 7.56(d, J=5.3 Hz, 1H), 7.45(d, J=8.6 Hz, 2H), 6.96(d, J=8.6 Hz, 2H), 4.36(m, 1H), 3.84(s, 3H), 3.70(m, 2H), 3.55(m, 2H), 1.99(m, 1H), 1.87(m, 1H), 1.68(m, 5H), 1.27(m, 6H), 0.89(m, 2H); LCMS: 505.5(M+H)$^+$.

Example 144

(S)-Biphenyl-3-carboxylic acid {3-cyclohexyl-1-[2-(4-methoxy-phenylamino)-ethylcarbamoyl]-propyl}-amide*

$C_{32}H_{39}N_3O_3$; $^1$H NMR (CD$_3$Cl) δ(ppm) 8.79(bs, 1H), 7.98(s, 1H), 7.74(d, J=7.6 Hz, 2H), 7.45(m, 9H), 6.91(d, J=8.7 Hz, 2H), 4.33(m, 1H), 3.80(s, 3H), 3.62(m, 4H), 1.97(m, 1H), 1.86(m, 1H), 1.68(m, 5H), 1.27(m, 6H), 0.88 (m, 2H); LCMS: 514.5(M+H)$^+$.

Example 145

(S)-N-{2-Cyclohexyl-1-[2-(4-methoxy-phenylamino)-ethylcarbamoyl]-ethyl}-2-fluoro-benzamide*

$C_{25}H_{32}FN_3O_3$; $^1$H NMR (CD$_3$Cl) δ(ppm) 8.58(bs, 1H), 7.71(m, 1H), 7.44(m, 3H), 7.33(m, 1H), 7.13(m, 2H), 6.92 (d, J=8.6 Hz, 2H), 4.31(m, 1H), 3.79(s, 3H), 3.61(m, 2H), 3.46(M, 2H), 1.72(m, 7H), 1.41(m, 1H), 1.19(m, 3H), 0.96 (m, 2H); LCMS: 442.4(M+H)$^+$.

Example 146

(S)-N-{2-Cyclohexyl-1-[2-(4-methoxy-phenylamino)-ethylcarbamoyl]-ethyl}-3,4-difluoro-benzamide*

$C_{25}H_{31}F_2N_3O_3$; $^1$H NMR (CD$_3$Cl) δ(ppm) 8.68(bs, 1H), 7.57(m, 2H), 7.44(m, 3H), 7.21(m, 1H), 6.97(d, J=8.6 Hz, 2H), 4.44(m, 1H), 3.85(s, 3H), 3.64(m, 3H), 3.48(m, 1H), 1.77(m, 7H), 1.45(m, 1H), 1.20(m, 3H), 0.96(m, 2H); LCMS: 460.5(M+H)$^+$.

Example 147

(S)-N-{2-Cyclohexyl-1-[2-(4-methoxy-phenylamino)-ethylcarbamoyl]-ethyl}-3-fluoro-2-methyl-benzamide*

$C_{26}H_{34}FN_3O_3$; $^1$H NMR (CD$_3$Cl) δ(ppm) 8.51(bs, 1H), 7.32(d, J=8.3 Hz, 2H), 7.09(m, 3H), 6.82 (d, J=8.4 Hz, 2H), 6.58(m, 1H), 4.36(m, 1H), 3.72(s, 3H), 3.68(m, 1H), 3.45(m, 3H), 2.18(s, 3H), 1.62(m, 7H), 1.31(m, 1H), 1.16(m, 3H), 0.89(m, 2H); LCMS: 456.5(M+H)$^+$.

Example 148

(S)-2-Chloro-N-{2-cyclohexyl-1-[2-(4-methoxy-phenylamino)-ethylcarbamoyl]-ethyl}-5-methyl-benzamide*

$C_{26}H_{34}ClN_3O_3$; $^1$H NMR (CD$_3$Cl) δ(ppm) 8.58(bs, 1H), 7.53(d, J=8.5 Hz, 2H), 7.43(s, 1H), 7.33(m, 1H), 7.24(m, 2H), 6.99(d, J=8.5 Hz, 2H), 4.49(m, 1H), 3.87(s, 3H), 3.67(m, 4H), 2.33(s, 3H), 1.85(m, 7H), 1.53(m, 1H), 1.27(m, 3H), 1.03(m, 2H); LCMS: 472.4($^{35}$ClM+H)$^+$, 474.4($^{37}$ClM+H)$^+$.

Example 149

(S)-N-{2-Cyclohexyl-1-[2-(4-methoxy-phenylamino)-ethylcarbamoyl]-ethyl}-4-fluoro-3-trifluoromethyl-benzamide*

$C_{26}H_{31}F_4N_3O_3$; $^1$H NMR (CD$_3$Cl) δ(ppm) 8.68(bs, 1H), 8.09(m, 1H), 8.03(m, 1H), 7.80(m, 1H), 7.41(d, J=8.0 Hz, 2H), 7.23(m, 1H), 6.95(d, J=7.9 Hz, 2H), 4.49(m, 1H), 3.84(s, 3H), 3.63(m, 3H), 3.48(m, 1H), 1.74(m, 7H), 1.46(m, 1H), 1.22 (m, 3H), 0.98(m, 2H); LCMS: 510.4(M+H)$^+$.

Example 150

(S)-5-Methyl-1-phenyl-1H-pyrazole-4-carboxylic acid {2-cyclohexyl-1-[2-(4-methoxy-phenylamino)-ethylcarbamoyl]-ethyl}-amide*

$C_{29}H_{37}N_5O_3$; $^1$H NMR (CD$_3$Cl) δ(ppm) 8.71(bs, 1H), 7.89 (bs, 1H), 7.44(m, 5H), 7.28(m, 2H), 6.90(m, 3H), 4.30(m, 1H), 3.78(s, 3H), 3.65(m, 3H), 3.40(m, 1H), 2.21(s, 3H), 1.70(m, 7H), 1.45(m, 1H), 1.20(m, 3H), 0.98(m, 2H); LCMS: 504.5(M+H)$^+$.

Example 151

(S)-N-{2-Cyclohexyl-1-[2-(4-methoxy-phenylamino)-ethylcarbamoyl]-ethyl}-4-propyl-benzamide*

$C_{28}H_{39}N_3O_3$; $^1$H NMR (CD$_3$Cl) δ(ppm) 8.69(bs, 1H), 7.66(d, J=7.8 Hz, 2H), 7.47(d, J=8.6 Hz, 2H), 7.30(m, 1H), 7.21(d, J=7.8 Hz, 2H), 6.95(d, J=8.5 Hz, 2H), 4.43(m, 1H), 3.84(s, 3H), 3.63(m, 3H), 3.48(m, 1H), 2.62(m, 2H), 1.72(m, 10H), ?(m, 1H), 1.22(m, 3H), 0.94(m, 4H); LCMS: 466.5 (M+H)$^+$.

Example 152

3-Cyclohexyl-2-(S)-[2-(4-fluoro-phenyl)-acetylamino]-N-[2-(4-fluoro-phenylamino)-ethyl]-propionamide*

$C_{25}H_{31}F_2N_3O_2$; $^1$H NMR (CDCl$_3$) δ(ppm) 8.44(m, 1H), 7.34(m, 2H), 7.19(m, 2H), 7.11(m, 2H), 6.94(m, 2H), 6.42 (m, 1H), 4.11(m, 1H), 3.62(m, 5H), 3.39(m, 1H), 1.66(m, 6H), 1.32(m, 1H), 1.18(m, 4H), 0.89(m, 2H); LCMS: 444.5 (M+H)$^+$.

Example 153

(S)-N-{2-Cyclohexyl-1-[2-(4-methoxy-phenylamino)-ethylcarbamoyl]-ethyl}-4-methoxy-benzamide*

$C_{26}H_{35}N_3O_4$; $^1$H NMR (CD$_3$Cl) δ(ppm) 8.66(bs, 1H), 7.72(d, J=8.4 Hz, 2H), 7.46(d, J=8.6 Hz, 2H), 7.34(m, 1H), 6.96(d, J=8.5 Hz, 2H), 6.88(d, J=8.4 Hz, 2H), 4.43(dd, J=6.1 Hz, J=13.6 Hz, 1H), 3.84(s, 6H), 3.60(m, 3H), 3.48(m, 1H), 1.71(m, 7H), 1.46(m, 1H), 1.23(m, 3H), 0.96(m, 2H); LCMS: 454.5(M+H)$^+$.

Example 154

(S)-N-{2-Cyclohexyl-1-[2-(4-methoxy-phenylamino)-ethylcarbamoyl]-ethyl}-2-fluoro-5-trifluoromethyl-benzamide*

$C_{26}H_{31}F_4N_3O_3$; $^1$H NMR (CD$_3$Cl) δ(ppm) 8.66(bs, 1H), 8.13(d, J=6.5 Hz, 1H), 7.79(m, 1H), 7.46(m, 3H), 7.33(m, 1H), 6.98(d, J=8.4 Hz, 2H), 4.44(m, 1H), 3.85(s, 3H), 3.73(m, 2H), 3.62(m, 2H), 1.75(m, 7H), 1.47(m, 1H), 1.25 (m, 3H), 1.04(m, 2H); LCMS: 510.5(M+H)$^+$.

Example 155

(S)-3-Chloro-N-{2-cyclohexyl-1-[2-(4-methoxy-phenylamino)-ethylcarbamoyl]-ethyl}-2-fluoro-benzamide*

$C_{25}H_{31}ClFN_3O_3$; $^1$H NMR (CD$_3$Cl) δ(ppm) 8.60(bs, 1H), 7.68(m, 1H), 7.58(m, 1H), 7.47(d, J=8.6 Hz, 2H), 7.37(m, 1H), 7.15(m, 1H), 6.98(d, J=8.6 Hz, 2H), 4.43(m, 1H), 3.85(s, 3H), 3.66(m, 3H), 3.55(m, 1H), 1.78(m, 7H), 1.47(m, 1H), 1.24(m, 3H), 1.04(m, 2H); LCMS: 476.4(M+H)$^+$.

Example 156

(S)-5-Chloro-N-{2-cyclohexyl-1-[2-(4-methoxy-phenylamino)-ethylcarbamoyl]-ethyl}-2-fluoro-benzamide*

$C_{25}H_{31}ClFN_3O_3$; $^1$H NMR (CD$_3$Cl) δ(ppm) 8.55(bs, 1H), 7.69(m, 1H), 7.35(m, 3H), 7.24(m, 1H), 7.03(m, 1H), 6.89 (d, J=8.5 HZ, 2H), 4.32(m, 1H), 3.75(s, 3H), 3.63(m, 2H), 3.49(m, 2H), 1.66(m, 7H), 1.35(m, 1H), 1.18(m, 3H), 0.92 (m, 2H); 476.4($^{35}$ClM+H)$^+$, 478.4($^{37}$ClM+H)$^+$.

Example 157

(S)-N-{2-Cyclohexyl-1-[2-(4-methoxy-phenylamino)-ethylcarbamoyl]-ethyl}-5-fluoro-2-methyl-benzamide*

$C_{26}H_{34}FN_3O_3$; $^1$H NMR (CD$_3$Cl) δ(ppm) 8.75(bs, 1H), 7.61(d, J=8.5 Hz, 2H), 7.36(m, 2H), 7.24(m, 1H), 7.11(d, J=8.4 Hz, 2H), 6.88(m, 1H), 4.63(m, 1H), 4.00(s, 3H), 3.98(m, 3H), 3.75(m, 3H), 2.53(s, 3H), 1.93(m, 7H), 1.60(m, 1H), 1.42(m, 3H), 1.18(m, 2H); LCMS: 456.5(M+H)$^+$.

Example 158

(S)-1-Phenyl-cyclopropanecarboxylic acid {2-cyclohexyl-1-[2-(4-methoxy-phenylamino)-ethylcarbamoyl]-ethyl}-amide*

$C_{28}H_{37}N_3O_3$; $^1$H NMR (CD$_3$Cl) δ(ppm) 8.49(bs, 1H), 7.42(m, 7H), 7.00(d, J=8.7 Hz, 2H), 4.01(m, 1H), 3.86(s, 3H), 3.67(m, 3H), 3.48(m, 1H), 1.60(m, 9H), 1.30(m, 1H), 1.21(m, 5H), 0.82(m, 3H); LCMS: 464.5(M+H)$^+$.

Example 159

(S)-3-Cyclohexyl-N-[2-(4-methoxy-phenylamino)-ethyl]-2-(2-phenylamino-acetylamino)-propionamide*

$C_{26}H_{36}N_4O_3$; $^1$H NMR (CD$_3$Cl) δ(ppm) 8.31(bs, 1H), 7.79(m, 1H), 7.35(d, J=8.2 Hz, 2H), 7.24(m, 2H), 6.95(m, 1H), 6.88(d, J=8.3 Hz, 2H), 6.80(d, J=7.9 Hz, 2H), 4.20(m, 1H), 3.86(m, 2H), 3.75(s, 3H), 3.55(m, 3H), 3.37(m, 1H), 1.52(m, 7H), 0.95(m, 4H), 0.76(m, 2H); LCMS: 453.5(M+H)$^+$.

Example 160

3-Cyclohexyl-2-(S)-(2-(R)-hydroxy-2-phenyl-acetylamino)-N-[2-(4-methoxy-phenylamino)-ethyl]-propionamide*

$C_{26}H_{35}N_3O_4$; $^1$H NMR (CD$_3$Cl) δ(ppm) 8.42(bs, 1H), 7.50(m, 1H), 7.41(m, 2H), 7.32(m, 3H), 7.19(d, J=8.6 Hz, 2H), 6.85(d, J=8.5 Hz, 2H), 5.00(s, 1H), 4.17(m, 1H), 3.83(s, 3H), 3.73(m, 1H), 3.56(m, 2H), 3.31(m, 1H), 1.63(m, 7H), 1.10(m, 4H); 0.89(m, 2H).

Example 161

(S)-1-(4-Fluoro-phenyl)-5-methyl-1H-pyrazole-4-carboxylic acid {2-cyclohexyl-1-[2-(4-methoxy-phenylamino)-ethylcarbamoyl]-ethyl}-amide*

$C_{29}H_{36}FN_5O_3$; $^1$H NMR (CD$_3$Cl) δ(ppm) 8.76(bs, 1H), 7.94(bs, 1H), 7.47(d, J=8.7 Hz, 2H), 7.31(m, 2H), 7.17(m, 2H), 6.96(m, 3H), 4.36(m, 1H), 3.83(s, 3H), 3.73(m, 3H), 3.44(m, 1H): 2.24(s, 3H), 1.75(m, 7H), 1.49(m, 1H), 1.24(m, 3H), 1.01(m, 2H); LCMS: 522.5(M+H)$^+$.

Example 162

(S)-1-(4-Methoxy-phenyl)-5-methyl-1H-pyrazole-4-carboxylic acid {2-cyclohexyl-1-[2-(4-methoxy-phenylamino)-ethylcarbamoyl]-ethyl}-amide*

$C_{30}H_{39}N_5O_4$; LCMS: 534.5(M+H)$^+$.

Example 163

(S)-1-(4-Chloro-phenyl)-5-methyl-1H-pyrazole-4-carboxylic acid {2-cyclohexyl-1-[2-(4-methoxy-phenylamino)-ethylcarbamoyl]-ethyl}-amide*

$C_{29}H_{36}ClN_5O_3$; $^H$ $^{NMR}$ $^{(CD}$$_3$Cl) δ(ppm) 7.81(m, 2H), 7.36(m, 2H), 7.22(m, 2H), 7.01(m, 2H), 6.77(m, 2H), 6.53(m, 1H), 4.35(m, 1H), 3.69(s, 3H), 3.51(m, 3H), 3.27(m, 1H), 2.29(s, 3H), 1.69(m, 7H), 1.34(m, 1H), 1.10(m, 3H), 0.90(m, 2H); LCMS: 538.4(M+H)$^+$.

Example 164

N-{2-Cyclohexyl-1-(S)-[2-(4-methoxy-phenylamino)-ethylcarbamoyl]-ethyl}-2-(S)-phenyl-butyramide*

$C_{28}H_{39}N_3O_3$; $^1$H NMR (CD$_3$Cl) δ(ppm) 8.34(m, 1H), 7.33(m, 2H), 7.25(m, 5H), 6.94(m, 2H), 6.53(m, 1H), 4.13(m, 1H), 3.80(s, 3H), 3.57(m, 2H), 3.40(m, 3H), 2.05(m, 1H), 1.84(m, 1H), 1.67(m, 7H), 1.15(m, 4H), 0.86(m, 5H); LCMS: 466.5(M+H)$^+$.

Example 165

(S)-N-{2-Cyclohexyl-1-[2-(4-methoxy-phenylamino)-ethylcarbamoyl]-ethyl}-3-fluoro-5-trifluoromethyl-benzamide*

$C_{26}H_{31}F_4N_3O_3$; $^1$H NMR (CD$_3$Cl) δ(ppm) 8.62(bs, 1H), 7.75(s, 1H), 7.58(m, 1H), 7.35(m, 4H), 6.88(m, 3H), 4.35(m, 1H), 3.75(s, 3H), 3.56(m, 3H), 3.40(m, 1H), 1.70(m, 7H), 1.37(m, 1H), 1.17(m, 3H), 0.91(m, 2H); LCMS: 510.4(M+H)$^+$.

Example 166

(S)-N-{2-Cyclohexyl-1-[2-(4-methoxy-phenylamino)-ethylcarbamoyl]-ethyl}-2-fluoro-3-trifluoromethyl-benzamide*

$C_{26}H_{31}F_4N_3O_3$; $^1$H NMR (CD$_3$Cl) δ(ppm) 8.50(bs, 1H), 7.87(m, 1H), 7.64(m, 1H), 7.32(m, 2H), 7.15(m, 2H), 6.83(m, 2H), 4.30(m, 1H), 3.72(s, 3H), 3.54(m, 3H), 3.37(m, 1H), 1.65(m, 7H), 1.35(m, 1H), 1.12(m, 3H), 0.89(m, 2H); LCMS: 510.4(M+H)$^+$.

Example 167

(S)-N-{2-Cyclohexyl-1-[2-(4-methoxy-phenylamino)-ethylcarbamoyl]-ethyl}-4-fluoro-3-methyl-benzamide*

$C_{26}H_{34}FN_3O_3$; $^1$H NMR (CD$_3$Cl) δ(ppm) 8.62(m, 1H), 7.50(m, 2H), 7.34(m, 2H), 7.09(m, 1H), 6.90(m, 1H): 6.85(m, 2H), 4.32(m, 1H), 3.74(s, 3H), 3.53(m, 3H), 3.38(m, 1H), 2.16(s, 3H), 1.68(m, 7H), 1.34(m, 1H), 1.09(m, 3H) 0.89(m, 2H); LCMS: 456.5(M+H)$^+$.

Example 168

(S)-5-(4-Chloro-phenyl)-furan-2-carboxylic acid {2-cyclohexyl-1-[2-(4-methoxy-phenylamino)-ethylcarbamoyl]-ethyl}-amide*

$C_{29}H_{34}ClN_3O_4$; $^1$H NMR (CD$_3$Cl) δ(ppm) 8.62(m, 1H), 7.53(m, 2H), 7.37(d, J=9.0 Hz, 2H), 7.29(m, 2H), 7.19(m, 1H), 6.97(d, J=3.6 Hz, 1H), 6.87(m, 2H), 6.58(d, J=3.6 Hz, 1H), 4.34(m, 1H), 3.74(s, 3H), 3.60(m, 2H), 3.46(m, 2H), 1.70(m, 7H), 1.39(m, 1H), 1.14(m, 3H), 0.91(m, 2H); LCMS: 524.4(M+H)$^+$.

Example 169

(S)-N-{2-Cyclohexyl-1-[2-(4-methoxy-phenylamino)-ethylcarbamoyl]-ethyl}-2-fluoro-4-trifluoromethyl-benzamide*

$C_{26}H_{31}F_4N_3O_3$; $^1$H NMR (CD$_3$Cl) δ(ppm) 8.57(bs, 1H), 7.81(m, 1H), 7.33(m, 5H), 6.89(m, 2H), 4.32(m, 1H), 3.76(s, 3H), 3.59(m, 3H), 3.43(m, 1H), 1.66(m, 7H), 1.37(m, 1H), 1.15(m, 3H), 0.92(m, 2H); LCMS: 510.5(M+H)$^+$.

Example 170

(S)-4'-Chloro-biphenyl-4-carboxylic acid {2-cyclohexyl-1-[2-(4-methoxy-phenylamino)-ethylcarbamoyl]-ethyl}-amide*

$C_{31}H_{36}ClN_3O_3$; $^1$H NMR (CD$_3$Cl) δ(ppm) 7.74(bs, 1H), 7.47(d, J=8.4 Hz, 2H), 7.40(m, 2H), 7.39(m, 2H), 7.32(m, 4H), 7.13(m, 1H), 6.84(m, 2H), 4.38(m, 1H), 3.73(s, 3H), 3.54(m, 2H), 3.45(m, 1H), 3.36(m, 1H), 1.66(m, 7H), 1.38(m, 1H), 1.12(m, 3H), 0.89(m, 2H); LCMS: 534.4(M+H)$^+$.

Example 171

(S)-3',5'-Dichloro-biphenyl-4-carboxylic acid {2-cyclohexyl-1-[2-(4-methoxy-phenylamino)-ethylcarbamoyl]-ethyl}-amide*

$C_{31}H_{35}Cl_2N_3O_3$; $^1$H NMR (CD$_3$Cl) δ(ppm) 8.04(bs, 1H), 7.74(d, J=8.5 Hz, 2H), 7.46(d, J=8.4 Hz, 2H), 7.34(m, 2H), 7.29(m, 1H), 7.10(m, 2H), 7.00(m, 1H), 6.79(m, 2H), 4.41 (m, 1H), 3.71(s, 3H), 3.52(m, 2H), 3.35(m, 2H), 1.64(m, 7H), 1.36(m, 1H), 1.16(m, 3H), 0.89(m, 2H); LCMS: 568.4 ($^{35}$ClM+H)$^+$, 570.4($^{37}$ClM+H)$^+$.

Example 172

(S)-3'-Methoxy-biphenyl-4-carboxylic acid {2-cyclohexyl-1-[2-(4methoxy-phenylamino)-ethylcarbamoyl]-ethyl}-amide*

$C_{32}H_{39}N_3O_4$; $^1$H NMR (CD$_3$Cl) δ(ppm) 8.54(bs, 1H), 7.60(d, J=8.4 Hz, 2H), 7.41(d, J=8.4 Hz, 2H), 7.29(d, J=9.0 Hz, 2H), 7.16(m, 1H), 7.08(m, 1H), 6.97(m, 1H), 6.90(m, 1H), 6.76(m, 3H), 4.24(m, 1H), 3.67(s, 3H), 3.64(s, 3H), 3.47(m, 3H), 3.31(m, 1H), 1.57(m, 7H), 1.29(m, 1H), 1.01 (m, 3H), 0.81(m, 2H); LCMS: 530.5(M+H)$^+$.

Example 173

(S)-3'-Chloro-biphenyl-4-carboxylic acid {2-cyclohexyl-1-[2-(4-methoxy-phenylamino)-ethylcarbamoyl]-ethyl}-amide*

$C_{31}H_{36}ClN_3O_3$; $^1$H NMR (CD$_3$Cl) δ(ppm) 8.66(m, 1H), 7.74(d, J=8.4 Hz, 2H), 7.46(m, 3H), 7.39(m, 6H), 6.85(m, 2h), 4.37(m, 1H), 3.73(s, 3H), 3.51(m, 3H), 3.39(m, 1H), 1.69(m, 7H), 1.38(m, 1H), 1.13(m, 3H), 0.90(m, 2H); LCMS: 534.5(M+H)$^+$.

Example 174

(S)-2'-Methoxy-biphenyl-4-carboxylic acid {2-cyclohexyl-1-[2-(4-methoxy-phenylamino)-ethylcarbamoyl]-ethyl}-amide*

$C_{32}H_{39}N_3O_4$; $^1$H NMR (CD$_3$Cl) δ(ppm) 8.66(m, 1H), 7.69(d, J=8.4 Hz, 2H), 7.48(d, J=8.4 Hz, 2H), 7.39(d, J=9.0 Hz, 2H), 7.27(m, 1H), 7.20(m, 1H), 7.08(m, 1H), 6.89(m, 4H), 4.34(m, 1H), 3.73(s, 3H), 3.72(s, 3H), 3.56(m, 3H), 3.39(m, 1H), 1.67(m, 7H), 1.38(m, 1H), 1.13(m, 3H), 0.90 (m, 2H); LCMS: 530.5(M+H)$^+$.

Example 175

(S)-4'-Chloro-biphenyl-3-carboxylic acid {2-cyclohexyl-1-[2-(4-methoxy-phenylamino)-ethylcarbamoyl]-ethyl}-amide*

$C_{31}H_{36}ClN_3O_3$; $^1$H NMR (CD$_3$Cl) δ(ppm) 8.43(m, 1H), 7.49(m, 1H), 7.42(m, 1H), 7.31(m, 8H), 6.84(d, J=9.0 Hz, 2H), 5.98(m, 1H), 3.96(m, 1H), 3.74(s, 3H), 3.59(m, 2H), 3.45(m, 1H), 3.38(m, 1H), 1.58(m, 3H), 1.46(m, 3H), 1.09 (m, 4H), 0.76(m, 3H); LCMS: 534.4(M+H)$^+$.

Example 176

(S)-4-Benzo[1,3]dioxol-5-yl-N-{2-cyclohexyl-1-[2-(4phenylamino)-ethylcarbamoyl]-ethyl}-benzamide*

$C_{32}H_{37}N_3O_5$; $^1$H NMR (CD$_3$Cl) δ(ppm) 8.68(m, 1H), 7.68(d, J=8.4 Hz, 2H), 7.40(m, 4H), 7.11(m, 1H), 6.97(m, 2H), 6.88(m, 2H), 6.79(m, 1H), 5.93(s, 2H), 4.33(m, 1H), 3.74(s, 3H), 3.55(m, 3H), 3.40(m, 1H), 1.70(m, 7H), 1.39(m, 1H), 1.13(m, 3H) 0.92(m, 2H); LCMS: 544.5(M+H)$^+$.

Example 177

(S)-5-Bromo-furan-2-carboxylic acid {2-cyclohexyl-1-[2-(4-methoxy-phenylamino)-ethylcarbamoyl]-ethyl}-amide*

$C_{23}H_{30}BrN_3O_4$; $^1$H NMR (CD$_3$Cl) δ(ppm) 8.3(m, 1H), 7.21 (m, 2H), 6.83(m, 1H), 6.72(m, 3H), 6.20(d, J=3.5 Hz, 1H), 4.14(dd, J=3.8 Hz, J=5.2 Hz, 1H), 3.61(s, 3H), 3.45(m, 2H), 3.34(m, 1H), 3.28(m, 1H), 1.52(m, 7H), 1.22(m, 1H), 1.02(m, 3H), 0.77(m, 2H); LCMS: 492.3($^{79}$BrM+H)$^+$, 494.3 ($^{80}$BrM+H)$^+$.

Example 178

(S)-3,5-Dibromo-N-{2-cyclohexyl-1-[2-(4-methoxy-phenylamino)-ethylcarbamoyl]-ethyl}-benzamide*

$C_{25}H_{31}Br_2N_3O_3$; $^1$H NMR (CD$_3$Cl) δ(ppm) 8.61(m, 1H), 7.78(m, 2H), 7.69(s, 1H), 7.45(m, 1H), 7.31(m, 2H), 6.86(m, 2H), 4.36(m, 1H), 3.74(s, 3H), 3.59(m, 1H), 3.42(m, 3H), 1.60(m, 7H), 1.35(m, 1H), 1.14(m, 3H), 0.86(m, 2H); LCMS: 580.2, 582.2, 584.3.

Example 179

(S)-3,5-Dichloro-N-{2-cyclohexyl-1-[2-(4-methoxy-phenylamino)-ethylcarbamoyl]-ethyl}-benzamide*

$C_{25}H_{31}Cl_2N_3O_3$; $^1$H NMR (CD$_3$Cl) δ(ppm) 8.60(m, 1H), 7.58(s, 2H), 7.51(m, 1H), 7.38(m, 1H), 7.30(d, J=9.0 Hz, 2H), 6.83(m, 2H), 4.37(m, 1H), 3.74(s, 3H), 3.57(m, 1H), 3.43(m, 3H), 1.61(m, 7H), 1.32(m, 1H), 1.15(m, 3H), 0.85 (m, 2H), LCMS: 492.4($^{35}$ClM+H)$^+$, 494.3($^{37}$ClM+H)$^+$.

Example 180

(S)-N-{2-Cyclohexyl-1-[2-(4-methoxy-phenylamino)-ethylcarbamoyl]-ethyl}-3,5-dimethoxy-benzamide*

$C_{27}H_{37}N_3O_5$; $^1$H NMR (CD$_3$Cl) δ(ppm) 8.59(m, 1H), 7.37(m, 2H), 7.11(m, 1H), 6.85(m, 2H), 6.76(m, 2H), 6.49 (m, 1H), 4.30(m, 1H), 3.73(s, 3H), 3.65(s, 6H), 3.56(m, 2H), 3.44(m, 2H), 1.66(m, 7H), 1.35(m, 1H), 1.15(m, 3H), 0.89 (m, 2H); LCMS: 484.5(M+H)$^+$.

Example 181

(S)-Biphenyl-3-carboxylic acid {2-cyclohexyl-1-[2-(4-methoxy-phenylamino)-ethylcarbamoyl]-ethyl}-amide*

$C_{31}H_{37}N_3O_3$; $^1$H NMR (CD$_3$Cl) δ(ppm) 8.71(m, 1H), 7.90(s, 1H), 7.71(m, 1H), 7.65(m, 1H), 7.44(m, 9H), 6.89(d, J=9.0 Hz, 2H), 4.40(m, 1H), 3.77(s, 3H), 3.63(m, 3H), 3.50(m, 1H), 1.72(m, 7H), 1.37(m, 1H), 1.19(m, 3H), 0.96 (m, 2H); LCMS: 500.5(M+H)$^+$.

Example 182

(S)-5-Bromo-thiophene-2-carboxylic acid {2-cyclohexyl-1-[2-(4-methoxy-phenylamino)-ethylcarbamoyl]-ethyl}-amide*

$C_{23}H_{30}BrN_3O_3S$; $^1$H NMR (CD$_3$Cl) δ(ppm) 8.63(m, 1H), 7.47(d, J=5.5 Hz, 1H), 7.35(m, 2H), 7.29(s, J=4.0 Hz, 1H), 6.93(s, J=4.0 Hz, 1H), 6.88(m, 2H), 4.29(m, 1H), 3.76(s, 3H), 3.57(m, 1H), 3.47(m, 2H), 3.40(m, 1H), 1.60(m, 7H), 1.34(m, 1H), 1.11(m, 3H), 0.84(m, 2H); LCMS: 508.3 ($^{79}$BrM+H)$^+$, 510.3($^{80}$BrM+H)$^+$.

Example 183

(S)-N-{2-Cyclohexyl-1-[2-(4-methoxy-phenylamino)-ethylcarbamoyl]-ethyl}-4-phenoxy-benzamide*

$C_{31}H_{37}N_3O_4$; $^1$H NMR (CD$_3$Cl) δ(ppm) 8.62(m, 1H), 7.60(d, J=8.8 Hz, 2H), 7.38(d, J=9.0 Hz, 2H), 7.28(m, 2H), 7.28(m, 2H), 7.09(m, 2H), 6.94(m, 2H), 6.86(m, 4H), 4.30 (m, 1H), 3.74(s, 3H), 3.54(m, 3H), 3.37(m, 1H), 1.66(m, 7H), 1.37(m, 1H), 1.12(m, 3H), 0.87(m, 2H); LCMS: 516.5 (M+H)$^+$.

Example 184

(S)-N-{2-Cyclohexyl-1-[2-(4-methoxy-phenylamino)-ethylcarbamoyl]-ethyl}-3-phenoxy-benzamide*

$C_{31}H_{37}N_3O_4$; $^1$H NMR (CD$_3$Cl) δ(ppm) 8.60(m, 1H), 7.34(m, 3H), 7.23(m, 4H), 7.02(m, 3H), 6.87(m, 2H), 6.81 (d, J=9 Hz, 2H), 4.28(m, 1H), 3.73(s, 3H), 3.52(m, 3H), 3.38(m, 1H), 1.64(m, 7H), 1.34(m, 1H), 1.10(m, 3H), 0.88 (m, 2H); LCMS: 516.5(M+H)$^+$.

Example 185

(S)-1H-Indole-3-carboxylic acid {2-cyclohexyl-1-[2-(4-methoxy-phenylamino)-ethylcarbamoyl]-ethyl}-amide*

$C_{27}H_{34}N_4O_3$; LCMS: 463.5(M+H)$^+$.

Example 186

(S)-Benzothiazole-6-carboxylic acid {2-cyclohexyl-1-[2-(4-methoxy-phenylamino)-ethylcarbamoyl]-ethyl}-amide*

$C_{26}H_{32}N_4O_3S$; $^1$H NMR (CD$_3$Cl) δ(ppm) 9.07(bs, 1H), 8.62(bs, 1H), 8.33(s, 1H), 8.05(m, 1H), 7.79(m, 1H), 7.37 (m, 3H), 6.87(m, 2H), 4.40(dd, J=5.2 Hz, J=9.3 Hz, 1H), 3.74(s, 3H), 3.55(m, 3H), 3.41(m, 2H), 1.69(m, 7H), 1.41(m, 1H), 1.16(m, 3H), 0.89(m, 2H); LCMS: 481.4(M+H)$^+$.

Example 187

(S)-2-Amino-benzothiazole-6-carboxylic acid {2-cyclohexyl-1-[2-(4-methoxy-phenylamino)-ethylcarbamoyl]-ethyl}-amide*

$C_{26}H_{33}N_5O_3S$; $^1$H NMR (CD$_3$Cl) δ(ppm) 9.65(bs, 1H), 8.17(m, 1H), 7.71(s, 1H), 7.57(d, J=8.6 Hz, 2H), 7.48(d, J=9.0 Hz, 2H), 7.29(m, 2H), 6.92(d, J=9.0 Hz, 2H), 4.25(m, 1H), 3.76(s, 3H), 3.62(m, 3H), 3.43(m, 1H), 1.73(m, 8H), 1.18(m, 3H), 0.93(m, 2H); LCMS: 496.4(M+H)$^+$.

Example 188

(S)-4-Methyl-2-(4-trifluoromethyl-phenyl)-thiazole-5-carboxylic acid {2-cyclohexyl-1-[2-(4-methoxy-phenylamino)-ethylcarbamoyl]-ethyl}-amide*

$C_{30}H_{35}F_3N_4O_3S$; $^1$H NMR (CD$_3$Cl) δ(ppm) 8.61(m, 1H), 7.91(d, J=8.1 Hz, 2H), 7.61(d, J=8.3 Hz, 2H), 7.38(m, 2H), 6.90(m, 2H), 6.72(d, J=4.8 Hz, 1H), 4.31(m, 1H), 3.75(s, 3H), 3.61(m, 3H), 3.44(m, 3H), 2.54(s, 3H), 1.67(m, 7H), 1.37(m, 1H), 1.17(m, 3H), 0.92(m, 2H); LCMS: 589.4(M+H)$^+$.

Example 189

(S)-4-(4-Chloro-phenyl)-thiophene-2-carboxylic acid {2-cyclohexyl-1-[2-(4-methoxy-phenylamino)-ethylcarbamoyl]-ethyl}-amide*

$C_{29}H_{34}ClN_3O_3S$; $^1$H NMR (CD$_3$Cl) δ(ppm) 8.72(m, 1H), 7.83(m, 1H), 7.46(s, 1H), 7.36(m, 4H), 7.23(m, 2H), 6.86(d, J=9.0 Hz, 2H), 4.38(m, 1H), 3.74(s, 3H), 3.55(m, 1H), 3.44(m, 3H), 1.60(m, 7H), 1.39(m, 1H), 1.10(m, 3H), 0.89 (m, 2H); LCMS: 540.4(M+H)$^+$.

Example 190

(S)-2-Methyl-5-trifluoromethyl-oxazole-4-carboxylic acid {2-cyclohexyl-1-[2-(4-methoxy-phenylamino)-ethylcarbamoyl]-ethyl}-amide*

$C_{24}H_{31}F_3N_4O_4$; $^1$H NMR (CD$_3$Cl) δ(ppm) 8.62(m, 1H), 7.68(m, 1H), 7.40(m, 2H), 6.92(m, 2H), 4.26(m, 1H), 3.81(s, 3H), 3.74(m, 2H), 3.59(m, 1H), 3.35(m, 1H), 2.51(s, 3H), 1.74(m, 7H), 1.44(m, 1H), 1.20(m, 3H), 0.97(m, 2H); LCMS: 497.4(M+H)$^+$.

Example 191

(S)-4-(4-Methoxy-phenyl)-thiophene-2-carboxylic acid {2-cyclohexyl-1-[2-(4-methoxy-phenylamino)-ethylcarbamoyl]-ethyl}-amide*

$C_{30}H_{37}N_3O_4S$; $^1$H NMR (CD$_3$Cl) δ(ppm) 8.72(m, 1H), 7.82(m, 1H), 7.74(m, 1H), 7.35(m, 5H), 6.85(m, 2H), 6.78 (m, 2H), 4.37(m, 1H), 3.73(s, 3H), 3.69(s, 3H), 3.53(m, 1H), 3.42(m, 3H), 1.66(m, 7H), 1.41(m, 1H), 1.10(m, 3H), 0.86 (m, 2H); LCMS: 536.5(M+H)$^+$.

Example 192

N-{2-Cyclohexyl-1-(S)-[2-(4-methoxy-phenylamino)-ethylcarbamoyl]-ethyl}-2-(S)-phenyl-propionamide*

$C_{27}H_{37}N_3O_3$; $^1$H NMR (CD$_3$Cl) δ(ppm) 8.30(m, 1H), 7.23(m, 6H), 7.18(m, 1H), 6.83(m, 2H), 6.26(m, 1H), 3.96 (m, 1H), 3.74(s, 3H), 3.56(m, 2H), 3.49(m, 1H), 3.38(m, 1H), 3.31(m, 1H), 1.49(m, 7H), 1.39(d, J=7.2 Hz, 3H), 1.00(m, 4H), 0.78(m, 2H); LCMS: 452.5(M+H)$^+$.

Example 193

(S)-5-(2-Chloro-5-trifluoromethyl-phenyl)-furan-2-carboxylic acid {2-cyclohexyl-1-[2-(4-methoxy-phenylamino)-ethylcarbamoyl]-ethyl}-amide*

$C_{30}H_{33}ClF_3N_3O_4$; $^1$H NMR (CD$_3$Cl) δ(ppm) 8.56(m, 1H), 7.97(m, 1H), 7.50(m, 1H), 7.40(m, 1H), 7.39(m, 2H), 7.25 (m, 1H), 7.10(d, J=3.7, 1H), 7.01(d, J=3.7, 1H), 6.89(m, 2H), 4.29(m, 1H), 3.75(s, 3H), 3.59(m, 3H), 3.46(m, 1H), 1.72(m, 7H), 1.40(m, 1H), 1.13(m, 3H), 0.91(m, 2H); LCMS: 592.4(M+H)$^+$.

Example 194

(S)-2'-Chloro-biphenyl-4-carboxylic acid {2-cyclohexyl-1-[2-(4-trifluoromethoxy-phenylamino)-ethylcarbamoyl]-ethyl}-amide*

$C_{31}H_{33}ClF_3N_3O_3$; 1H NMR (CD3Cl) δ(ppm) 7.72(d, J=8.4 Hz, 2H), 7.52(m, 1H), 7.42(m, 3H), 7.24(m, 3H), 7.04(m, 2H), 6.92(m, 2H), 6.83(m, 1H), 4.47(m, 1H), 3.49 (m, 2H), 3.33(m, 2H), 1.64(m, 7H), 1.34(m, 1H), 1.13(m, 3H), 0.91(m, 2H); LCMS: 558.4(M+H)$^+$.

Example 195

(S)-1-(5-Bromo-pyrimidin-2-yl)-piperidine-4-carboxylic acid {2-cyclohexyl-1-[2-(4-methoxy-phenylamino)-ethylcarbamoyl]-ethyl}-amide*

$C_{28}H_{39}BrN_6O_3$; $^1$H NMR (CD$_3$Cl) δ(ppm) 8.51(m, 1H), 8.17(m, 2H), 7.33(m, 2H), 6.84(m, 2H), 6.44(d, J=4.7 Hz, 1H), 4.60(m, 2H), 4.07(m, 1H), 3.74(s, 3H), 3.53(m, 3H), 3.31(m, 2H), 2.76(m, 2H), 2.43(m, 1H), 1.81(m, 1H), 1.55 (m, 10H), 1.27(m, 1H), 1.10(m, 3H), 0.86(m, 2H); LCMS: 587.4($^{79}$BrM+H)$^+$, 589.5($^{80}$BrM+H)$^+$.

Example 196

(S)-N-{2-Cyclohexyl-1-[2-(4-methoxy-phenylamino)-ethylcarbamoyl]-ethyl}-4-(4,6-dimethyl-pyrimidin-2-ylamino)-benzamide*

$C_{31}H_{40}N_6O_3$; $^1$H NMR (CD$_3$Cl) δ(ppm) 12.17(bs, 1H), 8.65(m, 1H), 7.68(m, 4H), 7.37(m, 3H), 6.85(m, 2H), 6.57(s, 1H), 4.35(m, 1H), 3.74(s, 3H), 3.55(m, 2H), 3.41(m, 2H), 2.49(s, 6H), 1.66(m, 7H), 1.37(m, 1H), 1.14(m, 3H), 0.88(m, 2H); LCMS: 545.5(M+H)$^+$.

Example 197

(S)-1-(5-Bromo-pyrimidin-2-yl)-piperidine-3-carboxylic acid {2-cyclohexyl-1-[2-(4-methoxy-phenylamino)-ethylcarbamoyl]-ethyl}-amide*

$C_{28}H_{39}BrN_6O_3$; $^1$H NMR (CD$_3$Cl) δ(ppm) 8.42(m, 1H), 8.32(s, 1H), 8.20(s, 1H), 7.36(m, 2H), 7.03(m, 1H), 6.87(m, 2H), 3.90(m, 2H), 3.74(s, 3H), 3.59(m, 5H), 2.45(m, 1H), 1.80(m, 2H), 1.54(m, 11H), 1.03(m, 6H); LCMS: 587.5 ($^{79}$BrM+H)$^+$, 589.4($^{80}$BrM+H)$^+$.

Example 198

(S)-3'-Fluoro-biphenyl-4-carboxylic acid {2-cyclohexyl-1-[2-(4-trifluoromethoxy-phenylamino)-ethylcarbamoyl]-ethyl}-amide*

$C_{31}H_{33}F_4N_3O_3$; 1H NMR (CD3Cl) δ(ppm) 7.73(m, 2H), 7.53(d, J=8.4 Hz, 2H), 7.52(m, 3H), 7.20(m, 1H), 6.98(m, 3H), 6.71(m, 3H), 4.52(m, 1H), 3.46(m, 2H), 3.26(m, 2H), 1.63(m, 7H), 1.31(m, 1H), 1.09(m, 3H), 0.90(m, 2H); LCMS: 572.5(M+H)$^+$.

Example 199

(S)-3-Aminomethyl-N-{2-cyclohexyl-1-[2-(4-methoxy-phenylamino)-ethylcarbamoyl]-ethyl}-benzamide*

$C_{26}H_{36}N_4O_3$; $^1$H NMR (CD$_3$Cl) δ(ppm) 8.44(bs, 3H), 7.91(s, 1H), 7.61(m, 1H), 7.33(m, 4H), 6.86(m, 2H), 4.42(m, 1H), 3.98(bs, 2H), 3.74(s, 3H), 3.37(m, 4H), 2.59(s, 2H), 1.68(m, 7H), 1.35(m, 1H), 1.14(m, 3H), 0.89(m, 2H); LCMS: 453.5(M+H)$^+$.

Example 200

(S)-N-{2-Cyclohexyl-1-[2-(4-trifluoromethoxy-phenylamino)-ethylcarbamoyl]-ethyl}-3-morpholin-4-ylmethyl-benzamide*

$C_{30}H_{39}F_3N_4O_4$; LCMS: 557.5(M+H)$^+$.

Example 201

(S)-5-(2-Fluoro-phenyl)-thiophene-2-carboxylic acid {2-cyclohexyl-1-[2-(4-trifluoromethoxy-phenylamino)-ethylcarbamoyl]-ethyl}-amide*

$C_{29}H_{31}F_4N_3O_3S$; 1H NMR (CD3Cl) δ(ppm) 7.51(m, 1H), 7.45(m, 1H), 7.39(m, 1H), 7.31(m, 1H), 7.23(m, 1H), 7.08 (m, 2H), 6.99(m, 2H), 6.77(m, 3H), 4.48(dd, J=6.8 Hz, J=15.2 Hz, 1H), 3.47(m, 2H), 3.26(m, 2H), 1.62(m, 7H), 1.32(m, 1H), 1.10(m, 3H), 0.88(m, 2H); LCMS: 578.4(M+ H)$^+$.

Example 202

(S)-N-{3-Cyclohexyl-1-[2-(4-methoxy-phenylamino)-ethylcarbamoyl]-propyl}-3-methyl-benzamide*

Following the procedure of Preparation 1, except substituting Fmoc-(L)-phenyl alanine for Fmoc-(L)-homo-cyclohexyl alanine in Step B and 3-methoxy benzoic acid for m-toluic acid in Step D, the title compound was prepared as a white solid (12 mg, 53%): MS calcd. for $C_{27}H_{38}N_3O_3$ (M+H$^+$) 452.29. found 452.3.

Example 203

(S)-N-{4-Cyclohexyl-1-[2-(4-methoxy-phenylamino)-ethylcarbamoyl]-butyl}-3-methyl-benzamide

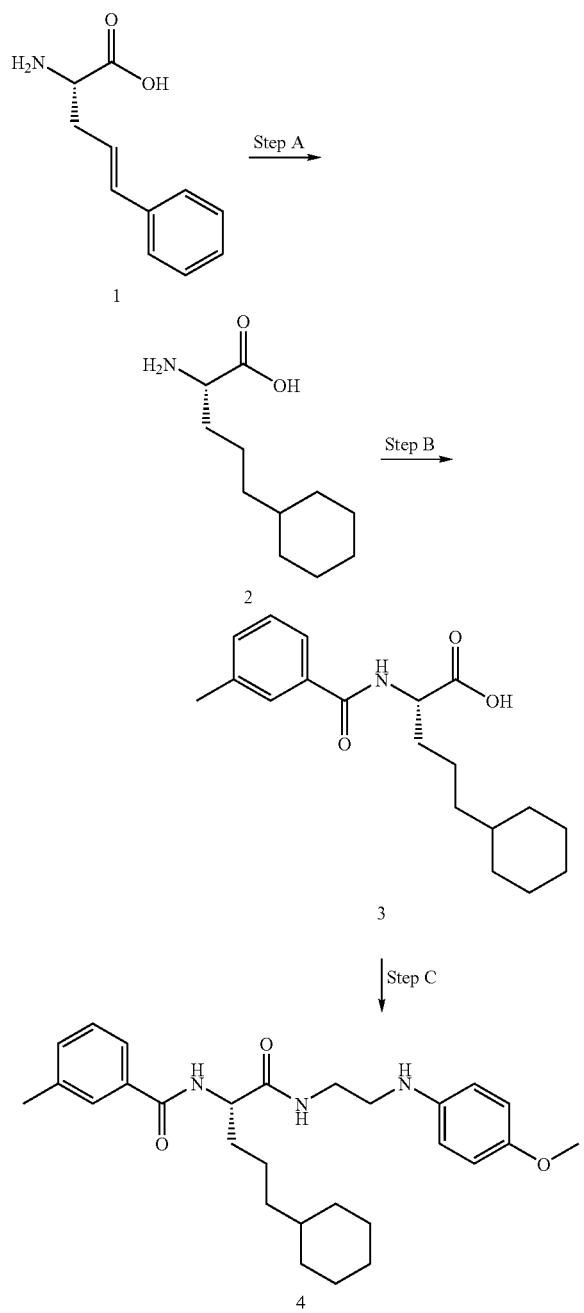

Step A: L-Styryl alanine 1 (50 mg, 0.26 mmol) was dissolved in MeOH (5 mL) and placed into a Parr-hydrogenation apparatus. Catalytic amounts of rhodium (5% on Al$_2$O$_3$) were added and the reaction vessel was placed under a hydrogen at 55 psi. The mixture was shaken for 20 h at room temperature, then filtered over celite. The organic solvent was removed in vacuo to yield (S)-2-Amino-5-cyclohexyl-pentanoic acid 2 (52 mg, quant.) as a white solid: ¹H-NMR (400 MHz, CD$_3$OD) δ=3.50 (dd, J=5.2, J=6.9, 1H), 1.88–1.64 (m, 7H), 1.47–1.37 (m, 2H), 1.31–1.11 (m, 6H), 0.94–0.86 (m, 2H). MS calcd. for $C_{11}H_{22}NO_2$ (M+H$^+$) 200.17. found 200.4.

Step B: (S)-2-Amino-5-cyclohexyl-pentanoic acid 2 (24 mg, 0.12 mmol) was dissolved in H$_2$O (1 mL) containing equimolar amounts of NaOH (5 mg, 0.12 mmol). The solution was cooled to 0° C., then m-Toluic acid chloride (16 μL, 0.12 mmol) was added dropwise under vigorous stirring. The mixture was allowed to warm to room temperature and stirred for approx. 12 h. After acidification with 1 M HCl (1 mL), the product was extracted from the reaction mixture with DCM (4 mL). The organic layer was separated and the solvent was removed in vacuo to yield (S)-5-Cyclohexyl-2-(3-methyl-benzoylamino)-pentanoic acid 3 (19 mg, 50%) as a white solid: ¹H-NMR (400 MHz, CD$_3$OD) δ=7.67–7.62 (m, 2H), 7.37–7.31 (m, 2H), 4.56 (dd, J=5.0, J=9.4, 1H), 2.40 (s, 3H), 1.96–0.84 (m, 17H). MS calcd. for $C_{19}H_{28}NO_3$ (M+H$^+$) 318.21. found 318.4.

Step C: (S)-5-Cyclohexyl-2-(3-methyl-benzoylamino)-pentanoic acid 3 (19 mg, 0.06 mmol) was dissolved in DCM (2 mL), HOBt (20 mg, 0.14 mmol) and DIC (23 μL, 0.14 mmol) were added and the solution was stirred for 10 min at room temperature. N-(4-Methoxyphenyl)-ethane-1,2-diamine (24 mg, 0.14 mmol) was added and the solution was stirred for 3 h at room temperature. The solvent was removed in vacuo, and the remainder was purified by reverse HPLC to afford the title compound (S)-N-{4-Cyclohexyl-1-[2-(4-methoxy-phenylamino)-ethylcarbamoyl]-butyl}-3-methyl-benzamide 4 (15 mg, 0.03 mmol, 50%) as a white solid: ¹H-NMR (400 MHz, CD$_3$OD) δ=7.70–7.65 (m, 2H), 7.38–7.32 (m, 4H), 7.03–6.99 (m, 2H), 4.39 (dd, J=6.4, J=8.4, 1H), 3.80 (s, 3H), 3.67–3.61 (m, 1H), 3.54–3.41 (m, 3H), 2.38 (s, 3H), 1.88–1.80 (m, 2H), 1.72–1.66 (m, 5H), 1.64–1.36 (m, 2H), 1.29–1.07 (m, 6H), 0.92–0.83 (m, 2H). MS calcd. for $C_{28}H_{40}N_3O_3$ (M+H$^+$) 466.31. found 466.5.

Example 204

(S)-N-{[2-(4-Methoxy-phenylamino)-ethylcarbamoyl]-phenyl-methyl}-3-methyl-benzamide*

Following the procedure of Preparation 1, except substituting Fmoc-(L)-phenyl alanine for Fmoc-(L)-phenylglycine in Step B and 3-methoxy benzoic acid for m-toluic acid in Step D, the title compound was prepared as a white solid (7 mg, 34%): MS calcd. for $C_{25}H_{28}N_3O_3$ (M+H$^+$) 418.21. found 418.2.

Example 205

(S)-5-(4-Trifluoromethyl-phenyl)-thiophene-2-carboxylic acid {2-cyclohexyl-1-[2-(4-trifluoromethoxy-phenylamino)-ethylcarbamoyl]-ethyl}-amide*

$C_{30}H_{31}F_6N_3O_3S$; 1H NMR (CD3Cl) δ(ppm) 7.58(m, 4H), 7.49(m, 1H), 7.44(d, J=4 Hz, 1H), 7.24(d, J=4 Hz, 1H), 7.07(d, J=8.8 Hz, 2H), 6.96(d, J=8.8 Hz, 2H), 6.78(m, 1H), 4.42(dd, J=6.4 Hz, J=15.2 Hz, 1H), 3.53(m, 2H), 3.32(m, 2H), 1.63(m, 7H), 1.31(m, 1H), 1.14(m, 3H), 0.90(m, 2H); LCMS: 628.4(M+H)$^+$.

Example 206

(S)-N-{1-[2-(4-Methoxy-phenylamino)-ethylcarbamoyl]-3-phenyl-propyl}-3-methyl-benzamide*

Following the procedure of Preparation 1, except substituting Fmoc-(L)-phenyl alanine for Fmoc-(L)-homo phenyl alanine in Step B and 3-methoxy benzoic acid for m-toluic acid in Step D, the title compound was prepared as a white solid (9 mg, 40%): MS calcd. for $C_{27}H_{32}N_3O_3$ (M+H$^+$) 446.24. found 446.2.

Example 207

(S)-5-(4-Trifluoromethoxy-phenyl)-thiophene-2-carboxylic acid {2-cyclohexyl-1-[2-(4-trifluoromethoxy-phenylamino)-ethylcarbamoyl]-ethyl}-amide*

$C_{30}H_{31}F_6N_3O_4S$; 1H NMR (CD3Cl) δ(ppm) 7.49(m, 3H), 7.43(d, J=4 Hz, 1H), 7.17(m, 3H), 7.06(m, 2H), 6.92(m, 2H), 6.83(m, 1H), 4.43(m, 1H), 3.51(m, 2H), 3.25(m, 2H), 1.62(m, 7H), 1.32(m, 1H), 1.14(m, 3H), 0.89(m, 2H); LCMS: 644.4(M+H)$^+$.

Example 208

(S)-N-{1-[2-(4-Methoxy-phenylamino)-ethylcarbamoyl]-4-phenyl-but-3-enyl}-3-methyl-benzamide*

Following the procedure of Preparation 1, except substituting Fmoc-(L)-phenyl alanine for Fmoc-(L)-styryl alanine in Step B and 3-methoxy benzoic acid for m-toluic acid in Step D, the title compound was prepared as a white solid (9 mg, 39%): MS calcd. for $C_{28}H_{32}N_3O_3$ (M+H$^+$) 458.24. found 458.2.

Example 209

(S)-5-(3-Trifluoromethoxy-phenyl)-thiophene-2-carboxylic acid {2-cyclohexyl-1-[2-(4-trifluoromethoxy-phenylamino)-ethylcarbamoyl]-ethyl}-amide*

$C_{30}H_{31}F_6N_3O_4S$; 1H NMR (CD3Cl) δ(ppm) 7.41(m, 2H), 7.34(m, 2H), 7.20(m, 1H), 7.16(m, 2H), 6.99(d, J=8.0 Hz, 2H), 6.74(m, 3H), 4.47(m, 1H), 3.47(m, 2H), 3.26(m, 2H), 1.61(m, 7H), 1.30(m, 1H), 1.12(m, 3H), 0.88(m, 2H); LCMS: 644.4(M+H)$^+$.

Example 210

(S)-5-(2-Methoxy-phenyl)-furan-2-carboxylic acid {2-cyclohexyl-1-[2-(4-trifluoromethoxy-phenylamino)-ethylcarbamoyl]-ethyl}-amide*

$C_{30}H_{34}F_3N_3O_5$; 1H NMR (CD3Cl) δ(ppm) 7.77(d, 1H), 7.29(m, 2H), 7.07(d, J=3.6 Hz, 1H), 6.98(m, 5H), 6.84(m, 2H), 6.77(m, 1H), 4.46(m, 1H), 3.87(s, 3H), 3.49(m, 2H), 3.30(m, 2H), 1.63(m, 7H), 1.32(m, 1H), 1.14(m, 3H), 0.90 (m, 2H); LCMS: 628.4(M+H)$^+$.

Example 211

N-{(4-Methoxy-phenyl)-[2-(4-methoxy-phenylamino)-ethylcarbamoyl]-methyl}-3-methyl-benzamide**

Following the procedure of Example 227, except substituting 4-fluoro-phenyl glycine for 4-methoxy-phenyl glycine in Step A, the title compound was prepared as a white solid (16 mg, 30%): $^1$H-NMR (400 MHz, CD$_3$OD) δ=7.69–6.94 (m, 12H), 5.43 (s, 1H), 3.82 (s, 3H), 3.80 (s, 3H), 3.71–3.37 (m, 4H), 2.37 (s, 3H). MS calcd. for $C_{26}H_{30}N_3O_4$ (M+H$^+$) 448.22. found 448.5.

Example 212

(S)-5-(2-Fluoro-phenyl)-furan-2-carboxylic acid {2-cyclohexyl-1-[2-(4-trifluoromethoxy-phenylamino)-ethylcarbamoyl]-ethyl}-amide*

$C_{29}H_{31}F_4N_3O_4$; 1H NMR (CD3Cl) δ(ppm) 7.75(m, 2H), 7.27(m, 1H), 7.12(m, 7H), 6.99(m, 1H), 6.83(m, 1H), 4.42 (dd, J=6.4 Hz, J=14.8 Hz, 1H), 3.55(m, 2H), 3.38(m, 2H), 1.65(m, 7H), 1.35(m, 1H), 1.13(m, 3H), 0.91(m, 2H); LCMS: 644.4(M+H)$^+$.

Example 213

(S)-5-(4-Trifluoromethyl-phenyl)-furan-2-carboxylic acid {2-cyclohexyl-1-[2-(4-trifluoromethoxy-phenylamino)-ethylcarbamoyl]-ethyl}-amide*

C30H31F6N3O4; 1H NMR (CD3Cl) δ(ppm) 7.72(d, J=8.0, 2H); 7.59(m, 3H); 7.06(m, 6H); 6.75(d, J=3.6 Hz, 1H); 4.45(m, 1H); 3.54(m, 2H); 3.36(m, 2H); 1.65(m, 7H); 1.33(m, 1H); 1.13(m, 3H); 0.89(m, 2H); LCMS: 574.5(M+H)$^+$.

Example 214

N-{(2-Benzyloxy-phenyl)-[2-(4-methoxy-phenylamino)-ethylcarbamoyl]-methyl}-3-methyl-benzamide**

Following the procedure of Example 227, except substituting 4-fluoro-phenyl glycine for 2-benzyloxy-phenyl glycine in Step A, the title compound was prepared as a white solid (7 mg, 11%): $^1$H-NMR (400 MHz, CD$_3$OD) δ=7.64–6.99 (m, 17H), 5.94 (s, 1H), 5.18 (s, 2H), 3.82 (s, 3H), 3.63–3.37 (m, 4H), 2.36 (s, 3H). MS calcd. for $C_{32}H_{34}N_3O_4$ (M+H$^+$) 524.25. found 524.6.

Example 215

(S)-5-(4-Trifluoromethoxy-phenyl)-furan-2-carboxylic acid {2-cyclohexyl-1-[2-(4-trifluoromethoxy-phenylamino)-ethylcarbamoyl]-ethyl}-amide*

$C_{30}H_{31}F_6N_3O_5$; $^1$H NMR (CD$_3$Cl) δ(ppm) 7.65(d, J=8.8, 2H), 7.56(m, 1H), 7.21(m, 1H), 7.04(m, 6H), 6.64(d, J=3.6 Hz, 1H), 4.42(dd, J=2.4 Hz, J=6.4 Hz, 1H), 3.54(m, 2H), 3.33(m, 2H), 1.66(m, 7H), 1.33(m, 1H), 1.15(m, 3H), 0.91 (m, 2H); LCMS: 562.4(M+H)$^+$.

Example 216

N-{(2-Chloro-phenyl)-[2-(4-methoxy-phenylamino)-ethylcarbamoyl]-methyl}-3-methyl-benzamide**

Following the procedure of Example 227, except substituting 4-fluoro-phenyl glycine for 2-chloro-phenyl glycine in Step A, the title compound was prepared as a white solid (20 mg, 37%): $^1$H-NMR (400 MHz, CD$_3$OD) δ=7.70–7.01 (m, 12H), 5.98 (s, 1H), 3.82 (s, 3H), 3.75–3.43 (m, 4H), 2.37 (s, 3H). MS calcd. for C$_{25}$H$_{27}$ClN$_3$O$_3$ (M+H$^+$) 452.17. found 452.5.

Example 217

N-{(4-Benzyloxy-phenyl)-[2-(4-methoxy-phenylamino)-ethylcarbamoyl]-methyl}-3-methyl-benzamide**

Following the procedure of Example 227, except substituting 4-fluoro-phenyl glycine for 4-benzyloxy-phenyl glycine in Step A, the title compound was prepared as a white solid (14 mg, 22%): $^1$H-NMR (400 MHz, CD$_3$OD) δ=7.69–7.01 (m, 17H), 5.42 (s, 1H), 5.10 (s, 2H), 3.81 (s, 3H), 3.72–3.35 (m, 4H), 2.37 (s, 3H). MS calcd. for C$_{32}$H$_{34}$N$_3$O$_4$ (M+H$^+$) 524.25. found 524.5.

Example 218

N-{[2-(4-Methoxy-phenylamino)-ethylcarbamoyl]-naphthalen-1-yl-methyl}-3-methyl-benzamide**

Following the procedure of Example 227, except substituting 4-fluoro-phenyl glycine for 1-naphtyl glycine in Step A, the title compound was prepared as a white solid (20 mg, 36%): $^1$H-NMR (400 MHz, CD$_3$OD) δ=8.15–7.04 (m, 15H), 6.39 (s, 1H), 3.82 (s, 3H), 3.80–3.42 (m, 4H), 2.34 (s, 3H). MS calcd. for C$_{29}$H$_{30}$N$_3$O$_3$ (M+H$^+$) 468.23. found 468.5.

Example 219

(S)-5-(2-Trifluoromethyl-phenyl)-furan-2-carboxylic acid {2-cyclohexyl-1-[2-(4-trifluoromethoxy-phenylamino)-ethylcarbamoyl]-ethyl}-amide*

C$_{30}$H$_{31}$F$_6$N$_3$O$_4$; $^1$H NMR (CD$_3$Cl) δ(ppm) 7.83(d, J=8.0, 1H), 7.70(m, 1H), 7.64(m, 1H), 7.30(m, 1H), 7.25(m, 1H), 7.13(m, 3H), 6.91(m, 2H), 6.74(m, 2H), 4.47(dd, J=3.2 Hz, J=6.0 Hz, 1H), 3.58(m, 2H), 3.37(m, 2H), 1.69(m, 7H), 1.40(m, 1H), 1.21(m, 3H), 0.98(m, 2H); LCMS: 612.4(M+H)$^+$.

Example 220

N-{[2-(4-Methoxy-phenylamino)-ethylcarbamoyl]-o-tolyl-methyl}-3-methyl-benzamide**

Following the procedure of Example 227, except substituting 4-fluoro-phenyl glycine for 2-methyl-phenyl glycine in Step A, the title compound was prepared as a white solid (19 mg, 37%): $^1$H-NMR (400 MHz, CD$_3$OD) δ=7.70–7.05 (m, 12H), 5.78 (s, 1H), 3.83 (s, 3H), 3.77–3.41 (m, 4H), 2.45 (s, 3H), 2.37 (s, 3H). MS calcd. for C$_{26}$H$_{30}$N$_3$O$_3$ (M+H$^+$) 432.23. found 432.23.

Example 221

(S)-N-{2-Cyclohexyl-1-[2-(4-trifluoromethoxy-phenylamino)-ethylcarbamoyl]-ethyl}-4-[1,2,4]triazol-1-yl-benzamide*

C$_{27}$H$_{31}$F$_3$N$_6$O$_3$; $^1$H NMR (CD$_3$Cl) δ(ppm) 8.60(s, 1H), 8.07(s, 1H), 7.82(m, 2H), 7.68(d, J=8.8 Hz, 2H), 7.32(m, 1H), 7.04(d, J=8.4 Hz, 2H), 6.92(d, J=6.8 Hz, 1H), 6.84(m, 2H), 4.49(m, 1H), 3.50(m, 2H), 3.30(m, 2H), 1.65(m, 7H), 1.32(m, 1H), 1.10(m, 3H), 0.88(m, 2H); LCMS: 545.4(M+H)$^+$.

Example 222

N-{(2,4-Dichloro-phenyl)-[2-(4-methoxy-phenylamino)-ethylcarbamoyl]-methyl}-3-methyl-benzamide**

Following the procedure of Example 227, except substituting 4-fluoro-phenyl glycine for 2,4-dichloro-phenyl glycine in Step A, the title compound was prepared as a white solid (10 mg, 17%): $^1$H-NMR (400 MHz, CD$_3$OD) δ=7.70–7.04 (m, 11H), 5.93 (s, 1H), 3.82 (s, 3H), 3.74–3.44 (m, 4H), 2.38 (s, 3H). MS calcd. for C$_{25}$H$_{26}$Cl$_2$N$_3$O$_3$ (M+H$^+$) 486.14. found 486.4.

Example 223

N-{(2,3-Dichloro-phenyl)-[2-(4-methoxy-phenylamino)-ethylcarbamoyl]-methyl}-3-methyl-benzamide**

Following the procedure of Example 227, except substituting 4-fluoro-phenyl glycine for 2,3-dichloro-phenyl glycine in Step A, the title compound was prepared as a white solid (32 mg, 55%): $^1$H-NMR (400 MHz, CD$_3$OD) δ=7.70–7.00 (m, 11H), 6.03 (s, 1H), 3.80 (s, 3H), 3.70–3.43 (m, 4H), 2.37 (s, 3H). MS calcd. for C$_{25}$H$_{26}$Cl$_2$N$_3$O$_3$ (M+H$^+$) 486.14. found 486.4.

Example 224

N-{(2,4-Dimethyl-phenyl)-[2-(4-methoxy-phenylamino)-ethylcarbamoyl]-methyl}-3-methyl-benzamide**

Following the procedure of Example 227, except substituting 4-fluoro-phenyl glycine for 2,4-dimethyl-phenyl glycine in Step A, the title compound was prepared as a white solid (16 mg, 30%): $^1$H-NMR (400 MHz, CD$_3$OD) δ=7.69–7.01 (m, 11H), 5.73 (s, 1H), 3.82 (s, 3H), 3.75–3.40 (m, 4H), 2.40 (s, 3H), 2.37 (s, 3H), 2.30 (s, 3H). MS calcd. for C$_{27}$H$_{32}$N$_3$O$_3$ (M+H$^+$) 446.24. found 446.5.

Example 225

N-{(2,4-Dimethoxy-phenyl)-[2-(4-methoxy-phenylamino)-ethylcarbamoyl]-methyl}-3-methyl-benzamide**

Following the procedure of Example 227, except substituting 4-fluoro-phenyl glycine for 2,4-dimethoxy-phenyl glycine in Step A, the title compound was prepared as a white solid (16 mg, 28%): $^1$H-NMR (400 MHz, CD$_3$OD) δ=7.68–6.54 (m, 11H), 5.78 (s, 1H), 3.87 (s, 3H), 3.82 (s, 3H), 3.80 (s, 3H), 3.71–3.40 (m, 4H), 2.37 (s, 3H). MS calcd. for $C_{27}H_{32}N_3O_5$ (M+H$^+$) 478.23. found 478.5.

Example 226

N-{[2-(4-Methoxy-phenylamino)-ethylcarbamoyl]-thiophen-2-yl-methyl}-3-methyl-benzamide**

Following the procedure of Example 227, except substituting 4-fluoro-phenyl glycine for 2-thienyl glycine in Step A, the title compound was prepared as a white solid (5 mg, 10%): $^1$H-NMR (400 MHz, CD$_3$OD) δ=7.70–7.04 (m, 11H), 5.80 (s, 1H), 3.82 (s, 3H), 3.75–3.40 (m, 4H), 2.38 (s, 3H). MS calcd. for $C_{23}H_{26}N_3O_3S$ (M+H$^+$) 424.17. found 424.5.

Example 227

N-{(4-Fluoro-phenyl)-[2-(4-methoxy-phenylamino)-ethylcarbamoyl]-methyl}-3-methyl-benzamide

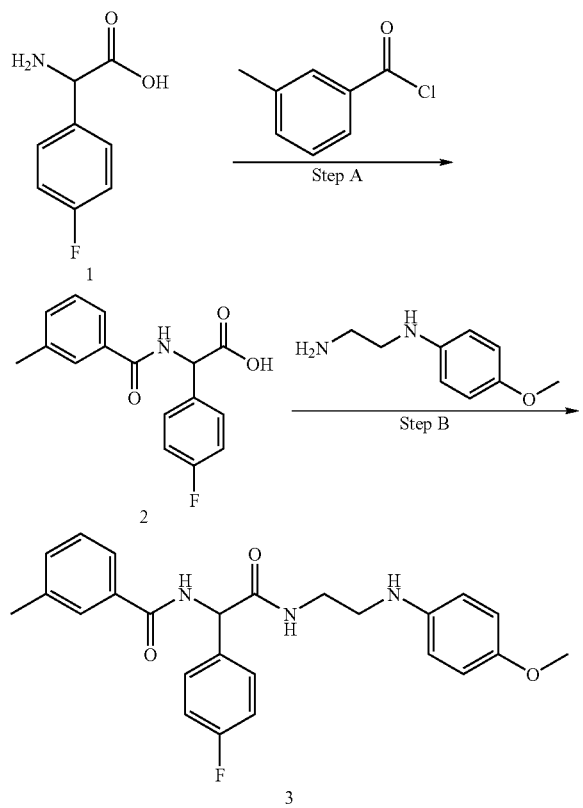

Step A: 4-Fluoro-phenyl glycine 1 (20 mg, 0.12 mmol) was dissolved in H$_2$O (1 mL) containing equimolar amounts of NaOH (5 mg, 0.12 mmol). The solution was cooled to 0° C., then m-toluoyl chloride (16 μL, 0.12 mmol) was added dropwise under vigorous stirring. The mixture was allowed to warm to room temperature and stirred for approx. 12 h. After acidification with 1 M HCl (1 mL), the product was extracted from the reaction mixture with DCM (4 mL). The organic layer was separated and the solvent was removed in vacuo to yield (4-Fluoro-phenyl)-(3-methyl-benzoylamino)-acetic acid 2 (34 mg, 0.12 mmol, quant.) as a white solid: $^1$H-NMR (400 MHz, CD$_3$OD) δ=7.67–7.08 (m, 8H), 5.66 (s, 1H), 2.38 (s, 3H). MS calcd. for $C_{16}H_{15}FNO_3$ (M+H$^+$) 288.10. found 288.4.

Step B: (4-Fluoro-phenyl)-(3-methyl-benzoylamino)-acetic acid 2 (34 mg, 0.12 mmol) was dissolved in DCM (2 mL), HOBt (20 mg, 0.14 mmol) and DIC (23 μL, 0.14 mmol) were added and the solution was stirred for 10 min at room temperature. N-(4-Methoxyphenyl)-ethane-1,2-diamine (24 mg, 0.14 mmol) was added and the solution was stirred for 3 h at room temperature. The solvent was removed in vacuo, and the remainder was purified by reverse HPLC to afford N-{(4-Fluoro-phenyl)-[2-(4-methoxy-phenylamino)-ethylcarbamoyl]-methyl}-3-methyl-benzamide 3 (19 mg, 0.04 mmol, 36%) as a white solid:
$^1$H-NMR (400 MHz, CD$_3$OD) δ=7.62–6.83 (m, 12H), 5.51 (s, 1H), 3.79 (s, 3H), 3.77–3.46 (m, 4H), 2.32 (s, 3H). MS calcd. for $C_{25}H_{27}FN_3O_3$ (M+H$^+$) 436.20. found 436.5.

Example 228

(S)-N-{2-(4-Hydroxy-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-O-t-butyl-tyrosine in Step B and 3-methoxy benzoic acid for m-toluic acid in Step D, the title compound was prepared as a white solid (10 mg, 45%): $^1$H-NMR (400 MHz, CD$_3$OD) δ=7.62–7.57 (m, 2H), 7.40–7.33 (m, 2H), 7.14–7.12 (m, 2H), 6.85–6.73 (m, 6H), 4.68 (t, J=7.6, 1H), 3.75 (s, 3H), 3.41–3.38 (m, 2H), 3.25–3.01 (m, 4H), 2.41 (s, 3H). MS calcd. for $C_{26}H_{30}N_3O_4$ (M+H$^+$) 448.22. found 448.2.

Example 229

(S)-N-{2-(2,4-Dichloro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-2,4-dichloro phenyl alanine in Step B and 3-methoxy benzoic acid for m-toluic acid in Step D, the title compound was prepared as a white solid (14 mg, 56%): MS calcd. for $C_{26}H_{28}Cl_2N_3O_3$ (M+H$^+$) 500.15. found 500.1.

Example 230

(S)-N-{2-(3,5-Difluoro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-3,5-difluoro phenyl alanine in Step B and 3-methoxy benzoic acid for m-toluic acid in Step D, the title compound was prepared as a white solid (15 mg, 64%): MS calcd. for $C_{26}H_{28}F_2N_3O_3$ (M+H$^+$) 468.21. found 468.2.

Example 231

(S)-N-{2-(3,4-Dichloro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-3,4-dichloro phenyl alanine in Step B and 3-methoxy benzoic acid for m-toluic acid in Step D, the title compound was prepared as

Example 232

(S)-4-Benzyloxy-N-{2-cyclohexyl-1-[2-(4-trifluoromethoxy-phenylamino)-ethylcarbamoyl]-ethyl}-benzamide*

$C_{32}H_{36}F_3N_3O_4$; $^1H$ NMR (CD$_3$Cl) δ(ppm) 7.61(m, 2H), 7.32(m, 5H), 6.96(m, 5H), 6.65(m, 2H), 6.42(m, 1H), 5.03(s, 2H), 4.46(dd, J=6.8 Hz, J=15.2 Hz, 1H), 3.44(m, 2H), 3.23(m, 2H), 1.59(m, 7H), 1.28(m, 1H), 1.11(m, 3H), 0.88 (m, 2H); LCMS: 584.4(M+H)$^+$.

Example 233

(S)-N-{2-(4-Acetylamino-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-acetylamino phenyl alanine in Step B and 3-methoxy benzoic acid for m-toluic acid in Step D, the title compound was prepared as a white solid (13 mg, 53%): MS calcd. for $C_{28}H_{33}N_4O_4$ (M+H$^+$) 489.25. found 489.2.

Example 234

(S)-Biphenyl-4-carboxylic acid {2-cyclohexyl-1-[2-(4-trifluoromethoxy-phenylamino)-ethylcarbamoyl]-ethyl}-amide*

$C_{31}H_{34}F_3N_3O_3$; $^1H$ NMR (CD$_3$Cl) δ(ppm) 7.67(d, J=8.4, 2H), 7.51(d, J=8.4, 2H), 7.46(m, 3H), 7.27(m, 3H), 7.01(m, 2H), 6.89(d, J=8.8, 2H), 6.70(m, 1H), 4.41(m, 1H), 3.47(m, 2H), 3.28(m, 2H), 1.59(m, 7H), 1.28(m, 1H), 1.06(m, 3H), 0.84(m, 2H); LCMS: 554.4(M+H)$^+$.

Example 235

(S)-N-{1-[2-(4-Methoxy-phenylamino)-ethylcarbamoyl]-2-p-tolyl-ethyl}-3-methyl-benzamide*

Following the procedure of Preparation 1, except substituting Fmoc-(L)-phenyl alanine for Fmoc-(L)-4-methyl phenyl alanine in Step B and 3-methoxy benzoic acid for m-toluic acid in Step D, the title compound was prepared as a white solid (12 mg, 54%): MS calcd. for $C_{27}H_{32}N_3O_3$ (M+H$^+$) 446.24. found 446.3.

Example 236

(S)-N-{2-(3-Fluoro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-3-fluoro phenyl alanine in Step B and 3-methoxy benzoic acid for m-toluic acid in Step D, the title compound was prepared as a white solid (13 mg, 58%): MS calcd. for $C_{26}H_{29}FN_3O_3$ (M+H$^+$) 450.22. found 450.2.

a white solid (12 mg, 48%): MS calcd. for $C_{26}H_{28}Cl_2N_3O_3$ (M+H$^+$) 500.15, found 500.1.

Example 237

(S)-N-{2-(3,4-Difluoro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-3,4-difluoro phenyl alanine in Step B and 3-methoxy benzoic acid for m-toluic acid in Step D, the title compound was prepared as a white solid (13 mg, 56%): MS calcd. for $C_{26}H_{28}F_2N_3O_3$ (M+H$^+$) 468.21. found 468.2.

Example 238

(S)-N-{1-[2-(4-Methoxy-phenylamino)-ethylcarbamoyl]-2-m-tolyl-ethyl}-3-methyl-benzamide*

Following the procedure of Preparation 1, except substituting Fmoc-(L)-phenyl alanine for Fmoc-(L)-3-methyl phenyl alanine in Step B and 3-methoxy benzoic acid for m-toluic acid in Step D, the title compound was prepared as a white solid (13 mg, 58%): MS calcd. for $C_{27}H_{32}N_3O_3$ (M+H$^+$) 446.24. found 446.3.

Example 239

(S)-N-[1-[2-(4-Methoxy-phenylamino)-ethylcarbamoyl]-2-(2-trifluoromethyl-phenyl)-ethyl]-3-methyl-benzamide*

Following the procedure of Preparation 1, except substituting Fmoc-(L)-phenyl alanine for Fmoc-(L)-2-trifluoromethyl phenyl alanine in Step B and 3-methoxy benzoic acid for m-toluic acid in Step D, the title compound was prepared as a white solid (14 mg, 56%): MS calcd. for $C_{27}H_{29}F_3N_3O_3$ (M+H$^+$) 500.22. found 500.2.

Example 240

(S)-N-{2-(4-Cyano-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-cyano phenyl alanine in Step B and 3-methoxy benzoic acid for m-toluic acid in Step D, the title compound was prepared as a white solid (14 mg, 61%): MS calcd. for $C_{27}H_{29}N_4O_3$ (M+H$^+$) 457.22. found 457.2.

Example 241

(S)-N-{2-(4-Bromo-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-bromo phenyl alanine in Step B and 3-methoxy benzoic acid for m-toluic acid in Step D, the title compound was prepared as a white solid (12 mg, 47%): MS calcd. for $C_{26}H_{29}BrN_3O_3$ (M+H$^+$) 510.14. found 510.1.

Example 242

(S)-N-{2-(4-Iodo-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-iodo phenyl alanine in Step B and 3-methoxy benzoic acid for m-toluic acid in Step D, the title compound was prepared as a white solid (13 mg, 47%): $^1$H-NMR (400 MHz, CD$_3$OD) δ=7.59–7.6.60 (m, 12H), 4.71 (dd, J=7.0, J=8.2, 1H), 3.69 (s, 3H), 3.38–2.97 (m, 6H), 2.37 (s, 3H). MS calcd. for $C_{26}H_{29}IN_3O_3$ (M+H$^+$) 558.12. found 558.1.

Example 243

(S)-N-{2-(4-Chloro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-chloro phenyl alanine in Step B and 3-methoxy benzoic acid for m-toluic acid in Step D, the title compound was prepared as a white solid (14 mg, 60%): MS calcd. for $C_{26}H_{29}ClN_3O_3$ (M+H$^+$) 466.19. found 466.2.

Example 244

(S)-N-[1-[2-(4-Methoxy-phenylamino)-ethylcarbamoyl]-2-(4-nitro-phenyl)-ethyl]-3-methyl-benzamide*

Following the procedure of Preparation 1, except substituting Fmoc-(L)-phenyl alanine for Fmoc-(L)-4-nitro phenyl alanine in Step B and 3-methoxy benzoic acid for m-toluic acid in Step D, the title compound was prepared as a white solid (15 mg, 63%): MS calcd. for $C_{26}H_{29}N_4O_5$ (M+H$^+$) 477.21. found 477.2.

Example 245

(S)-N-{2-(4-Fluoro-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-fluoro phenyl alanine in Step B and 3-methoxy benzoic acid for m-toluic acid in Step D, the title compound was prepared as a white solid (13 mg, 58%): MS calcd. for $C_{26}H_{29}FN_3O_3$ (M+H$^+$) 500.15. found 500.1.

Example 246

(S)-5-(3-Trifluoromethyl-phenyl)-furan-2-carboxylic acid {2-cyclohexyl-1-[2-(4-trifluoromethoxy-phenylamino)-ethylcarbamoyl]-ethyl}-amide*

$C_{30}H_{31}F_6N_3O_4$; $^1$H NMR (CD$_3$Cl) δ(ppm) 7.80(m, 2H), 7.46(m, 2H), 7.07(d, J=4.0 Hz, 1H), 6.87(m, 2H), 6.69(m, J=3.6 Hz, 1H), 6.60(m, 2H), 6.47(m, 2H), 4.48(m, 1H), 3.40(m, 2H), 3.16(m, 2H), 1.60(m, 7H), 1.26(m, 1H), 1.12 (m, 3H), 0.86(m, 2H); LCMS: 612.4(M+H)$^+$.

Example 247

(S)-N-{2-(4-Benzyloxy-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-benzyloxy phenyl alanine in Step B and 3-methoxy benzoic acid for m-toluic acid in Step D, the title compound was prepared as a white solid (13 mg, 48%): MS calcd. for $C_{33}H_{35}N_3O_4$ (M+H$^+$) 538.27. found 538.3.

Example 248

(S)-N-{2-[4-(2,6-Dichloro-benzyloxy)-phenyl]-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-(2,6-dichloro-benzyloxy) phenyl alanine in Step B and 3-methoxy benzoic acid for m-toluic acid in Step D, the title compound was prepared as a white solid (11 mg, 36%): MS calcd. for $C_{33}H_{34}Cl_2N_3O_4$ (M+H$^+$) 606.19. found 606.2.

Example 249

(S)-N-{2-(4-Methoxy-phenyl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-4-methoxy phenyl alanine in Step B and 3-methoxy benzoic acid for m-toluic acid in Step D, the title compound was prepared as a white solid (14 mg, 61%): MS calcd. for $C_{27}H_{32}N_3O_4$ (M+H$^+$) 462.24. found 462.2.

Example 250

2-Amino-4-methyl-thiazole-5-carboxylic acid (S)-{2-cyclohexyl-1-[2-(4-trifluoromethoxy-phenylamino)-ethylcarbamoyl]-ethyl}-amide*

$C_{23}H_{30}F_3N_5O_3S$; LCMS: 514.4(M+H)$^+$.

Example 251

(S)-5-(2-Chloro-5-trifluoromethyl-phenyl)-furan-2-carboxylic acid {2-cyclohexyl-1-[2-(4-trifluoromethoxy-phenylamino)-ethylcarbamoyl]-ethyl}-amide*

$C_{30}H_{30}ClF_6N_3O_4$; $^1$H NMR (CD$_3$Cl) δ(ppm) 7.92(m, 1H), 7.49(d, J=8.52 Hz, 1H), 7.42(m, 1H), 7.28(m, 1H), 7.08(d, J=3.6 Hz, 1H), 7.05(d, J=4 Hz, 1H), 7.00(d, J=8.8 Hz, 2H), 6.85(d, J=8.8 Hz, 2H), 6.78(m, 1H), 4.37(m, 1H), 3.48(m, 2H), 3.28(m, 2H), 1.64(m, 7H), 1.30(m, 1H), 1.06 (m, 3H), 0.85(m, 2H); LCMS: 646.3(M+H)$^+$.

Example 252

(S)-N-[1-[2-(4-Methoxy-phenylamino)-ethylcarbamoyl]-2-(3-trifluoromethyl-phenyl)-ethyl]-3-methyl-benzamide*

Following the procedure of Preparation 1, except substituting Fmoc-(L)-phenyl alanine for Fmoc-(L)-3-trifluorom-

Example 253

(S)-N-[1-[2-(4-Methoxy-phenylamino)-ethylcarbamoyl]-2-(4-trifluoromethyl-phenyl)-ethyl]-3-methylbenzamide*

Following the procedure of Preparation 1, except substituting Fmoc-(L)-phenyl alanine for Fmoc-(L)-4-trifluoromethyl phenyl alanine in Step B and 3-methoxy benzoic acid for m-toluic acid in Step D, the title compound was prepared as a white solid (15 mg, 60%): MS calcd. for $C_{27}H_{29}F_3N_3O_3$ (M+H$^+$) 500.22. found 500.2.

Example 254

(S)-N-{2-Benzyloxy-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-O-benzyl serine in Step B and 3-methoxy benzoic acid for m-toluic acid in Step D, the title compound was prepared as a white solid (10 mg, 43%): MS calcd. for $C_{27}H_{32}N_3O_4$ (M+H$^+$) 462.24. found 462.2.

Example 255

(S)-N-{2-(4-tert-Butyl-phenyl)-1-[2-(4-methoxyphenylamino)-ethylcarbamoyl]-ethyl}-3-methylbenzamide*

Following the procedure of Preparation 1, except substituting Fmoc-(L)-phenyl alanine for Fmoc-(L)-4-tert-butyl phenyl alanine in Step B and 3-methoxy benzoic acid for m-toluic acid in Step D, the title compound was prepared as a white solid (13 mg, 53%): MS calcd. for $C_{30}H_{38}N_3O_3$ (M+H$^+$) 488.29. found 488.3.

Example 256

4-Cyclohexyl-N-[2-(4-methoxy-phenylamino)-ethyl]-2-(S)-(2-(S)-phenyl-propionylamino)-butyramide;*

$C_{28}H_{39}N_3O_3$; LCMS: 466.6 (M+H)$^+$.

Example 257

(S)-N-{2-(1H-Indol-3-yl)-1-[2-(4-methoxy-phenylamino)-ethylcarbamoyl]-ethyl}-3-methyl-benzamide*

Following the procedure of Preparation 1, except substituting Fmoc-(L)-phenyl alanine for Fmoc-(L)-N-Boc-tryptophane in Step B and 3-methoxy benzoic acid for m-toluic acid in Step D, the title compound was prepared as a white solid (8 mg, 34%): $^1$H-NMR (400 MHz, CD$_3$OD) δ=7.69–6.71 (m, 13H), 4.80 (t, J=7.3, 1H), 3.72 (s, 3H), 3.43–3.30 (m, 4H), 3.15–3.02 (m, 2H), 2.40 (s, 3H). MS calcd. for $C_{28}H_{31}N_4O_3$ (M+H$^+$) 471.24. found 471.2.

Example 258

(S)-N-{1-[2-(4-Methoxy-phenylamino)-ethylcarbamoyl]-2-naphthalen-1-yl-ethyl}-3-methyl-benzamide*

Following the procedure of Preparation 1, except substituting Fmoc-(L)-phenyl alanine for Fmoc-(S)-2-amino-3-(1-naphtyl)-propionic acid in Step B and 3-methoxy benzoic acid for m-toluic acid in Step D, the title compound was prepared as a white solid (12 mg, 50%): MS calcd. for $C_{30}H_{32}N_3O_3$ (M+H$^+$) 482.24. found 482.2.

Example 259

(S)-N-{2-Benzyloxy-1-[2-(4-methoxy-phenylamino)-ethylcarbamoyl]-propyl}-3-methyl-benzamide*

Following the procedure of Preparation 1, except substituting Fmoc-(L)-phenyl alanine for Fmoc-(L)-O-benzyl threonine in Step B and 3-methoxy benzoic acid for m-toluic acid in Step D, the title compound was prepared as a white solid (8 mg, 34%): MS calcd. for $C_{28}H_{34}N_3O_4$ (M+H$^+$) 476.25. found 476.2.

Example 260

3-Cyclohexyl-2-(S)-[2-(3-fluoro-phenyl)-acetylamino]-N-[2-(4-fluoro-phenylamino)-ethyl]-propionamide*

$C_{25}H_{31}F_2N_3O_2$; $^1$H NMR (CDCl$_3$) δ(ppm) 8.60(m, 1H), 7.52(m, 2H), 7.40(m, 1H), 7.28(m, 2H), 7.11(m, 3H), 6.60 (m, 1H), 4.28(m, 1H), 3.75(m, 5H), 3.55(m, 1H), 1.85(m, 6H), 1.70(m, 1H), 1.34(m, 4H), 1.05(m, 2H); LCMS: 444.5 (M+H)$^+$.

Example 261

(S)-N-{1-[2-(4-Methoxy-phenylamino)-ethylcarbamoyl]-2-naphthalen-2-yl-ethyl}-3-methyl-benzamide*

Following the procedure of Preparation 1, except substituting Fmoc-(L)-phenyl alanine for Fmoc-(S)-2-amino-3-(2-naphtyl)-propionic acid in Step B and 3-methoxy benzoic acid for m-toluic acid in Step D, the title compound was prepared as a white solid (13 mg, 54%): MS calcd. for $C_{30}H_{32}N_3O_3$ (M+H$^+$) 482.24. found 482.2.

Example 262

(S)-N-{1-[2-(4-Methoxy-phenylamino)-ethylcarbamoyl]-2-pyridin-3-yl-ethyl}-3-methyl-benzamide*

Following the procedure of Preparation 1, except substituting Fmoc-(L)-phenyl alanine for Fmoc-(L)-3-pyridyl alanine in Step B and 3-methoxy benzoic acid for m-toluic acid in Step D, the title compound was prepared as a white solid (3 mg, 14%): MS calcd. for $C_{25}H_{29}N_4O_3$ (M+H$^+$) 433.22. found 433.2.

Example 263

(S)-N-{1-[2-(4-Methoxy-phenylamino)-ethylcarbamoyl]-2-pyridin-4-yl-ethyl}-3-methyl-benzamide*

Following the procedure of Preparation 1, except substituting Fmoc-(L)-phenyl alanine for Fmoc-(L)-4-pyridyl alanine in Step B and 3-methoxy benzoic acid for m-toluic acid in Step D, the title compound was prepared as a white solid (5 mg, 23%): MS calcd. for $C_{25}H_{29}N_4O_3$ $(M+H^+)$ 433.22. found 433.2.

Example 264

Furan-2-carboxylic acid (S)-{2-cyclohexyl-1-[2-(4-fluoro-phenylamino)-ethylcarbamoyl]-ethyl}-amide*

$C_{22}H_{22}FN_3O_3$; $^1H$ NMR $(CDCl_3)$ $\delta$(ppm) 8.42(m, 1H), 7.41(m, 3H), 7.08(m, 3H), 6.89(m, 1H), 6.40(m, 1H), 4.30 (m, 1H), 3.52(m, 4H), 1.66(m, 7H), 1.34(m, 1H), 1.12(m, 3H), 0.90(m, 2H); LCMS: 402.5 $(M+H)^+$.

Example 265

3-Cyclohexyl-N-[2-(4-fluoro-phenylamino)-ethyl]-2-(S)-(2-tetrazol-1-yl-acetylamino)-propionamide*

$C_{20}H_{28}FN_7O_2$; $^1H$ NMR $(CDCl_3)$ $\delta$(ppm) 8.85(s, 1H), 8.32(m, 1H), 7.96(m, 1H), 7.31(m, 2H), 7.07(m, 2H), 5.28 (d, J=16.8 Hz, 1H), 5.15(d, J=16.8 Hz, 1H), 4.28(m, 1H), 3.45(m, 4H), 1.52(m, 7H), 1.30(m, 4H), 0.82(m, 2H); LCMS: 418.5 $(M+H)^+$.

Example 266

N-[1-[2-(4-Methoxy-phenylamino)-ethylcarbamoyl]-2-(4-nitro-phenyl)-propyl]-3-methyl-benzamide**

Following the procedure of Example 227, except substituting 4-fluoro-phenyl glycine for 2-amino-3-(4-nitro-phenyl)-butyric acid in Step A, the title compound was prepared as a white solid (7 mg, 29%): MS calcd. for $C_{27}H_{32}N_4O_5$ $(M+H^+)$ 491.23. found 491.6.

Example 267

(S)-N-[1-[2-(4-Methoxy-phenylamino)-ethylcarbamoyl]-2-(4-m-tolyloxy-phenyl)-ethyl]-3-methyl-benzamide$^{\$\$}$ Following the procedure of Example 327, except substituting phenyl-boronic acid for 3-methylphenyl-boronic acid in Step D, the title compound was prepared as a white solid (7 mg, 26%): $^1$H-NMR (400 MHz, $CD_3OD$) $\delta$=7.60–6.67 (m, 16H), 4.64 (dd, J=7.1, J=8.5, 1H), 3.81 (s, 3H), 3.60–3.07 (m, 6H), 2.37 (s, 3H), 2.26 (s, 3H). MS calcd. for $C_{33}H_{36}N_3O_4$ $(M+H^+)$ 538.27. found 538.4.

Example 268 threo-N-{1-[2-(4-Methoxy-phenylamino)-ethylcarbamoyl]-2-phenyl-propyl}-3-methyl-benzamide**

Following the procedure of Example 227, except substituting 4-fluoro-phenyl glycine for threo-DL-β-methyl phenylalanine in Step A, the title compound was prepared as a white solid (5 mg, 22%): $^1$H-NMR (400 MHz, $CD_3OD$) $\delta$=7.41–7.02 (m, 13H), 4.65 (d, J=10.0, 1H), 3.81 (s, 3H), 3.77–2.96 (m, 5H), 2.30 (s, 3H), 1.33 (d, J=7.0, 3H). MS calcd. for $C_{27}H_{32}N_3O_3$ $(M+H^+)$ 446.24. found 446.6.

Example 269 erythro-N-{1-[2-(4-Methoxy-phenylamino)-ethylcarbamoyl]-2-phenyl-propyl}-3-methyl-benzamide**

Following the procedure of Example 227, except substituting 4-fluoro-phenyl glycine for erythro-DL-β-methyl phenylalanine in Step A, the title compound was prepared as a white solid (6 mg, 27%): $^1$H-NMR (400 MHz, $CD_3OD$) $\delta$=7.68–7.01 (m, 13H), 4.61 (d, J=10.2, 1H), 3.80 (s, 3H), 3.77–2.96 (m, 5H), 2.40 (s, 3H), 1.41 (d, J=6.9, 3H). MS calcd. for $C_{27}H_{32}N_3O_3$ $(M+H^+)$ 446.24. found 446.5.

Example 270

(S)-N-{2-Biphenyl-4-yl-1-[2-(4-methoxy-phenylamino)-ethylcarbamoyl]-ethyl}-3-methyl-benzamide.

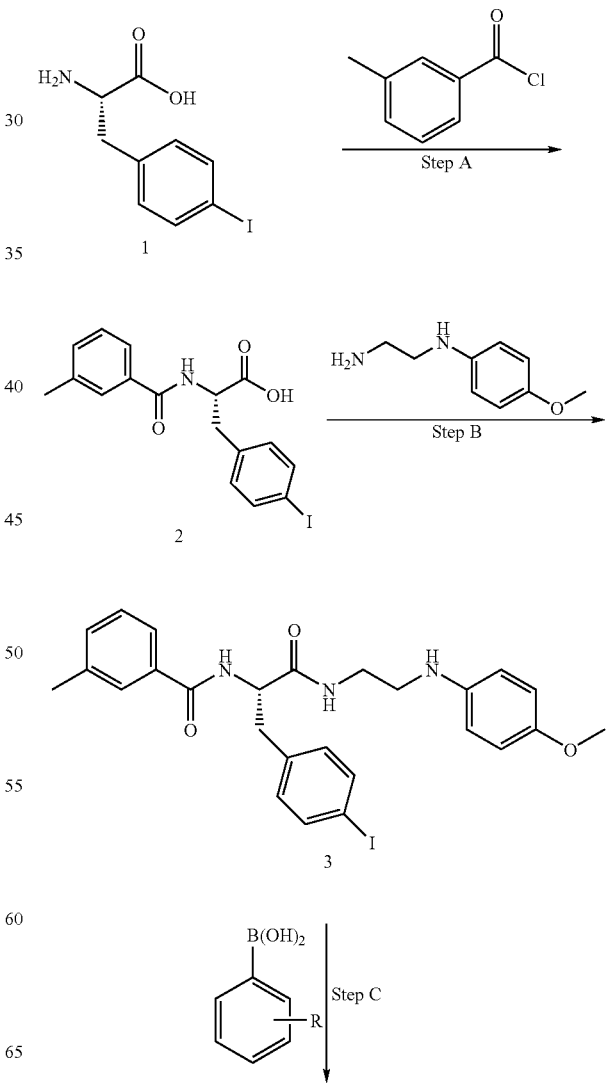

-continued

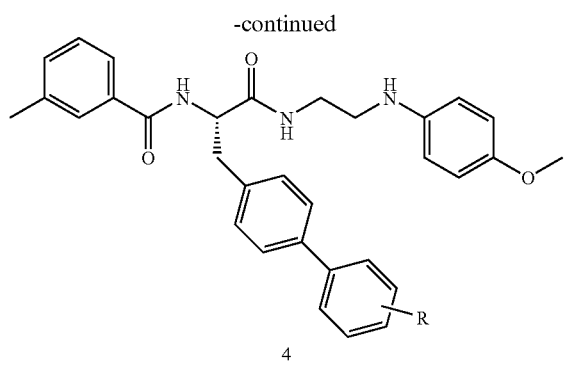

4

Step A: L-p-Iodo-phenylalanine (3.00 g, 10 mmol) was dissolved in H$_2$O (25 mL) containing equimolar amounts of NaOH (0.40 g, 10 mmol). The solution was cooled to 0° C., then m-toluoyl chloride (1.32 mL, 10 mmol) was added dropwise under vigorous stirring. The mixture was allowed to warm to room temperature and stirred for approx. 2 h. After neutralization with 0.5 M HCl, the product was extracted from the reaction mixture three times with EtOAc. The combined organic layers were dried (MgSO$_4$), filtered and the solvent was removed in vacuo to yield (S)-(3-(4-Iodo-phenyl)-2-(3-methyl-benzoylamino)-propionic acid 2 (3.36 g, 82%): $^1$H-NMR (400 MHz, CD$_3$OD) δ=7.62–7.05 (m, 8H), 4.82 (dd, J=5.0, J=9.7, 1H), 3.32–3.26 (m, 1H), 3.08–3.03 (m, 1H), 2.36 (s, 3H). MS calcd. for C$_{17}$H$_{17}$INO$_3$ (M+H$^+$) 410.22. found 410.2.

Step B: (S)-(3-(4-Iodo-phenyl)-2-(3-methyl-benzoylamino)-propionic acid 2 (3.36 g, 8.2 mmol) was dissolved in DMF (40 mL), HOBt (1.20 g, 9 mmol) and DIC (1.38 ml, 8.9 mmol) were added and the solution was stirred for 10 min at room temperature. N-(4-Mthoxyphenyl)-ethane-1,2-diamine (1.48 g, 8.9 mmol) was added and the solution was stirred for 4 h at room temperature. The reaction mixture was then diluted with EtOAc and washed with H$_2$O three times. The organic solvent was partially removed, upon which the product precipitated. The precipitate was collected by filtration, recrystallized from EtOAc and dried under high vacuum to yield (S)-N-{2-(4-Iodo-phenyl)-1-[2-(4-methoxy-phenylamino)-ethylcarbamoyl]-ethyl}-3-methyl-benzamide 3 (3.03 g, 68%): $^1$H-NMR (400 MHz, CD$_3$OD) δ=7.59–7.6.60 (m, 12H), 4.71 (dd, J=7.0, J=8.2, 1H), 3.69 (s, 3H), 3.38–2.97 (m, 6H), 2.37 (s, 3H). MS calcd. for C$_{26}$H$_{29}$IN$_3$O$_3$ (M+H$^+$) 558.12. found 558.1.

Step C: (S)-N-{2-(4-Iodo-phenyl)-1-[2-(4-methoxy-phenylamino)-ethylcarbamoyl]-ethyl}-3-methyl-benzamide 3 (20 mg, 0.04 mmol) was suspended in a 2:1 mixture of dioxane and water (3 mL) together with phenyl-boronic acid (13 mg, 0.12 mmol), Na$_2$CO$_3$ (15 mg, 0.16 mmol) and Pd(PPh$_3$)$_4$ (4 mg, 0.004 mmol). The mixture was heated to 150° C. (microwave-assisted) for 5 min and filtered. The filtrate was subjected to reverse phase HPLC, the fractions containing the product were combined and lyophilized to yield the title compound as a white solid (9 mg, 44%): $^1$H-NMR (400 MHz, CD$_3$OD) δ=7.57–6.74 (m, 17H), 4.83 (m, 1H), 3.74 (s, 3H), 3.72–3.23 (m, 4H), 2.36 (s, 3H). MS calcd. for C$_{32}$H$_{34}$N$_3$O$_3$ (M+H$^+$) 508.26. found 508.2.

For the examples which were prepared according to the procedures in Example 270, partial or complete racemization at the stereogenic center of the a-amino acids may have occurred.

Example 271

(S)-N-[1-[2-(4-Methoxy-phenylamino)-ethylcarbamoyl]-2-(3'-nitro-biphenyl-4-yl)-ethyl]-3-methyl-benzamide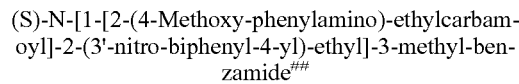

Following the procedure of Example 270, except substituting phenyl-boronic acid for 3-nitrophenyl-boronic acid in Step C, the title compound was prepared as a white solid (8 mg, 36%): MS calcd. for C$_{32}$H$_{33}$N$_4$O$_5$ (M+H$^+$) 553.25. found 553.2.

Example 272

Furan-3-carboxylic acid (S)-{2-cyclohexyl-1-[2-(4-fluoro-phenylamino)-ethylcarbamoyl]-ethyl}-amide*

C$_{22}$H$_{28}$FN$_3$O$_3$; $^1$H NMR (CDCl$_3$) δ(ppm) 8.48(m, 1H), 7.83(s, 1H), 7.40(m, 2H), 7.32(m, 1H), 7.07(m, 3H), 6.54(m, 1H), 4.31(m, 1H), 3.53(m, 3H), 3.40(m, 1H), 1.60(m, 7H), 1.30(m, 1H), 1.14(m, 3H), 0.87(m, 2H); LCMS: 402.5 (M+H)$^+$.

Example 273

(S)-N-[1-[2-(4-Methoxy-phenylamino)-ethylcarbamoyl]-2-(2'-nitro-biphenyl-4-yl)-ethyl]-3-methyl-benzamide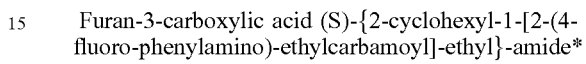

Following the procedure of Example 270, except substituting phenyl-boronic acid for 2-nitrophenyl-boronic acid in Step C, the title compound was prepared as a white solid (8 mg, 36%): MS calcd. for C$_{32}$H$_{33}$N$_4$O$_5$ (M+H$^+$) 553.25. found 553.2.

Example 274

(S)-N-[1-[2-(4-Methoxy-phenylamino)-ethylcarbamoyl]-2-(4-pyridin-3-yl-phenyl)-ethyl]-3-methyl-benzamide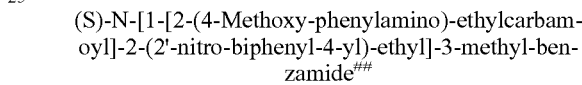

Following the procedure of Example 270, except substituting phenyl-boronic acid for 3-pyridyl-boronic acid in Step C, the title compound was prepared as a white solid (4 mg, 20%): MS calcd. for C$_{31}$H$_{33}$N$_4$O$_3$ (M+H$^+$) 509.26. found 509.2.

Example 275

(S)-N-[1-[2-(4-Methoxy-phenylamino)-ethylcarbamoyl]-2-(4-thiophen-3-yl-phenyl)-ethyl]-3-methyl-benzamide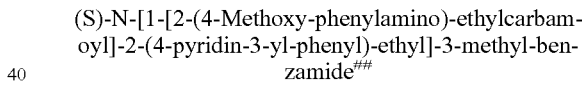

Following the procedure of Example 270, except substituting phenyl-boronic acid for 3-thienyl-boronic acid in Step C, the title compound was prepared as a white solid (9 mg, 44%): MS calcd. for C$_{30}$H$_{32}$N$_3$O$_3$S (M+H$^+$) 514.22. found 514.2.

Example 276

(S)-N-{2-(4'-Cyano-biphenyl-4-yl)-1-[2-(4-methoxy-phenylamino)-ethylcarbamoyl]-ethyl}-3-methyl-benzamide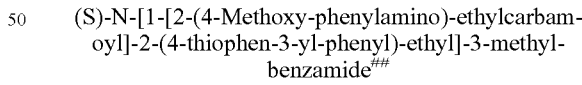

Following the procedure of Example 270, except substituting phenyl-boronic acid for 4-cyanophenyl-boronic acid in Step C, the title compound was prepared as a white solid (8 mg, 38%): MS calcd. for $C_{33}H_{33}N_4O_{3}S$ (M+H$^+$) 533.26. found 533.2.

Example 277

(S)-N-[1-[2-(4-Methoxy-phenylamino)-ethylcarbamoyl]-2-(4-pyridin-4-yl-phenyl)-ethyl]-3-methyl-benzamide$^{\#\#}$ Following the procedure of Example 270, except substituting phenyl-boronic acid for 4-pyridyl-boronic acid in Step C, the title compound was prepared as a white solid (4 mg, 20%): MS calcd. for $C_{31}H_{33}N_4O_3$ (M+H$^+$) 509.26. found 509.2.

Example 278

(S)-N-{2-(4'-Chloro-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 4-chlorophenyl-boronic acid in Step C, the title compound was prepared as a white solid (8 mg, 37%): MS calcd. for $C_{32}H_{33}ClN_3O_3$ (M+H$^+$) 542.22. found 542.2.

Example 279

(S)-N-{2-(2',3'-Dimethoxy-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 2,3-dimethoxyphenyl-boronic acid in Step C, the title compound was prepared as a white solid (10 mg, 44%): MS calcd. for $C_{34}H_{38}N_3O_5$ (M+H$^+$) 568.28. found 568.3.

Example 280

(S)-N-{2-(3'-Amino-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 3-aminophenyl-boronic acid in Step C, the title compound was prepared as a white solid (8 mg, 38%): MS calcd. for $C_{32}H_{35}N_4O_3$ (M+H$^+$) 523.27. found 523.3.

Example 281

(S)-N-{2-(3',4'-Dimethoxy-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 3,4-dimethoxyphenyl-boronic acid in Step C, the title compound was prepared as a white solid (12 mg, 53%): MS calcd. for $C_{34}H_{38}N_3O_5$ (M+H$^+$) 568.28. found 568.3.

Example 282

(S)-N-{2-(4'-Hydroxymethyl-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 4-hydroxymethylphenyl-boronic acid in Step C, the title compound was prepared as a white solid (11 mg, 51%): MS calcd. for $C_{33}H_{36}N_3O_4$ (M+H$^+$) 538.27. found 538.2.

Example 283

(S)-N-{2-(5'-Fluoro-2'-methoxy-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 5-fluoro-2-methoxyphenyl-boronic acid in Step C, the title compound was prepared as a white solid (10 mg, 45%): MS calcd. for $C_{33}H_{35}FN_3O_4$ (M+H$^+$) 556.26. found 556.3.

Example 284

(S)-N-{2-(3'-Hydroxymethyl-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 3-hydroxymethylphenyl-boronic acid in Step C, the title compound was prepared as a white solid (11 mg, 51%): MS calcd. for $C_{33}H_{36}N_3O_4$ (M+H$^+$) 538.27. found 538.3.

Example 285

(S)-N-{2-(2',5'-Dimethoxy-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 2,5-dimethoxyphenyl-boronic acid in Step C, the title compound was prepared as a white solid (9 mg, 40%): MS calcd. for $C_{34}H_{38}N_3O_5$ (M+H$^+$) 568.28. found 568.3.

Example 286

(S)-N-{2-(2',5'-Dichloro-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 2,5-dichlorophenyl-boronic acid in Step C, the title compound was prepared as a white solid (10 mg, 43%): MS calcd. for $C_{32}H_{32}Cl_2N_3O_3$ (M+H$^+$) 576.18. found 576.2.

Example 287

(S)-N-{2-(4'-Dimethylamino-biphenyl-4-yl)-1-[2-(4-methoxy-phenylamino)-ethylcarbamoyl]-ethyl}-3-methyl-benzamide$^{\#\#}$ Following the procedure of Example 270, except substituting phenyl-boronic acid for 4-dimethylaminophenyl-boronic acid in Step C, the title compound was prepared as a white solid (5 mg, 23%): MS calcd. for $C_{34}H_{39}N_4O_3$ (M+H$^+$) 551.30. found 551.3.

Example 288

(S)-N-{2-(2'-Acetyl-biphenyl-4-yl)-1-[2-(4-methoxy-phenylamino)-ethylcarbamoyl]-ethyl}-3-methyl-benzamide[##]

Following the procedure of Example 270, except substituting phenyl-boronic acid for 2-acetylphenyl-boronic acid in Step C, the title compound was prepared as a white solid (7 mg, 32%): MS calcd. for $C_{34}H_{36}N_3O_4$ (M+H$^+$) 550.27. found 550.3.

Example 289

(S)-N-{2-(4'-Hydroxy-biphenyl-4-yl)-1-[2-(4-methoxy-phenylamino)-ethylcarbamoyl]-ethyl}-3-methyl-benzamide[##]

Following the procedure of Example 270, except substituting phenyl-boronic acid for 4-hydroxyphenyl-boronic acid in Step C, the title compound was prepared as a white solid (8 mg, 38%): MS calcd. for $C_{32}H_{34}N_3O_4$ (M+H$^+$) 524.25. found 524.3.

Example 290

(S)-N-{2-(3'-Acetyl-biphenyl-4-yl)-1-[2-(4-methoxy-phenylamino)-ethylcarbamoyl]-ethyl}-3-methyl-benzamide[##]

Following the procedure of Example 270, except substituting phenyl-boronic acid for 3-acetylphenyl-boronic acid in Step C, the title compound was prepared as a white solid (12 mg, 55%): MS calcd. for $C_{34}H_{36}N_3O_4$ (M+H$^+$) 550.27. found 550.3.

Example 291

(S)-N-{2-[4-(2,4-Dimethoxy-pyrimidin-5-yl)-phenyl]-1-[2-(4-methoxy-phenylamino)-ethylcarbamoyl]-ethyl}-3-methyl-benzamide[##]

Following the procedure of Example 270, except substituting phenyl-boronic acid for 2,4-dimethoxy-5-pyrimidinyl-boronic acid in Step C, the title compound was prepared as a white solid (10 mg, 44%): MS calcd. for $C_{32}H_{36}N_5O_5$ (M+H$^+$) 570.27. found 570.3.

Example 292

(S)-N-{1-[2-(4-Methoxy-phenylamino)-ethylcarbamoyl]-2-[4-(6-methoxy-pyridin-3-yl)-phenyl]-ethyl}-3-methyl-benzamide[##]

Following the procedure of Example 270, except substituting phenyl-boronic acid for 2-methoxy-5-pyridyl-boronic acid in Step C, the title compound was prepared as a white solid (9 mg, 42%): MS calcd. for $C_{32}H_{35}N_4O_4$ (M+H$^+$) 539.27. found 539.3.

Example 293

5-Methanesulfonyl-thiophene-2-carboxylic acid (S)-{2-cyclohexyl-1-[2-(4-fluoro-phenylamino)-ethylcarbamoyl]-ethyl}-amide*

$C_{23}H_{30}FN_3O_4S_2$; $^1$H NMR (CDCl$_3$) δ(ppm) 8.58(m, 1H), 7.69(d, J=5.2, 1H), 7.54(d, J=4.0 Hz, 1H), 7.50(d, J=4.0 Hz, 1H), 7.44(m, 2H), 7.13(m, 2H), 4.34(m, 1H), 3.59(m, 3H), 3.38(m, 1H), 3.08(s, 3H), 1.66(m, 7H), 1.35(m, 1H), 1.13(m, 3H), 0.88(m, 2H); LCMS: 496.4 (M+H)$^+$.

Example 294

N-(S)-{2-cyclohexyl-1-[2-(4-fluoro-phenylamino)-ethylcarbamoyl]-ethyl}-2-(S)-phenyl-propionamide*

$C_{26}H_{34}FN_3O_2$; $^1$H NMR (CDCl$_3$) δ(ppm) 7.62(m, 1H), 7.20(m, 5H), 6.95(m, 4H), 6.00(d, J=5.6 Hz, 1H), 4.07(m, 1H), 3.46(m, 3H), 3.23(m, 2H), 1.56(m, 6H), 1.42(m, 4H), 1.04(m, 4H), 0.81(m, 2H); LCMS: 440.5 (M+H)$^+$.

Example 295

Pyridazine-4-carboxylic acid (S)-{2-cyclohexyl-1-[2-(4-fluoro-phenylamino)-ethylcarbamoyl]-ethyl}-amide*

$C_{22}H_{28}FN_5O_2$; $^1$H NMR (CDCl$_3$) δ(ppm) 9.62(m, 1H), 9.28(m, 1H), 8.59(d, J=6.4 Hz, 1H), 8.47(m, 1H), 8.12(m, 1H), 7.43(m, 2H), 7.08(m, 2H), 4.53(m, 1H), 3.53(m, 4H), 1.62(m, 7H), 1.36(m, 1H), 1.14(m, 3H), 0.90(m, 2H); LCMS: 414.5 (M+H)$^+$.

Example 296

N-(S)-{2-cyclohexyl-1-[2-(4-fluoro-phenylamino)-ethylcarbamoyl]-ethyl}-3-methanesulfonyl-benzamide*

$C_{25}H_{32}FN_3O_4S$; $^1$H NMR (CDCl$_3$) δ(ppm) 8.57(m, 1H), 8.31(s, 1H), 7.95(m, 2H), 7.73(m, 1H), 7.49(m, 3H), 7.10(m, 2H), 4.42(m, 1H), 3.58(m, 3H), 3.45(m, 1H), 2.97(s, 3H), 1.62(m, 7H), 1.36(m, 1H), 1.14(m, 3H), 0.90(m, 2H); LCMS: 490.4 (M+H)$^+$.

Example 297

3-Cyclohexyl-N-[2-(4-fluoro-phenylamino)-ethyl]-2-(S)-(2-1H-tetrazol-5-yl-acetylamino)-propionamide*

$C_{20}H_{28}FN_7O_2$; $^1$H NMR (CDCl$_3$) δ(ppm) 9.14(s, 1H), 8.62(m, 1H), 8.26(d, J=5.6 Hz, 1H), 7.59(m, 2H), 7.36(m, 2H), 5.58(d, J=16.4 Hz, 1H), 5.44(d, J=16.4 Hz, 1H), 4.56(m, 1H), 3.73(m, 4H), 1.81(m, 7H), 1.41(m, 4H), 1.12(m, 2H); LCMS: 418.5(M+H)$^+$.

Example 298

Cyclopropanecarboxylic acid (S)-{2-cyclohexyl-1-[2-(4-fluoro-phenylamino)-ethylcarbamoyl]-ethyl}-amide*

$C_{21}H_{30}FN_3O_2$; $^1$H NMR (CDCl$_3$) δ(ppm) 8.60(m, 1H), 7.52(m, 2H), 7.20(m, 2H), 6.78(d, J=4 Hz, 1H), 4.18(m, 1H), 3.69(m, 3H), 3.42(m, 1H), 1.74(m, 8H), 1.54(m, 1H), 1.26(m, 3H), 1.00(m, 2H), 0.85(m, 3H), 1.44(m, 1H); LCMS: 376.5(M+H)$^+$.

Example 299

N-(S)-{2-cyclohexyl-1-[2-(4-fluoro-phenylamino)-ethylcarbamoyl]-ethyl}-4-methanesulfonylamino-benzamide*

$C_{25}H_{33}FN_4O_4S$; $^1$H NMR (CDCl$_3$) δ(ppm) 8.68(s, 1H), 8.05(m, 1H), 7.61(m, 2H), 7.43(d, J=8.8 Hz, 2H), 7.21(m, 1H), 7.17(m, 2H), 6.83(d, J=8.8 Hz, 2H), 4.20(m, 1H), 3.82(m, 1H), 3.67(m, 1H), 3.43(m, 2H), 2.88(s, 3H), 1.74(m, 7H), 1.43(m, 1H), 1.20(m, 3H), 0.94(m, 2H); LCMS: 505.4 (M+H)$^+$.

Example 300

(S)-N-{2-[4-(4-Chloro-phenoxy)-phenyl]-1-[2-(4-methoxy-phenylamino)-ethylcarbamoyl]-ethyl}-3-methyl-benzamide$^{\$\$}$ Following the procedure of Example 327, except substituting phenyl-boronic acid for 4-chlorophenyl-boronic acid in Step D, the title compound was prepared as a white solid (4 mg, 14%): $^1$H-NMR (400 MHz, CD$_3$OD) δ=7.60–6.86 (m, 16H), 4.66 (dd, J=7.0, J=8.6, 1H), 3.81 (s, 3H), 3.60–3.07 (m, 6H), 2.38 (s, 3H). MS calcd. for $C_{32}H_{33}ClN_3O_4$ (M+H$^+$) 558.22. found 558.4.

Example 301

3-Cyclohexyl-N-[2-(4-fluoro-phenylamino)-ethyl]-2-(S)-[2-(4-methoxy-phenyl)-acetylamino]-propionamide*

$C_{26}H_{34}FN_3O_3$; $^1$H NMR (CDCl$_3$) δ(ppm) 8.26(m, 1H), 7.24(m, 2H), 7.08(m, 2H), 7.01(m, 2H), 6.75(m, 2H), 6.09 (d, J=4.0 Hz, 1H), 3.99(m, 1H), 3.69(s, 3H), 3.48(m, 5H), 3.28(m, 1H), 1.56(m, 6H), 1.42(m, 1H), 1.05(m, 4H), 0.79 (m, 2H); LCMS: 456.5(M+H)$^+$.

Example 302

2-(S)-[2-(3-Chloro-phenyl)-acetylamino]-3-cyclohexyl-N-[2-(4-fluoro-phenylamino)-ethyl]-propionamide*

$C_{25}H_{31}FN_3O_2$; $^1$H NMR (CDCl$_3$) δ(ppm) 8.42(m, 1H), 7.34(m, 5H), 7.16(m, 3H), 6.47(d, J=4.4 Hz, 1H), 4.17(m, 1H), 3.61(m, 5H), 3.41(m, 1H), 1.71(m, 6H), 1.59(m, 1H), 1.13(m, 4H), 0.86(m, 2H); LCMS: 460.5($^{35}$ClM+H)$^+$, 462.4 ($^{37}$ClM+H)$^+$.

Example 303

3-Cyclohexyl-N-[2-(4-fluoro-phenylamino)-ethyl]-2-(S)-phenylacetylamino-propionamide*

$C_{25}H_{32}FN_3O_2$; $^1$H NMR (CDCl$_3$) δ(ppm) 8.37(m, 1H), 7.29(m, 6H), 7.24(m, 1H), 7.08(m, 2H), 6.23(d, J=4.0 Hz, 1H), 4.09(m, 1H), 3.57(m, 5H), 3.37(m, 1H), 1.65(m, 6H), 1.59(m, 1H), 1.13(m, 4H), 0.86(m, 2H); LCMS: 426.4(M+H)$^+$.

Example 304

3-Cyclohexyl-N-[2-(4-fluoro-phenylamino)-ethyl]-2-(S)-(2-o-tolyl-acetylamino)-propionamide*

$C_{26}H_{34}FN_3O_2$; $^1$H NMR (CDCl$_3$) δ(ppm) 8.42(m, 1H), 7.34(m, 2H), 7.22(m, 4H), 7.09(m, 2H), 6.10(d, J=3.6 Hz, 1H), 4.08(m, 1H), 3.57(m, 5H), 3.44(m, 1H), 2.25(s, 3H), 1.58(m, 7H), 1.11(m, 4H), 0.85(m, 2H); LCMS: 440.5(M+H)$^+$.

Example 305

2-(S)-[2-(4-Chloro-phenyl)-acetylamino]-3-cyclohexyl-N-[2-(4-fluoro-phenylamino)-ethyl]-propionamide*

$C_{25}H_{31}ClFN_3O_2$; $^1$H NMR (CDCl$_3$) δ(ppm) 8.33(m, 1H), 7.13(m, 8H), 6.29(d, J=4.0 Hz, 1H), 4.02(m, 1H), 3.48(m, 5H), 3.28(m, 1H), 1.62(m, 6H), 1.45(m, 1H), 1.12(m, 4H), 0.82(m, 2H); LCMS: 460.4($^{35}$ClM+H)$^+$, 462.5($^{37}$ClM+H)$^+$.

Example 306

3-Cyclohexyl-2-(S)-[2-(2-fluoro-phenyl)-acetylamino]-N-[2-(4-fluoro-phenylamino)-ethyl]-propionamide*

$C_{25}H_{31}F_2N_3O_2$; $^1$H NMR (CDCl$_3$) δ(ppm) 8.20(m, 1H), 7.19(m, 3H), 7.16(m, 2H), 6.98(m, 4H), 6.29(d, J=4.0 Hz, 1H), 4.06(m, 1H), 3.48(m, 5H), 3.28(m, 1H), 1.61(m, 6H), 1.47(m, 1H), 1.08(m, 4H), 0.81(m, 2H); LCMS: 444.5(M+H)$^+$.

Example 307

3-Cyclohexyl-2-(S)-diphenylacetylamino-N-[2-(4-fluoro-phenylamino)-ethyl]-propionamide*

$C_{31}H_{36}FN_3O_2$; $^1$H NMR (CDCl$_3$) δ(ppm) 8.46(m, 1H), 7.18(m, 10H), 6.91(m, 2H), 6.80(m, 2H), 6.20(d, J=3.6 Hz, 1H), 4.05(m, 1H), 3.51(m, 3H), 3.18(m, 1H), 1.50(m, 7H), 1.43(m, 1H), 1.01(m, 4H), 0.75(m, 2H); LCMS: 502.5(M+H)$^+$.

Example 308

N-(S)-{2-cyclohexyl-1-[2-(4-fluoro-phenylamino)-ethylcarbamoyl]-ethyl}-2-(2-fluoro-biphenyl-4-yl)-propionamide*

$C_{32}H_{37}F_2N_3O_2$; $^1$H NMR (CDCl$_3$) δ(ppm) 8.33(m, 1H), 7.35(m, 8H), 7.01(m, 4H), 6.30(m, 1H), 4.02(m, 1H), 3.60 (m, 3H), 3.37(m, 2H), 1.52(m, 9H), 1.42(m, 1H), 1.04(m, 4H), 0.78(m, 2H); LCMS: 534.5(M+H)$^+$.

Example 309

N-{2-cyclohexyl-1-(S)-[2-(4-fluoro-phenylamino)-ethylcarbamoyl]-ethyl}-2-p-tolyl-propionamide*

$C_{27}H_{36}FN_3O_2$; $^1$H NMR (CDCl$_3$) δ(ppm) 8.18(m, 1H), 7.37(m, 1H), 7.23(m, 1H), 7.02(m, 6H), 6.02(m, 1H), 3.95 (m, 1H): 3.53(m, 3H), 3.31(m, 2H), 2.22(d, J=15.2 Hz, 3H), 1.55(m, 5H), 1.37(m, 5H), 1.01(m, 4H), 0.74(m, 2H); LCMS: 454.5(M+H)$^+$.

Example 310

N-{2-cyclohexyl-1-(S)-[2-(4-fluoro-phenylamino)-ethylcarbamoyl]-ethyl}-2-(4-fluoro-phenyl)-propionamide*

$C_{26}H_{33}F_2N_3O_2$; $^1$H NMR (CDCl$_3$) δ(ppm) 8.25(m, 1H), 7.38(m, 1H), 7.21(m, 1H), 6.97(m, 6H), 6.18(m, 1H), 3.98(m, 1H), 3.55(m, 4H), 3.34(m, 1H), 1.58(m, 9H), 1.27(m, 1H), 1.06(m, 4H), 0.77(m, 2H); LCMS: 458.5 (M+H)$^+$.

Example 311

N-{2-cyclohexyl-1-(S)-[2-(4-fluoro-phenylamino)-ethylcarbamoyl]-ethyl}-2-(4-hydroxy-phenyl)-propionamide*

$C_{26}H_{34}FN_3O_3$; $^1$H NMR (CDCl$_3$) δ(ppm) 8.18(m, 1H), 7.39(m, 1H), 7.26(m, 1H), 7.03(m, 4H), 6.68(m, 2H), 6.13(m, 1H), 3.96(m, 2H), 3.52(m, 4H), 3.31(m, 2H), 1.56(m, 8H), 1.18(m, 1H), 1.04(m, 4H), 0.74(m, 2H); LCMS: 465.5 (M+H)$^+$.

Example 312

2-(4-Chloro-phenyl)-N-{2-cyclohexyl-1-(S)-[2-(4-fluoro-phenylamino)-ethylcarbamoyl]-ethyl}-propionamide*

$C_{26}H_{33}FN_3O_2$; $^1$H NMR (CDCl$_3$) δ(ppm) 8.24(m, 1H), 7.31(m, 1H), 7.16(m, 2H), 7.04(m, 5H), 6.13(m, 1H), 3.92(m, 1H), 3.50(m, 4H), 3.28(m, 1H), 1.54(m, 7H), 1.28(m, 3H), 0.99(m, 4H), 0.71(m, 2H); LCMS: 474.5($^{35}$ClM+H)$_+$, 476.5($^{37}$ClM+H)$^+$.

Example 313

N-(S)-{2-cyclohexyl-1-[2-(4-fluoro-phenylamino)-ethylcarbamoyl]-ethyl}-4-methanesulfonyl-benzamide*

$C_{25}H_{32}FN_3O_4S$; $^1$H NMR (CDCl$_3$) δ(ppm) 8.55(m, 1H), 7.90(m, 4H), 7.52(m, 2H), 7.45(m, 1H), 7.19(m, 2H), 4.44(m, 1H), 3.68(m, 3H), 3.45(m, 1H), 3.04(s, 3H), 1.75(m, 7H), 1.46(m, 1H), 1.21(m, 3H), 0.99(m, 2H); LCMS: 490.4 (M+H)$^+$.

Example 314

Thiazole-4-carboxylic acid (S)-{2-cyclohexyl-1-[2-(4-fluoro-phenylamino)-ethylcarbamoyl]-ethyl}-amide*

$C_{21}H_{27}FN_4O_2S$; $^1$H NMR (CDCl$_3$) δ(ppm) 8.97(m, 1H), 8.61(m, 1H), 8.15(m, 1H), 8.11(m, 1H), 7.70(m, 2H), 7.35(m, 2H), 4.56(m, 1H), 3.80(m, 4H), 1.96(m, 7H), 1.63(m, 1H), 1.39(m, 3H), 1.17(m, 2H); LCMS: 419.4(M+H)$^+$.

Example 315

N-{2-cyclohexyl-1-(S)-[2-(4-fluoro-phenylamino)-ethylcarbamoyl]-ethyl}-2-(R)-phenyl-propionamide*

$C_{26}H_{34}FN_3O_2$; $^1$H NMR (CDCl$_3$) δ(ppm) 8.46(m, 1H), 7.50(m, 2H), 7.34(m, 5H), 7.17(m, 2H), 6.16(m, 1H), 4.07(m, 1H), 3.65(m, 4H), 3.42(m, 1H), 1.47(m, 10H), 1.02(m, 4H), 0.76(m, 2H); LCMS: 440.5 (M+H)$^+$.

Example 316

4-Cyano-N-(S)-{2-cyclohexyl-1-[2-(4-fluoro-phenylamino)-ethylcarbamoyl]-ethyl}-benzamide*

$C_{25}H_{29}FN_4O_2$; $^1$H NMR (CDCl$_3$) δ(ppm) 8.32(m, 1H), 7.64(d, J=8.4 Hz, 2H), 7.47(d, J=8.4 Hz, 2H), 7.38(d, J=6.0 Hz, 1H), 7.25(m, 2H), 6.91(m, 2H), 4.26(m, 1H), 3.38(m, 3H), 3.26(m, 1H), 1.47(m, 7H), 1.18(m, 1H), 0.96(m, 3H), 0.76(m, 2H); LCMS: 437.5 (M+H)$^+$.

Example 317

3-Cyclohexyl-N-[2-(4-fluoro-phenylamino)-ethyl]-2-(S)-(2-(R)-hydroxy-2-phenyl-acetylamino)-propionamide*

$C_{25}H_{32}FN_3O_3$; $^1$H NMR (CDCl$_3$) δ(ppm) 8.36(m, 1H), 7.44(m, 2H), 7.28(m, 8H), 4.96(s, 1H), 4.12(m, 1H), 3.79(m, 2H), 3.45(m, 1H), 3.15(m, 1H), 1.75(m, 1H), 1.53(m, 6H), 0.89(m, 6H); LCMS: 442.5 (M+H)$^+$.

Example 318

N-{2-cyclohexyl-1-(S)-[2-(4-fluoro-phenylamino)-ethylcarbamoyl]-ethyl}-2-(R)-phenyl-butyramide*

$C_{27}H_{36}FN_3O_2$; $^1$H NMR (CDCl$_3$) δ(ppm) 8.02(m, 1H), 7.16(m, 7H), 6.98(m, 2H), 6.49(d, J=5.6 Hz, 1H), 4.08(m, 1H), 3.45(m, 2H), 3.25(m, 3H), 1.94(m, 1H), 1.73(m, 1H), 1.55(m, 7H), 1.07(m, 4H), 0.79(m, 5H); LCMS: 454.5(M+H)$^+$.

Example 319

1-Phenyl-cyclopropanecarboxylic acid (S)-{2-cyclohexyl-1-[2-(4-fluoro-phenylamino)-ethylcarbamoyl]-ethyl}-amide*

$C_{27}H_{34}FN_3O_2$; $^1$H NMR (CDCl$_3$) δ(ppm) 8.31(m, 1H), 7.37(m, 4H), 7.27(m, 3H), 7.05(m, 2H), 5.77(d, J=2.8 Hz, 1H), 3.82(m, 1H), 3.53(m, 3H), 3.29(m, 1H), 1.12(m, 14H), 0.80(m, 1H), 0.64(m, 2H); LCMS: 452.5(M+H)$^+$.

Example 320

N-(S)-{2-cyclohexyl-1-[2-(4-fluoro-phenylamino)-ethylcarbamoyl]-ethyl}-2-(R,S)-(4-fluoro-phenyl)-propionamide*

$C_{26}H_{33}F_2N_3O_2$; $^1$H NMR (CDCl$_3$) δ(ppm) 8.06(m, 1H), 7.22(m, 1H), 7.07(m, 1H), 6.89(m, 5H), 6.69(m, 2H), 3.82(m, 1H), 3.42(m, 4H), 3.20(m, 1H), 1.23(m, 9H), 1.16(m, 3H), 0.90(m, 3H), 0.66(m, 1H); LCMS: 496.5 (M+H)$^+$.

Example 321

3-Cyano-N-(S)-{2-cyclohexyl-1-[2-(4-fluoro-phenylamino)-ethylcarbamoyl]-ethyl}-benzamide*

$C_{25}H_{29}FN_4O_2$; $^1$H NMR (CDCl$_3$) δ(ppm) 8.67(m, 1H), 8.04(m, 2H), 7.92(m, 3H), 7.62(m, 2H), 7.36(m, 2H), 4.65(m, 1H), 3.85(m, 4H), 1.90(m, 7H), 1.63(m, 1H), 1.37(m, 3H), 1.16(m, 2H); LCMS: 437.5(M+H)$^+$.

Example 322

5-(4-Fluoro-phenyl)-furan-2-carboxylic acid (S)-{2-cyclohexyl-1-[2-(4-fluoro-phenylamino)-ethylcarbamoyl]-ethyl}-amide*

$C_{28}H_{31}F_2N_3O_3$; LCMS: 496.5 (M+H)$^+$.

Example 323

3-Cyclohexyl-N-[2-(4-fluoro-phenylamino)-ethyl]-2-(S)-[2-(3-trifluoromethyl-phenyl)-acetylamino]-propionamide*

$C_{26}H_{31}F_4N_3O_2$; $^1$H NMR (CDCl$_3$) δ(ppm) 8.26(m, 1H), 7.45(m, 4H), 7.24(m, 2H), 7.07(m, 2H), 6.39(d, J=4.8 Hz, 1H), 4,17(m, 1H), 3.71(s, 2H), 3.57(m, 3H), 3.35(m, 1H), 1.68(m, 7H), 1.19(m, 4H), 0.91(m, 2H); LCMS: 494.5(M+H)$^+$.

Example 324

3-Cyano-N-(S)-{2-cyclohexyl-1-[2-(4-fluoro-phenylamino)-ethylcarbamoyl]-ethyl}-benzamide*

$C_{25}H_{29}FN_4O_2$; $^1$H NMR (CDCl$_3$) δ(ppm) 8.09(m, 1H), 7.99(s, 1H), 7.91(m, 1H), 7.69(m, 1H), 7.46(m, 1H), 7.29(m, 1H), 7.24(m, 2H), 7.03(m, 2H), 4.42(m, 1H), 3.45(m, 3H), 3.37(m, 1H), 1.66(m, 7H), 1.34(m, 1H), 1.16(m, 3H), 0.90(m, 2H); LCMS: 437.5 (M+H)$^+$.

Example 325

3-Cyclohexyl-N-[2-(4-fluoro-phenylamino)-ethyl]-2-(S)-[2-(4-trifluoromethyl-phenyl)-acetylamino]-propionamide*

$C_{26}H_{31}F_4N_3O_2$; $^1$H NMR (CDCl$_3$) δ(ppm) 8.57(M, 1H), 7.62(m, 2H), 7.43(m, 4H), 7.21(m, 2H), 6.63(m, 1H), 4.25(m, 1H), 3.85(m, 1H), 3.83(s, 2H), 3.72(m, 2H), 3.47(m, 1H), 1.73(m, 7H), 1.35(m, 4H), 1.05(m, 2H); LCMS: 494.5 (M+H)$^+$.

Example 326

3-Cyclohexyl-N-[2-(4-fluoro-phenylamino)-ethyl]-2-(S)-[2-(4-methanesulfonyl-phenyl)-acetylamino]-propionamide*

$C_{26}H_{34}FN_3O_4S$; $^1$H NMR (CDCl$_3$) δ(ppm) 8.31(m, 1H), 7.72(d, J=8.4 Hz, 2H), 7.36(d, J=8.4 Hz, 2H), 7.24(m, 2H), 7.05(m, 2H), 6.60(m, 1H), 4.09(m, 1H), 3.65(s, 2H), 3.61(m, 1H), 3.50(m, 2H), 3.26(m, 1H), 2.93(s, 3H), 1.62(m, 7H), 1.12(m, 4H), 0.85(m, 2H); LCMS: 504.5(M+H)$^+$.

Example 327

(S)-N-[1-[2-(4-Methoxy-phenylamino)-ethylcarbamoyl]-2-(4-phenoxy-phenyl)-ethyl]-3-methyl-benzamide

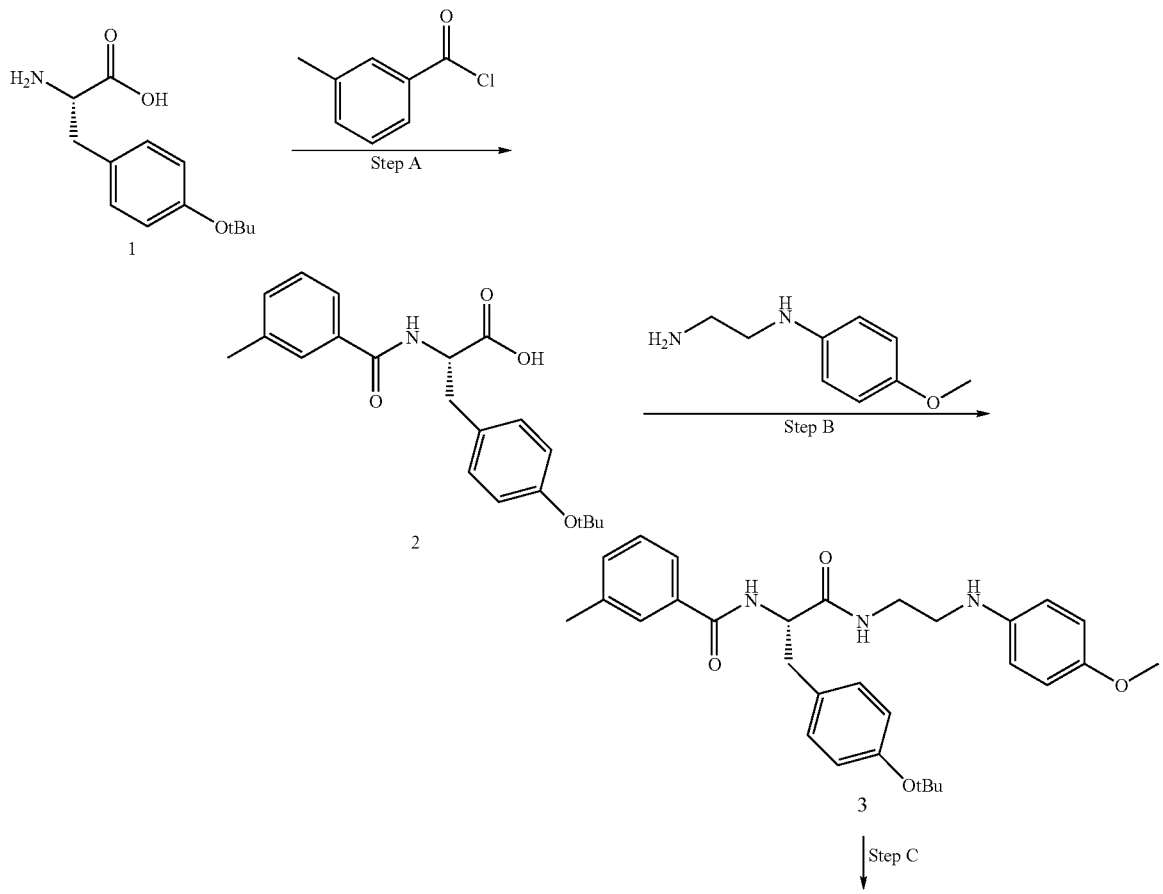

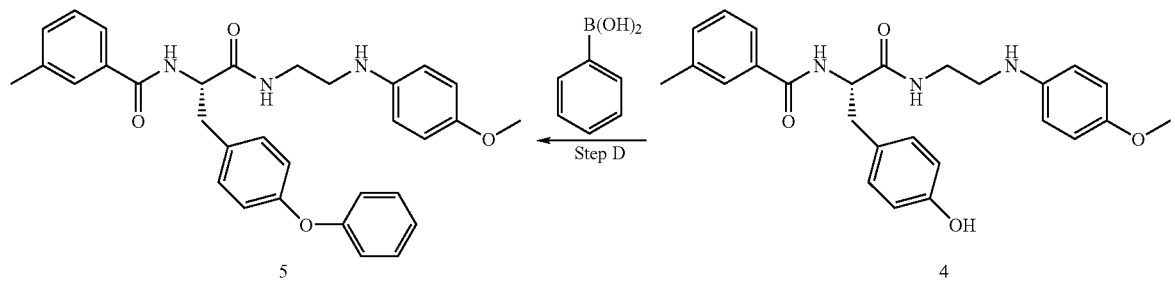

Step A: O-t-Butyl-L-tyrosine 1 (2.00 g, 7.8 mmol) was dissolved in H₂O (10 mL) containing equimolar amounts of NaOH (0.31 g, 7.8 mmol). The solution was cooled to 0° C., then m-toluoyl chloride (1.04 mL, 7.8 mmol) was added dropwise under vigorous stirring. The mixture was allowed to warm to room temperature and stirred for approx. 2 h. After acidification with 0.25 M phosphate buffer (pH 6.2), the product was extracted from the reaction mixture three times with EtOAc. The combined organic layers were dried (MgSO₄), filtered and the solvent was removed in vacuo to yield (S)-3-(4-tert-Butoxy-phenyl)-2-(3-methyl-benzoylamino)-propionic acid 2 (2.17 g, 6.1 mmol, 78%) as a white solid: ¹H-NMR (400 MHz, CD₃OD) δ=7.51–6.87 (m, 8H), 4.82 (dd, J=5.0, J=9.8, 1H), 3.33–3.28 (m, 1H), 3.09–3.03 (m, 1H), 2.35 (s, 3H), 1.27 (s, 9H). MS calcd. for C₂₁H₂₆NO₄ (M+H⁺) 356.19. found 356.4.

Step B: (S)-3-(4-tert-Butoxy-phenyl)-2-(3-methyl-benzoylamino)-propionic acid 2 (0.80 g, 2.25 mmol) was dissolved in DCM (20 mL), HOBt (0.37 g, 2.7 mmol) and DIC (0.42 ml, 2.7 mmol) were added and the solution was stirred for 10 min at room temperature. N-(4-Mthoxyphenyl)-ethane-1,2-diamine (0.45 g, 2.7 mmol) was added and the solution was stirred for 6 h at room temperature. The reaction mixture was then diluted with DCM and washed with H₂O three times. The organic layer was dried (MgSO₄), filtered and the solvent was removed in vacuo. The remainder was purified by chromatography (silica, DCM/MeOH gradient) and dried under high vacuum to afford (S)-N-{2-(4-tert-Butoxy-phenyl)-1-[2-(4-methoxy-phenylamino)-ethylcarbamoyl]-ethyl}-3-methyl-benzamide 3 (0.71 g, 1.4 mmol, 63%) as a white solid: ¹H-NMR (400 MHz, CD₃OD) δ=7.55–6.79 (m, 12H), 4.80 (m, 1H), 3.76 (s, 3H), 3.52–3.47 (m, 2H), 3.24–3.15 (m, 4H), 2.37 (s, 3H), 1.32 (s, 9H). MS calcd. for C₃₀H₃₈N₃O₄ (M+H⁺) 504.29. found 504.6.

Step C: (S)-N-{2-(4-tert-Butoxy-phenyl)-1-[2-(4-methoxy-phenylamino)-ethylcarbamoyl]-ethyl}-3-methyl-benzamide (0.50 g, 1.0 mmol) was dissolved in DCM containing 10% trifluoroacetic acid. The solution was stirred at room temperature for 1 h, then the solvents were removed in vacuo. The remaining crude material was purified by chromatography (silica, DCM/MeOH gradient) and dried under high vacuum to yield (S)-N-{2-(4-Hydroxy-phenyl)-1-[2-(4-methoxy-phenylamino)-ethylcarbamoyl]-ethyl}-3-methyl-benzamide 4 (0.40 g, 0.9 mmol, 90%): ¹H-NMR (400 MHz, CD₃OD) δ=7.62–7.57 (m, 2H), 7.40–7.33 (m, 2H), 7.14–7.12 (m, 2H), 6.85–6.73 (m, 6H), 4.68 (t, J=7.6, 1H), 3.75 (s, 3H), 3.41–3.38 (m, 2H), 3.25–3.01 (m, 4H), 2.41 (s, 3H). MS calcd. for C₂₆H₃₀N₃O₄ (M+H⁺) 448.22. found 448.2.

Step D:. (S)-N-{2-(4-Hydroxy-phenyl)-1-[2-(4-methoxy-phenylamino)-ethylcarbamoyl]-ethyl}-3-methyl-benzamide (0.02 g, 0.05 mmol) 4 was suspended in DCM (1 mL) together with phenyl-boronic acid (7 mg, 0.06 mmol), Cu(OAc)₂ (16 mg, 0.09 mmol) and NEt₃ (30 μL, 0.23 mmol). The mixture was stirred at room temperature for 14 h. The solvent was removed and the crude products were separated on reversed phase HPLC. The fraction containing the title compound 5(S)-N-[1-[2-(4-Methoxy-phenylamino)-ethylcarbamoyl]-2-(4-phenoxy-phenyl)-ethyl]-3-methyl-benzamide (R═H) was lyophilized to yield a white solid (5 mg, 0.009 mmol, 19%): ¹H-NMR (400 MHz, CD₃OD) δ=7.60–6.89 (m, 17H), 4.65 (dd, J=7.1, J=8.4, 1H), 3.81 (s, 3H), 3.61–3.07 (m, 6H), 2.37 (s, 3H). MS calcd. for C₃₂H₃₄N₃O₄ (M+H⁺) 524.25. found 524.4.

For the examples which were prepared according to the procedures in Example 327, partial or complete racemization at the stereogenic center of the a-amino acids may have occurred.

Example 328

(S)-N-{2-[4-(4-Methoxy-phenoxy)-phenyl]-1-[2-(4-methoxy-phenylamino)-ethylcarbamoyl]-ethyl}-3-methyl-benzamide$$

Following the procedure of Example 327, except substituting phenyl-boronic acid for 4-methoxyphenyl-boronic acid in Step D, the title compound was prepared as a white solid (6 mg, 22%): ¹H-NMR (400 MHz, CD₃OD) δ=7.60–6.82 (m, 16H), 4.62 (dd, J=7.2, J=8.3, 1H), 3.81 (s, 3H), 3.77 (s, 3H), 3.61–3.05 (m, 6H), 2.38 (s, 3H). MS calcd. for C₃₃H₃₆N₃O₅ (M+H⁺) 554.27. found 554.4.

Example 329

(S)-N-{2-[4-(3-Chloro-phenoxy)-phenyl]-1-[2-(4-methoxy-phenylamino)-ethylcarbamoyl]-ethyl}-3-methyl-benzamide$$

Following the procedure of Example 327, except substituting phenyl-boronic acid for 3-chlorophenyl-boronic acid in Step D, the title compound was prepared as a white solid (4 mg, 14%): ¹H-NMR (400 MHz, CD₃OD) δ=7.61–6.82 (m, 16H), 4.66 (dd, J=7.1, J=8.5, 1H), 3.81 (s, 3H), 3.61–3.09 (m, 6H), 2.38 (s, 3H). MS calcd. for C₃₂H₃₃ClN₃O₄ (M+H⁺) 558.22. found 558.4.

Example 330

(S)-N-{2-[4-(3,5-Dimethyl-phenoxy)-phenyl]-1-[2-(4-methoxy-phenylamino)-ethylcarbamoyl]-ethyl}-3-methyl-benzamide$^{\$\$}$ Following the procedure of Example 327, except substituting phenyl-boronic acid for 3,5-dimethylphenyl-boronic acid in Step D, the title compound was prepared as a white solid (6 mg, 22%): $^1$H-NMR (400 MHz, CD$_3$OD) δ=7.52–6.43 (m, 15H), 4.56 (dd, J=7.1, J=8.5, 1H), 3.73 (s, 3H), 3.55–2.99 (m, 6H), 2.29 (s, 3H), 2.13 (s, 6H). MS calcd. for C$_{34}$H$_{38}$N$_3$O$_4$ (M+H$^+$) 552.29. found 552.4.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754–9). Kinetic measurements are performed in a total reaction volume of 30 μl in 384-well microtiter plates. Cathepsin S, at a final concentration of 0.3–3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45–50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754–9). Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45–50) and are then used to calculate the inhibition constants for competitive inhibitors.

Cathepsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754–9). Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45–50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci U S A* 2000, 97(14), 7754–9). Kinetic measurements are performed in a total reaction volume of 30 μl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45–50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE II

Assay Data for Inhibitors of Cathepsin S

| Compound | $K_i$ Cat. S[a] | Selectivity for Cat. S over Cat. K[b] |
|---|---|---|
| 1 | ++ | ++ |
| 2 | +++ | + |
| 3 | +++ | +++ |
| 4 | +++ | +++ |
| 5 | ++ | + |
| 6 | +++ | ++ |
| 7 | ++ | ++ |
| 8 | +++ | +++ |
| 9 | ++ | + |
| 10 | +++ | +++ |
| 11 | +++ | + |
| 12 | +++ | + |
| 13 | +++ | +++ |
| 14 | ++ | ++ |
| 15 | ++ | + |
| 16 | ++ | + |
| 17 | +++ | ++ |
| 18 | + | + |
| 19 | ++ | + |
| 20 | ++ | ++ |
| 21 | +++ | + |
| 22 | ++ | + |
| 23 | +++ | ++ |
| 24 | +++ | + |
| 25 | +++ | ++ |
| 26 | +++ | ++ |
| 27 | +++ | +++ |
| 28 | ++ | + |
| 29 | +++ | ++ |
| 30 | +++ | + |
| 31 | +++ | + |
| 32 | +++ | + |
| 33 | + | + |
| 34 | +++ | +++ |
| 35 | +++ | + |
| 36 | +++ | ++ |
| 37 | +++ | ++ |
| 38 | +++ | ++ |
| 39 | ++ | ++ |
| 40 | ++ | + |
| 41 | ++ | ++ |
| 42 | ++ | + |
| 43 | +++ | + |
| 44 | ++ | ++ |
| 45 | +++ | +++ |
| 46 | ++ | ++ |
| 47 | +++ | +++ |
| 48 | ++ | ++ |
| 49 | +++ | ++ |
| 50 | +++ | +++ |
| 51 | +++ | +++ |
| 52 | + | + |
| 53 | +++ | +++ |
| 54 | +++ | + |
| 55 | ++ | ++ |
| 56 | ++ | ++ |
| 57 | ++ | + |
| 58 | +++ | ++ |
| 59 | ++ | ++ |
| 60 | +++ | + |
| 61 | ++ | + |
| 62 | +++ | ++ |
| 63 | + | + |
| 64 | + | + |
| 65 | +++ | ++ |
| 66 | ++ | ++ |
| 67 | +++ | + |
| 68 | +++ | +++ |
| 69 | +++ | + |
| 70 | +++ | +++ |
| 71 | +++ | ++ |
| 72 | + | ++ |
| 73 | +++ | ++ |
| 74 | +++ | +++ |
| 75 | +++ | +++ |
| 76 | +++ | +++ |
| 77 | +++ | ++ |
| 78 | +++ | + |
| 79 | + | + |
| 80 | ++ | +++ |
| 81 | ++ | ++ |
| 82 | ++ | + |
| 83 | +++ | ++ |
| 84 | +++ | ++ |
| 85 | +++ | ++ |
| 86 | +++ | ++ |
| 87 | +++ | ++ |
| 88 | ++ | + |
| 89 | ++ | + |
| 90 | ++ | + |
| 91 | + | + |
| 92 | +++ | + |
| 93 | ++ | +++ |
| 94 | + | + |
| 95 | +++ | ++ |
| 96 | + | + |
| 97 | ++ | + |
| 98 | ++ | ++ |
| 99 | +++ | ++ |
| 100 | +++ | +++ |
| 101 | ++ | + |
| 102 | +++ | ++ |
| 103 | ++ | ++ |
| 104 | + | + |
| 105 | +++ | + |
| 106 | +++ | ++ |
| 107 | +++ | +++ |
| 108 | +++ | ++ |
| 109 | +++ | +++ |
| 110 | +++ | ++ |
| 111 | +++ | ++ |
| 112 | +++ | ++ |
| 113 | +++ | + |
| 114 | +++ | ++ |
| 115 | +++ | +++ |
| 116 | +++ | +++ |
| 117 | +++ | ++ |
| 118 | +++ | ++ |
| 119 | +++ | + |
| 120 | +++ | ++ |
| 121 | +++ | + |
| 122 | +++ | +++ |
| 123 | +++ | ++ |
| 124 | +++ | + |
| 125 | +++ | ++ |
| 126 | +++ | +++ |
| 127 | ++ | ++ |
| 128 | +++ | +++ |
| 129 | + | + |
| 130 | + | + |
| 131 | + | + |
| 132 | ++ | ++ |
| 133 | ++ | ++ |
| 134 | ++ | ++ |
| 135 | +++ | +++ |
| 136 | ++ | ++ |
| 137 | +++ | +++ |
| 138 | +++ | +++ |
| 139 | +++ | +++ |

TABLE II-continued

Assay Data for Inhibitors of Cathepsin S

| Compound | $K_i$ Cat. S[a] | Selectivity for Cat. S over Cat. K[b] |
|---|---|---|
| 140 | +++ | +++ |
| 141 | +++ | + |
| 142 | +++ | +++ |
| 143 | ++ | ++ |
| 144 | ++ | +++ |
| 145 | +++ | +++ |
| 146 | +++ | +++ |
| 147 | +++ | +++ |
| 148 | +++ | +++ |
| 149 | +++ | +++ |
| 150 | +++ | + |
| 151 | +++ | + |
| 152 | +++ | ++ |
| 153 | +++ | + |
| 154 | +++ | ++ |
| 155 | +++ | +++ |
| 156 | +++ | +++ |
| 157 | +++ | +++ |
| 158 | +++ | ++ |
| 159 | +++ | +++ |
| 160 | + | ++ |
| 161 | +++ | ++ |
| 162 | +++ | + |
| 163 | +++ | + |
| 164 | +++ | +++ |
| 165 | +++ | +++ |
| 166 | +++ | +++ |
| 167 | +++ | +++ |
| 168 | +++ | +++ |
| 169 | ++ | ++ |
| 170 | + | + |
| 171 | +++ | +++ |
| 172 | +++ | +++ |
| 173 | +++ | +++ |
| 174 | +++ | + |
| 175 | +++ | +++ |
| 176 | +++ | +++ |
| 177 | +++ | ++ |
| 178 | +++ | +++ |
| 179 | +++ | +++ |
| 180 | +++ | + |
| 181 | +++ | +++ |
| 182 | +++ | + |
| 183 | +++ | +++ |
| 184 | +++ | +++ |
| 185 | +++ | ++ |
| 186 | +++ | ++ |
| 187 | +++ | + |
| 188 | +++ | +++ |
| 189 | +++ | ++ |
| 190 | +++ | +++ |
| 191 | +++ | + |
| 192 | +++ | +++ |
| 193 | +++ | ++ |
| 194 | ++ | + |
| 195 | ++ | +++ |
| 196 | +++ | ++ |
| 197 | +++ | +++ |
| 198 | ++ | + |
| 199 | ++ | ++ |
| 200 | +++ | + |
| 201 | +++ | ++ |
| 202 | +++ | +++ |
| 203 | +++ | +++ |
| 204 | ++ | ++ |
| 205 | +++ | ++ |
| 206 | ++ | ++ |
| 207 | ++ | ++ |
| 208 | +++ | +++ |
| 209 | +++ | +++ |
| 210 | +++ | ++ |
| 211 | ++ | ++ |
| 212 | +++ | ++ |
| 213 | +++ | +++ |
| 214 | +++ | +++ |
| 215 | +++ | +++ |
| 216 | ++ | +++ |
| 217 | ++ | +++ |
| 218 | ++ | +++ |
| 219 | +++ | ++ |
| 220 | ++ | ++ |
| 221 | +++ | + |
| 222 | +++ | +++ |
| 223 | ++ | ++ |
| 224 | ++ | ++ |
| 225 | + | + |
| 226 | + | + |
| 227 | ++ | ++ |
| 228 | +++ | +++ |
| 229 | +++ | +++ |
| 230 | +++ | +++ |
| 231 | +++ | +++ |
| 232 | +++ | + |
| 233 | +++ | +++ |
| 234 | +++ | + |
| 235 | +++ | +++ |
| 236 | +++ | +++ |
| 237 | +++ | +++ |
| 238 | +++ | + |
| 239 | +++ | +++ |
| 240 | +++ | +++ |
| 241 | +++ | +++ |
| 242 | +++ | +++ |
| 243 | +++ | +++ |
| 244 | ++ | +++ |
| 245 | +++ | +++ |
| 246 | +++ | ++ |
| 247 | +++ | +++ |
| 248 | +++ | +++ |
| 249 | +++ | +++ |
| 250 | +++ | ++ |
| 251 | +++ | +++ |
| 252 | +++ | +++ |
| 253 | +++ | +++ |
| 254 | ++ | ++ |
| 255 | ++ | ++ |
| 256 | +++ | +++ |
| 257 | +++ | +++ |
| 258 | +++ | +++ |
| 259 | ++ | ++ |
| 260 | +++ | ++ |
| 261 | +++ | +++ |
| 262 | + | + |
| 263 | + | + |
| 264 | +++ | ++ |
| 265 | ++ | ++ |
| 266 | ++ | + |
| 267 | +++ | +++ |
| 268 | ++ | ++ |
| 269 | + | + |
| 270 | +++ | +++ |
| 271 | ++ | ++ |
| 272 | +++ | ++ |
| 273 | ++ | ++ |
| 274 | +++ | +++ |

TABLE II-continued

Assay Data for Inhibitors of Cathepsin S

| Compound | $K_i$ Cat. S[a] | Selectivity for Cat. S over Cat. K[b] |
|---|---|---|
| 275 | +++ | +++ |
| 276 | +++ | +++ |
| 277 | +++ | ++ |
| 278 | ++ | ++ |
| 279 | ++ | ++ |
| 280 | ++ | ++ |
| 281 | ++ | ++ |
| 282 | ++ | ++ |
| 283 | ++ | ++ |
| 284 | ++ | ++ |
| 285 | ++ | ++ |
| 286 | + | + |
| 287 | ++ | ++ |
| 288 | ++ | ++ |
| 289 | ++ | ++ |
| 290 | +++ | +++ |
| 291 | ++ | ++ |
| 292 | +++ | +++ |
| 293 | +++ | ++ |
| 294 | +++ | ++ |
| 295 | ++ | ++ |
| 296 | +++ | +++ |
| 297 | ++ | ++ |
| 298 | +++ | ++ |
| 299 | +++ | + |
| 300 | +++ | ++ |
| 301 | +++ | ++ |
| 302 | +++ | ++ |
| 303 | +++ | ++ |
| 304 | +++ | +++ |
| 305 | +++ | ++ |
| 306 | +++ | +++ |
| 307 | +++ | +++ |
| 308 | +++ | ++ |
| 309 | +++ | ++ |
| 310 | +++ | ++ |
| 311 | +++ | + |
| 312 | +++ | ++ |
| 313 | ++ | + |
| 314 | +++ | + |
| 315 | +++ | ++ |
| 316 | +++ | ++ |
| 317 | +++ | ++ |
| 318 | +++ | + |
| 319 | +++ | ++ |
| 320 | +++ | ++ |
| 321 | ++ | ++ |
| 322 | +++ | ++ |
| 323 | +++ | ++ |
| 324 | +++ | ++ |
| 325 | +++ | ++ |
| 326 | ++ | ++ |
| 327 | ++ | ++ |
| 328 | ++ | ++ |
| 329 | ++ | ++ |
| 330 | ++ | ++ |

[a]Cathepsin S inhibition constant for compounds of Formula I: +, <10 μM; ++, <1.0 μM; +++, <0.1 μM.
[b]Selectivity of compounds of Formula I for cathepsin S over cathepsin K: +, >10; ++, >100; +++, >1000.

C. Comparison Activity

In order to show the superiority of the compounds of the present invention versus compound in the art, several compounds were tested in assays discussed herein. The compounds of the present invention showed superior unexpected properties, especially with respect to Cats inhibition. Moreover, the compounds of the present invention were also in inhibiting Cat S over Cat K.

| Compound | Ki (CatS)[a] μM | Ki (CatK)[b] μM | Selectivity for Cat. S over Cat. K[c] |
|---|---|---|---|
| | ++ | +++ | <10 |

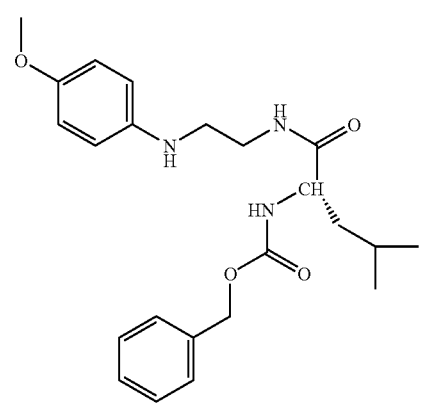

-continued

| Compound | Ki (CatS)[a] μM | Ki (CatK)[b] μM | Selectivity for Cat. S over Cat. K[c] |
|---|---|---|---|
| 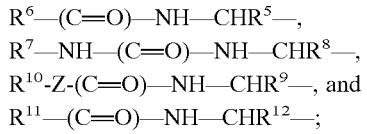 | ++ | +++ | <10 |
|  | +++ | +++ | <10 |

[a]Cathepsin S inhibition constant for the compounds +, <10 μM; ++, <1.0 μM; +++, <0.1 μM.
[a]Cathepsin K inhibition constant for the compounds +, <10 μM; ++, <1.0 μM; +++, <0.1 μM.
[c]Selectivity of the compounds for cathepsin S over cathepsin K: <10

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A compound of Formula I:

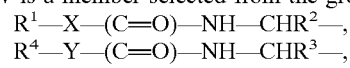

(I)

or a pharmaceutically acceptable salt or prodrug thereof, wherein:

W is a member selected from the group consisting of
$R^1$—X—(C=O)—NH—CHR$^2$—,
$R^4$—Y—(C=O)—NH—CHR$^3$—,
$R^6$—(C=O)—NH—CHR$^5$—,
$R^7$—NH—(C=O)—NH—CHR$^8$—,
$R^{10}$-Z-(C=O)—NH—CHR$^9$—, and
$R^{11}$—(C=O)—NH—CHR$^{12}$—;

$R^1$ is a member selected from the group consisting of phenyl substituted with 0–2 $R^{1a}$, pyridyl substituted with 0–2 $R^{1a}$, and pyridinium N-oxide substituted with 0–2 $R^{1a}$;

each $R^{1a}$ is independently a member selected from the group consisting of Cl, F, OCF$_3$, OCH$_3$, CH$_3$ and CF$_3$;

X is a member selected from the group consisting of furanylene substituted with 0–1 $R^X$, thienylene substituted with 0–1 $R^X$, pyrazolylene substituted with 0–1 $R^X$, thiazolylene substituted with 0–1 $R^X$, and oxazolylene substituted with 0–1 $R^X$;

$R^X$ is a member selected from the group consisting of F, Cl, CH$_3$ and CF$_3$;

$R^2$ is a member selected from the group consisting of phenyl substituted with 0–2 $R^{2a}$, and (CH$_2$)$_n$R$^{2b}$;

each $R^{2a}$ is independently a member selected from the group consisting of Cl, F, $OCF_3$, $OCH_3$, $CH_3$ and $CF_3$;

$R^{2b}$ is independently a member selected from the group consisting of phenyl substituted with 0–2 $R^{2a}$; cyclopentyl, cyclohexyl and tetrahydropyranyl;

n is the integer 1 or 2;

$R^3$ is $(CH_2)_m R^{3b}$;

$R^{3b}$ is selected from the group consisting of phenyl substituted with 0–2 $R^{2a}$, cyclopentyl and cyclohexyl;

m is the integer 1 or 2;

$R^4$ is a member selected from the group consisting of phenyl substituted with 0–3 $R^{4a}$, thienyl, tetrazolyl, cyclopentenyl and indolyl;

each $R^{4a}$ is a member selected from the group consisting of phenyl, OH, $C_1$–$C_4$ alkyl, $C_1$–$C_4$ alkoxy, $CF_3$, $OCF_3$, F, Cl, $CH_3S(=O)_2$—, morpholinyl, pyrrolidinyl, piperidinyl and 4-acetylpiperazinyl;

Y is a member selected from the group consisting of —$CR^{17}R^{18}$, —NH—$CH_2$— and —O—$CH_2$—;

$R^5$ is a member selected from the group consisting of phenyl substituted with 0–2 $R^{5a}$, thienyl, naphthyl, and $CH_2R^{5b}$, $CH_2CH_2$(cyclohexyl), $CH_2CH_2CH_2$(cyclohexyl), $CH_2CH_2Ph$, $CH(CH_3)R^{5e}$, $CH_2CH=CHPh$, —$CH_2OCH_2Ph$, —$CH(CH_3)OCH_2Ph$;

each $R^{5a}$ is independently a member selected from the group consisting of F, Cl, $NO_2$, $OCH_3$, $OCH_2Ph$, OPh, $CH_3$, $OCF_3$ and $CF_3$;

$R^{5b}$ is independently a member selected from the group consisting of phenyl substituted with 0–2 $R^{5c}$; cyclopentyl, cyclohexyl, naphthyl, indolyl and pyridyl;

$R^{5c}$ is independently a member selected from the group consisting of OH, Cl, F, Br, I, CN, $NO_2$, $CH_3$, $OCH_3$, $^tBu$, O—$^tBu$, —NHC(=O)$CH_3$, $CF_3$, $OCF_3$; phenyl substituted with 0–2 $R^{5d}$; phenoxy substituted with 0–2 $R^{5d}$; benzyloxy substituted with 0–2 $R^{5d}$; pyridyl substituted with 0–2 $R^{5d}$; pyrimidinyl substituted with 0–2 $R^{5d}$; thienyl substituted with 0–2 $R^{5d}$;

$R^{5d}$ is independently a member selected from the group consisting of $CH_3$, Cl, F, $OCH_3$, $CF_3$, $OCF_3$, $N(CH_3)_2$, acetyl, OH, $CH_2OH$, $NH_2$, CN and $NO_2$;

$R^{5e}$ is phenyl substituted with 0–2 $R^{5a}$;

$R^6$ is a member selected from the group consisting of phenyl substituted with 0–3 $R^{6a}$, furanyl substituted with 0–2 $R^{6b}$, thienyl substituted with 0–2 $R^{6b}$, oxazolyl substituted with 0–2 $R^{6b}$, thiazolyl substituted with 0–2 $R^{6b}$, pyridyl, pyridazinyl and cyclopropyl;

each $R^{6a}$ is independently a member selected from the group consisting of Cl, F, Br, $OCF_3$, $CF_3$, $C_1$–$C_4$ alkyl, $C_1$–$C_4$ alkoxy, —$S(=O)_2CH_3$, CN, —$N(CH_3)_2$, $OCF_2H$, —$CH_2$-benzimidazole, —NH—$S(=O)_2CH_3$, —$NR^{13}R^{14}$, $OR^{14}$, $CH_2$-morpholine, $CH_2NH_2$, $OCH_2Ph$, and OPh;

alternatively, two $R^{6a}$ substituents on adjacent atoms may be combined to form a 5 to 6 membered heterocyclic fused radical, wherein said 5 to 6 membered heterocyclic fused radical has 1 or 2 oxygen atom(s);

each $R^{6b}$ is independently a member selected from the group consisting of $NH_2$, F, Cl, Br, —$S(=O)_2R^{15}$, $CH_3$, and $CF_3$;

$R^7$ is a member selected from the group consisting of $(CH_2)_p R^{7a}$, and naphthyl substituted with 0–2 $R^{7b}$;

p is the integer 0, 1, or 2;

$R^{7a}$ is phenyl substituted with 0–2 $R^{7b}$;

$R^{7b}$ is a member selected from the group consisting of F, Cl, $CF_3$, $C_1$–$C_4$ alkyl, $C_1$–$C_4$ alkoxy, $OCF_3$, phenoxy and acetyl;

alternatively, two $R^{7b}$ substituents on adjacent atoms may be combined to form a 5 to 6 membered heterocyclic fused radical, wherein said 5 to 6 membered heterocyclic fused radical has 1 or 2 oxygen atom(s);

$R^8$ is —$CH_2$—$R^{3b}$;

$R^9$ is $(CH_2)_q R^{9a}$;

$R^{9a}$ is a member selected from the group consisting of cyclopentyl, phenyl and cyclohexyl;

q is the integer 1 or 2;

$R^{10}$ is a member selected from the group consisting of phenyl substituted with 0–2 $R^{10a}$, 5 membered heteroaryl containing 1 to 4 heteroatoms each independently a member selected from the group consisting of N, O and S, wherein said heteroaryl is substituted with 0–2 $R^{10a}$, 6 membered heteroaryl containing 1 to 2 N, wherein said heteroaryl is substituted with 0–2 $R^{10a}$, morpholinyl substituted with 0–2 $R^{10a}$, piperazinyl substituted with 0–2 $R^{10a}$ and piperidinyl substituted with 0–2 $R^{10a}$;

each $R^{10a}$ is independently a member selected from the group consisting of Cl, F, $C_1$–$C_4$ alkyl, $C_1$–$C_4$ alkoxy, $OCF_3$, and $CF_3$;

alternatively, two $R^{10a}$ substituents on adjacent atoms may be combined to form a 5 to 6 membered heterocyclic fused radical, wherein said 5 to 6 membered heterocyclic fused radical comprises 1 or 2 heteroatom(s);

Z is phenylene;

$R^{11}$ is a member selected from the group consisting of indolyl substituted with 0–2 $R^{11a}$, benzofuranyl substituted with 0–2 $R^{11a}$, benzothienyl substituted with 0–2 $R^{11a}$, benzothiazole substituted with 0–2 $R^{11a}$, benzisoxazolyl substituted with 0–2 $R^{11a}$, benzoxazolyl substituted with 0–2 $R^{11a}$, and pyrazolo[1,5-a]pyrimidinyl substituted with 0–2 $R^{11a}$, piperidinyl N-substituted with 0–1 $R^{11b}$, morpholinyl N-substituted with 0–1 $R^{11b}$; and 2-oxo-pyrrolidinyl with 0–1 $R^{11b}$;

each $R^{11a}$ is independently a member selected from the group consisting of Cl, F, $NH_2$, $CH_3$, $OCH_3$, —C(=O)$OCH_3$, $OCF_3$, and $CF_3$;

each $R^{11b}$ is independently a member selected from the group consisting of pyrimidinyl substituted with 0–2 $R^{11c}$; benzyl, acetyl, $CH_2$-furanyl, and $CH_2$-thienyl;

each $R^{11c}$ is independently a member selected from the group consisting of Br and $CH_3$;

$R^{12}$ is $(CH_2)_s R^{12a}$;

$R^{12a}$ is a member selected from the group consisting of cyclopentyl and cyclohexyl;

s is the integer 1 or 2;

$R^{13}$ is a member selected from the group consisting of H and $C_1$–$C_4$ alkyl;

$R^{14}$ is pyrimidinyl substituted with 0–2 $R^{16}$;

$R^{15}$ is a member selected from the group consisting of $C_1$–$C_4$ alkyl, morpholinyl, pyrrolidinyl and piperidinyl;

$R^{16}$ is a member selected from the group consisting of $CH_3$ and $OCH_3$;

each of $R^{17}$ and $R^{18}$ is independently a member of H, OH, F, phenyl and $C_1$–$C_3$ alkyl;

alternatively, $R^{17}$ and $R^{18}$ may be taken together to form a $C_3$–$C_6$ cycloalkyl;

Ar is a phenyl substituted with 0–2 $R^{19}$; and each $R^{19}$ is independently a member selected from the group consisting of F, Cl, COOH, $C_1$–$C_4$alkoxy, $OCHF_2$ and $OCF_3$.

2. The compound of claim 1, wherein said compound has the formula:

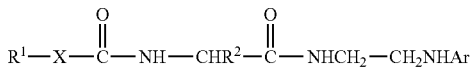

Ia wherein:
- $R^1$ is a member selected from the group consisting of phenyl substituted with 0–2 $R^{1a}$, pyridyl substituted with 0–2 $R^{1a}$, and pyridinium N-oxide substituted with 0–2 $R^{1a}$;
- each $R^{1a}$ is independently a member selected from the group consisting of Cl, F, $OCF_3$, $OCH_3$, $CH_3$ and $CF_3$;
- X is a member selected from the group consisting of furanylene substituted with 0–1 $R^X$, thienylene substituted with 0–1 $R^X$, pyrazolylene substituted with 0–1 $R^X$, thiazolylene substituted with 0–1 $R^X$, and oxazolylene substituted with 0–1 $R^X$;
- $R^X$ is a member selected from the group consisting of F, Cl, $CH_3$ and $CF_3$;
- $R^2$ is a member selected from the group consisting of phenyl substituted with 0–2 $R^{2a}$, and $(CH_2)_n R^{2b}$;
- each $R^{2a}$ is independently a member selected from the group consisting of Cl, F, $OCF_3$, $OCH_3$, $CH_3$ and $CF_3$;
- $R^{2b}$ is independently a member selected from the group consisting of phenyl substituted with 0–2 $R^{2a}$, cyclopentyl, cyclohexyl and tetrahydropyranyl;
- n is the integer 1 or 2;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

3. The compound of claim 1, wherein said compound has the formula:

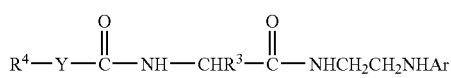

Ib wherein:
- $R^4$ is a member selected from the group consisting of phenyl substituted with 0–3 $R^{4a}$, thienyl, tetrazolyl, cyclopentenyl and indolyl;
- each $R^{4a}$ is a member selected from the group consisting of phenyl, OH, $C_1$–$C_4$ alkyl, $C_1$–$C_4$ alkoxy, $CF_3$, $OCF_3$, F, Cl, $CH_3S(=O)_2$—, morpholinyl, pyrrolidinyl, piperidinyl and 4-acetylpiperazinyl;
- Y is a member selected from the group consisting of —$CR^{17}R^{18}$, —NH—$CH_2$— and —O—$CH_2$—;
- $R^3$ is $(CH_2)_m R^{3b}$;
- $R^{3b}$ is selected from the group consisting of phenyl substituted with 0–2 $R^{2a}$, cyclopentyl and cyclohexyl;
- each $R^{2a}$ is independently a member selected from the group consisting of Cl, F, $OCF_3$, $OCH_3$, $CH_3$ and $CF_3$;
- m is the integer 1 or 2;
- each of $R^{17}$ and $R^{18}$ is independently a member of H, OH, F, phenyl and $C_1$–$C_3$ alkyl;
- alternatively, $R^{17}$ and $R^{18}$ may be taken together to form a $C_3$–$C_6$ cycloalkyl;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

4. The compound of claim 1, wherein said compound has the formula:

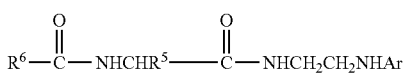

Ic wherein:
- $R^5$ is a member selected from the group consisting of phenyl substituted with 0–2 $R^{5a}$, thienyl, naphthyl, and $CH_2R^{5b}$, $CH_2CH_2$(cyclohexyl), $CH_2CH_2CH_2$(cyclohexyl), $CH_2CH_2Ph$, $CH(CH_3)R^{5e}$, $CH_2CH=CHPh$, —$CH_2OCH_2Ph$, and —$CH(CH_3)OCH_2Ph$;
- each $R^{5a}$ is independently a member selected from the group consisting of F, Cl, $NO_2$, $OCH_3$, $OCH_2Ph$, OPh, $CH_3$, $OCF_3$ and $CF_3$;
- $R^{5b}$ is independently a member selected from the group consisting of phenyl substituted with 0–2 $R^{5c}$; cyclopentyl, cyclohexyl, naphthyl, indolyl and pyridyl;
- $R^{5c}$ is independently a member selected from the group consisting of OH, Cl, F, Br, I, CN, $NO_2$, $CH_3$, $OCH_3$, $^tBu$, O-$^tBu$, —NHC(=O)$CH_3$, $CF_3$, $OCF_3$, phenyl substituted with 0–2 $R^{5d}$, phenoxy substituted with 0–2 $R^{5d}$, benzyloxy substituted with 0–2 $R^{5d}$, pyridyl substituted with 0–2 $R^{5d}$, pyrimidinyl substituted with 0–2 $R^{5d}$, and thienyl substituted with 0–2 $R^{5d}$;
- $R^{5d}$ is independently a member selected from the group consisting of $CH_3$, Cl, F, $OCH_3$, $CF_3$, $OCF_3$, $N(CH_3)_2$, acetyl, OH, $CH_2OH$, $NH_2$, CN and $NO_2$;
- $R^{5e}$ is phenyl substituted with 0–2 $R^{5a}$;
- $R^6$ is a member selected from the group consisting of phenyl substituted with 0–3 $R^{6a}$, furanyl substituted with 0–2 $R^{6b}$; thienyl substituted with 0–2 $R^{6b}$; oxazolyl substituted with 0–2 $R^{6b}$; thiazolyl substituted with 0–2 $R^{6b}$; pyridyl, pyridazinyl and cyclopropyl;
- each $R^{6a}$ is independently a member selected from the group consisting of Cl, F, Br, $OCF_3$, $CF_3$, $C_1$–$C_4$ alkyl, $C_1$–$C_4$ alkoxy, —$S(=O)_2CH_3$, CN, —$N(CH_3)_2$, $OCF_2H$, —$CH_2$-benzimidazole, —NH—$S(=O)_2CH_3$, —$NR^{13}R^{14}$, $OR^{14}$, $CH_2$-morpholine, $CH_2NH_2$, $OCH_2Ph$, and OPh;
- alternatively, two $R^{6a}$ substituents on adjacent atoms may be combined to form a 5 to 6 membered heterocyclic fused radical, wherein said 5 to 6 membered heterocyclic fused radical has 1 or 2 oxygen atom(s);
- each $R^{6b}$ is independently a member selected from the group consisting of $NH_2$, F, Cl, Br, —$S(=O)_2R^{15}$, $CH_3$, and $CF_3$;
- $R^{13}$ is a member selected from the group consisting of H and $C_1$–$C_4$ alkyl;
- $R^{14}$ is pyrimidinyl substituted with 0–2 $R^{16}$;
- $R^{15}$ is a member selected from the group consisting of $C_1$–$C_4$ alkyl, morpholinyl, pyrrolidinyl and piperidinyl;
- $R^{16}$ is a member selected from the group consisting of $CH_3$ and $OCH_3$;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

5. The compound of claim 1, wherein said compound has the formula:

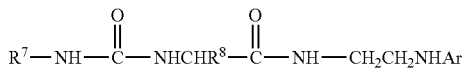

Id wherein:
- $R^7$ is a member selected from the group consisting of $(CH_2)_p R^{7a}$; and naphthyl substituted with 0–2 $R^{7b}$;
- p is the integer 0, 1, or 2;
- $R^{7a}$ is a member selected from the group consisting of phenyl substituted with 0–2 $R^{7b}$;
- $R^{7b}$ is a member selected from the group consisting of F, Cl, $CF_3$, $C_1$–$C_4$ alkyl, $C_1$–$C_4$ alkoxy, $OCF_3$, phenoxy and acetyl;
- alternatively, two $R^{7b}$ substituents on adjacent atoms may be combined to form a 5 to 6 membered heterocyclic fused radical, wherein said 5 to 6 membered heterocyclic fused radical has 1 or 2 oxygen atom(s);
- $R^8$ is —$CH_2$—$R^{3b}$;
- $R^{3b}$ is selected from the group consisting of phenyl substituted with 0–2 $R^{2a}$, cyclopentyl and cyclohexyl;
- each $R^{2a}$ is independently a member selected from the group consisting of Cl, F, $OCF_3$, $OCH_3$, $CH_3$ and $CF_3$;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

6. The compound of claim 1, wherein said compound has the formula:

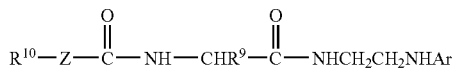

Ie wherein:
- $R^{10}$ is a member selected from the group consisting of phenyl substituted with 0–2 $R^{10a}$, 5 membered heteroaryl containing 1 to 4 heteroatoms each independently a member selected from the group consisting of N, O and S, wherein said heteroaryl is substituted with 0–2 $R^{10a}$, 6 membered heteroaryl containing 1 to 2 N, wherein said heteroaryl is substituted with 0–2 $R^{10a}$, morpholinyl substituted with 0–2 $R^{10a}$, piperazinyl substituted with 0–2 $R^{10a}$ and piperidinyl substituted with 0–2 $R^{10a}$;
- each $R^{10a}$ is independently a member selected from the group consisting of Cl, F, $C_1$–$C_4$ alkyl, $C_1$–$C_4$ alkoxy, $OCF_3$, and $CF_3$;
- alternatively, two $R^{10a}$ substituents on adjacent atoms may be combined to form a 5 to 6 membered heterocyclic fused radical, wherein said 5 to 6 membered heterocyclic fused radical comprises 1 or 2 heteroatom(s);
- Z is phenylene;
- $R^9$ is $(CH_2)_q R^{9a}$;
- $R^{9a}$ is a member selected from the group consisting of cyclopentyl, phenyl and cyclohexyl;
- q is the integer 1 or 2;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

7. The compound of claim 1, wherein said compound has the formula:

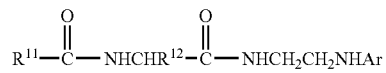

If wherein:
- $R^{11}$ is a member selected from the group consisting of indolyl substituted with 0–2 $R^{11a}$; benzofuranyl substituted with 0–2 $R^{11a}$; benzothienyl substituted with 0–2 $R^{11a}$; benzothiazole substituted with 0–2 $R^{11a}$; benzisoxazolyl substituted with 0–2 $R^{11a}$; benzoxazolyl substituted with 0–2 $R^{11a}$; and pyrazolo[1,5-a]pyrimidinyl substituted with 0–2 $R^{11a}$; piperidinyl N-substituted with 0–1 $R^{11b}$; morpholinyl N-substituted with 0–1 $R^{11b}$; and 2-oxo-pyrrolidinyl with 0–1 $R^{11b}$;
- each $R^{11a}$ is independently a member selected from the group consisting of Cl, F, $NH_2$, $CH_3$, $OCH_3$, —C(=O)$OCH_3$, $OCF_3$, and $CF_3$;
- each $R^{11b}$ is independently a member selected from the group consisting of pyrimidinyl substituted with 0–2 $R^{11c}$; benzyl, acetyl, $CH_2$-furanyl, and $CH_2$-thienyl;
- each $R^{11c}$ is independently a member selected from the group consisting of Br and $CH_3$;
- $R^{12}$ is $(CH_2)_s R^{12a}$;
- $R^{12a}$ is a member selected from the group consisting of cyclopentyl and cyclohexyl;
- s is the integer 1 or 2;
- Ar is a phenyl substituted with 0–2 $R^{19}$; and
- each $R^{19}$ is independently a member selected from the group consisting of F, Cl, COOH, $C_1$–$C_4$ alkoxy, $OCHF_2$ and $OCF_3$.

8. The compound of claim 1, wherein said compound is a member selected from the compounds of Table I:

TABLE I

| | |
|---|---|
| i. | N-((S)-1-(2-(4-methoxyphenylamino)ethylcarbamoyl)-3-phenylpropyl)-5-(3-(trifluoromethyl)phenyl)furan-2-carboxamide; |
| ii. | N-((S)-1-(2-(4-methoxyphenylamino)ethylcarbamoyl)-2-(2-chlorophenyl)ethyl)-5-(3-(trifluoromethyl)phenyl)furan-2-carboxamide; |
| iii. | N-((S)-1-(2-(4-methoxyphenylamino)ethylcarbamoyl)-2-(3-chlorophenyl)ethyl)-5-(3-(trifluoromethyl)phenyl)furan-2-carboxamide; |
| iv. | N-((S)-1-(2-(4-methoxyphenylamino)ethylcarbamoyl)-2-(4-chlorophenyl)ethyl)-5-(3-(trifluoromethyl)phenyl)furan-2-carboxamide; |
| v. | N-((S)-1-(2-(4-methoxyphenylamino)ethylcarbamoyl)-2-(tetrahydro-2H-pyran-4-yl)ethyl)-5-(3-(trifluoromethyl)-phenyl)furan-2-carboxamide; |
| vi. | N-((S)-1-(2-(4-methoxyphenylamino)ethylcarbamoyl)-2-cyclopentylethyl)-5-(3-(trifluoromethyl)phenyl)furan-2-carboxamide; |
| vii. | (S)-N-{2-[4-(2,3-Dimethyl-phenoxy)-phenyl]-1-[2-(4-methoxy-phenylamino)ethylcarbamoyl]-ethyl}-3-methyl-benzamide; |
| viii. | (±)-N-((2-(4-methoxyphenylamino)ethylcarbamoyl)(4-chlorophenyl)methyl)-3-methylbenzamide; |
| ix. | (±)-N-((2-(4-methoxyphenylamino)ethylcarbamoyl)(phenyl)-methyl)-5-(3-(trifluoromethyl)phenyl)furan-2-carboxamide; |
| x. | N-((S)-1-(2-(4-(difluoromethoxy)phenylamino)-ethylcarbamoyl)-2-cyclohexylethyl)-5-(3-(trifluoromethyl)-phenyl)furan-2-carboxamide; |

TABLE I-continued

| | |
|---|---|
| xi. | 4-[2-(3-Cyclohexyl-2-(S)-{[5-(3-trifluoromethyl-phenyl)-furan-2-carbonyl]-amino}-propionylamino)-ethylamino]-benzoic acid; |
| xii. | 2-[2-(3-Cyclohexyl-2-(S)-{[5-(3-trifluoromethyl-phenyl)-furan-2-carbonyl]-amino}-propionylamino)-ethylamino]-benzoic acid; |
| xiii. | 4-Cyclohexyl-2-(S)-(2-(R)-phenyl-propionylamino)-N-[2-(4-trifluoromethoxy-phenylamino)-ethyl]-butyramide; |
| xiv. | Acetyl-piperidine-4-carboxylic acid (S)-{2-cyclohexyl-1-[2-(4-trifluoromethoxy-phenylamino)-ethylcarbamoyl]-ethyl}-amide; |
| xv. | (S)-2-{2-[4-(4-Acetyl-piperazin-1-yl)-phenoxy]-acetylamino}-3-cyclohexyl-N-[2-(4-trifluoromethoxy-phenylamino)-ethyl]-propionamide; |
| xvi. | (S)-2-Chloro-N-{1-[2-(4-methoxy-phenylamino)-ethylcarbamoyl]-2-phenyl-ethyl}-3-methyl-benzamide; |
| xvii. | Cyclohexyl-2-[2-(4-methoxy-phenyl)-acetylamino]-N-[2-(4-trifluoromethoxy-phenylamino)-ethyl]-propionamide; |
| xviii. | (S)-N-{2-[4-(3,5-Dichloro-phenoxy)-phenyl]-1-[2-(4-methoxy-phenylamino)-ethylcarbamoyl]-ethyl}-3-methyl-benzamide; |
| xix. | N-(S)-{2-cyclohexyl-1-[2-(4-trifluoromethoxy-phenylamino)-ethylcarbamoyl]-ethyl}-4-methanesulfonyl-benzamide; |
| xx. | (S)-4-Benzyloxy-N-{1-[2-(4-methoxy-phenylamino)-ethylcarbamoyl]-2-phenyl-ethyl}-3,5-dimethyl-benzamide; |
| xxi. | (S)-4-Methoxy-N-{1-[2-(4-methoxy-phenylamino)-ethylcarbamoyl]-2-phenyl-ethyl}-3,5-dimethyl-benzamide; |
| xxii. | 5-Methoxy-1H-indole-2-carboxylic acid (S)-{2-cyclohexyl-1-[2-(4-trifluoromethoxy-phenylamino)-ethylcarbamoyl]-ethyl}-amide; |
| xxiii. | (S)-3-Bromo-N-{1-[2-(4-methoxy-phenylamino)-ethylcarbamoyl]-2-phenyl-ethyl}-4-methyl-benzamide; |
| xxiv. | Furan-2-carboxylic acid (S)-{2-cyclohexyl-1-[2-(4-trifluoromethoxy-phenylamino)-ethylcarbamoyl]-ethyl}-amide; |
| xxv. | Thiophene-2-carboxylic acid (S)-{2-cyclohexyl-1-[2-(4-trifluoromethoxy-phenylamino)-ethylcarbamoyl]-ethyl}-amide; |
| xxvi. | Furan-3-carboxylic acid (S)-{2-cyclohexyl-1-[2-(4-trifluoromethoxy-phenylamino)-ethylcarbamoyl]-ethyl}-amide; |
| xxvii. | N-(S)-{2-cyclohexyl-1-[2-(4-trifluoromethoxy-phenylamino)-ethylcarbamoyl]-ethyl}-4-(5-methyl-[1,2,4]oxadiazol-3-yl)-benzamide; |
| xxviii. | 5-(4-Fluoro-phenyl)-thiophene-2-carboxylic acid (S)-{2-cyclohexyl-1-[2-(4-trifluoromethoxy-phenylamino)-ethylcarbamoyl]-ethyl}-amide; |
| xxix. | (S)-N-{1-[2-(4-Methoxy-phenylamino)-ethylcarbamoyl]-2-phenyl-ethyl}-2,4,5-trimethyl-benzamide; |
| xxx. | (S)-N-{1-[2-(4-Methoxy-phenylamino)-ethylcarbamoyl]-2-phenyl-ethyl}-2,4,5-trimethyl-benzamide; |
| xxxi. | 5-(3-Fluoro-phenyl)-furan-2-carboxylic acid (S)-{2-cyclohexyl-1-[2-(4-trifluoromethoxy-phenylamino)-ethylcarbamoyl]-ethyl}-amide; |
| xxxii. | Benzyl-morpholine-2-carboxylic acid (S)-{2-cyclohexyl-1-[2-(4-trifluoromethoxy-phenylamino)-ethylcarbamoyl]-ethyl}-amide; |
| xxxiii. | (S)-N-{2-[4-(4-Dimethylamino-phenoxy)-phenyl]-1-[2-(4-methoxy-phenylamino)-ethylcarbamoyl]-ethyl}-3-methyl-benzamide; |
| xxxiv. | 2'-Chloro-biphenyl-3-carboxylic acid (S)-{2-cyclohexyl-1-[2-(4-trifluoromethoxy-phenylamino)-ethylcarbamoyl]-ethyl}-amide; |
| xxxv. | 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| xxxvi. | 5-(3-Fluoro-phenyl)-thiophene-2-carboxylic acid (S)-{2-cyclohexyl-1-[2-(4-trifluoromethoxy-phenylamino)-ethylcarbamoyl]-ethyl}-amide; |
| xxxvii. | Thiophene-3-carboxylic acid (S)-{2-cyclohexyl-1-[2-(4-trifluoromethoxy-phenylamino)-ethylcarbamoyl]-ethyl}-amide; |
| xxxviii. | Oxo-1-thiophen-2-ylmethyl-pyrrolidine-3-carboxylic acid (S)-{2-cyclohexyl-1-[2-(4-trifluoromethoxy-phenylamino)-ethylcarbamoyl]-ethyl}-amide; |
| xxxix. | Furan-2-ylmethyl-5-oxo-pyrrolidine-3-carboxylic acid (S)-{2-cyclohexyl-1-[2-(4-trifluoromethoxy-phenylamino)-ethylcarbamoyl]-ethyl}-amide; |
| xl. | Methyl-5-(pyrrolidine-1-sulfonyl)-furan-3-carboxylic acid (S)-{2-cyclohexyl-1-[2-(4-trifluoromethoxy-phenylamino)-ethylcarbamoyl]-ethyl}-amide; |
| xli. | (S)-1-Phenyl-5-trifluoromethyl-1H-pyrazole-4-carboxylic acid {1-[2-(4-methoxy-phenylamino)-ethylcarbamoyl]-2-phenyl-ethyl}-amide; |
| xlii. | 5-p-Tolyl-thiophene-2-carboxylic acid (S)-{2-cyclohexyl-1-[2-(4-trifluoromethoxy-phenylamino)-ethylcarbamoyl]-ethyl}-amide; |
| xliii. | Benzoimidazol-1-ylmethyl-N-{2-cyclohexyl-1-(S)-[2-(4-trifluoromethoxy-phenylamino)-ethylcarbamoyl]-ethyl}-benzamide; |
| xliv. | (S)-1-(4-Chloro-phenyl)-5-trifluoromethyl-1H-pyrazole-4-carboxylic acid {1-[2-(4-methoxy-phenylamino)-ethylcarbamoyl]-2-phenyl-ethyl}-amide; |
| xlv. | (S)-N-[1-[2-(4-Methoxy-phenylamino)-ethylcarbamoyl]-2-(4-p-tolyloxy-phenyl)-ethyl]-3-methyl-benzamide; |
| xlvi. | Cyclohexyl-2-(S)-(2-tetrazol-1-yl-acetylamino)-N-[2-(4-trifluoromethoxy-phenylamino)-ethyl]-propionamide; |
| xlvii. | 5-m-Tolyl-thiophene-2-carboxylic acid (S)-{2-cyclohexyl-1-[2-(4-trifluoromethoxy-phenylamino)-ethylcarbamoyl]-ethyl}-amide; |
| xlviii. | 2,7-Dimethyl-pyrazolo[1,5-a]pyrimidine-6-carboxylic acid (S)-{2-cyclohexyl-1-[2-(4-trifluoromethoxy-phenylamino)-ethylcarbamoyl]-ethyl}-amide; |
| xlix. | 2-Methyl-5-(morpholine-4-sulfonyl)-furan-3-carboxylic acid (S)-{2-cyclohexyl-1-[2-(4-trifluoromethoxy-phenylamino)-ethylcarbamoyl]-ethyl}-amide; |
| l. | 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| li. | 5-m-Tolyl-furan-2-carboxylic acid (S)-{2-cyclohexyl-1-[2-(4-trifluoromethoxy-phenylamino)-ethylcarbamoyl]-ethyl}-amide; |
| lii. | (S)-2,3-Dihydro-benzofuran-7-carboxylic acid {1-[2-(4-methoxy-phenylamino)-ethylcarbamoyl]-2-phenyl-ethyl}-amide; |
| liii. | Methanesulfonyl-thiophene-2-carboxylic acid (S)-{2-cyclohexyl-1-[2-(4-trifluoromethoxy-phenylamino)-ethylcarbamoyl]-ethyl}-amide; |
| liv. | 2-Phenyl-thiazole-4-carboxylic acid (S)-{2-cyclohexyl-1-[2-(4-trifluoromethoxy-phenylamino)-ethylcarbamoyl]-ethyl}-amide; |
| lv. | (S)-3-Cyano-N-{1-[2-(4-methoxy-phenylamino)-ethylcarbamoyl]-2-phenyl-ethyl}-benzamide; |
| lvi. | (S)-N-{1-[2-(4-Methoxy-phenylamino)-ethylcarbamoyl]-2-phenyl-ethyl}-3-(2-methyl-thiazol-4-yl)-benzamide; |
| lvii. | (S)-N-[2-(4-Methoxy-phenylamino)-ethyl]-3-phenyl-2-(3-phenyl-ureido)-propionamide; |
| lviii. | 3-Cyclohexyl-2-(S)-(2-(S)-hydroxy-2-phenyl-acetylamino)-N-[2-(4-trifluoromethoxy-phenylamino)-ethyl]-propionamide; |
| lix. | Benzo[c]isoxazole-3-carboxylic acid (S)-{2-cyclohexyl-1-[2-(4-trifluoromethoxy-phenylamino)-ethylcarbamoyl]-ethyl}-amide; |
| lx. | N-(S)-{2-cyclohexyl-1-[2-(4-trifluoromethoxy-phenylamino)-ethylcarbamoyl]-ethyl}-4-difluoromethoxy-benzamide; |
| lxi. | N-(S)-{2-cyclohexyl-1-[2-(4-trifluoromethoxy-phenylamino)-ethylcarbamoyl]-ethyl}-4-isopropoxy-benzamide; |
| lxii. | Phenyl-thiophene-2-carboxylic acid (S)-{2-cyclohexyl-1-[2-(4-trifluoromethoxy-phenylamino)-ethylcarbamoyl]-ethyl}-amide; |
| lxiii. | (S)-N-{1-[2-(4-Methoxy-phenylamino)-ethylcarbamoyl]-2-phenyl-ethyl}-nicotinamide; |
| lxiv. | (S)-N-{1-[2-(4-Methoxy-phenylamino)-ethylcarbamoyl]-2-phenyl-ethyl}-isonicotinamide; |
| lxv. | Phenyl-furan-2-carboxylic acid (S)-{2-cyclohexyl-1-[2-(4-trifluoromethoxy-phenylamino)-ethylcarbamoyl]-ethyl}-amide; |
| lxvi. | (S)-N-[1-[2-(4-Methoxy-phenylamino)-ethylcarbamoyl]-2-(4-o-tolyloxy-phenyl)-ethyl]-3-methyl-benzamide; |
| lxvii. | N-(S)-{2-cyclohexyl-1-[2-(4-trifluoromethoxy-phenylamino)-ethylcarbamoyl]-ethyl}-4-oxazol-5-yl-benzamide; |
| lxviii. | 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| lxix. | 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |

TABLE I-continued

| | |
|---|---|
| lxx. | 5-p-Tolyl-furan-2-carboxylic acid (S)-{2-cyclohexyl-1-[2-(4-trifluoromethoxy-phenylamino)-ethylcarbamoyl]-ethyl}-amide; |
| lxxi. | N-(S)-{2-cyclohexyl-1-[2-(4-trifluoromethoxy-phenylamino)-ethylcarbamoyl]-ethyl}-3-[(4,6-dimethyl-pyrimidin-2-yl)-methyl-amino]-benzamide; |
| lxxii. | 1-(4,6-Dimethyl-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxiii. | N-(S)-{2-cyclohexyl-1-[2-(4-trifluoromethoxy-phenylamino)-ethylcarbamoyl]-ethyl}-3-(4,6-dimethyl-pyrimidin-2-yloxy)-benzamide; |
| lxxiv. | 3'-Methoxy-biphenyl-3-carboxylic acid (S)-{2-cyclohexyl-1-[2-(4-trifluoromethoxy-phenylamino)-ethylcarbamoyl]-ethyl}-amide; |
| lxxv. | N-{3-Cyclohexyl-1-(S)-[2-(4-methoxy-phenylamino)-ethylcarbamoyl]-propyl}-2-(R)-phenyl-butyramide; |
| lxxvi. | 3-Cyclohexyl-N-[2-(4-fluoro-phenylamino)-ethyl]-2-(S)-(2-thiophen-2-yl-acetylamino)-propionamide; |
| lxxvii. | 3-Cyclohexyl-N-[2-(4-fluoro-phenylamino)-ethyl]-2-(S)-(2-thiophen-3-yl-acetylamino)-propionamide; |
| lxxviii. | (S)-3-Bromo-N-{1-[2-(4-methoxy-phenylamino)-ethylcarbamoyl]-2-phenyl-ethyl}-benzamide; |
| lxxix. | Acetyl-piperidine-4-carboxylic acid (S)-{2-cyclohexyl-1-[2-(4-fluoro-phenylamino)-ethylcarbamoyl]-ethyl}-amide; |
| lxxx. | N-(S)-{2-cyclohexyl-1-[2-(4-trifluoromethoxy-phenylamino)-ethylcarbamoyl]-ethyl}-4-(4,6-dimethoxy-pyrimidin-2-yl)-benzamide; |
| lxxxi. | 1-(5-Bromo-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxxii. | (S)-2-(2-Cyclopent-2-enyl-acetylamino)-N-[2-(4-methoxy-phenylamino)-ethyl]-3-phenyl-propionamide; |
| lxxxiii. | Cyclohexyl-N-[2-(4-fluoro-phenylamino)-ethyl]-2-(2-1H-indol-3-yl-acetylamino)-propionamide; |
| lxxxiv. | N-(S)-{2-cyclohexyl-1-[2-(4-fluoro-phenylamino)-ethylcarbamoyl]-ethyl}-3-methanesulfonylamino-benzamide; |
| lxxxv. | 5-(3-Trifluoromethyl-phenyl)-furan-2-carboxylic acid (S)-{2-cyclohexyl-1-[2-(4-fluoro-phenylamino)-ethylcarbamoyl]-ethyl}-amide; |
| lxxxvi. | Cyclohexyl-2-(S)-(2-(R,S)-fluoro-2-phenyl-acetylamino)-N-[2-(4-fluoro-phenylamino)-ethyl]-propionamide; |
| lxxxvii. | Cyclohexyl-N-(S)-[2-(4-fluoro-phenylamino)-ethyl]-2-[2-(4-trifluoromethoxy-phenyl)-acetylamino]-propionamide; |
| lxxxviii. | (S)-2-[3-(4-Chloro-phenyl)-ureido]-N-[2-(4-methoxy-phenylamino)-ethyl]-3-phenyl-propionamide; |
| lxxxix. | (S)-N-[2-(4-Methoxy-phenylamino)-ethyl]-2-[3-(4-phenoxy-phenyl)-ureido]-3-phenyl-propionamide; |
| xc. | (S)-N-[2-(4-Methoxy-phenylamino)-ethyl]-2-(3-phenethyl-ureido)-3-phenyl-propionamide; |
| xci. | (S)-2-[3-(4-Fluoro-benzyl)-ureido]-N-[2-(4-methoxy-phenylamino)-ethyl]-3-phenyl-propionamide; |
| xcii. | N-(S)-{2-cyclohexyl-1-[2-(4-trifluoromethoxy-phenylamino)-ethylcarbamoyl]-ethyl}-4-(4,6-dimethyl-pyrimidin-2-ylamino)-benzamide; |
| xciii. | 1-(5-Bromo-pyrimidin-2-yl)-piperidine-3-carboxylic acid (S)-{2-cyclohexyl-1-[2-(4-trifluoromethoxy-phenylamino)-ethylcarbamoyl]-ethyl}-amide; |
| xciv. | (S)-2-(3-Benzo[1,3]dioxol-5-yl-ureido)-N-[2-(4-methoxy-phenylamino)-ethyl]-3-phenyl-propionamide; |
| xcv. | 3-Cyclohexyl-2-(S)-[2-(2,5-difluorophenyl-acetylamino)-N-[2-(4-fluoro-phenylamino)-ethyl]-propionamide; |
| xcvi. | (S)-2-[3-(3-Fluoro-benzyl)-ureido]-N-[2-(4-methoxy-phenylamino)-ethyl]-3-phenyl-propionamide; |
| xcvii. | (S)-N-[2-(4-Methoxy-phenylamino)-ethyl]-3-phenyl-2-(3-o-tolyl-ureido)-propionamide; |
| xcviii. | (S)-N-{2-[4-(3,4-Dichloro-phenoxy)-phenyl]-1-[2-(4-methoxy-phenylamino)-ethylcarbamoyl]-ethyl}-3-methyl-benzamide; |
| xcix. | 3-Cyclohexyl-2-(S)-[2-(3,4-difluoro-phenyl)-acetylamino]-N-[2-(4-fluoro-phenylamino)-ethyl]-propionamide; |
| c. | 3-Cyclohexyl-2-(S)-[2-(2,4-difluoro-phenyl)-acetylamino]-N-[2-(4-fluoro-phenylamino)-ethyl]-propionamide; |
| ci. | (S)-N-[2-(4-Methoxy-phenylamino)-ethyl]-2-(3-naphthalen-1-yl-ureido)-3-phenyl-propionamide; |
| cii. | (S)-2-[3-(2-tert-Butyl-6-methyl-phenyl)-ureido]-N-[2-(4-methoxy-phenylamino)-ethyl]-3-phenyl-propionamide; |
| ciii. | (S)-2-[3-(4-Acetyl-phenyl)-ureido]-N-[2-(4-methoxy-phenylamino)-ethyl]-3-phenyl-propionamide; |
| civ. | (S)-N-[2-(4-Methoxy-phenylamino)-ethyl]-2-[3-(3-methoxy-phenyl)-ureido]-3-phenyl-propionamide; |
| cv. | (S)-Biphenyl-4-carboxylic acid {2-cyclohexyl-1-[2-(4-methoxy-phenylamino)-ethylcarbamoyl]-ethyl}-amide; |
| cvi. | (S)-N-{2-Cyclohexyl-1-[2-(4-methoxy-phenylamino)-ethylcarbamoyl]-ethyl}-3-trifluoromethyl-benzamide; |
| cvii. | 2-(S)-[2-(2-Chloro-4-fluoro-phenyl)-acetylamino]-3-cyclohexyl-N-[2-(4-fluoro-phenylamino)-ethyl]-propionamide; |
| cviii. | (S)-2-Chloro-N-{2-cyclohexyl-1-[2-(4-methoxy-phenylamino)-ethylcarbamoyl]-ethyl}-3-methyl-benzamide; |
| cix. | (S)-4-Benzyloxy-N-{2-cyclohexyl-1-[2-(4-methoxy-phenylamino)-ethylcarbamoyl]-ethyl}-benzamide; |
| cx. | (S)-4-Benzyloxy-N-{2-cyclohexyl-1-[2-(4-methoxy-phenylamino)-ethylcarbamoyl]-ethyl}-3,5-dimethyl-benzamide; |
| cxi. | (S)-N-{2-Cyclohexyl-1-[2-(4-methoxy-phenylamino)-ethylcarbamoyl]-ethyl}-4-methoxy-3,5-dimethyl-benzamide; |
| cxii. | (S)-3-Bromo-N-{2-cyclohexyl-1-[2-(4-methoxy-phenylamino)-ethylcarbamoyl]-ethyl}-4-methyl-benzamide; |
| cxiii. | (S)-5-Fluoro-1H-indole-2-carboxylic acid {2-cyclohexyl-1-[2-(4-methoxy-phenylamino)-ethylcarbamoyl]-ethyl}-amide; |
| cxiv. | (S)-2-Amino-4-methyl-thiazole-5-carboxylic acid {2-cyclohexyl-1-[2-(4-methoxy-phenylamino)-ethylcarbamoyl]-ethyl}-amide; |
| cxv. | (S)-1-Phenyl-5-trifluoromethyl-1H-pyrazole-4-carboxylic acid {2-cyclohexyl-1-[2-(4-methoxy-phenylamino)-ethylcarbamoyl]-ethyl}-amide; |
| cxvi. | (S)-1-(4-Chloro-phenyl)-5-trifluoromethyl-1H-pyrazole-4-carboxylic acid {2-cyclohexyl-1-[2-(4-methoxy-phenylamino)-ethylcarbamoyl]-ethyl}-amide; |
| cxvii. | (S)-5-(3-Trifluoromethyl-phenyl)-furan-2-carboxylic acid {2-cyclohexyl-1-[2-(4-methoxy-phenylamino)-ethylcarbamoyl]-ethyl}-amide; |
| cxviii. | (S)-3-Chloro-N-{2-cyclohexyl-1-[2-(4-methoxy-phenylamino)-ethylcarbamoyl]-ethyl}-benzamide; |
| cxix. | (S)-N-{2-Cyclohexyl-1-[2-(4-methoxy-phenylamino)-ethylcarbamoyl]-ethyl}-3-dimethylamino-benzamide; |
| cxx. | (S)-3-Cyano-N-{2-cyclohexyl-1-[2-(4-methoxy-phenylamino)-ethylcarbamoyl]-ethyl}-benzamide; |
| cxxi. | (S)-4-Cyano-N-{2-cyclohexyl-1-[2-(4-methoxy-phenylamino)-ethylcarbamoyl]-ethyl}-benzamide; |
| cxxii. | N-{2-cyclohexyl-1-(S)-[2-(4-trifluoromethoxy-phenylamino)-ethylcarbamoyl]-ethyl}-2-(R)-phenyl-propionamide; |
| cxxiii. | (S)-N-{2-Cyclohexyl-1-[2-(4-methoxy-phenylamino)-ethylcarbamoyl]-ethyl}-3-(2-methyl-thiazol-4-yl)-benzamide; |
| cxxiv. | (S)-N-{2-Cyclohexyl-1-[2-(4-methoxy-phenylamino)-ethylcarbamoyl]-ethyl}-4-[1,2,4]triazol-1-yl-benzamide; |
| cxxv. | 3-Cyclohexyl-2-(S)-[2-(3,5-difluoro-phenyl)-acetylamino]-N-[2-(4-fluoro-phenylamino)-ethyl]-propionamide; |
| cxxvi. | (S)-N-{3-Cyclohexyl-1-[2-(4-methoxy-phenylamino)-ethylcarbamoyl]-propyl}-3-trifluoromethyl-benzamide; |
| cxxvii. | (S)-N-{3-Cyclohexyl-1-[2-(4-methoxy-phenylamino)-ethylcarbamoyl]-propyl}-4-morpholin-4-yl-benzamide; |
| cxxviii. | (4-Cyclohexyl-N-[2-(4-methoxy-phenylamino)-ethyl]-2-(S)-(2-(S)-phenyl-propionylamino)-butyramide; |
| cxxix. | (S)-4-Benzyloxy-N-{3-cyclohexyl-1-[2-(4-methoxy-phenylamino)-ethylcarbamoyl]-propyl}-benzamide; |
| cxxx. | (S)-Biphenyl-4-carboxylic acid {3-cyclohexyl-1-[2-(4-methoxy-phenylamino)-ethylcarbamoyl]-propyl}-amide; |
| cxxxi. | (S)-5-Chloro-1H-indole-2-carboxylic acid {3-cyclohexyl-1-[2-(4-methoxy-phenylamino)-ethylcarbamoyl]-propyl}-amide; |
| cxxxii. | (S)-5-Fluoro-1H-indole-2-carboxylic acid {3-cyclohexyl-1-[2-(4-methoxy-phenylamino)-ethylcarbamoyl]-propyl}-amide; |
| cxxxiii. | (S)-2-Amino-4-methyl-thiazole-5-carboxylic acid {3-cyclohexyl-1-[2-(4-methoxy-phenylamino)-ethylcarbamoyl]-propyl}-amide; |
| cxxxiv. | (S)-5-Chloro-benzofuran-2-carboxylic acid {3-cyclohexyl-1-[2-(4-methoxy-phenylamino)-ethylcarbamoyl]-propyl}-amide; |
| cxxxv. | N-{2-cyclohexyl-1-(S)-[2-(4-trifluoromethoxy-phenylamino)-ethylcarbamoyl]-ethyl}-2-(R)-phenyl-butyramide; |
| cxxxvi. | (S)-5-(3-Trifluoromethyl-phenyl)-furan-2-carboxylic acid {3-cyclohexyl-1-[2-(4-methoxy-phenylamino)-ethylcarbamoyl]-propyl}-amide; |
| cxxxvii. | (S)-Benzothiazole-6-carboxylic acid {3-cyclohexyl-1-[2-(4-methoxy-phenylamino)-ethylcarbamoyl]-propyl}-amide; |
| cxxxviii. | (S)-N-{3-Cyclohexyl-1-[2-(4-methoxy-phenylamino)-ethylcarbamoyl]-propyl}-3-trifluoromethoxy-benzamide; |
| cxxxix. | (S)-3-Cyano-N-{3-cyclohexyl-1-[2-(4-methoxy-phenylamino)-ethylcarbamoyl]-propyl}-benzamide; |

TABLE I-continued

| | |
|---|---|
| cxl. | (S)-4-Cyano-N-{3-cyclohexyl-1-[2-(4-methoxy-phenylamino)-ethylcarbamoyl]-propyl}-benzamide; |
| cxli. | N-{2-cyclohexyl-1-(S)-[2-(4-trifluoromethoxy-phenylamino)-ethylcarbamoyl]-ethyl}-4-phenoxy-benzamide; |
| cxlii. | (S)-N-{3-Cyclohexyl-1-[2-(4-methoxy-phenylamino)-ethylcarbamoyl]-propyl}-3-(2-methyl-thiazol-4-yl)-benzamide; |
| cxliii. | (S)-N-{3-Cyclohexyl-1-[2-(4-methoxy-phenylamino)-ethylcarbamoyl]-propyl}-4-[1,2,4]triazol-1-yl-benzamide; |
| cxliv. | (S)-Biphenyl-3-carboxylic acid {3-cyclohexyl-1-[2-(4-methoxy-phenylamino)-ethylcarbamoyl]-propyl}-amide; |
| cxlv. | (S)-N-{2-Cyclohexyl-1-[2-(4-methoxy-phenylamino)-ethylcarbamoyl]-ethyl}-2-fluoro-benzamide; |
| cxlvi. | (S)-N-{2-Cyclohexyl-1-[2-(4-methoxy-phenylamino)-ethylcarbamoyl]-ethyl}-3,4-difluoro-benzamide; |
| cxlvii. | (S)-N-{2-Cyclohexyl-1-[2-(4-methoxy-phenylamino)-ethylcarbamoyl]-ethyl}-3-fluoro-2-methyl-benzamide; |
| cxlviii. | (S)-2-Chloro-N-{2-cyclohexyl-1-[2-(4-methoxy-phenylamino)-ethylcarbamoyl]-ethyl}-5-methyl-benzamide; |
| cxlix. | (S)-N-{2-Cyclohexyl-1-[2-(4-methoxy-phenylamino)-ethylcarbamoyl]-ethyl}-4-fluoro-3-trifluoromethyl-benzamide; |
| cl. | (S)-5-Methyl-1-phenyl-1H-pyrazole-4-carboxylic acid {2-cyclohexyl-1-[2-(4-methoxy-phenylamino)-ethylcarbamoyl]-ethyl}-amide; |
| cli. | (S)-N-{2-Cyclohexyl-1-[2-(4-methoxy-phenylamino)-ethylcarbamoyl]-ethyl}-4-propyl-benzamide; |
| clii. | 3-Cyclohexyl-2-(S)-[2-(4-fluoro-phenyl)-acetylamino]-N-[2-(4-fluoro-phenylamino)-ethyl]-propionamide; |
| cliii. | (S)-N-{2-Cyclohexyl-1-[2-(4-methoxy-phenylamino)-ethylcarbamoyl]-ethyl}-4-methoxy-benzamide; |
| cliv. | (S)-N-{2-Cyclohexyl-1-[2-(4-methoxy-phenylamino)-ethylcarbamoyl]-ethyl}-2-fluoro-5-trifluoromethyl-benzamide; |
| clv. | (S)-3-Chloro-N-{2-cyclohexyl-1-[2-(4-methoxy-phenylamino)-ethylcarbamoyl]-ethyl}-2-fluoro-benzamide; |
| clvi. | (S)-5-Chloro-N-{2-cyclohexyl-1-[2-(4-methoxy-phenylamino)-ethylcarbamoyl]-ethyl}-2-fluoro-benzamide; |
| clvii. | (S)-N-{2-Cyclohexyl-1-[2-(4-methoxy-phenylamino)-ethylcarbamoyl]-ethyl}-5-fluoro-2-methyl-benzamide; |
| clviii. | (S)-1-Phenyl-cyclopropanecarboxylic acid {2-cyclohexyl-1-[2-(4-methoxy-phenylamino)-ethylcarbamoyl]-ethyl}-amide; |
| clix. | (S)-3-Cyclohexyl-N-[2-(4-methoxy-phenylamino)-ethyl]-2-(2-phenylamino-acetylamino)-propionamide; |
| clx. | 3-Cyclohexyl-2-(S)-(2-(R)-hydroxy-2-phenyl-acetylamino)-N-[2-(4-methoxy-phenylamino)-ethyl]-propionamide; |
| clxi. | (S)-1-(4-Fluoro-phenyl)-5-methyl-1H-pyrazole-4-carboxylic acid {2-cyclohexyl-1-[2-(4-methoxy-phenylamino)-ethylcarbamoyl]-ethyl}-amide; |
| clxii. | (S)-1-(4-Methoxy-phenyl)-5-methyl-1H-pyrazole-4-carboxylic acid {2-cyclohexyl-1-[2-(4-methoxy-phenylamino)-ethylcarbamoyl]-ethyl}-amide; |
| clxiii. | (S)-1-(4-Chloro-phenyl)-5-methyl-1H-pyrazole-4-carboxylic acid {2-cyclohexyl-1-[2-(4-methoxy-phenylamino)-ethylcarbamoyl]-ethyl}-amide; |
| clxiv. | N-{2-Cyclohexyl-1-(S)-[2-(4-methoxy-phenylamino)-ethylcarbamoyl]-ethyl}-2-(S)-phenyl-butyramide; |
| clxv. | (S)-N-{2-Cyclohexyl-1-[2-(4-methoxy-phenylamino)-ethylcarbamoyl]-ethyl}-3-fluoro-5-trifluoromethyl-benzamide; |
| clxvi. | (S)-N-{2-Cyclohexyl-1-[2-(4-methoxy-phenylamino)-ethylcarbamoyl]-ethyl}-2-fluoro-3-trifluoromethyl-benzamide; |
| clxvii. | (S)-N-{2-Cyclohexyl-1-[2-(4-methoxy-phenylamino)-ethylcarbamoyl]-ethyl}-4-fluoro-3-methyl-benzamide; |
| clxviii. | (S)-5-(4-Chloro-phenyl)-furan-2-carboxylic acid {2-cyclohexyl-1-[2-(4-methoxy-phenylamino)-ethylcarbamoyl]-ethyl}-amide; |
| clxix. | (S)-N-{2-Cyclohexyl-1-[2-(4-methoxy-phenylamino)-ethylcarbamoyl]-ethyl}-2-fluoro-4-trifluoromethyl-benzamide; |
| clxx. | (S)-4'-Chloro-biphenyl-4-carboxylic acid {2-cyclohexyl-1-[2-(4-methoxy-phenylamino)-ethylcarbamoyl]-ethyl}-amide; |
| clxxi. | (S)-3',5'-Dichloro-biphenyl-4-carboxylic acid {2-cyclohexyl-1-[2-(4-methoxy-phenylamino)-ethylcarbamoyl]-ethyl}-amide; |
| clxxii. | (S)-3'-Methoxy-biphenyl-4-carboxylic acid {2-cyclohexyl-1-[2-(4-methoxy-phenylamino)-ethylcarbamoyl]-ethyl}-amide; |
| clxxiii. | (S)-3'-Chloro-biphenyl-4-carboxylic acid {2-cyclohexyl-1-[2-(4-methoxy-phenylamino)-ethylcarbamoyl]-ethyl}-amide; |
| clxxiv. | (S)-2'-Chloro-biphenyl-4-carboxylic acid {2-cyclohexyl-1-[2-(4-methoxy-phenylamino)-ethylcarbamoyl]-ethyl}-amide; |
| clxxv. | (S)-4'-Chloro-biphenyl-3-carboxylic acid {2-cyclohexyl-1-[2-(4-methoxy-phenylamino)-ethylcarbamoyl]-ethyl}-amide; |
| clxxvi. | (S)-4-Benzo[1,3]dioxol-5-yl-N-{2-cyclohexyl-1-[2-(4-methoxy-phenylamino)-ethylcarbamoyl]-ethyl}-benzamide; |
| clxxvii. | (S)-5-Bromo-furan-2-carboxylic acid {2-cyclohexyl-1-[2-(4-methoxy-phenylamino)-ethylcarbamoyl]-ethyl}-amide; |
| clxxviii. | (S)-3,5-Dibromo-N-{2-cyclohexyl-1-[2-(4-methoxy-phenylamino)-ethylcarbamoyl]-ethyl}-benzamide; |
| clxxix. | (S)-3,5-Dichloro-N-{2-cyclohexyl-1-[2-(4-methoxy-phenylamino)-ethylcarbamoyl]-ethyl}-benzamide; |
| clxxx. | (S)-N-{2-Cyclohexyl-1-[2-(4-methoxy-phenylamino)-ethylcarbamoyl]-ethyl}-3,5-dimethoxy-benzamide; |
| clxxxi. | (S)-Biphenyl-3-carboxylic acid {2-cyclohexyl-1-[2-(4-methoxy-phenylamino)-ethylcarbamoyl]-ethyl}-amide; |
| clxxxii. | (S)-5-Bromo-thiophene-2-carboxylic acid {2-cyclohexyl-1-[2-(4-methoxy-phenylamino)-ethylcarbamoyl]-ethyl}-amide; |
| clxxxiii. | (S)-N-{2-Cyclohexyl-1-[2-(4-methoxy-phenylamino)-ethylcarbamoyl]-ethyl}-4-phenoxy-benzamide; |
| clxxxiv. | (S)-N-{2-Cyclohexyl-1-[2-(4-methoxy-phenylamino)-ethylcarbamoyl]-ethyl}-3-phenoxy-benzamide; |
| clxxxv. | (S)-1H-Indole-3-carboxylic acid {2-cyclohexyl-1-[2-(4-methoxy-phenylamino)-ethylcarbamoyl]-ethyl}-amide; |
| clxxxvi. | (S)-Benzothiazole-6-carboxylic acid {2-cyclohexyl-1-[2-(4-methoxy-phenylamino)-ethylcarbamoyl]-ethyl}-amide; |
| clxxxvii. | (S)-2-Amino-benzothiazole-6-carboxylic acid {2-cyclohexyl-1-[2-(4-methoxy-phenylamino)-ethylcarbamoyl]-ethyl}-amide; |
| clxxxviii. | (S)-4-Methyl-2-(4-trifluoromethyl-phenyl)-thiazole-5-carboxylic acid {2-cyclohexyl-1-[2-(4-methoxy-phenylamino)-ethylcarbamoyl]-ethyl}-amide; |
| clxxxix. | (S)-4-(4-Chloro-phenyl)-thiophene-2-carboxylic acid {2-cyclohexyl-1-[2-(4-methoxy-phenylamino)-ethylcarbamoyl]-ethyl}-amide; |
| cxc. | (S)-2-Methyl-5-trifluoromethyl-oxazole-4-carboxylic acid {2-cyclohexyl-1-[2-(4-methoxy-phenylamino)-ethylcarbamoyl]-ethyl}-amide; |
| cxci. | (S)-4-(4-Methoxy-phenyl)-thiophene-2-carboxylic acid {2-cyclohexyl-1-[2-(4-methoxy-phenylamino)-ethylcarbamoyl]-ethyl}-amide; |
| cxcii. | N-{2-Cyclohexyl-1-(S)-[2-(4-methoxy-phenylamino)-ethylcarbamoyl]-ethyl}-2-(S)-phenyl-propionamide; |
| cxciii. | (S)-5-(2-Chloro-5-trifluoromethyl-phenyl)-furan-2-carboxylic acid {2-cyclohexyl-1-[2-(4-methoxy-phenylamino)-ethylcarbamoyl]-ethyl}-amide; |
| cxciv. | (S)-2'-Chloro-biphenyl-4-carboxylic acid {2-cyclohexyl-1-[2-(4-trifluoromethoxy-phenylamino)-ethylcarbamoyl]-ethyl}-amide; |
| cxcv. | (S)-1-(5-Bromo-pyrimidin-2-yl)-piperidine-4-carboxylic acid {2-cyclohexyl-1-[2-(4-methoxy-phenylamino)-ethylcarbamoyl]-ethyl}-amide; |
| cxcvi. | (S)-N-{2-Cyclohexyl-1-[2-(4-methoxy-phenylamino)-ethylcarbamoyl]-ethyl}-4-(4,6-dimethyl-pyrimidin-2-ylamino)-benzamide; |
| cxcvii. | (S)-1-(5-Bromo-pyrimidin-2-yl)-piperidine-3-carboxylic acid {2-cyclohexyl-1-[2-(4-methoxy-phenylamino)-ethylcarbamoyl]-ethyl}-amide; |
| cxcviii. | (S)-3'-Fluoro-biphenyl-4-carboxylic acid {2-cyclohexyl-1-[2-(4-trifluoromethoxy-phenylamino)-ethylcarbamoyl]-ethyl}-amide; |
| cxcix. | (S)-3-Aminomethyl-N-{2-cyclohexyl-1-[2-(4-methoxy-phenylamino)-ethylcarbamoyl]-ethyl}-benzamide; |
| cc. | (S)-N-{2-Cyclohexyl-1-[2-(4-trifluoromethoxy-phenylamino)-ethylcarbamoyl]-ethyl}-3-morpholin-4-ylmethyl-benzamide; |
| cci. | (S)-5-(2-Fluoro-phenyl)-thiophene-2-carboxylic acid {2-cyclohexyl-1-[2-(4-trifluoromethoxy-phenylamino)-ethylcarbamoyl]-ethyl}-amide; |
| ccii. | (S)-N-{3-Cyclohexyl-1-[2-(4-methoxy-phenylamino)-ethylcarbamoyl]-propyl}-3-methyl-benzamide; |
| cciii. | (S)-N-{4-Cyclohexyl-1-[2-(4-methoxy-phenylamino)-ethylcarbamoyl]-butyl}-3-methyl-benzamide; |
| cciv. | (S)-N-{[2-(4-Methoxy-phenylamino)-ethylcarbamoyl]-phenyl-methyl}-3-methyl-benzamide; |
| ccv. | (S)-5-(4-Trifluoromethyl-phenyl)-thiophene-2-carboxylic acid {2-cyclohexyl-1-[2-(4-trifluoromethoxy-phenylamino)-ethylcarbamoyl]-ethyl}-amide; |
| ccvi. | (S)-N-{1-[2-(4-Methoxy-phenylamino)-ethylcarbamoyl]-3-phenyl-propyl}-3-methyl-benzamide; |
| ccvii. | (S)-5-(4-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccviii. | (S)-N-{1-[2-(4-Methoxy-phenylamino)-ethylcarbamoyl]-4-phenyl-but-3-enyl}-3-methyl-benzamide; |

TABLE I-continued

| | |
|---|---|
| ccix. | (S)-5-(3-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccx. | (S)-5-(2-Methoxy-phenyl)-furan-2-carboxylic acid {2-cyclohexyl-1-[2-(4-trifluoromethoxy-phenylamino)-ethylcarbamoyl]-ethyl}-amide; |
| ccxi. | N-{(4-Methoxy-phenyl)-[2-(4-methoxy-phenylamino)-ethylcarbamoyl]-methyl}-3-methyl-benzamide; |
| ccxii. | (S)-5-(2-Fluoro-phenyl)-furan-2-carboxylic acid {2-cyclohexyl-1-[2-(4-trifluoromethoxy-phenylamino)-ethylcarbamoyl]-ethyl}-amide; |
| ccxiii. | (S)-5-(4-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxiv. | N-{(2-Benzyloxy-phenyl)-[2-(4-methoxy-phenylamino)-ethylcarbamoyl]-methyl}-3-methyl-benzamide; |
| ccxv. | (S)-5-(4-Trifluoromethoxy-phenyl)-furan-2-carboxylic acid {2-cyclohexyl-1-[2-(4-trifluoromethoxy-phenylamino)-ethylcarbamoyl]-ethyl}-amide; |
| ccxvi. | N-{(2-Chloro-phenyl)-[2-(4-methoxy-phenylamino)-ethylcarbamoyl]-methyl}-3-methyl-benzamide; |
| ccxvii. | N-{(4-Benzyloxy-phenyl)-[2-(4-methoxy-phenylamino)-ethylcarbamoyl]-methyl}-3-methyl-benzamide; |
| ccxviii. | N-{[2-(4-Methoxy-phenylamino)-ethylcarbamoyl]-naphthalen-1-yl-methyl}-3-methyl-benzamide; |
| ccxix. | (S)-5-(2-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxx. | N-{[2-(4-Methoxy-phenylamino)-ethylcarbamoyl]-o-tolyl-methyl}-3-methyl-benzamide; |
| ccxxi. | (S)-N-{2-Cyclohexyl-1-[2-(4-trifluoromethoxy-phenylamino)-ethylcarbamoyl]-ethyl}-4-[1,2,4]triazol-1-yl-benzamide; |
| ccxxii. | N-{(2,4-Dichloro-phenyl)-[2-(4-methoxy-phenylamino)-ethylcarbamoyl]-methyl}-3-methyl-benzamide; |
| ccxxiii. | N-{(2,3-Dichloro-phenyl)-[2-(4-methoxy-phenylamino)-ethylcarbamoyl]-methyl}-3-methyl-benzamide; |
| ccxxiv. | N-{(2,4-Dimethyl-phenyl)-[2-(4-methoxy-phenylamino)-ethylcarbamoyl]-methyl}-3-methyl-benzamide; |
| ccxxv. | N-{(2,4-Dimethoxy-phenyl)-[2-(4-methoxy-phenylamino)-ethylcarbamoyl]-methyl}-3-methyl-benzamide; |
| ccxxvi. | N-{[2-(4-Methoxy-phenylamino)-ethylcarbamoyl]-thiophen-2-yl-methyl}-3-methyl-benzamide; |
| ccxxvii. | N-{(4-Fluoro-phenyl)-[2-(4-methoxy-phenylamino)-ethylcarbamoyl]-methyl}-3-methyl-benzamide; |
| ccxxviii. | (S)-N-{2-(4-Hydroxy-phenyl)-1-[2-(4-methoxy-phenylamino)-ethylcarbamoyl]-ethyl}-3-methyl-benzamide; |
| ccxxix. | (S)-N-{2-(2,4-Dichloro-phenyl)-1-[2-(4-methoxy-phenylamino)-ethylcarbamoyl]-ethyl}-3-methyl-benzamide; |
| ccxxx. | (S)-N-{2-(3,5-Difluoro-phenyl)-1-[2-(4-methoxy-phenylamino)-ethylcarbamoyl]-ethyl}-3-methyl-benzamide; |
| ccxxxi. | (S)-N-{2-(3,4-Dichloro-phenyl)-1-[2-(4-methoxy-phenylamino)-ethylcarbamoyl]-ethyl}-3-methyl-benzamide; |
| ccxxxii. | (S)-4-Benzyloxy-N-{2-cyclohexyl-1-[2-(4-trifluoromethoxy-phenylamino)-ethylcarbamoyl]-ethyl}-benzamide; |
| ccxxxiii. | (S)-N-{2-(4-Acetylamino-phenyl)-1-[2-(4-methoxy-phenylamino)-ethylcarbamoyl]-ethyl}-3-methyl-benzamide; |
| ccxxxiv. | (S)-Biphenyl-4-carboxylic acid {2-cyclohexyl-1-[2-(4-trifluoromethoxy-phenylamino)-ethylcarbamoyl]-ethyl}-amide; |
| ccxxxv. | (S)-N-{1-[2-(4-Methoxy-phenylamino)-ethylcarbamoyl]-2-p-tolyl-ethyl}-3-methyl-benzamide; |
| ccxxxvi. | (S)-N-{2-(3-Fluoro-phenyl)-1-[2-(4-methoxy-phenylamino)-ethylcarbamoyl]-ethyl}-3-methyl-benzamide; |
| ccxxxvii. | (S)-N-{2-(3,4-Difluoro-phenyl)-1-[2-(4-methoxy-phenylamino)-ethylcarbamoyl]-ethyl}-3-methyl-benzamide; |
| ccxxxviii. | (S)-N-{1-[2-(4-Methoxy-phenylamino)-ethylcarbamoyl]-2-m-tolyl-ethyl}-3-methyl-benzamide; |
| ccxxxix. | (S)-N-[1-[2-(4-Methoxy-phenylamino)-ethylcarbamoyl]-2-(2-trifluoromethyl-phenyl)-ethyl]-3-methyl-benzamide; |
| ccxl. | (S)-N-{2-(4-Cyano-phenyl)-1-[2-(4-methoxy-phenylamino)-ethylcarbamoyl]-ethyl}-3-methyl-benzamide; |
| ccxli. | (S)-N-{2-(4-Bromo-phenyl)-1-[2-(4-methoxy-phenylamino)-ethylcarbamoyl]-ethyl}-3-methyl-benzamide; |
| ccxlii. | (S)-N-{2-(4-Iodo-phenyl)-1-[2-(4-methoxy-phenylamino)-ethylcarbamoyl]-ethyl}-3-methyl-benzamide; |
| ccxliii. | (S)-N-{2-(4-Chloro-phenyl)-1-[2-(4-methoxy-phenylamino)-ethylcarbamoyl]-ethyl}-3-methyl-benzamide; |
| ccxliv. | (S)-N-[1-[2-(4-Methoxy-phenylamino)-ethylcarbamoyl]-2-(4-nitro-phenyl)-ethyl]-3-methyl-benzamide; |
| ccxlv. | (S)-N-{2-(4-Fluoro-phenyl)-1-[2-(4-methoxy-phenylamino)-ethylcarbamoyl]-ethyl}-3-methyl-benzamide; |
| ccxlvi. | (S)-5-(3-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxlvii. | (S)-N-{2-(4-Benzyloxy-phenyl)-1-[2-(4-methoxy-phenylamino-ethylcarbamoyl]-ethyl}-3-methyl-benzamide; |
| ccxlviii. | (S)-N-{2-[4-(2,6-Dichloro-benzyloxy)-phenyl]-1-[2-(4-methoxy-phenylamino)-ethylcarbamoyl]-ethyl}-3-methyl-benzamide; |
| ccxlix. | (S)-N-{2-(4-Methoxy-phenyl)-1-[2-(4-methoxy-phenylamino)-ethylcarbamoyl]-ethyl}-3-methyl-benzamide; |
| ccl. | 2-Amino-4-methyl-thiazole-5-carboxylic acid (S)-{2-cyclohexyl-1-[2-(4-trifluoromethoxy-phenylamino)-ethylcarbamoyl]-ethyl}-amide; |
| ccli. | (S)-5-(2-Chloro-5-trifluoromethyl-phenyl)-furan-2-carboxylic acid {2-cyclohexyl-1-[2-(4-trifluoromethoxy-phenylamino)-ethylcarbamoyl]-ethyl}-amide; |
| cclii. | (S)-N-[1-[2-(4-Methoxy-phenylamino)-ethylcarbamoyl]-2-(3-trifluoromethyl-phenyl)-ethyl]-3-methyl-benzamide; |
| ccliii. | (S)-N-[1-[2-(4-Methoxy-phenylamino)-ethylcarbamoyl]-2-(4-trifluoromethyl-phenyl)-ethyl]-3-methyl-benzamide; |
| ccliv. | (S)-N-{2-Benzyloxy-1-[2-(4-methoxy-phenylamino)-ethylcarbamoyl]-ethyl}-3-methyl-benzamide; |
| cclv. | (S)-N-{2-(4-tert-Butyl-phenyl)-1-[2-(4-methoxy-phenylamino)-ethylcarbamoyl]-ethyl}-3-methyl-benzamide; |
| cclvi. | Cyclohexyl-N-[2-(4-methoxy-phenylamino)-ethyl]-2-(S)-(2-(S)-phenyl-propionylamino)-butyramide; |
| cclvii. | (S)-N-{2-(1H-Indol-3-yl)-1-[2-(4-methoxy-phenylamino)-ethylcarbamoyl]-ethyl}-3-methyl-benzamide; |
| cclviii. | (S)-N-{1-[2-(4-Methoxy-phenylamino)-ethylcarbamoyl]-2-naphthalen-1-yl-ethyl}-3-methyl-benzamide; |
| cclix. | (S)-N-{2-Benzyloxy-1-[2-(4-methoxy-phenylamino)-ethylcarbamoyl]-propyl}-3-methyl-benzamide; |
| cclx. | 3-Cyclohexyl-2-(S)-[2-(3-fluoro-phenyl)-acetylamino]-N-[2-(4-fluoro-phenylamino)-ethyl]-propionamide; |
| cclxi. | (S)-N-{1-[2-(4-Methoxy-phenylamino)-ethylcarbamoyl]-2-naphthalen-2-yl-ethyl}-3-methyl-benzamide; |
| cclxii. | (S)-N-{1-[2-(4-Methoxy-phenylamino)-ethylcarbamoyl]-2-pyridin-3-yl-ethyl}-3-methyl-benzamide; |
| cclxiii. | (S)-N-{1-[2-(4-Methoxy-phenylamino)-ethylcarbamoyl]-2-pyridin-4-yl-ethyl}-3-methyl-benzamide; |
| cclxiv. | Furan-2-carboxylic acid (S)-{2-cyclohexyl-1-[2-(4-fluoro-phenylamino)-ethylcarbamoyl]-ethyl}-amide; |
| cclxv. | 3-Cyclohexyl-N-[2-(4-fluoro-phenylamino)-ethyl]-2-(S)-(2-tetrazol-1-yl-acetylamino)-propionamide; |
| cclxvi. | N-[1-[2-(4-Methoxy-phenylamino)-ethylcarbamoyl]-2-(4-nitro-phenyl)-propyl]-3-methyl-benzamide; |
| cclxvii. | (S)-N-[1-[2-(4-Methoxy-phenylamino)-ethylcarbamoyl]-2-(4-m-tolyloxy-phenyl)-ethyl]-3-methyl-benzamide; |
| cclxviii. | threo-N-{1-[2-(4-Methoxy-phenylamino)-ethylcarbamoyl]-2-phenyl-propyl}-3-methyl-benzamide; |
| cclxix. | erythro-N-{1-[2-(4-Methoxy-phenylamino)-ethylcarbamoyl]-2-phenyl-propyl}-3-methyl-benzamide; |
| cclxx. | (S)-N-{2-Biphenyl-4-yl-1-[2-(4-methoxy-phenylamino)-ethylcarbamoyl]-ethyl}-3-methyl-benzamide; |
| cclxxi. | (S)-N-[1-[2-(4-Methoxy-phenylamino)-ethylcarbamoyl]-2-(3'-nitro-biphenyl-4-yl)-ethyl]-3-methyl-benzamide; |
| cclxxii. | Furan-3-carboxylic acid (S)-{2-cyclohexyl-1-[2-(4-fluoro-phenylamino)-ethylcarbamoyl]-ethyl}-amide; |
| cclxxiii. | (S)-N-[1-[2-(4-Methoxy-phenylamino)-ethylcarbamoyl]-2-(2'-nitro-biphenyl-4-yl)-ethyl]-3-methyl-benzamide; |
| cclxxiv. | (S)-N-[1-[2-(4-Methoxy-phenylamino)-ethylcarbamoyl]-2-(4-pyridin-3-yl-phenyl)-ethyl]-3-methyl-benzamide; |
| cclxxv. | (S)-N-[1-[2-(4-Methoxy-phenylamino)-ethylcarbamoyl]-2-(4-thiophen-3-yl-phenyl)-ethyl]-3-methyl-benzamide; |
| cclxxvi. | (S)-N-{2-(4'-Cyano-biphenyl-4-yl)-1-[2-(4-methoxy-phenylamino)-ethylcarbamoyl]-ethyl}-3-methyl-benzamide; |
| cclxxvii. | (S)-N-[1-[2-(4-Methoxy-phenylamino)-ethylcarbamoyl]-2-(4-pyridin-4-yl-phenyl)-ethyl]-3-methyl-benzamide; |
| cclxxviii. | (S)-N-{2-(4'-Chloro-biphenyl-4-yl)-1-[2-(4-methoxy-phenylamino)-ethylcarbamoyl]-ethyl}-3-methyl-benzamide; |
| cclxxix. | (S)-N-{2-(2',3'-Dimethoxy-biphenyl-4-yl)-1-[2-(4-methoxy-phenylamino)-ethylcarbamoyl]-ethyl}-3-methyl-benzamide; |
| cclxxx. | (S)-N-{2-(3'-Amino-biphenyl-4-yl)-1-[2-(4-methoxy-phenylamino)-ethylcarbamoyl]-ethyl}-3-methyl-benzamide; |
| cclxxxi. | (S)-N-{2-(3',4'-Dimethoxy-biphenyl-4-yl)-1-[2-(4-methoxy-phenylamino)-ethylcarbamoyl]-ethyl}-3-methyl-benzamide; |

TABLE I-continued

| | |
|---|---|
| cclxxxii. | (S)-N-[2-(4'-Hydroxymethyl-biphenyl-4-yl)-1-[2-(4-methoxy-phenylamino)-ethylcarbamoyl]-ethyl}-3-methyl-benzamide; |
| cclxxxiii. | (S)-N-{2-(5'-Fluoro-2'-methoxy-biphenyl-4-yl)-1-[2-(4-methoxy-phenylamino)-ethylcarbamoyl]-ethyl}-3-methyl-benzamide; |
| cclxxxiv. | (S)-N-{2-(3'-Hydroxymethyl-biphenyl-4-yl)-1-[2-(4-methoxy-phenylamino)-ethylcarbamoyl]-ethyl}-3-methyl-benzamide; |
| cclxxxv. | (S)-N-{2-(2',5'-Dimethoxy-biphenyl-4-yl)-1-[2-(4-methoxy-phenylamino)-ethylcarbamoyl]-ethyl}-3-methyl-benzamide; |
| cclxxxvi. | (S)-N-{2-(2',5'-Dichloro-biphenyl-4-yl)-1-[2-(4-methoxy-phenylamino)-ethylcarbamoyl]-ethyl}-3-methyl-benzamide; |
| cclxxxvii. | (S)-N-{2-(4'-Dimethylamino-biphenyl-4-yl)-1-[2-(4-methoxy-phenylamino)-ethylcarbamoyl]-ethyl}-3-methyl-benzamide; |
| cclxxxviii. | (S)-N-{2-(2'-Acetyl-biphenyl-4-yl)-1-[2-(4-methoxy-phenylamino)-ethylcarbamoyl]-ethyl}-3-methyl-benzamide; |
| cclxxxix. | (S)-N-{2-(4'-Hydroxy-biphenyl-4-yl)-1-[2-(4-methoxy-phenylamino)-ethylcarbamoyl]-ethyl}-3-methyl-benzamide; |
| ccxc. | (S)-N-{2-(3'-Acetyl-biphenyl-4-yl)-1-[2-(4-methoxy-phenylamino)-ethylcarbamoyl]-ethyl}-3-methyl-benzamide; |
| ccxci. | (S)-N-{2-[4-(2,4-Dimethoxy-pyrimidin-5-yl)-phenyl]-1-[2-(4-methoxy-phenylamino)-ethylcarbamoyl]-ethyl}-3-methyl-benzamide; |
| ccxcii. | (S)-N-{1-[2-(4-Methoxy-phenylamino)-ethylcarbamoyl]-2-[4-(6-methoxy-pyridin-3-yl)-phenyl]-ethyl}-3-methyl-benzamide; |
| ccxciii. | Methanesulfonyl-thiophene-2-carboxylic acid (S)-{2-cyclohexyl-1-[2-(4-fluoro-phenylamino)-ethylcarbamoyl]-ethyl}-amide; |
| ccxciv. | N-(S)-{2-cyclohexyl-1-[2-(4-fluoro-phenylamino)-ethylcarbamoyl]-ethyl}-2-(S)-phenyl-propionamide; |
| ccxcv. | Pyridazine-4-carboxylic acid (S)-{2-cyclohexyl-1-[2-(4-fluoro-phenylamino)-ethylcarbamoyl]-ethyl}-amide; |
| ccxcvi. | N-(S)-{2-cyclohexyl-1-[2-(4-fluoro-phenylamino)-ethylcarbamoyl]-ethyl}-3-methanesulfonyl-benzamide; |
| ccxcvii. | 3-Cyclohexyl-N-[2-(4-fluoro-phenylamino)-ethyl]-2-(S)-(2-1H-tetrazol-5-yl-acetylamino)-propionamide; |
| ccxcviii. | Cyclopropanecarboxylic acid (S)-{2-cyclohexyl-1-[2-(4-fluoro-phenylamino)-ethylcarbamoyl]-ethyl}-amide; |
| ccxcix. | N-(S)-{2-cyclohexyl-1-[2-(4-fluoro-phenylamino)-ethylcarbamoyl]-ethyl}-4-methanesulfonylamino-benzamide; |
| ccc. | (S)-N-{2-[4-(4-Chloro-phenoxy)-phenyl]-1-[2-(4-methoxy-phenylamino)-ethylcarbamoyl]-ethyl}-3-methyl-benzamide; |
| ccci. | 3-Cyclohexyl-N-[2-(4-fluoro-phenylamino)-ethyl]-2-(S)-[2-(4-methoxy-phenyl)-acetylamino]-propionamide; |
| cccii. | 2-(S)-[2-(3-Chloro-phenyl)-acetylamino]-3-cyclohexyl-N-[2-(4-fluoro-phenylamino)-ethyl]-propionamide; |
| ccciii. | 3-Cyclohexyl-N-[2-(4-fluoro-phenylamino)-ethyl]-2-(S)-phenylacetylamino-propionamide; |
| ccciv. | 3-Cyclohexyl-N-[2-(4-fluoro-phenylamino)-ethyl]-2-(S)-(2-o-tolyl-acetylamino)-propionamide; |
| cccv. | 2-(S)-[2-(4-Chloro-phenyl)-acetylamino]-3-cyclohexyl-N-[2-(4-fluoro-phenylamino)-ethyl]-propionamide; |
| cccvi. | 3-Cyclohexyl-2-(S)-[2-(2-fluoro-phenyl)-acetylamino]-N-[2-(4-fluoro-phenylamino)-ethyl]-propionamide; |
| cccvii. | 3-Cyclohexyl-2-(S)-diphenylacetylamino-N-[2-(4-fluoro-phenylamino-ethyl]-propionamide; |
| cccviii. | N-(S)-{2-cyclohexyl-1-[2-(4-fluoro-phenylamino)-ethylcarbamoyl]-ethyl}-2-(2-fluoro-biphenyl-4-yl)-propionamide; |
| cccix. | N-{2-cyclohexyl-1-(S)-[2-(4-fluoro-phenylamino)-ethylcarbamoyl]-ethyl}-2-p-tolyl-propionamide; |
| cccx. | N-{2-cyclohexyl-1-(S)-[2-(4-fluoro-phenylamino)-ethylcarbamoyl]-ethyl}-2-(4-fluoro-phenyl)-propionamide; |
| cccxi. | N-{2-cyclohexyl-1-(S)-[2-(4-fluoro-phenylamino)-ethylcarbamoyl]-ethyl}-2-(4-hydroxy-phenyl)-propionamide; |
| cccxii. | 2-(4-Chloro-phenyl)-N-{2-cyclohexyl-1-(S)-[2-(4-fluoro-phenylamino)-ethylcarbamoyl]-ethyl}-propionamide; |
| cccxiii. | N-(S)-{2-cyclohexyl-1-[2-(4-fluoro-phenylamino)-ethylcarbamoyl]-ethyl}-4-methanesulfonyl-benzamide; |
| cccxiv. | Thiazole-4-carboxylic acid (S)-{2-cyclohexyl-1-[2-(4-fluoro-phenylamino)-ethylcarbamoyl]-ethyl}-amide; |
| cccxv. | N-{2-cyclohexyl-1-(S)-[2-(4-fluoro-phenylamino)-ethylcarbamoyl]-ethyl}-2-(R)-phenyl-propionamide; |
| cccxvi. | 4-Cyano-N-(S)-{2-cyclohexyl-1-[2-(4-fluoro-phenylamino)-ethylcarbamoyl]-ethyl}-benzamide; |
| cccxvii. | 3-Cyclohexyl-N-[2-(4-fluoro-phenylamino)-ethyl]-2-(S)-(2-(R)-hydroxy-2-phenyl-acetylamino)-propionamide; |
| cccxviii. | N-{2-cyclohexyl-1-(S)-[2-(4-fluoro-phenylamino)-ethylcarbamoyl]-ethyl}-2-(R)-phenyl-butyramide; |
| cccxix. | Phenyl-cyclopropanecarboxylic acid (S)-{2-cyclohexyl-1-[2-(4-fluoro-phenylamino)-ethylcarbamoyl-ethyl}-amide; |
| cccxx. | N-(S)-{2-cyclohexyl-1-[2-(4-fluoro-phenylamino)-ethylcarbamoyl]-ethyl}-2-(R,S)-(4-fluoro-phenyl)-propionamide; |
| cccxxi. | Cyano-N-(S)-{2-cyclohexyl-1-[2-(4-fluoro-phenylamino)-ethylcarbamoyl]-ethyl}-benzamide; |
| cccxxii. | 5-(4-Fluoro-phenyl)-furan-2-carboxylic acid (S)-{2-cyclohexyl-1-[2-(4-fluoro-phenylamino)-ethylcarbamoyl]-ethyl}-amide; |
| cccxxiii. | Cyclohexyl-N-[2-(4-fluoro-phenylamino)-ethyl]-2-(S)-[2-(3-trifluoromethyl-phenyl)-acetylamino]-propionamide; |
| cccxxiv. | Cyano-N-(S)-{2-cyclohexyl-1-[2-(4-fluoro-phenylamino)-ethylcarbamoyl]-ethyl}-benzamide; |
| cccxxv. | 3-Cyclohexyl-N-[2-(4-fluoro-phenylamino)-ethyl]-2-(S)-[2-(4-trifluoromethyl-phenyl)-acetylamino]-propionamide; |
| cccxxvi. | 3-Cyclohexyl-N-[2-(4-fluoro-phenylamino)-ethyl]-2-(S)-[2-(4-methanesulfonyl-phenyl)-acetylamino]-propionamide; |
| cccxxvii. | (S)-N-[1-[2-(4-Methoxy-phenylamino)-ethylcarbamoyl]-2-(4-phenoxy-phenyl)-ethyl]-3-methyl-benzamide; |
| cccxxviii. | (S)-N-{2-[4-(4-Methoxy-phenoxy)-phenyl]-1-[2-(4-methoxy-phenylamino)-ethylcarbamoyl]-ethyl}-3-methyl-benzamide; |
| cccxxix. | (S)-N-{2-[4-(3-Chloro-phenoxy)-phenyl]-1-[2-(4-methoxy-phenylamino)-ethylcarbamoyl]-ethyl}-3-methyl-benzamide; |
| cccxxx. | (S)-N-{2-[4-(3,5-Dimethyl-phenoxy)-phenyl]-1-[2-(4-methoxy-phenylamino)-ethylcarbamoyl]-ethyl}-3-methyl-benzamide. |

9. A pharmaceutical composition, said composition comprising a compound of Formula I:

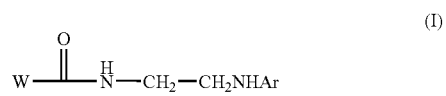

(I)

or a pharmaceutically acceptable salt or prodrug thereof, wherein:

W is a member selected from the group consisting of
$R^1$—X—(C=O)—NH—CHR$^2$—,
$R^4$—Y—(C=O)—NH—CHR$^3$—,
$R^6$—(C=O)—NH—CHR$^5$—,
$R^7$—NH—(C=O)—NH—CHR$^8$—,
$R^{10}$-Z-(C=O)—NH—CHR$^9$—, and
$R^{11}$—(C=O)—NH—CHR$^{12}$—;

$R^1$ is a member selected from the group consisting of phenyl substituted with 0–2 $R^{1a}$, pyridyl substituted with 0–2 $R^{1a}$, and pyridinium N-oxide substituted with 0–2 $R^{1a}$;

each $R^{1a}$ is independently a member selected from the group consisting of Cl, F, OCF$_3$, OCH$_3$, CH$_3$ and CF$_3$;

X is a member selected from the group consisting of furanylene substituted with 0–1 $R^X$, thienylene substituted with 0–1 $R^X$, pyrazolylene substituted with 0–1 $R^X$, thiazolylene substituted with 0–1 $R^X$, and oxazolylene substituted with 0–1 $R^X$;

$R^X$ is a member selected from the group consisting of F, Cl, CH$_3$ and CF$_3$;

$R^2$ is a member selected from the group consisting of phenyl substituted with 0–2 $R^{2a}$, and (CH$_2$)$_n$R$^{2b}$;

each $R^{2a}$ is independently a member selected from the group consisting of Cl, F, OCF$_3$, OCH$_3$, CH$_3$ and CF$_3$;

$R^{2b}$ is independently a member selected from the group consisting of phenyl substituted with 0–2 $R^{2a}$; cyclopentyl, cyclohexyl and tetrahydropyranyl;

n is the integer 1 or 2;

$R^3$ is (CH$_2$)$_m$R$^{3b}$;

$R^{3b}$ is selected from the group consisting of phenyl substituted with 0–2 $R^{2a}$, cyclopentyl and cyclohexyl;

m is the integer 1 or 2;

$R^4$ is a member selected from the group consisting of phenyl substituted with 0–3 $R^{4a}$, thienyl, tetrazolyl, cyclopentenyl and indolyl;

each $R^{4a}$ is a member selected from the group consisting of phenyl, OH, $C_1$–$C_4$ alkyl, $C_1$–$C_4$ alkoxy, $CF_3$, $OCF_3$, F, Cl, $CH_3S(=O)_2$—, morpholinyl, pyrrolidinyl, piperidinyl and 4-acetylpiperazinyl;

Y is a member selected from the group consisting of —$CR^{17}R^{18}$, —NH—$CH_2$— and —O—$CH_2$—;

$R^5$ is a member selected from the group consisting of phenyl substituted with 0–2 $R^{5a}$, thienyl, naphthyl, and $CH_2R^{5b}$, $CH_2CH_2$(cyclohexyl), $CH_2CH_2CH_2$(cyclohexyl), $CH_2CH_2Ph$, $CH(CH_3)R^{5e}$, $CH_2CH=CHPh$, —$CH_2OCH_2Ph$, —$CH(CH_3)OCH_2Ph$;

each $R^{5a}$ is independently a member selected from the group consisting of F, Cl, $NO_2$, $OCH_3$, $OCH_2Ph$, OPh, $CH_3$, $OCF_3$ and $CF_3$;

$R^{5b}$ is independently a member selected from the group consisting of phenyl substituted with 0–2 $R^{5c}$; cyclopentyl, cyclohexyl, naphthyl, indolyl and pyridyl;

$R^{5c}$ is independently a member selected from the group consisting of OH, Cl, F, Br, I, CN, $NO_2$, $CH_3$, $OCH_3$, $^tBu$, $O$-$^tBu$, —$NHC(=O)CH_3$, $CF_3$, $OCF_3$; phenyl substituted with 0–2 $R^{5d}$; phenoxy substituted with 0–2 $R^{5d}$; benzyloxy substituted with 0–2 $R^{5d}$; pyridyl substituted with 0–2 $R^{5d}$; pyrimidinyl substituted with 0–2 $R^{5d}$; thienyl substituted with 0–2 $R^{5d}$;

$R^{5d}$ is independently a member selected from the group consisting of $CH_3$, Cl, F, $OCH_3$, $CF_3$, $OCF_3$, $N(CH_3)_2$, acetyl, OH, $CH_2OH$, $NH_2$, CN and $NO_2$;

$R^{5e}$ is phenyl substituted with 0–2 $R^{5a}$;

$R^6$ is a member selected from the group consisting of phenyl substituted with 0–3 $R^{6a}$, furanyl substituted with 0–2 $R^{6b}$, thienyl substituted with 0–2 $R^{6b}$, oxazolyl substituted with 0–2 $R^{6b}$, thiazolyl substituted with 0–2 $R^{6b}$, pyridyl, pyridazinyl and cyclopropyl;

each $R^{6a}$ is independently a member selected from the group consisting of Cl, F, Br, $OCF_3$, $CF_3$, $C_1$–$C_4$ alkyl, $C_1$–$C_4$ alkoxy, —$S(=O)_2CH_3$, CN, —$N(CH_3)_2$, $OCF_2H$, —$CH_2$-benzimidazole, —NH—$S(=O)_2CH_3$, —$NR^{13}R^{14}$, $OR^{14}$, $CH_2$-morpholine, $CH_2NH_2$, $OCH_2Ph$, and OPh;

alternatively, two $R^{6a}$ substituents on adjacent atoms may be combined to form a 5 to 6 membered heterocyclic fused radical, wherein said 5 to 6 membered heterocyclic fused radical has 1 or 2 oxygen atom(s);

each $R^{6b}$ is independently a member selected from the group consisting of $NH_2$, F, Cl, Br, —$S(=O)_2R^5$, $CH_3$, and $CF_3$;

$R^7$ is a member selected from the group consisting of $(CH_2)_pR^{7a}$, and naphthyl substituted with 0–2 $R^{7b}$;

p is the integer 0, 1, or 2;

$R^{7a}$ is phenyl substituted with 0–2 $R^{7b}$;

$R^{7b}$ is a member selected from the group consisting of F, Cl, $CF_3$, $C_1$–$C_4$ alkyl, $C_1$–$C_4$ alkoxy, $OCF_3$, phenoxy and acetyl;

alternatively, two $R^{7b}$ substituents on adjacent atoms may be combined to form a 5 to 6 membered heterocyclic fused radical, wherein said 5 to 6 membered heterocyclic fused radical has 1 or 2 oxygen atom(s);

$R^8$ is —$CH_2$—$R^{3b}$;

$R^9$ is $(CH_2)_qR^{9a}$;

$R^{9a}$ is a member selected from the group consisting of cyclopentyl, phenyl and cyclohexyl;

q is the integer 1 or 2;

$R^{10}$ is a member selected from the group consisting of phenyl substituted with 0–2 $R^{10a}$, 5 membered heteroaryl containing 1 to 4 heteroatoms each independently a member selected from the group consisting of N, O and S, wherein said heteroaryl is substituted with 0–2 $R^{10a}$, 6 membered heteroaryl containing 1 to 2 N, wherein said heteroaryl is substituted with 0–2 $R^{10a}$, morpholinyl substituted with 0–2 $R^{10a}$, piperazinyl substituted with 0–2 $R^{10a}$ and piperidinyl substituted with 0–2 $R^{10a}$;

each $R^{10a}$ is independently a member selected from the group consisting of Cl, F, $C_1$–$C_4$ alkyl, $C_1$–$C_4$ alkoxy, $OCF_3$, and $CF_3$;

alternatively, two $R^{10a}$ substituents on adjacent atoms may be combined to form a 5 to 6 membered heterocyclic fused radical, wherein said 5 to 6 membered heterocyclic fused radical comprises 1 or 2 heteroatom(s);

Z is phenylene;

$R^{11}$ is a member selected from the group consisting of indolyl substituted with 0–2 $R^{11a}$, benzofuranyl substituted with 0–2 $R^{11a}$, benzothienyl substituted with 0–2 $R^{11a}$, benzothiazole substituted with 0–2 $R^{11a}$, benzisoxazolyl substituted with 0–2 $R^{11a}$, benzoxazolyl substituted with 0–2 $R^{11a}$, and pyrazolo[1,5-a]pyrimidinyl substituted with 0–2 $R^{11a}$, piperidinyl N-substituted with 0–1 $R^{11b}$, morpholinyl N-substituted with 0–1 $R^{11b}$; and 2-oxo-pyrrolidinyl with 0–1 $R^{11b}$;

each $R^{11a}$ is independently a member selected from the group consisting of Cl, F, $NH_2$, $CH_3$, $OCH_3$, —$C(=O)OCH_3$, $OCF_3$, and $CF_3$;

each $R^{11b}$ is independently a member selected from the group consisting of pyrimidinyl substituted with 0–2 $R^{11c}$; benzyl, acetyl, $CH_2$-furanyl, and $CH_2$-thienyl;

each $R^{11c}$ is independently a member selected from the group consisting of Br and $CH_3$;

$R^{12}$ is $(CH_2)_sR^{12a}$;

$R^{12a}$ is a member selected from the group consisting of cyclopentyl and cyclohexyl;

s is the integer 1 or 2;

$R^{13}$ is a member selected from the group consisting of H and $C_1$–$C_4$ alkyl;

$R^{14}$ is pyrimidinyl substituted with 0–2 $R^{16}$;

$R^{15}$ is a member selected from the group consisting of $C_1$–$C_4$ alkyl, morpholinyl, pyrrolidinyl and piperidinyl;

$R^{16}$ is a member selected from the group consisting of $CH_3$ and $OCH_3$;

each of $R^{17}$ and $R^{18}$ is independently a member of H, OH, F, phenyl and $C_1$–$C_3$ alkyl;

alternatively, $R^{17}$ and $R^{18}$ may be taken together to form a $C_3$–$C_6$ cycloalkyl;

Ar is a phenyl substituted with 0–2 $R^{19}$;

each $R^{19}$ is independently a member selected from the group consisting of F, Cl, COOH, $C_1$–$C_4$ alkoxy, $OCHF_2$ and $OCF_3$;

and a pharmaceutically acceptable excipient.

10. The composition of claim 9, wherein said compound is a member selected from the compounds of Table I.

TABLE I

| | |
|---|---|
| i. | N-((S)-1-(2-(4-methoxyphenylamino)ethylcarbamoyl)-3-phenylpropyl)-5-(3-(trifluoromethyl)phenyl)furan-2-carboxamide; |

TABLE I-continued ii. N-((S)-1-(2-(4-methoxyphenylamino)ethylcarbamoyl)-2-(2-chlorophenyl)ethyl)-5-(3-(trifluoromethyl)phenyl)furan-2-carboxamide;
iii. N-((S)-1-(2-(4-methoxyphenylamino)ethylcarbamoyl)-2-(3-chlorophenyl)ethyl)-5-(3-(trifluoromethyl)phenyl)furan-2-carboxamide;
iv. N-((S)-1-(2-(4-methoxyphenylamino)ethylcarbamoyl)-2-(4-chlorophenyl)ethyl)-5-(3-(trifluoromethyl)phenyl)furan-2-carboxamide;
v. N-((S)-1-(2-(4-methoxyphenylamino)ethylcarbamoyl)-2-(tetrahydro-2H-pyran-4-yl)ethyl)-5-(3-(trifluoromethyl)phenyl)furan-2-carboxamide;
vi. N-((S)-1-(2-(4-methoxyphenylamino)ethylcarbamoyl)-2-cyclopentylethyl)-5-(3-(trifluoromethyl)phenyl)furan-2-carboxamide;
vii. (S)-N-{2-[4-(2,3-Dimethyl-phenoxy)-phenyl]-1-[2-(4-methoxy-phenylamino)-ethylcarbamoyl]-ethyl}-3-methyl-benzamide;
viii. (±)-N-((2-(4-methoxyphenylamino)ethylcarbamoyl)(4-chlorophenyl)methyl)-3-methylbenzamide;
ix. (±)-N-((2-(4-methoxyphenylamino)ethylcarbamoyl)(phenyl)methyl)-5-(3-(trifluoromethyl)phenyl)furan-2-carboxamide;
x. N-((S)-1-(2-(4-(difluoromethoxy)phenylamino)ethyl-carbamoyl)-2-cyclohexylethyl)-5-(3-(trifluoromethyl)phenyl)furan-2-carboxamide;
xi. 4-[2-(3-Cyclohexyl-2-(S)-{[5-(3-trifluoromethyl-phenyl)-furan-2-carbonyl]-amino}-propionylamino)-ethylamino]-benzoic acid;
xii. 2-[2-(3-Cyclohexyl-2-(S)-{[5-(3-trifluoromethyl-phenyl)-furan-2-carbonyl]-amino}-propionylamino)-ethylamino]-benzoic acid;
xiii. 4-Cyclohexyl-2-(S)-(2-(R)-phenyl-propionylamino)-N-[2-(4-trifluoromethoxy-phenylamino)-ethyl]-butyramide;
xiv. Acetyl-piperidine-4-carboxylic acid (S)-{2-cyclohexyl-1-[2-(4-trifluoromethoxy-phenylamino)-ethylcarbamoyl]-ethyl}-amide;
xv. (S)-2-{2-[4-(4-Acetyl-piperazin-1-yl)-phenoxy]-acetylamino}-3-cyclohexyl-N-[2-(4-trifluoromethoxy-phenylamino)-ethyl]-propionamide;
xvi. (S)-2-Chloro-N-{1-[2-(4-methoxy-phenylamino)-ethylcarbamoyl]-2-phenyl-ethyl}-3-methyl-benzamide;
xvii. Cyclohexyl-2-[2-(4-methoxy-phenyl)-acetylamino]-N-[2-(4-trifluoromethoxy-phenylamino)-ethyl]-propionamide;
xviii. (S)-N-{2-[4-(3,5-Dichloro-phenoxy)-phenyl]-1-[2-(4-methoxy-phenylamino)-ethylcarbamoyl]-ethyl}-3-methyl-benzamide;
xix. N-(S)-{2-cyclohexyl-1-[2-(4-trifluoromethoxy-phenylamino)-ethylcarbamoyl]-ethyl}-4-methanesulfonyl-benzamide;
xx. (S)-4-Benzyloxy-N-{1-[2-(4-methoxy-phenylamino)-ethylcarbamoyl]-2-phenyl-ethyl}-3,5-dimethyl-benzamide;
xxi. (S)-4-Methoxy-N-{1-[2-(4-methoxy-phenylamino)-ethylcarbamoyl]-2-phenyl-ethyl}-3,5-dimethyl-benzamide;
xxii. 5-Methoxy-1H-indole-2-carboxylic acid (S)-{2-cyclohexyl-1-[2-(4-trifluoromethoxy-phenylamino)-ethylcarbamoyl]-ethyl}-amide;
xxiii. (S)-3-Bromo-N-{1-[2-(4-methoxy-phenylamino)-ethylcarbamoyl]-2-phenyl-ethyl}-4-methyl-benzamide;
xxiv. Furan-2-carboxylic acid (S)-{2-cyclohexyl-1-[2-(4-trifluoromethoxy-phenylamino)-ethylcarbamoyl]-ethyl}-amide;
xxv. Thiophene-2-carboxylic acid (S)-{2-cyclohexyl-1-[2-(4-trifluoromethoxy-phenylamino)-ethylcarbamoyl]-ethyl}-amide;
xxvi. Furan-3-carboxylic acid (S)-{2-cyclohexyl-1-[2-(4-trifluoromethoxy-phenylamino)-ethylcarbamoyl]-ethyl}-amide;
xxvii. N-(S)-{2-cyclohexyl-1-[2-(4-trifluoromethoxy-phenylamino)-ethylcarbamoyl]-ethyl}-4-(5-methyl-[1,2,4]oxadiazol-3-yl)-benzamide;
xxviii. 5-(4-Fluoro-phenyl)-thiophene-2-carboxylic acid (S)-{2-cyclohexyl-1-[2-(4-trifluoromethoxy-phenylamino)-ethylcarbamoyl]-ethyl}-amide;
xxix. (S)-N-{1-[2-(4-Methoxy-phenylamino)-ethylcarbamoyl]-2-phenyl-ethyl}-2,4,5-trimethyl-benzamide;
xxx. (S)-N-{1-[2-(4-Methoxy-phenylamino)-ethylcarbamoyl]-2-phenyl-ethyl}-2,4,5-trimethyl-benzamide;
xxxi. 5-(3-Fluoro-phenyl)-furan-2-carboxylic acid (S)-{2-cyclohexyl-1-[2-(4-trifluoromethoxy-phenylamino)-ethylcarbamoyl]-ethyl}-amide;
xxxii. Benzyl-morpholine-2-carboxylic acid (S)-{2-cyclohexyl-1-[2-(4-trifluoromethoxy-phenylamino)-ethylcarbamoyl]-ethyl}-amide;
xxxiii. (S)-N-{2-[4-(4-Dimethylamino-phenoxy)-phenyl]-1-[2-(4-methoxy-phenylamino)-ethylcarbamoyl]-ethyl}-3-methyl-benzamide;
xxxiv. 2'-Chloro-biphenyl-3-carboxylic acid (S)-{2-cyclohexyl-1-[2-(4-trifluoromethoxy-phenylamino)-ethylcarbamoyl]-ethyl}-amide;
xxxv. 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
xxxvi. 5-(3-Fluoro-phenyl)-thiophene-2-carboxylic acid (S)-{2-cyclohexyl-1-[2-(4-trifluoromethoxy-phenylamino)-ethylcarbamoyl]-ethyl}-amide;
xxxvii. Thiophene-3-carboxylic acid (S)-{2-cyclohexyl-1-[2-(4-trifluoromethoxy-phenylamino)-ethylcarbamoyl]-ethyl}-amide;
xxxviii. Oxo-1-thiophen-2-ylmethyl-pyrrolidine-3-carboxylic acid (S)-{2-cyclohexyl-1-[2-(4-trifluoromethoxy-phenylamino)-ethylcarbamoyl]-ethyl}-amide;
xxxix. Furan-2-ylmethyl-5-oxo-pyrrolidine-3-carboxylic acid (S)-{2-cyclohexyl-1-[2-(4-trifluoromethoxy-phenylamino)-ethylcarbamoyl]-ethyl}-amide;
xl. Methyl-5-(pyrrolidine-1-sulfonyl)-furan-3-carboxylic acid (S)-{2-cyclohexyl-1-[2-(4-trifluoromethoxy-phenylamino)-ethylcarbamoyl]-ethyl}-amide;
xli. (S)-1-Phenyl-5-trifluoromethyl-1H-pyrazole-4-carboxylic acid {1-[2-(4-methoxy-phenylamino)-ethylcarbamoyl]-2-phenyl-ethyl}-amide;
xlii. 5-p-Tolyl-thiophene-2-carboxylic acid (S)-{2-cyclohexyl-1-[2-(4-trifluoromethoxy-phenylamino)-ethylcarbamoyl]-ethyl}-amide;
xliii. Benzoimidazol-1-ylmethyl-N-{2-cyclohexyl-1-(S)-[2-(4-trifluoromethoxy-phenylamino)-ethylcarbamoyl]-ethyl}-benzamide;
xliv. (S)-1-(4-Chloro-phenyl)-5-trifluoromethyl-1H-pyrazole-4-carboxylic acid {1-[2-(4-methoxy-phenylamino)-ethylcarbamoyl]-2-phenyl-ethyl}-amide;
xlv. (S)-N-[1-[2-(4-Methoxy-phenylamino)-ethylcarbamoyl]-2-(4-p-tolyloxy-phenyl)-ethyl]-3-methyl-benzamide;
xlvi. Cyclohexyl-2-(S)-(2-tetrazol-1-yl-acetylamino)-N-[2-(4-trifluoromethoxy-phenylamino)-ethyl]-propionamide;
xlvii. 5-m-Tolyl-thiophene-2-carboxylic acid (S)-{2-cyclohexyl-1-[2-(4-trifluoromethoxy-phenylamino)-ethylcarbamoyl]-ethyl}-amide;
xlviii. 2,7-Dimethyl-pyrazolo[1,5-a]pyrimidine-6-carboxylic acid (S)-{2-cyclohexyl-1-[2-(4-trifluoromethoxy-phenylamino)-ethylcarbamoyl]-ethyl}-amide;
xlix. 2-Methyl-5-(morpholine-4-sulfonyl)-furan-3-carboxylic acid (S)-{2-cyclohexyl-1-[2-(4-trifluoromethoxy-phenylamino)-ethylcarbamoyl]-ethyl}-amide;
l. 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide;
li. 5-m-Tolyl-furan-2-carboxylic acid (S)-{2-cyclohexyl-1-[2-(4-trifluoromethoxy-phenylamino)-ethylcarbamoyl]-ethyl}-amide;
lii. (S)-2,3-Dihydro-benzofuran-7-carboxylic acid {1-[2-(4-methoxy-phenylamino)-ethylcarbamoyl]-2-phenyl-ethyl}-amide;
liii. Methanesulfonyl-thiophene-2-carboxylic acid (S)-{2-cyclohexyl-1-[2-(4-trifluoromethoxy-phenylamino)-ethylcarbamoyl]-ethyl}-amide;
liv. 2-Phenyl-thiazole-4-carboxylic acid (S)-{2-cyclohexyl-1-[2-(4-trifluoromethoxy-phenylamino)-ethylcarbamoyl]-ethyl}-amide;
lv. (S)-3-Cyano-N-{1-[2-(4-methoxy-phenylamino)-ethylcarbamoyl]-2-phenyl-ethyl}-benzamide;
lvi. (S)-N-{1-[2-(4-Methoxy-phenylamino)-ethylcarbamoyl]-2-phenyl-ethyl}-3-(2-methyl-thiazol-4-yl)-benzamide;
lvii. (S)-N-[2-(4-Methoxy-phenylamino)-ethyl]-3-phenyl-2-(3-phenyl-ureido)-propionamide;
lviii. 3-Cyclohexyl-2-(S)-(2-(S)-hydroxy-2-phenyl-acetylamino)-N-[2-(4-trifluoromethoxy-phenylamino)-ethyl]-propionamide;
lix. Benzo[c]isoxazole-3-carboxylic acid (S)-{2-cyclohexyl-1-[2-(4-trifluoromethoxy-phenylamino)-ethylcarbamoyl]-ethyl}-amide;

TABLE I-continued

| | |
|---|---|
| lx. | N-(S)-{2-cyclohexyl-1-[2-(4-trifluoromethoxy-phenylamino)-ethylcarbamoyl]-ethyl}-4-difluoromethoxy-benzamide; |
| lxi. | N-(S)-{2-cyclohexyl-1-[2-(4-trifluoromethoxy-phenylamino)-ethylcarbamoyl]-ethyl}-4-isopropoxy-benzamide; |
| lxii. | Phenyl-thiophene-2-carboxylic acid (S)-{2-cyclohexyl-1-[2-(4-trifluoromethoxy-phenylamino)-ethylcarbamoyl]-ethyl}-amide; |
| lxiii. | (S)-N-{1-[2-(4-Methoxy-phenylamino)-ethylcarbamoyl]-2-phenyl-ethyl}-nicotinamide; |
| lxiv. | (S)-N-{1-[2-(4-Methoxy-phenylamino)-ethylcarbamoyl]-2-phenyl-ethyl}-isonicotinamide; |
| lxv. | Phenyl-furan-2-carboxylic acid (S)-{2-cyclohexyl-1-[2-(4-trifluoromethoxy-phenylamino)-ethylcarbamoyl]-ethyl}-amide; |
| lxvi. | (S)-N-[1-[2-(4-Methoxy-phenylamino)-ethylcarbamoyl]-2-(4-o-tolyloxy-phenyl)-ethyl]-3-methyl-benzamide; |
| lxvii. | N-(S)-{2-cyclohexyl-1-[2-(4-trifluoromethoxy-phenylamino)-ethylcarbamoyl]-ethyl}-4-oxazol-5-yl-benzamide; |
| lxviii. | 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| lxix. | 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| lxx. | 5-p-Tolyl-furan-2-carboxylic acid (S)-{2-cyclohexyl-1-[2-(4-trifluoromethoxy-phenylamino)-ethylcarbamoyl]-ethyl}-amide; |
| lxxi. | N-(S)-{2-cyclohexyl-1-[2-(4-trifluoromethoxy-phenylamino)-ethylcarbamoyl]-ethyl}-3-[(4,6-dimethyl-pyrimidin-2-yl)-methyl-amino]-benzamide; |
| lxxii. | 1-(4,6-Dimethyl-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxiii. | N-(S)-{2-cyclohexyl-1-[2-(4-trifluoromethoxy-phenylamino)-ethylcarbamoyl]-ethyl}-3-(4,6-dimethoxy-pyrimidin-2-yloxy)-benzamide; |
| lxxiv. | 3'-Methoxy-biphenyl-3-carboxylic acid (S)-{2-cyclohexyl-1-[2-(4-trifluoromethoxy-phenylamino)-ethylcarbamoyl]-ethyl}-amide; |
| lxxv. | N-{3-Cyclohexyl-1-(S)-[2-(4-methoxy-phenylamino)-ethylcarbamoyl]-propyl}-2-(R)-phenyl-butyramide; |
| lxxvi. | 3-Cyclohexyl-N-[2-(4-fluoro-phenylamino)-ethyl]-2-(S)-(2-thiophen-2-yl-acetylamino)-propionamide; |
| lxxvii. | 3-Cyclohexyl-N-[2-(4-fluoro-phenylamino)-ethyl]-2-(S)-(2-thiophen-3-yl-acetylamino)-propionamide; |
| lxxviii. | (S)-3-Bromo-N-{1-[2-(4-methoxy-phenylamino)-ethylcarbamoyl]-2-phenyl-ethyl}-benzamide; |
| lxxix. | Acetyl-piperidine-4-carboxylic acid (S)-{2-cyclohexyl-1-[2-(4-fluoro-phenylamino)-ethylcarbamoyl]-ethyl}-amide; |
| lxxx. | N-(S)-{2-cyclohexyl-1-[2-(4-trifluoromethoxy-phenylamino)-ethylcarbamoyl]-ethyl}-4-(4,6-dimethoxy-pyrimidin-2-yl)-benzamide; |
| lxxxi. | 1-(5-Bromo-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxxii. | (S)-2-(2-Cyclopent-2-enyl-acetylamino)-N-[2-(4-methoxy-phenylamino)-ethyl]-3-phenyl-propionamide; |
| lxxxiii. | Cyclohexyl-N-[2-(4-fluoro-phenylamino)-ethyl]-2-(2-1H-indol-3-yl-acetylamino)-propionamide; |
| lxxxiv. | N-(S)-{2-cyclohexyl-1-[2-(4-fluoro-phenylamino)-ethylcarbamoyl]-ethyl}-3-methanesulfonylamino-benzamide; |
| lxxxv. | 5-(3-Trifluoromethyl-phenyl)-furan-2-carboxylic acid (S)-{2-cyclohexyl-1-[2-(4-fluoro-phenylamino)-ethylcarbamoyl]-ethyl}-amide; |
| lxxxvi. | Cyclohexyl-2-(S)-(2-(R,S)-fluoro-2-phenyl-acetylamino)-N-[2-(4-fluoro-phenylamino)-ethyl]-propionamide; |
| lxxxvii. | Cyclohexyl-N-(S)-[2-(4-fluoro-phenylamino)-ethyl]-2-(4-trifluoromethoxy-phenyl)-acetylamino)-propionamide; |
| lxxxviii. | (S)-2-[3-(4-Chloro-phenyl)-ureido]-N-[2-(4-methoxy-phenylamino)-ethyl]-3-phenyl-propionamide; |
| lxxxix. | (S)-N-[2-(4-Methoxy-phenylamino)-ethyl]-2-[3-(4-phenoxy-phenyl)-ureido]-3-phenyl-propionamide; |
| xc. | (S)-N-[2-(4-Methoxy-phenylamino)-ethyl]-2-(3-phenethyl-ureido)-3-phenyl-propionamide; |
| xci. | (S)-2-[3-(4-Fluoro-benzyl)-ureido]-N-[2-(4-methoxy-phenylamino)-ethyl]-3-phenyl-propionamide; |
| xcii. | N-(S)-{2-cyclohexyl-1-[2-(4-trifluoromethoxy-phenylamino)-ethylcarbamoyl]-ethyl}-4-(4,6-dimethyl-pyrimidin-2-ylamino)-benzamide; |
| xciii. | 1-(5-Bromo-pyrimidin-2-yl)-piperidine-3-carboxylic acid (S)-{2-cyclohexyl-1-[2-(4-trifluoromethoxy-phenylamino)-ethylcarbamoyl]-ethyl}-amide; |
| xciv. | (S)-2-(3-Benzo[1,3]dioxol-5-yl-ureido)-N-[2-(4-methoxy-phenylamino)-ethyl]-3-phenyl-propionamide; |
| xcv. | 3-Cyclohexyl-2-(S)-[2-(2,5-difluorophenyl)-acetylamino]-N-[2-(4-fluoro-phenylamino)-ethyl]-propionamide; |
| xcvi. | (S)-2-[3-(3-Fluoro-benzyl)-ureido]-N-[2-(4-methoxy-phenylamino)-ethyl]-3-phenyl-propionamide; |
| xcvii. | (S)-N-[2-(4-Methoxy-phenylamino)-ethyl]-3-phenyl-2-(3-o-tolyl-ureido)-propionamide; |
| xcviii. | (S)-N-{2-[4-(3,4-Dichloro-phenoxy)-phenyl]-1-[2-(4-methoxy-phenylamino)-ethylcarbamoyl]-ethyl}-3-methyl-benzamide; |
| xcix. | 3-Cyclohexyl-2-(S)-[2-(3,4-difluoro-phenyl)-acetylamino]-N-[2-(4-fluoro-phenylamino)-ethyl]-propionamide; |
| c. | 3-Cyclohexyl-2-(S)-[2-(2,4-difluoro-phenyl)-acetylamino]-N-[2-(4-fluoro-phenylamino)-ethyl]-propionamide; |
| ci. | (S)-N-[2-(4-Methoxy-phenylamino)-ethyl]-2-(3-naphthalen-1-yl-ureido)-3-phenyl-propionamide; |
| cii. | (S)-2-[3-(2-tert-Butyl-6-methyl-phenyl)-ureido]-N-[2-(4-methoxy-phenylamino)-ethyl]-3-phenyl-propionamide; |
| ciii. | (S)-2-[3-(4-Acetyl-phenyl)-ureido]-N-[2-(4-methoxy-phenylamino)-ethyl]-3-phenyl-propionamide; |
| civ. | (S)-N-[2-(4-Methoxy-phenylamino)-ethyl]-2-[3-(3-methoxy-phenyl)-ureido]-3-phenyl-propionamide; |
| cv. | (S)-Biphenyl-4-carboxylic acid {2-cyclohexyl-1-[2-(4-methoxy-phenylamino)-ethylcarbamoyl]-ethyl}-amide; |
| cvi. | (S)-N-{2-Cyclohexyl-1-[2-(4-methoxy-phenylamino)-ethylcarbamoyl]-ethyl}-3-trifluoromethyl-benzamide; |
| cvii. | 2-(S)-[2-(2-Chloro-4-fluoro-phenyl)-acetylamino]-3-cyclohexyl-N-[2-(4-fluoro-phenylamino)-ethyl]-propionamide; |
| cviii. | (S)-2-Chloro-N-{2-cyclohexyl-1-[2-(4-methoxy-phenylamino)-ethylcarbamoyl]-ethyl}-3-methyl-benzamide; |
| cix. | (S)-4-Benzyloxy-N-{2-cyclohexyl-1-[2-(4-methoxy-phenylamino)-ethylcarbamoyl]-ethyl}-benzamide; |
| cx. | (S)-4-Benzyloxy-N-{2-cyclohexyl-1-[2-(4-methoxy-phenylamino)-ethylcarbamoyl]-ethyl}-3,5-dimethyl-benzamide; |
| cxi. | (S)-N-{2-Cyclohexyl-1-[2-(4-methoxy-phenylamino)-ethylcarbamoyl]-ethyl}-4-methoxy-3,5-dimethyl-benzamide; |
| cxii. | (S)-3-Bromo-N-{2-cyclohexyl-1-[2-(4-methoxy-phenylamino)-ethylcarbamoyl]-ethyl}-4-methyl-benzamide; |
| cxiii. | (S)-5-Fluoro-1H-indole-2-carboxylic acid {2-cyclohexyl-1-[2-(4-methoxy-phenylamino)-ethylcarbamoyl]-ethyl}-amide; |
| cxiv. | (S)-2-Amino-4-methyl-thiazole-5-carboxylic acid {2-cyclohexyl-1-[2-(4-methoxy-phenylamino)-ethylcarbamoyl]-ethyl}-amide; |
| cxv. | (S)-1-Phenyl-5-trifluoromethyl-1H-pyrazole-4-carboxylic acid {2-cyclohexyl-1-[2-(4-methoxy-phenylamino)-ethylcarbamoyl]-ethyl}-amide; |
| cxvi. | (S)-1-(4-Chloro-phenyl)-5-trifluoromethyl-1H-pyrazole-4-carboxylic acid {2-cyclohexyl-1-[2-(4-methoxy-phenylamino)-ethylcarbamoyl]-ethyl}-amide; |
| cxvii. | (S)-5-(3-Trifluoromethyl-phenyl)-furan-2-carboxylic acid {2-cyclohexyl-1-[2-(4-methoxy-phenylamino)-ethylcarbamoyl]-ethyl}-amide; |
| cxviii. | (S)-3-Chloro-N-{2-cyclohexyl-1-[2-(4-methoxy-phenylamino)-ethylcarbamoyl]-ethyl}-benzamide; |
| cxix. | (S)-N-{2-Cyclohexyl-1-[2-(4-methoxy-phenylamino)-ethylcarbamoyl]-ethyl}-3-dimethylamino-benzamide; |
| cxx. | (S)-3-Cyano-N-{2-cyclohexyl-1-[2-(4-methoxy-phenylamino)-ethylcarbamoyl]-ethyl}-benzamide; |
| cxxi. | (S)-4-Cyano-N-{2-cyclohexyl-1-[2-(4-methoxy-phenylamino)-ethylcarbamoyl]-ethyl}-benzamide; |
| cxxii. | N-{2-cyclohexyl-1-(S)-[2-(4-trifluoromethoxy-phenylamino)-ethylcarbamoyl]-ethyl}-2-(R)-phenyl-propionamide; |
| cxxiii. | (S)-N-{2-Cyclohexyl-1-[2-(4-methoxy-phenylamino)-ethylcarbamoyl]-ethyl}-3-(2-methyl-thiazol-4-yl)-benzamide; |
| cxxiv. | (S)-N-{2-Cyclohexyl-1-[2-(4-methoxy-phenylamino)-ethylcarbamoyl]-ethyl}-4-[1,2,4]triazol-1-yl-benzamide; |
| cxxv. | 3-Cyclohexyl-2-(S)-[2-(3,5-difluoro-phenyl)-acetylamino]-N-[2-(4-fluoro-phenylamino)-ethyl]-propionamide; |
| cxxvi. | (S)-N-{3-Cyclohexyl-1-[2-(4-methoxy-phenylamino)-ethylcarbamoyl]-propyl}-3-trifluoromethyl-benzamide; |
| cxxvii. | (S)-N-{3-Cyclohexyl-1-[2-(4-methoxy-phenylamino)-ethylcarbamoyl]-propyl}-4-morpholin-4-yl-benzamide; |
| cxxviii. | (4-Cyclohexyl-N-[2-(4-methoxy-phenylamino)-ethyl]-2-(S)-(2-(S)-phenyl-propionylamino)-butyramide; |

TABLE I-continued

| | |
|---|---|
| cxxix. | (S)-4-Benzyloxy-N-{3-cyclohexyl-1-[2-(4-methoxy-phenylamino)-ethylcarbamoyl]-propyl}-benzamide; |
| cxxx. | (S)-Biphenyl-4-carboxylic acid {3-cyclohexyl-1-[2-(4-methoxy-phenylamino)-ethylcarbamoyl]-propyl}-amide; |
| cxxxi. | (S)-5-Chloro-1H-indole-2-carboxylic acid {3-cyclohexyl-1-[2-(4-methoxy-phenylamino)-ethylcarbamoyl]-propyl}-amide; |
| cxxxii. | (S)-5-Fluoro-1H-indole-2-carboxylic acid {3-cyclohexyl-1-[2-(4-methoxy-phenylamino)-ethylcarbamoyl]-propyl}-amide; |
| cxxxiii. | (S)-2-Amino-4-methyl-thiazole-5-carboxylic acid {3-cyclohexyl-1-[2-(4-methoxy-phenylamino)-ethylcarbamoyl]-propyl}-amide; |
| cxxxiv. | (S)-5-Chloro-benzofuran-2-carboxylic acid {3-cyclohexyl-1-[2-(4-methoxy-phenylamino)-ethylcarbamoyl]-propyl}-amide; |
| cxxxv. | N-{2-cyclohexyl-1-(S)-[2-(4-trifluoromethoxy-phenylamino)-ethylcarbamoyl]-ethyl}-2-(R)-phenyl-butyramide; |
| cxxxvi. | (S)-5-(3-Trifluoromethyl-phenyl)-furan-2-carboxylic acid {3-cyclohexyl-1-[2-(4-methoxy-phenylamino)-ethylcarbamoyl]-propyl}-amide; |
| cxxxvii. | (S)-Benzothiazole-6-carboxylic acid {3-cyclohexyl-1-[2-(4-methoxy-phenylamino)-ethylcarbamoyl]-propyl}-amide; |
| cxxxviii. | (S)-N-{3-Cyclohexyl-1-[2-(4-methoxy-phenylamino)-ethylcarbamoyl]-propyl}-3-trifluoromethoxy-benzamide; |
| cxxxix. | (S)-3-Cyano-N-{3-cyclohexyl-1-[2-(4-methoxy-phenylamino)-ethylcarbamoyl]-propyl}-benzamide; |
| cxl. | (S)-4-Cyano-N-{3-cyclohexyl-1-[2-(4-methoxy-phenylamino)-ethylcarbamoyl]-propyl}-benzamide; |
| cxli. | N-{2-cyclohexyl-1-(S)-[2-(4-trifluoromethoxy-phenylamino)-ethylcarbamoyl]-ethyl}-4-phenoxy-benzamide; |
| cxlii. | (S)-N-{3-Cyclohexyl-1-[2-(4-methoxy-phenylamino)-ethylcarbamoyl]-propyl}-3-(2-methyl-thiazol-4-yl)-benzamide; |
| cxliii. | (S)-N-{3-Cyclohexyl-1-[2-(4-methoxy-phenylamino)-ethylcarbamoyl]-propyl}-4-[1,2,4]triazol-1-yl-benzamide; |
| cxliv. | (S)-Biphenyl-3-carboxylic acid {3-cyclohexyl-1-[2-(4-methoxy-phenylamino)-ethylcarbamoyl]-propyl}-amide; |
| cxlv. | (S)-N-{2-Cyclohexyl-1-[2-(4-methoxy-phenylamino)-ethylcarbamoyl]-ethyl}-2-fluoro-benzamide; |
| cxlvi. | (S)-N-{2-Cyclohexyl-1-[2-(4-methoxy-phenylamino)-ethylcarbamoyl]-ethyl}-3,4-difluoro-benzamide; |
| cxlvii. | (S)-N-{2-Cyclohexyl-1-[2-(4-methoxy-phenylamino)-ethylcarbamoyl]-ethyl}-3-fluoro-2-methyl-benzamide; |
| cxlviii. | (S)-2-Chloro-N-{2-cyclohexyl-1-[2-(4-methoxy-phenylamino)-ethylcarbamoyl]-ethyl}-5-methyl-benzamide; |
| cxlix. | (S)-N-{2-Cyclohexyl-1-[2-(4-methoxy-phenylamino)-ethylcarbamoyl]-ethyl}-4-fluoro-3-trifluoromethyl-benzamide; |
| cl. | (S)-5-Methyl-1-phenyl-1H-pyrazole-4-carboxylic acid {2-cyclohexyl-1-[2-(4-methoxy-phenylamino)-ethylcarbamoyl]-ethyl}-amide; |
| cli. | (S)-N-{2-Cyclohexyl-1-[2-(4-methoxy-phenylamino)-ethylcarbamoyl]-ethyl}-4-propyl-benzamide; |
| clii. | 3-Cyclohexyl-2-(S)-[2-(4-fluoro-phenyl)-acetylamino]-N-[2-(4-fluoro-phenylamino)-ethyl]-propionamide; |
| cliii. | (S)-N-{2-Cyclohexyl-1-[2-(4-methoxy-phenylamino)-ethylcarbamoyl]-ethyl}-4-methoxy-benzamide; |
| cliv. | (S)-N-{2-Cyclohexyl-1-[2-(4-methoxy-phenylamino)-ethylcarbamoyl]-ethyl}-2-fluoro-5-trifluoromethyl-benzamide; |
| clv. | (S)-3-Chloro-N-{2-cyclohexyl-1-[2-(4-methoxy-phenylamino)-ethylcarbamoyl]-ethyl}-2-fluoro-benzamide; |
| clvi. | (S)-5-Chloro-N-{2-cyclohexyl-1-[2-(4-methoxy-phenylamino)-ethylcarbamoyl]-ethyl}-2-fluoro-benzamide; |
| clvii. | (S)-N-{2-Cyclohexyl-1-[2-(4-methoxy-phenylamino)-ethylcarbamoyl]-ethyl}-5-fluoro-2-methyl-benzamide; |
| clviii. | (S)-1-Phenyl-cyclopropanecarboxylic acid {2-cyclohexyl-1-[2-(4-methoxy-phenylamino)-ethylcarbamoyl]-ethyl}-amide; |
| clix. | (S)-3-Cyclohexyl-N-[2-(4-methoxy-phenylamino)-ethyl]-2-(2-phenylamino-acetylamino)-propionamide; |
| clx. | 3-Cyclohexyl-2-(S)-(2-(R)-hydroxy-2-phenyl-acetylamino)-N-[2-(4-methoxy-phenylamino)-ethyl]-propionamide; |
| clxi. | (S)-1-(4-Fluoro-phenyl)-5-methyl-1H-pyrazole-4-carboxylic acid {2-cyclohexyl-1-[2-(4-methoxy-phenylamino)-ethylcarbamoyl]-ethyl}-amide; |
| clxii. | (S)-1-(4-Methoxy-phenyl)-5-methyl-1H-pyrazole-4-carboxylic acid {2-cyclohexyl-1-[2-(4-methoxy-phenylamino)-ethylcarbamoyl]-ethyl}-amide; |
| clxiii. | (S)-1-(4-Chloro-phenyl)-5-methyl-1H-pyrazole-4-carboxylic acid {2-cyclohexyl-1-[2-(4-methoxy-phenylamino)-ethylcarbamoyl]-ethyl}-amide; |
| clxiv. | N-{2-Cyclohexyl-1-(S)-[2-(4-methoxy-phenylamino)-ethylcarbamoyl]-ethyl}-2-(S)-phenyl-butyramide; |
| clxv. | (S)-N-{2-Cyclohexyl-1-[2-(4-methoxy-phenylamino)-ethylcarbamoyl]-ethyl}-3-fluoro-5-trifluoromethyl-benzamide; |
| clxvi. | (S)-N-{2-Cyclohexyl-1-[2-(4-methoxy-phenylamino)-ethylcarbamoyl]-ethyl}-2-fluoro-3-trifluoromethyl-benzamide; |
| clxvii. | (S)-N-{2-Cyclohexyl-1-[2-(4-methoxy-phenylamino)-ethylcarbamoyl]-ethyl}-4-fluoro-3-methyl-benzamide; |
| clxviii. | (S)-5-(4-Chloro-phenyl)-furan-2-carboxylic acid {2-cyclohexyl-1-[2-(4-methoxy-phenylamino)-ethylcarbamoyl]-ethyl}-amide; |
| clxix. | (S)-N-{2-Cyclohexyl-1-[2-(4-methoxy-phenylamino)-ethylcarbamoyl]-ethyl}-2-fluoro-4-trifluoromethyl-benzamide; |
| clxx. | (S)-4'-Chloro-biphenyl-4-carboxylic acid {2-cyclohexyl-1-[2-(4-methoxy-phenylamino)-ethylcarbamoyl]-ethyl}-amide; |
| clxxi. | (S)-3',5'-Dichloro-biphenyl-4-carboxylic acid {2-cyclohexyl-1-[2-(4-methoxy-phenylamino)-ethylcarbamoyl]-ethyl}-amide; |
| clxxii. | (S)-3'-Methoxy-biphenyl-4-carboxylic acid {2-cyclohexyl-1-[2-(4-methoxy-phenylamino)-ethylcarbamoyl]-ethyl}-amide; |
| clxxiii. | (S)-3'-Chloro-biphenyl-4-carboxylic acid {2-cyclohexyl-1-[2-(4-methoxy-phenylamino)-ethylcarbamoyl]-ethyl}-amide; |
| clxxiv. | (S)-2'-Methoxy-biphenyl-4-carboxylic acid {2-cyclohexyl-1-[2-(4-methoxy-phenylamino)-ethylcarbamoyl]-ethyl}-amide; |
| clxxv. | (S)-4'-Chloro-biphenyl-3-carboxylic acid {2-cyclohexyl-1-[2-(4-methoxy-phenylamino)-ethylcarbamoyl]-ethyl}-amide; |
| clxxvi. | (S)-4-Benzo[1,3]dioxol-5-yl-N-{2-cyclohexyl-1-[2-(4-methoxy-phenylamino)-ethylcarbamoyl]-ethyl}-benzamide; |
| clxxvii. | (S)-5-Bromo-furan-2-carboxylic acid {2-cyclohexyl-1-[2-(4-methoxy-phenylamino)-ethylcarbamoyl]-ethyl}-amide; |
| clxxviii. | (S)-3,5-Dibromo-N-{2-cyclohexyl-1-[2-(4-methoxy-phenylamino-ethylcarbamoyl]-ethyl}-benzamide; |
| clxxix. | (S)-3,5-Dichloro-N-{2-cyclohexyl-1-[2-(4-methoxy-phenylamino)-ethylcarbamoyl]-ethyl}-benzamide; |
| clxxx. | (S)-N-{2-Cyclohexyl-1-[2-(4-methoxy-phenylamino)-ethylcarbamoyl]-ethyl}-3,5-dimethoxy-benzamide; |
| clxxxi. | (S)-Biphenyl-3-carboxylic acid {2-cyclohexyl-1-[2-(4-methoxy-phenylamino)-ethylcarbamoyl]-ethyl}-amide; |
| clxxxii. | (S)-5-Bromo-thiophene-2-carboxylic acid {2-cyclohexyl-1-[2-(4-methoxy-phenylamino)-ethylcarbamoyl]-ethyl}-amide; |
| clxxxiii. | (S)-N-{2-Cyclohexyl-1-[2-(4-methoxy-phenylamino)-ethylcarbamoyl]-ethyl}-4-phenoxy-benzamide; |
| clxxxiv. | (S)-N-{2-Cyclohexyl-1-[2-(4-methoxy-phenylamino)-ethylcarbamoyl]-ethyl}-3-phenoxy-benzamide; |
| clxxxv. | (S)-1H-Indole-3-carboxylic acid {2-cyclohexyl-1-[2-(4-methoxy-phenylamino)-ethylcarbamoyl]-ethyl}-amide; |
| clxxxvi. | (S)-Benzothiazole-6-carboxylic acid {2-cyclohexyl-1-[2-(4-methoxy-phenylamino)-ethylcarbamoyl]-ethyl}-amide; |
| clxxxvii. | (S)-2-Amino-benzothiazole-6-carboxylic acid {2-cyclohexyl-1-[2-(4-methoxy-phenylamino)-ethylcarbamoyl]-ethyl}-amide; |
| clxxxviii. | (S)-4-Methyl-2-(4-trifluoromethyl-phenyl)-thiazole-5-carboxylic acid {2-cyclohexyl-1-[2-(4-methoxy-phenylamino)-ethylcarbamoyl]-ethyl}-amide; |
| clxxxix. | (S)-4-(4-Chloro-phenyl)-thiophene-2-carboxylic acid {2-cyclohexyl-1-[2-(4-methoxy-phenylamino)-ethylcarbamoyl]-ethyl}-amide; |
| cxc. | (S)-2-Methyl-5-trifluoromethyl-oxazole-4-carboxylic acid {2-cyclohexyl-1-[2-(4-methoxy-phenylamino)-ethylcarbamoyl]-ethyl}-amide; |
| cxci. | (S)-4-(4-Methoxy-phenyl)-thiophene-2-carboxylic acid {2-cyclohexyl-1-[2-(4-methoxy-phenylamino)-ethylcarbamoyl]-ethyl}-amide; |
| cxcii. | N-{2-Cyclohexyl-1-(S)-[2-(4-methoxy-phenylamino)-ethylcarbamoyl]-ethyl}-2-(S)-phenyl-propionamide; |
| cxciii. | (S)-5-(2-Chloro-5-trifluoromethyl-phenyl)-furan-2-carboxylic acid {2-cyclohexyl-1-[2-(4-methoxy-phenylamino)-ethylcarbamoyl]-ethyl}-amide; |
| cxciv. | (S)-2'-Chloro-biphenyl-4-carboxylic acid {2-cyclohexyl-1-[2-(4-trifluoromethoxy-phenylamino)-ethylcarbamoyl]-ethyl}-amide; |
| cxcv. | (S)-1-(5-Bromo-pyrimidin-2-yl)-piperidine-4-carboxylic acid {2-cyclohexyl-1-[2-(4-methoxy-phenylamino)-ethylcarbamoyl]-ethyl}-amide; |
| cxcvi. | (S)-N-{2-Cyclohexyl-1-[2-(4-methoxy-phenylamino)-ethylcarbamoyl]-ethyl}-4-(4,6-dimethyl-pyrimidin-2-ylamino)-benzamide; |
| cxcvii. | (S)-1-(5-Bromo-pyrimidin-2-yl)-piperidine-3-carboxylic acid {2-cyclohexyl-1-[2-(4-methoxy-phenylamino)-ethylcarbamoyl]-ethyl}-amide; |
| cxcviii. | (S)-3'-Fluoro-biphenyl-4-carboxylic acid {2-cyclohexyl-1-[2-(4-trifluoromethoxy-phenylamino)-ethylcarbamoyl]-ethyl}-amide; |

TABLE I-continued

| | |
|---|---|
| cxcix. | (S)-3-Aminomethyl-N-{2-cyclohexyl-1-[2-(4-methoxy-phenylamino)-ethylcarbamoyl]-ethyl}-benzamide; |
| cc. | (S)-N-{2-Cyclohexyl-1-[2-(4-trifluoromethoxy-phenylamino)-ethylcarbamoyl]-ethyl}-3-morpholin-4-ylmethyl-benzamide; |
| cci. | (S)-5-(2-Fluoro-phenyl)-thiophene-2-carboxylic acid {2-cyclohexyl-1-[2-(4-trifluoromethoxy-phenylamino)-ethylcarbamoyl]-ethyl}-amide; |
| ccii. | (S)-N-{3-Cyclohexyl-1-[2-(4-methoxy-phenylamino)-ethylcarbamoyl]-propyl}-3-methyl-benzamide; |
| cciii. | (S)-N-{4-Cyclohexyl-1-[2-(4-methoxy-phenylamino)-ethylcarbamoyl]-butyl}-3-methyl-benzamide; |
| cciv. | (S)-N-{[2-(4-Methoxy-phenylamino)-ethylcarbamoyl]-phenyl-methyl}-3-methyl-benzamide; |
| ccv. | (S)-5-(4-Trifluoromethyl-phenyl)-thiophene-2-carboxylic acid {2-cyclohexyl-1-[2-(4-trifluoromethoxy-phenylamino)-ethylcarbamoyl]-ethyl}-amide; |
| ccvi. | (S)-N-{1-[2-(4-Methoxy-phenylamino)-ethylcarbamoyl]-3-phenyl-propyl}-3-methyl-benzamide; |
| ccvii. | (S)-5-(4-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccviii. | (S)-N-{1-[2-(4-Methoxy-phenylamino)-ethylcarbamoyl]-4-phenyl-but-3-enyl}-3-methyl-benzamide; |
| ccix. | (S)-5-(3-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccx. | (S)-5-(2-Methoxy-phenyl)-furan-2-carboxylic acid {2-cyclohexyl-1-[2-(4-trifluoromethoxy-phenylamino)-ethylcarbamoyl]-ethyl}-amide; |
| ccxi. | N-{(4-Methoxy-phenyl)-[2-(4-methoxy-phenylamino)-ethylcarbamoyl]-methyl}-3-methyl-benzamide; |
| ccxii. | (S)-5-(2-Fluoro-phenyl)-furan-2-carboxylic acid {2-cyclohexyl-1-[2-(4-trifluoromethoxy-phenylamino)-ethylcarbamoyl]-ethyl}-amide; |
| ccxiii. | (S)-5-(4-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxiv. | N-{(2-Benzyloxy-phenyl)-[2-(4-methoxy-phenylamino)-ethylcarbamoyl]-methyl}-3-methyl-benzamide; |
| ccxv. | (S)-5-(4-Trifluoromethoxy-phenyl)-furan-2-carboxylic acid {2-cyclohexyl-1-[2-(4-trifluoromethoxy-phenylamino)-ethylcarbamoyl]-ethyl}-amide; |
| ccxvi. | N-{(2-Chloro-phenyl)-[2-(4-methoxy-phenylamino)-ethylcarbamoyl]-methyl}-3-methyl-benzamide; |
| ccxvii. | N-{(4-Benzyloxy-phenyl)-[2-(4-methoxy-phenylamino)-ethylcarbamoyl]-methyl}-3-methyl-benzamide; |
| ccxviii. | N-{[2-(4-Methoxy-phenylamino)-ethylcarbamoyl]-naphthalen-1-yl-methyl}-3-methyl-benzamide; |
| ccxix. | (S)-5-(2-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxx. | N-{[2-(4-Methoxy-phenylamino)-ethylcarbamoyl]-o-tolyl-methyl}-3-methyl-benzamide; |
| ccxxi. | (S)-N-{2-Cyclohexyl-1-[2-(4-trifluoromethoxy-phenylamino)-ethylcarbamoyl]-ethyl}-4-[1,2,4]triazol-1-yl-benzamide; |
| ccxxii. | N-{(2,4-Dichloro-phenyl)-[2-(4-methoxy-phenylamino)-ethylcarbamoyl]-methyl}-3-methyl-benzamide; |
| ccxxiii. | N-{(2,3-Dichloro-phenyl)-[2-(4-methoxy-phenylamino)-ethylcarbamoyl]-methyl}-3-methyl-benzamide; |
| ccxxiv. | N-{(2,4-Dimethyl-phenyl)-[2-(4-methoxy-phenylamino)-ethylcarbamoyl]-methyl}-3-methyl-benzamide; |
| ccxxv. | N-{(2,4-Dimethoxy-phenyl)-[2-(4-methoxy-phenylamino)-ethylcarbamoyl]-methyl}-3-methyl-benzamide; |
| ccxxvi. | N-{[2-(4-Methoxy-phenylamino)-ethylcarbamoyl]-thiophen-2-yl-methyl}-3-methyl-benzamide; |
| ccxxvii. | N-{(4-Fluoro-phenyl)-[2-(4-methoxy-phenylamino)-ethylcarbamoyl]-methyl}-3-methyl-benzamide; |
| ccxxviii. | (S)-N-{2-(4-Hydroxy-phenyl)-1-[2-(4-methoxy-phenylamino)-ethylcarbamoyl]-ethyl}-3-methyl-benzamide; |
| ccxxix. | (S)-N-{2-(2,4-Dichloro-phenyl)-1-[2-(4-methoxy-phenylamino)-ethylcarbamoyl]-ethyl}-3-methyl-benzamide; |
| ccxxx. | (S)-N-{2-(3,5-Difluoro-phenyl)-1-[2-(4-methoxy-phenylamino)-ethylcarbamoyl]-ethyl}-3-methyl-benzamide; |
| ccxxxi. | (S)-N-{2-(3,4-Dichloro-phenyl)-1-[2-(4-methoxy-phenylamino)-ethylcarbamoyl]-ethyl}-3-methyl-benzamide; |
| ccxxxii. | (S)-4-Benzyloxy-N-{2-cyclohexyl-1-[2-(4-trifluoromethoxy-phenylamino)-ethylcarbamoyl]-ethyl}-benzamide; |
| ccxxxiii. | (S)-N-{2-(4-Acetylamino-phenyl)-1-[2-(4-methoxy-phenylamino)-ethylcarbamoyl]-ethyl}-3-methyl-benzamide; |
| ccxxxiv. | (S)-Biphenyl-4-carboxylic acid {2-cyclohexyl-1-[2-(4-trifluoromethoxy-phenylamino)-ethylcarbamoyl]-ethyl}-amide; |
| ccxxxv. | (S)-N-{1-[2-(4-Methoxy-phenylamino)-ethylcarbamoyl]-2-p-tolyl-ethyl}-3-methyl-benzamide; |
| ccxxxvi. | (S)-N-{2-(3-Fluoro-phenyl)-1-[2-(4-methoxy-phenylamino)-ethylcarbamoyl]-ethyl}-3-methyl-benzamide; |
| ccxxxvii. | (S)-N-{2-(3,4-Difluoro-phenyl)-1-[2-(4-methoxy-phenylamino)-ethylcarbamoyl]-ethyl}-3-methyl-benzamide; |
| ccxxxviii. | (S)-N-{1-[2-(4-Methoxy-phenylamino)-ethylcarbamoyl]-2-m-tolyl-ethyl}-3-methyl-benzamide; |
| ccxxxix. | (S)-N-{1-[2-(4-Methoxy-phenylamino)-ethylcarbamoyl]-2-(2-trifluoromethyl-phenyl)-ethyl}-3-methyl-benzamide; |
| ccxl. | (S)-N-{2-(4-Cyano-phenyl)-1-[2-(4-methoxy-phenylamino)-ethylcarbamoyl]-ethyl}-3-methyl-benzamide; |
| ccxli. | (S)-N-{2-(4-Bromo-phenyl)-1-[2-(4-methoxy-phenylamino)-ethylcarbamoyl]-ethyl}-3-methyl-benzamide; |
| ccxlii. | (S)-N-{2-(4-Iodo-phenyl)-1-[2-(4-methoxy-phenylamino)-ethylcarbamoyl]-ethyl}-3-methyl-benzamide; |
| ccxliii. | (S)-N-{2-(4-Chloro-phenyl)-1-[2-(4-methoxy-phenylamino)-ethylcarbamoyl]-ethyl}-3-methyl-benzamide; |
| ccxliv. | (S)-N-{1-[2-(4-Methoxy-phenylamino)-ethylcarbamoyl]-2-(4-nitro-phenyl)-ethyl}-3-methyl-benzamide; |
| ccxlv. | (S)-N-{2-(4-Fluoro-phenyl)-1-[2-(4-methoxy-phenylamino)-ethylcarbamoyl]-ethyl}-3-methyl-benzamide; |
| ccxlvi. | (S)-5-(3-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxlvii. | (S)-N-{2-(4-Benzyloxy-phenyl)-1-[2-(4-methoxy-phenylamino)-ethylcarbamoyl]-ethyl}-3-methyl-benzamide; |
| ccxlviii. | (S)-N-{2-[4-(2,6-Dichloro-benzyloxy)-phenyl]-1-[2-(4-methoxy-phenylamino)-ethylcarbamoyl]-ethyl}-3-methyl-benzamide; |
| ccxlix. | (S)-N-{2-(4-Methoxy-phenyl)-1-[2-(4-methoxy-phenylamino)-ethylcarbamoyl]-ethyl}-3-methyl-benzamide; |
| ccl. | 2-Amino-4-methyl-thiazole-5-carboxylic acid (S)-{2-cyclohexyl-1-[2-(4-trifluoromethoxy-phenylamino)-ethylcarbamoyl]-ethyl}-amide; |
| ccli. | (S)-5-(2-Chloro-5-trifluoromethyl-phenyl)-furan-2-carboxylic acid {2-cyclohexyl-1-[2-(4-trifluoromethoxy-phenylamino)-ethylcarbamoyl]-ethyl}-amide; |
| cclii. | (S)-N-{1-[2-(4-Methoxy-phenylamino)-ethylcarbamoyl]-2-(3-trifluoromethyl-phenyl)-ethyl}-3-methyl-benzamide; |
| ccliii. | (S)-N-{1-[2-(4-Methoxy-phenylamino)-ethylcarbamoyl]-2-(4-trifluoromethyl-phenyl)-ethyl}-3-methyl-benzamide; |
| ccliv. | (S)-N-{2-Benzyloxy-1-[2-(4-methoxy-phenylamino)-ethylcarbamoyl]-ethyl}-3-methyl-benzamide; |
| cclv. | (S)-N-{2-(4-tert-Butyl-phenyl)-1-[2-(4-methoxy-phenylamino)-ethylcarbamoyl]-ethyl}-3-methyl-benzamide; |
| cclvi. | Cyclohexyl-N-[2-(4-methoxy-phenylamino)-ethyl]-2-(S)-(2-(S)-phenyl-propionylamino)-butyramide; |
| cclvii. | (S)-N-{2-(1H-Indol-3-yl)-1-[2-(4-methoxy-phenylamino)-ethylcarbamoyl]-ethyl}-3-methyl-benzamide; |
| cclviii. | (S)-N-{1-[2-(4-Methoxy-phenylamino)-ethylcarbamoyl]-2-naphthalen-1-yl-ethyl}-3-methyl-benzamide; |
| cclix. | (S)-N-{2-Benzyloxy-1-[2-(4-methoxy-phenylamino)-ethylcarbamoyl]-propyl}-3-methyl-benzamide; |
| cclx. | 3-Cyclohexyl-2-(S)-[2-(3-fluoro-phenyl)-acetylamino]-N-[2-(4-fluoro-phenylamino)-ethyl]-propionamide; |
| cclxi. | (S)-N-{1-[2-(4-Methoxy-phenylamino)-ethylcarbamoyl]-2-naphthalen-2-yl-ethyl}-3-methyl-benzamide; |
| cclxii. | (S)-N-{1-[2-(4-Methoxy-phenylamino)-ethylcarbamoyl]-2-pyridin-3-yl-ethyl}-3-methyl-benzamide; |
| cclxiii. | (S)-N-{1-[2-(4-Methoxy-phenylamino)-ethylcarbamoyl]-2-pyridin-4-yl-ethyl}-3-methyl-benzamide; |
| cclxiv. | Furan-2-carboxylic acid (S)-{2-cyclohexyl-1-[2-(4-fluoro-phenylamino)-ethylcarbamoyl]-ethyl}-amide; |
| cclxv. | 3-Cyclohexyl-N-[2-(4-fluoro-phenylamino)-ethyl]-2-(S)-(2-tetrazol-1-yl-acetylamino)-propionamide; |
| cclxvi. | N-[1-[2-(4-Methoxy-phenylamino)-ethylcarbamoyl]-2-(4-nitro-phenyl)-propyl]-3-methyl-benzamide; |
| cclxvii. | (S)-N-[1-[2-(4-Methoxy-phenylamino)-ethylcarbamoyl]-2-(4-m-tolyloxy-phenyl)-ethyl]-3-methyl-benzamide; |
| cclxviii. | threo-N-{1-[2-(4-Methoxy-phenylamino)-ethylcarbamoyl]-2-phenyl-propyl}-3-methyl-benzamide; |
| cclxix. | erythro-N-{1-[2-(4-Methoxy-phenylamino)-ethylcarbamoyl]-2-phenyl-propyl}-3-methyl-benzamide; |

TABLE I-continued

| | |
|---|---|
| cclxx. | (S)-N-{2-Biphenyl-4-yl-1-[2-(4-methoxy-phenylamino)-ethylcarbamoyl]-ethyl}-3-methyl-benzamide; |
| cclxxi. | (S)-N-[1-[2-(4-Methoxy-phenylamino)-ethylcarbamoyl]-2-(3'-nitro-biphenyl-4-yl)-ethyl]-3-methyl-benzamide; |
| cclxxii. | Furan-3-carboxylic acid (S)-{2-cyclohexyl-1-[2-(4-fluoro-phenylamino)-ethylcarbamoyl]-ethyl}-amide; |
| cclxxiii. | (S)-N-[1-[2-(4-Methoxy-phenylamino)-ethylcarbamoyl]-2-(2'-nitro-biphenyl-4-yl)-ethyl]-3-methyl-benzamide; |
| cclxxiv. | (S)-N-[1-[2-(4-Methoxy-phenylamino)-ethylcarbamoyl]-2-(4-pyridin-3-yl-phenyl)-ethyl]-3-methyl-benzamide; |
| cclxxv. | (S)-N-[1-[2-(4-Methoxy-phenylamino)-ethylcarbamoyl]-2-(4-thiophen-3-yl-phenyl)-ethyl]-3-methyl-benzamide; |
| cclxxvi. | (S)-N-{2-(4'-Cyano-biphenyl-4-yl)-1-[2-(4-methoxy-phenylamino)-ethylcarbamoyl]-ethyl}-3-methyl-benzamide; |
| cclxxvii. | (S)-N-[1-[2-(4-Methoxy-phenylamino)-ethylcarbamoyl]-2-(4-pyridin-4-yl-phenyl)-ethyl]-3-methyl-benzamide; |
| cclxxviii. | (S)-N-{2-(4'-Chloro-biphenyl-4-yl)-1-[2-(4-methoxy-phenylamino)-ethylcarbamoyl]-ethyl}-3-methyl-benzamide; |
| cclxxix. | (S)-N-{2-(2',3'-Dimethoxy-biphenyl-4-yl)-1-[2-(4-methoxy-phenylamino)-ethylcarbamoyl]-ethyl}-3-methyl-benzamide; |
| cclxxx. | (S)-N-{2-(3'-Amino-biphenyl-4-yl)-1-[2-(4-methoxy-phenylamino)-ethylcarbamoyl]-ethyl}-3-methyl-benzamide; |
| cclxxxi. | (S)-N-{2-(3',4'-Dimethoxy-biphenyl-4-yl)-1-[2-(4-methoxy-phenylamino)-ethylcarbamoyl]-ethyl}-3-methyl-benzamide; |
| cclxxxii. | (S)-N-{2-(4'-Hydroxymethyl-biphenyl-4-yl)-1-[2-(4-methoxy-phenylamino)-ethylcarbamoyl]-ethyl}-3-methyl-benzamide; |
| cclxxxiii. | (S)-N-{2-(5'-Fluoro-2'-methoxy-biphenyl-4-yl)-1-[2-(4-methoxy-phenylamino)-ethylcarbamoyl]-ethyl}-3-methyl-benzamide; |
| cclxxxiv. | (S)-N-{2-(3'-Hydroxymethyl-biphenyl-4-yl)-1-[2-(4-methoxy-phenylamino)-ethylcarbamoyl]-ethyl}-3-methyl-benzamide; |
| cclxxxv. | (S)-N-{2-(2',5'-Dimethoxy-biphenyl-4-yl)-1-[2-(4-methoxy-phenylamino)-ethylcarbamoyl]-ethyl}-3-methyl-benzamide; |
| cclxxxvi. | (S)-N-{2-(2',5'-Dichloro-biphenyl-4-yl)-1-[2-(4-methoxy-phenylamino)-ethylcarbamoyl]-ethyl}-3-methyl-benzamide; |
| cclxxxvii. | (S)-N-{2-(4'-Dimethylamino-biphenyl-4-yl)-1-[2-(4-methoxy-phenylamino)-ethylcarbamoyl]-ethyl}-3-methyl-benzamide; |
| cclxxxviii. | (S)-N-{2-(2'-Acetyl-biphenyl-4-yl)-1-[2-(4-methoxy-phenylamino)-ethylcarbamoyl]-ethyl}-3-methyl-benzamide; |
| cclxxxix. | (S)-N-{2-(4'-Hydroxy-biphenyl-4-yl)-1-[2-(4-methoxy-phenylamino)-ethylcarbamoyl]-ethyl}-3-methyl-benzamide; |
| ccxc. | (S)-N-{2-(3'-Acetyl-biphenyl-4-yl)-1-[2-(4-methoxy-phenylamino)-ethylcarbamoyl]-ethyl}-3-methyl-benzamide; |
| ccxci. | (S)-N-{2-[4-(2,4-Dimethoxy-pyrimidin-5-yl)-phenyl]-1-[2-(4-methoxy-phenylamino)-ethylcarbamoyl]-ethyl}-3-methyl-benzamide; |
| ccxcii. | (S)-N-{1-[2-(4-Methoxy-phenylamino)-ethylcarbamoyl]-2-[4-(6-methoxy-pyridin-3-yl)-phenyl]-ethyl}-3-methyl-benzamide; |
| ccxciii. | Methanesulfonyl-thiophene-2-carboxylic acid (S)-{2-cyclohexyl-1-[2-(4-fluoro-phenylamino)-ethylcarbamoyl]-ethyl}-amide; |
| ccxciv. | N-(S)-{2-cyclohexyl-1-[2-(4-fluoro-phenylamino)-ethylcarbamoyl]-ethyl}-2-(S)-phenyl-propionamide; |
| ccxcv. | Pyridazine-4-carboxylic acid (S)-{2-cyclohexyl-1-[2-(4-fluoro-phenylamino)-ethylcarbamoyl]-ethyl}-amide; |
| ccxcvi. | N-(S)-{2-cyclohexyl-1-[2-(4-fluoro-phenylamino)-ethylcarbamoyl]-ethyl}-3-methanesulfonyl-benzamide; |
| ccxcvii. | 3-Cyclohexyl-N-[2-(4-fluoro-phenylamino)-ethyl]-2-(S)-(2-1H-tetrazol-5-yl-acetylamino)-propionamide; |
| ccxcviii. | Cyclopropanecarboxylic acid (S)-{2-cyclohexyl-1-[2-(4-fluoro-phenylamino)-ethylcarbamoyl]-ethyl}-amide; |
| ccxcix. | N-(S)-{2-cyclohexyl-1-[2-(4-fluoro-phenylamino)-ethylcarbamoyl]-ethyl}-4-methanesulfonylamino-benzamide; |
| ccc. | (S)-N-{2-[4-(4-Chloro-phenoxy)-phenyl]-1-[2-(4-methoxy-phenylamino)-ethylcarbamoyl]-ethyl}-3-methyl-benzamide; |
| ccci. | 3-Cyclohexyl-N-[2-(4-fluoro-phenylamino)-ethyl]-2-(S)-[2-(4-methoxy-phenyl)-acetylamino]-propionamide; |
| cccii. | 2-(S)-[2-(3-Chloro-phenyl-acetylamino]-3-cyclohexyl-N-[2-(4-fluoro-phenylamino)-ethyl]-propionamide; |
| ccciii. | 3-Cyclohexyl-N-[2-(4-fluoro-phenylamino)-ethyl]-2-(S)-phenylacetylamino-propionamide; |
| ccciv. | 3-Cyclohexyl-N-[2-(4-fluoro-phenylamino)-ethyl]-2-(S)-(2-o-tolyl-acetylamino)-propionamide; |
| cccv. | 2-(S)-[2-(4-Chloro-phenyl)-acetylamino]-3-cyclohexyl-N-[2-(4-fluoro-phenylamino)-ethyl]-propionamide; |
| cccvi. | 3-Cyclohexyl-2-(S)-[2-(2-fluoro-phenyl)-acetylamino]-N-[2-(4-fluoro-phenylamino)-ethyl]-propionamide; |
| cccvii. | 3-Cyclohexyl-2-(S)-diphenylacetylamino-N-[2-(4-fluoro-phenylamino)-ethyl]-propionamide; |
| cccviii. | N-(S)-{2-cyclohexyl-1-[2-(4-fluoro-phenylamino)-ethylcarbamoyl]-ethyl}-2-(2-fluoro-biphenyl-4-yl)-propionamide; |
| cccix. | N-{2-cyclohexyl-1-(S)-[2-(4-fluoro-phenylamino)-ethylcarbamoyl]-ethyl}-2-p-tolyl-propionamide; |
| cccx. | N-{2-cyclohexyl-1-(S)-[2-(4-fluoro-phenylamino)-ethylcarbamoyl]-ethyl}-2-(4-fluoro-phenyl)-propionamide; |
| cccxi. | N-{2-cyclohexyl-1-(S)-[2-(4-fluoro-phenylamino)-ethylcarbamoyl]-ethyl}-2-(4-hydroxy-phenyl)-propionamide; |
| cccxii. | 2-(4-Chloro-phenyl)-N-{2-cyclohexyl-1-(S)-[2-(4-fluoro-phenylamino)-ethylcarbamoyl]-ethyl}-propionamide; |
| cccxiii. | N-(S)-{2-cyclohexyl-1-[2-(4-fluoro-phenylamino)-ethylcarbamoyl]-ethyl}-4-methanesulfonyl-benzamide; |
| cccxiv. | Thiazole-4-carboxylic acid (S)-{2-cyclohexyl-1-[2-(4-fluoro-phenylamino)-ethylcarbamoyl]-ethyl}-amide; |
| cccxv. | N-{2-cyclohexyl-1-(S)-[2-(4-fluoro-phenylamino)-ethylcarbamoyl]-ethyl}-2-(R)-phenyl-propionamide; |
| cccxvi. | 4-Cyano-N-(S)-{2-cyclohexyl-1-[2-(4-fluoro-phenylamino)-ethylcarbamoyl]-ethyl}-benzamide; |
| cccxvii. | 3-Cyclohexyl-N-[2-(4-fluoro-phenylamino)-ethyl]-2-(S)-(2-(R)-hydroxy-2-phenyl-acetylamino)-propionamide; |
| cccxviii. | N-{2-cyclohexyl-1-(S)-[2-(4-fluoro-phenylamino)-ethylcarbamoyl]-ethyl}-2-(R)-phenyl-butyramide; |
| cccxix. | Phenyl-cyclopropanecarboxylic acid (S)-{2-cyclohexyl-1-[2-(4-fluoro-phenylamino)-ethylcarbamoyl]-ethyl}-amide; |
| cccxx. | N-(S)-{2-cyclohexyl-1-[2-(4-fluoro-phenylamino)-ethylcarbamoyl]-ethyl}-2-(R,S)-(4-fluoro-phenyl)-propionamide; |
| cccxxi. | Cyano-N-(S)-{2-cyclohexyl-1-[2-(4-fluoro-phenylamino)-ethylcarbamoyl]-ethyl}-benzamide; |
| cccxxii. | 5-(4-Fluoro-phenyl)-furan-2-carboxylic acid (S)-{2-cyclohexyl-1-[2-(4-fluoro-phenylamino)-ethylcarbamoyl]-ethyl}-amide; |
| cccxxiii. | Cyclohexyl-N-[2-(4-fluoro-phenylamino)-ethyl]-2-(S)-[2-(3-trifluoromethyl-phenyl)-acetylamino]-propionamide; |
| cccxxiv. | Cyano-N-(S)-{2-cyclohexyl-1-[2-(4-fluoro-phenylamino)-ethylcarbamoyl]-ethyl}-benzamide; |
| cccxxv. | 3-Cyclohexyl-N-[2-(4-fluoro-phenylamino)-ethyl]-2-(S)-[2-(4-trifluoromethyl-phenyl)-acetylamino]-propionamide; |
| cccxxvi. | 3-Cyclohexyl-N-[2-(4-fluoro-phenylamino)-ethyl]-2-(S)-[2-(4-methanesulfonyl-phenyl)-acetylamino]-propionamide; |
| cccxxvii. | (S)-N-[1-[2-(4-Methoxy-phenylamino)-ethylcarbamoyl]-2-(4-phenoxy-phenyl)-ethyl]-3-methyl-benzamide; |
| cccxxviii. | (S)-N-{2-[4-(4-Methoxy-phenoxy)-phenyl]-1-[2-(4-methoxy-phenylamino)-ethylcarbamoyl]-ethyl}-3-methyl-benzamide; |
| cccxxix. | (S)-N-{2-[4-(3-Chloro-phenoxy)-phenyl]-1-[2-(4-methoxy-phenylamino)-ethylcarbamoyl]-ethyl}-3-methyl-benzamide; |
| cccxxx. | (S)-N-{2-[4-(3,5-Dimethyl-phenoxy)-phenyl]-1-[2-(4-methoxy-phenylamino)-ethylcarbamoyl]-ethyl}-3-methyl-benzamide. |

11. A method of selectively inhibiting cathepsin S activity in a mammal in need thereof, comprising administering to said mammal a therapeutically effective amount of a compound of Formula I:

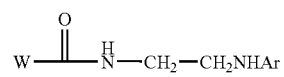

(I)

or a pharmaceutically acceptable salt or prodrug thereof, wherein:

W is a member selected from the group consisting of $R^1$—X—(C=O)—NH—$CHR^2$—, $R^4$—Y—(C=O)—NH—$CHR^3$—, $R^6$—(C=O)—NH—$CHR^5$—, $R^7$—NH—(C=O)—NH—$CHR^8$—, $R^{10}$-Z-(C=O)—NH—$CHR^9$—, and $R^{11}$—(C=O)—NH—$CHR^{12}$;

$R^1$ is a member selected from the group consisting of phenyl substituted with 0–2 $R^{1a}$, pyridyl substituted with 0–2 $R^{1a}$, and pyridinium N-oxide substituted with 0–2 $R^{1a}$;

each $R^{1a}$ is independently a member selected from the group consisting of Cl, F, $OCF_3$, $OCH_3$, $CH_3$ and $CF_3$;

X is a member selected from the group consisting of furanylene substituted with 0–1 $R^X$, thienylene substituted with 0–1 $R^X$, pyrazolylene substituted with 0–1 $R^X$, thiazolylene substituted with 0–1 $R^X$, and oxazolylene substituted with 0–1 $R^X$;

$R^X$ is a member selected from the group consisting of F, Cl, $CH_3$ and $CF_3$;

$R^2$ is a member selected from the group consisting of phenyl substituted with 0–2 $R^{2a}$ and $(CH_2)_n R^{2b}$;

each $R^{2a}$ is independently a member selected from the group consisting of Cl, F, $OCF_3$, $OCH_3$, $CH_3$ and $CF_3$;

$R^{2b}$ is independently a member selected from the group consisting of phenyl substituted with 0–2 $R^{2a}$; cyclopentyl, cyclohexyl and tetrahydropyranyl;

n is the integer 1 or 2;

$R^3$ is $(CH_2)_m R^{3b}$;

$R^{3b}$ is selected from the group consisting of phenyl substituted with 0–2 $R^{2a}$, cyclopentyl and cyclohexyl;

m is the integer 1 or 2;

$R^4$ is a member selected from the group consisting of phenyl substituted with 0–3 $R^{4a}$, thienyl, tetrazolyl, cyclopentenyl and indolyl;

each $R^{4a}$ is a member selected from the group consisting of phenyl, OH, $C_1$–$C_4$ alkyl, $C_1$–$C_4$ alkoxy, $CF_3$, $OCF_3$, F, Cl, $CH_3S(=O)_2$—, morpholinyl, pyrrolidinyl, piperidinyl and 4-acetylpiperazinyl;

Y is a member selected from the group consisting of —$CR^{17}R^{18}$, —NH—$CH_2$— and —O—$CH_2$—;

$R^5$ is a member selected from the group consisting of phenyl substituted with 0–2 $R^{5a}$, thienyl, naphthyl, and $CH_2R^{5b}$, $CH_2CH_2$(cyclohexyl), $CH_2CH_2CH_2$(cyclohexyl), $CH_2CH_2Ph$, $CH(CH_3)R^{5e}$, $CH_2CH=CHPh$, —$CH_2OCH_2Ph$, —$CH(CH_3)OCH_2Ph$;

each $R^{5a}$ is independently a member selected from the group consisting of F, Cl, $NO_2$, $OCH_3$, $OCH_2Ph$, OPh, $CH_3$, $OCF_3$ and $CF_3$;

$R^{5b}$ is independently a member selected from the group consisting of phenyl substituted with 0–2 $R^{5c}$; cyclopentyl, cyclohexyl, naphthyl, indolyl and pyridyl;

$R^{5c}$ is independently a member selected from the group consisting of OH, Cl, F, Br, I, CN, $NO_2$, $CH_3$, $OCH_3$, $^tBu$, O—$^tBu$, —$NHC(=O)CH_3$, $CF_3$, $OCF_3$; phenyl substituted with 0–2 $R^{5d}$; phenoxy substituted with 0–2 $R^{5d}$; benzyloxy substituted with 0–2 $R^{5d}$; pyridyl substituted with 0–2 $R^{5d}$; pyrimidinyl substituted with 0–2 $R^{5d}$; thienyl substituted with 0–2 $R^{5d}$;

$R^{5d}$ is independently a member selected from the group consisting of $CH_3$, Cl, F, $OCH_3$, $CF_3$, $OCF_3$, $N(CH_3)_2$, acetyl, OH, $CH_2OH$, $NH_2$, CN and $NO_2$;

$R^{5e}$ is phenyl substituted with 0–2 $R^{5a}$;

$R^6$ is a member selected from the group consisting of phenyl substituted with 0–3 $R^{6a}$ furanyl substituted with 0–2 $R^{6b}$, thienyl substituted with 0–2 $R^{6b}$, oxazolyl substituted with 0–2 $R^{6b}$, thiazolyl substituted with 0–2 $R^{6b}$, pyridyl, pyridazinyl and cyclopropyl;

each $R^{6a}$ is independently a member selected from the group consisting of Cl, F, Br, $OCF_3$, $CF_3$, $C_1$–$C_4$ alkyl, $C_1$–$C_4$ alkoxy, —$S(=O)_2CH_3$, CN, —$N(CH_3)_2$, $OCF_2H$, —$CH_2$-benzimidazole, —NH—$S(=O)_2CH_3$, —$NR^{13}R^{14}$, $OR^{14}$, $CH_2$-morpholine, $CH_2NH_2$, $OCH_2Ph$, and OPh;

alternatively, two $R^{6a}$ substituents on adjacent atoms may be combined to form a 5 to 6 membered heterocyclic fused radical, wherein said 5 to 6 membered heterocyclic fused radical has 1 or 2 oxygen atom(s);

each $R^{6b}$ is independently a member selected from the group consisting of $NH_2$, F, Cl, Br, —$S(=O)_2R^{15}$, $CH_3$, and $CF_3$ $R^7$ is a member selected from the group consisting of $(CH_2)_p R^{7a}$, and naphthyl substituted with 0–2 $R^{7b}$;

p is the integer 0, 1, or 2;

$R^{7a}$ is phenyl substituted with 0–2 $R^{7b}$;

$R^{7b}$ is a member selected from the group consisting of F, Cl, $CF_3$, $C_1$–$C_4$ alkyl, $C_1$–$C_4$ alkoxy, $OCF_3$, phenoxy and acetyl;

alternatively, two $R^{7b}$ substituents on adjacent atoms may be combined to form a 5 to 6 membered heterocyclic fused radical, wherein said 5 to 6 membered heterocyclic fused radical has 1 or 2 oxygen atom(s);

$R^8$ is —$CH_2$—$R^{3b}$;

$R^9$ is $(CH_2)_q R^{9a}$;

$R^{9a}$ is a member selected from the group consisting of cyclopentyl, phenyl and cyclohexyl;

q is the integer 1 or 2;

$R^{10}$ is a member selected from the group consisting of phenyl substituted with 0–2 $R^{10a}$, 5 membered heteroaryl containing 1 to 4 heteroatoms each independently a member selected from the group consisting of N, O and S, wherein said heteroaryl is substituted with 0–2 $R^{10a}$, 6 membered heteroaryl containing 1 to 2 N, wherein said heteroaryl is substituted with 0–2 $R^{10a}$, morpholinyl substituted with 0–2 $R^{10a}$, piperazinyl substituted with 0–2 $R^{10a}$ and piperidinyl substituted with 0–2 $R^{10a}$;

each $R^{10a}$ is independently a member selected from the group consisting of Cl, F, $C_1$–$C_4$ alkyl, $C_1$–$C_4$ alkoxy, $OCF_3$, and $CF_3$;

alternatively, two $R^{10a}$ substituents on adjacent atoms may be combined to form a 5 to 6 membered heterocyclic fused radical, wherein said 5 to 6 membered heterocyclic fused radical comprises 1 or 2 heteroatom(s);

Z is phenylene;

$R^{11}$ is a member selected from the group consisting of indolyl substituted with 0–2 $R^{11a}$, benzofuranyl substituted with 0–2 $R^{11a}$, benzothienyl substituted with 0–2 $R^{11a}$, benzothiazole substituted with 0–2 $R^{11a}$, benzisoxazolyl substituted with 0–2 $R^{11a}$, benzoxazolyl substituted with 0–2 $R^{11a}$, and pyrazolo[1,5-a]pyrimidinyl substituted with 0–2 $R^{11a}$, piperidinyl N-substituted with 0–1 $R^{11b}$, morpholinyl N-substituted with 0–1 $R^{11b}$; and 2-oxo-pyrrolidinyl with 0–1 $R^{11b}$;

each $R^{11a}$ is independently a member selected from the group consisting of Cl, F, $NH_2$, $CH_3$, $OCH_3$, —C(=O) $OCH_3$, $OCF_3$, and $CF_3$;

each $R^{11b}$ is independently a member selected from the group consisting of pyrimidinyl substituted with 0–2 $R^{11c}$; benzyl, acetyl, $CH_2$-furanyl, and $CH_2$-thienyl;

each $R^{11c}$ is independently a member selected from the group consisting of Br and $CH_3$;

$R^{12}$ is $(CH_2)_s R^{12a}$;

$R^{12a}$ is a member selected from the group consisting of cyclopentyl and cyclohexyl;

s is the integer 1 or 2;

$R^{13}$ is a member selected from the group consisting of H and $C_1$–$C_4$ alkyl;

$R^{14}$ is pyrimidinyl substituted with 0–2 $R^{16}$;

$R^{15}$ is a member selected from the group consisting of $C_1$–$C_4$ alkyl, morpholinyl, pyrrolidinyl and piperidinyl;

$R^{16}$ is a member selected from the group consisting of $CH_3$ and $OCH_3$;

each of $R^{17}$ and $R^{18}$ is independently a member of H, OH, F, phenyl and $C_1$–$C_3$ alkyl;

alternatively, $R^{17}$ and $R^{18}$ may be taken together to form a $C_3$–$C_6$ cycloalkyl;

Ar is a phenyl substituted with 0–2 $R^{19}$; and each $R^{19}$ is independently a member selected from the group consisting of F, Cl, COOH, $C_1$–$C_4$ alkoxy, $OCHF_2$ and $OCF_3$.

12. The method of claim 11, wherein the cathepsin S inhibition constant for a compound of Formula I is less than 10 μM.

13. The method of claim 12, wherein the cathepsin S inhibition constant for a compound of Formula I is less than 1.0 μM.

14. The method of claim 13, wherein the cathepsin S inhibition constant for a compound of Formula I is less than 0.1 μM.

15. The method of claim 11, wherein cathepsin S is selectively inhibited in the presence of cathepsin K.

16. The method of claim 15, wherein the inhibition constant of a compound of Formula I for cathepsin K is at least 10 times greater than a cathepsin S inhibition constant of a compound of Formula I.

17. The method of claim 16, wherein the inhibition constant of a compound of Formula I for cathepsin K is at least 100 times greater than said cathepsin S inhibition constant of a compound of Formula I.

18. The method of claim 17, wherein the inhibition constant of a compound of Formula I for cathepsin K is at least 1000 times greater than said cathepsin S inhibition constant of a compound of Formula I.

19. The method of claim 11, wherein said compound is a member selected from the compounds of Table I:

TABLE I

| | |
|---|---|
| i. | N-((S)-1-(2-(4-methoxyphenylamino)ethylcarbamoyl)-3-phenylpropyl)-5-(3-(trifluoromethyl)phenyl)furan-2-carboxamide; |
| ii. | N-((S)-1-(2-(4-methoxyphenylamino)ethylcarbamoyl)-2-(2-chlorophenyl)ethyl)-5-(3-(trifluoromethyl)phenyl)furan-2-carboxamide; |
| iii. | N-((S)-1-(2-(4-methoxyphenylamino)ethylcarbamoyl)-2-(3-chlorophenyl)ethyl)-5-(3-(trifluoromethyl)phenyl)furan-2-carboxamide; |
| iv. | N-((S)-1-(2-(4-methoxyphenylamino)ethylcarbamoyl)-2-(4-chlorophenyl)ethyl)-5-(3-(trifluoromethyl)phenyl)furan-2-carboxamide; |
| v. | N-((S)-1-(2-(4-methoxyphenylamino)ethylcarbamoyl)-2-(tetrahydro-2H-pyran-4-yl)ethyl)-5-(3-(trifluoromethyl)phenyl)furan-2-carboxamide; |
| vi. | N-((S)-1-(2-(4-methoxyphenylamino)ethylcarbamoyl)-2-cyclopentylethyl)-5-(3-(trifluoromethyl)phenyl)furan-2-carboxamide; |
| vii. | (S)-N-{2-[4-(2,3-Dimethyl-phenoxy)-phenyl]-1-[2-(4-methoxy-phenylamino)-ethylcarbamoyl]-ethyl}-3-methyl-benzamide; |
| viii. | (±)-N-((2-(4-methoxyphenylamino)ethylcarbamoyl)(4-chlorophenyl)methyl)-3-methylbenzamide; |
| ix. | (±)-N-((2-(4-methoxyphenylamino)ethylcarbamoyl)(phenyl)methyl)-5-(3-(trifluoromethyl)phenyl)furan-2-carboxamide; |
| x. | N-((S)-1-(2-(4-(difluoromethoxy)phenylamino)ethylcarbamoyl)-2-cyclohexylethyl)-5-(3-(trifluoromethyl)phenyl)furan-2-carboxamide; |
| xi. | 4-[2-3-Cyclohexyl-2-(S)-{[5-(3-trifluoromethyl-phenyl)-furan-2-carbonyl]-amino}-propionylamino]-ethylamino]-benzoic acid; |

TABLE I-continued

| | |
|---|---|
| xii. | 2-[2-(3-Cyclohexyl-2-(S)-{[5-(3-trifluoromethyl-phenyl)-furan-2-carbonyl]-amino}-propionylamino)-ethylamino]-benzoic acid; |
| xiii. | 4-Cyclohexyl-2-(S)-(2-(R)-phenyl-propionylamino)-N-[2-(4-trifluoromethoxy-phenylamino)-ethyl]-butyramide; |
| xiv. | Acetyl-piperidine-4-carboxylic acid (S)-{2-cyclohexyl-1-[2-(4-trifluoromethoxy-phenylamino)-ethylcarbamoyl]-ethyl}-amide; |
| xv. | (S)-2-{2-[4-(4-Acetyl-piperazin-1-yl)-phenoxy]-acetylamino}-3-cyclohexyl-N-[2-(4-trifluoromethoxy-phenylamino)-ethyl]-propionamide; |
| xvi. | (S)-2-Chloro-N-{1-[2-(4-methoxy-phenylamino)-ethylcarbamoyl]-2-phenyl-ethyl}-3-methyl-benzamide; |
| xvii. | Cyclohexyl-2-[2-(4-methoxy-phenyl)-acetylamino]-N-[2-(4-trifluoromethoxy-phenylamino)-ethyl]-propionamide; |
| xviii. | (S)-N-{2-[4-(3,5-Dichloro-phenoxy)-phenyl]-1-[2-(4-methoxy-phenylamino)-ethylcarbamoyl]-ethyl}-3-methyl-benzamide; |
| xix. | N-(S)-{2-cyclohexyl-1-[2-(4-trifluoromethoxy-phenylamino)-ethylcarbamoyl]-ethyl}-4-methanesulfonyl-benzamide; |
| xx. | (S)-4-Benzyloxy-N-{1-[2-(4-methoxy-phenylamino)-ethylcarbamoyl]-2-phenyl-ethyl}-3,5-dimethyl-benzamide; |
| xxi. | (S)-4-Methoxy-N-{1-[2-(4-methoxy-phenylamino)-ethylcarbamoyl]-2-phenyl-ethyl}-3,5-dimethyl-benzamide; |
| xxii. | 5-Methoxy-1H-indole-2-carboxylic acid (S)-{2-cyclohexyl-1-[2-(4-trifluoromethoxy-phenylamino)-ethylcarbamoyl]-ethyl}-amide; |
| xxiii. | (S)-3-Bromo-N-{1-[2-(4-methoxy-phenylamino)-ethylcarbamoyl]-2-phenyl-ethyl}-4-methyl-benzamide; |
| xxiv. | Furan-2-carboxylic acid (S)-{2-cyclohexyl-1-[2-(4-trifluoromethoxy-phenylamino)-ethylcarbamoyl]-ethyl}-amide; |
| xxv. | Thiophene-2-carboxylic acid (S)-{2-cyclohexyl-1-[2-(4-trifluoromethoxy-phenylamino)-ethylcarbamoyl]-ethyl}-amide; |
| xxvi. | Furan-3-carboxylic acid (S)-{2-cyclohexyl-1-[2-(4-trifluoromethoxy-phenylamino)-ethylcarbamoyl]-ethyl}-amide; |
| xxvii. | N-(S)-{2-cyclohexyl-1-[2-(4-trifluoromethoxy-phenylamino)-ethylcarbamoyl]-ethyl}-4-(5-methyl-[1,2,4]oxadiazol-3-yl)-benzamide; |
| xxviii. | 5-(4-Fluoro-phenyl)-thiophene-2-carboxylic acid (S)-{2-cyclohexyl-1-[2-(4-trifluoromethoxy-phenylamino)-ethylcarbamoyl]-ethyl}-amide; |
| xxix. | (S)-N-{1-[2-(4-Methoxy-phenylamino)-ethylcarbamoyl]-2-phenyl-ethyl}-2,4,5-trimethyl-benzamide; |
| xxx. | (S)-N-{1-[2-(4-Methoxy-phenylamino)-ethylcarbamoyl]-2-phenyl-ethyl}-2,4,5-trimethyl-benzamide; |
| xxxi. | 5-(3-Fluoro-phenyl)-furan-2-carboxylic acid (S)-{2-cyclohexyl-1-[2-(4-trifluoromethoxy-phenylamino)-ethylcarbamoyl]-ethyl}-amide; |
| xxxii. | Benzyl-morpholine-2-carboxylic acid (S)-{2-cyclohexyl-1-[2-(4-trifluoromethoxy-phenylamino)-ethylcarbamoyl]-ethyl}-amide; |
| xxxiii. | (S)-N-{2-[4-(4-Dimethylamino-phenoxy)-phenyl]-1-[2-(4-methoxy-phenylamino)-ethylcarbamoyl]-ethyl}-3-methyl-benzamide; |
| xxxiv. | 2'-Chloro-biphenyl-3-carboxylic acid (S)-{2-cyclohexyl-1-[2-(4-trifluoromethoxy-phenylamino)-ethylcarbamoyl]-ethyl}-amide; |
| xxxv. | 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| xxxvi. | 5-(3-Fluoro-phenyl)-thiophene-2-carboxylic acid (S)-{2-cyclohexyl-1-[2-(4-trifluoromethoxy-phenylamino)-ethylcarbamoyl]-ethyl}-amide; |
| xxxvii. | Thiophene-3-carboxylic acid (S)-{2-cyclohexyl-1-[2-(4-trifluoromethoxy-phenylamino)-ethylcarbamoyl]-ethyl}-amide; |
| xxxviii. | Oxo-1-thiophen-2-ylmethyl-pyrrolidine-3-carboxylic acid (S)-{2-cyclohexyl-1-[2-(4-trifluoromethoxy-phenylamino)-ethylcarbamoyl]-ethyl}-amide; |
| xxxix. | Furan-2-ylmethyl-5-oxo-pyrrolidine-3-carboxylic acid (S)-{2-cyclohexyl-1-[2-(4-trifluoromethoxy-phenylamino)-ethylcarbamoyl]-ethyl}-amide; |
| xl. | Methyl-5-(pyrrolidine-1-sulfonyl)-furan-3-carboxylic acid (S)-{2-cyclohexyl-1-[2-(4-trifluoromethoxy-phenylamino)-ethylcarbamoyl]-ethyl}-amide; |

TABLE I-continued

| | |
|---|---|
| xli. | (S)-1-Phenyl-5-trifluoromethyl-1H-pyrazole-4-carboxylic acid {1-[2-(4-methoxy-phenylamino)-ethylcarbamoyl]-2-phenyl-ethyl}-amide; |
| xlii. | 5-p-Tolyl-thiophene-2-carboxylic acid (S)-{2-cyclohexyl-1-[2-(4-trifluoromethoxy-phenylamino)-ethylcarbamoyl]-ethyl}-amide; |
| xliii. | Benzoimidazol-1-ylmethyl-N-{2-cyclohexyl-1-(S)-[2-(4-trifluoromethoxy-phenylamino)-ethylcarbamoyl]-ethyl}-benzamide; |
| xliv. | (S)-1-(4-Chloro-phenyl)-5-trifluoromethyl-1H-pyrazole-4-carboxylic acid {1-[2-(4-methoxy-phenylamino)-ethylcarbamoyl]-2-phenyl-ethyl}-amide; |
| xlv. | (S)-N-[1-[2-(4-Methoxy-phenylamino)-ethylcarbamoyl]-2-(4-p-tolyloxy-phenyl)-ethyl]-3-methyl-benzamide; |
| xlvi. | Cyclohexyl-2-(S)-(2-tetrazol-1-yl-acetylamino)-N-[2-(4-trifluoromethoxy-phenylamino)-ethyl]-propionamide; |
| xlvii. | 5-m-Tolyl-thiophene-2-carboxylic acid (S)-{2-cyclohexyl-1-[2-(4-trifluoromethoxy-phenylamino)-ethylcarbamoyl]-ethyl}-amide; |
| xlviii. | 2,7-Dimethyl-pyrazolo[1,5-a]pyrimidine-6-carboxylic acid (S)-{2-cyclohexyl-1-[2-(4-trifluoromethoxy-phenylamino)-ethylcarbamoyl]-ethyl}-amide; |
| xlix. | 2-Methyl-5-(morpholine-4-sulfonyl)-furan-3-carboxylic acid (S)-{2-cyclohexyl-1-[2-(4-trifluoromethoxy-phenylamino)-ethylcarbamoyl]-ethyl}-amide; |
| l. | 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| li. | 5-m-Tolyl-furan-2-carboxylic acid (S)-{2-cyclohexyl-1-[2-(4-trifluoromethoxy-phenylamino)-ethylcarbamoyl]-ethyl}-amide; |
| lii. | (S)-2,3-Dihydro-benzofuran-7-carboxylic acid {1-[2-(4-methoxy-phenylamino)-ethylcarbamoyl]-2-phenyl-ethyl}-amide; |
| liii. | Methanesulfonyl-thiophene-2-carboxylic acid (S)-{2-cyclohexyl-1-[2-(4-trifluoromethoxy-phenylamino)-ethylcarbamoyl]-ethyl}-amide; |
| liv. | 2-Phenyl-thiazole-4-carboxylic acid (S)-{2-cyclohexyl-1-[2-(4-trifluoromethoxy-phenylamino)-ethylcarbamoyl]-ethyl}-amide; |
| lv. | (S)-3-Cyano-N-{1-[2-(4-methoxy-phenylamino)-ethylcarbamoyl]-2-phenyl-ethyl}-benzamide; |
| lvi. | (S)-N-{1-[2-(4-Methoxy-phenylamino)-ethylcarbamoyl]-2-phenyl-ethyl}-3-(2-methyl-thiazol-4-yl)-benzamide; |
| lvii. | (S)-N-[2-(4-Methoxy-phenylamino)-ethyl]-3-phenyl-2-(3-phenyl-ureido)-propionamide; |
| lviii. | 3-Cyclohexyl-2-(S)-(2-(S)-hydroxy-2-phenyl-acetylamino)-N-[2-(4-trifluoromethoxy-phenylamino)-ethyl]-propionamide; |
| lix. | Benzo[c]isoxazole-3-carboxylic acid (S)-{2-cyclohexyl-1-[2-(4-trifluoromethoxy-phenylamino)-ethylcarbamoyl]-ethyl}-amide; |
| lx. | N-(S)-{2-cyclohexyl-1-[2-(4-trifluoromethoxy-phenylamino)-ethylcarbamoyl]-ethyl}-4-difluoromethoxy-benzamide; |
| lxi. | N-(S)-{2-cyclohexyl-1-[2-(4-trifluoromethoxy-phenylamino)-ethylcarbamoyl]-ethyl}-4-isopropoxy-benzamide; |
| lxii. | Phenyl-thiophene-2-carboxylic acid (S)-{2-cyclohexyl-1-[2-(4-trifluoromethoxy-phenylamino)-ethylcarbamoyl]-ethyl}-amide; |
| lxiii. | (S)-N-{1-[2-(4-Methoxy-phenylamino)-ethylcarbamoyl]-2-phenyl-ethyl}-nicotinamide; |
| lxiv. | (S)-N-{1-[2-(4-Methoxy-phenylamino)-ethylcarbamoyl]-2-phenyl-ethyl}-isonicotinamide; |
| lxv. | Phenyl-furan-2-carboxylic acid (S)-{2-cyclohexyl-1-[2-(4-trifluoromethoxy-phenylamino)-ethylcarbamoyl]-ethyl}-amide; |
| lxvi. | (S)-N-[1-[2-(4-Methoxy-phenylamino)-ethylcarbamoyl]-2-(4-o-tolyloxy-phenyl)-ethyl]-3-methyl-benzamide; |
| lxvii. | N-(S)-{2-cyclohexyl-1-[2-(4-trifluoromethoxy-phenylamino)-ethylcarbamoyl]-ethyl}-4-oxazol-5-yl-benzamide; |
| lxviii. | 5-(3-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| lxix. | 5-(2-Trifluoromethyl-phenyl)-thiophene-2-carboxylic acid (S)-{2-cyclohexyl-1-[2-(4-trifluoromethoxy-phenylamino)-ethylcarbamoyl]-ethyl}-amide; |
| lxx. | 5-p-Tolyl-furan-2-carboxylic acid (S)-{2-cyclohexyl-1-[2-(4-trifluoromethoxy-phenylamino)-ethylcarbamoyl]-ethyl}-amide; |
| lxxi. | N-(S)-{2-cyclohexyl-1-[2-(4-trifluoromethoxy-phenylamino)-ethylcarbamoyl]-ethyl}-3-[(4,6-dimethyl-pyrimidin-2-yl)-methyl-amino]-benzamide; |
| lxxii. | 1-(4,6-Dimethyl-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxiii. | N-(S)-{2-cyclohexyl-1-[2-(4-trifluoromethoxy-phenylamino)-ethylcarbamoyl]-ethyl}-3-(4,6-dimethoxy-pyrimidin-2-yloxy)-benzamide; |
| lxxiv. | 3'-Methoxy-biphenyl-3-carboxylic acid (S)-{2-cyclohexyl-1-[2-(4-trifluoromethoxy-phenylamino)-ethylcarbamoyl]-ethyl}-amide; |
| lxxv. | N-{3-Cyclohexyl-1-(S)-[2-(4-methoxy-phenylamino)-ethylcarbamoyl]-propyl}-2-(R)-phenyl-butyramide; |
| lxxvi. | 3-Cyclohexyl-N-[2-(4-fluoro-phenylamino)-ethyl]-2-(S)-(2-thiophen-2-yl-acetylamino)-propionamide; |
| lxxvii. | 3-Cyclohexyl-N-[2-(4-fluoro-phenylamino)-ethyl]-2-(S)-(2-thiophen-3-yl-acetylamino)-propionamide; |
| lxxviii. | (S)-3-Bromo-N-{1-[2-(4-methoxy-phenylamino)-ethylcarbamoyl]-2-phenyl-ethyl}-benzamide; |
| lxxix. | Acetyl-piperidine-4-carboxylic acid (S)-{2-cyclohexyl-1-[2-(4-fluoro-phenylamino)-ethylcarbamoyl]-ethyl}-amide; |
| lxxx. | N-(S)-{2-cyclohexyl-1-[2-(4-trifluoromethoxy-phenylamino)-ethylcarbamoyl]-ethyl}-4-(4,6-dimethoxy-pyrimidin-2-yl)-benzamide; |
| lxxxi. | 1-(5-Bromo-pyrimidin-2-yl)-piperidine-4-carboxylic acid (S)-{2-cyclohexyl-1-[2-(4-trifluoromethoxy-phenylamino)-ethylcarbamoyl]-ethyl}-amide; |
| lxxxii. | (S)-2-(2-Cyclopent-2-enyl-acetylamino)-N-[2-(4-methoxy-phenylamino)-ethyl]-3-phenyl-propionamide; |
| lxxxiii. | Cyclohexyl-N-[2-(4-fluoro-phenylamino)-ethyl]-2-(2-1H-indol-3-yl-acetylamino)-propionamide; |
| lxxxiv. | N-(S)-{2-cyclohexyl-1-[2-(4-fluoro-phenylamino)-ethylcarbamoyl]-ethyl}-3-methanesulfonylamino-benzamide; |
| lxxxv. | 5-(3-Trifluoromethyl-phenyl)-furan-2-carboxylic acid (S)-{2-cyclohexyl-1-[2-(4-fluoro-phenylamino)-ethylcarbamoyl]-ethyl}-amide; |
| lxxxvi. | Cyclohexyl-2-(S)-(2-(R,S)-fluoro-2-phenyl-acetylamino)-N-[2-(4-fluoro-phenylamino)-ethyl]-propionamide; |
| lxxxvii. | Cyclohexyl-N-(S)-[2-(4-fluoro-phenylamino)-ethyl]-2-[2-(4-trifluoromethoxy-phenyl)-acetylamino]-propionamide; |
| lxxxviii. | (S)-2-[3-(4-Chloro-phenyl)-ureido]-N-[2-(4-methoxy-phenylamino)-ethyl]-3-phenyl-propionamide; |
| lxxxix. | (S)-N-[2-(4-Methoxy-phenylamino)-ethyl]-2-[3-(4-phenoxy-phenyl)-ureido]-3-phenyl-propionamide; |
| xc. | (S)-N-[2-(4-Methoxy-phenylamino)-ethyl]-2-(3-phenethyl-ureido)-3-phenyl-propionamide; |
| xci. | (S)-2-[3-(4-Fluoro-benzyl)-ureido]-N-[2-(4-methoxy-phenylamino)-ethyl]-3-phenyl-propionamide; |
| xcii. | N-(S)-{2-cyclohexyl-1-[2-(4-trifluoromethoxy-phenylamino)-ethylcarbamoyl]-ethyl}-4-(4,6-dimethyl-pyrimidin-2-ylamino)-benzamide; |
| xciii. | 1-(5-Bromo-pyrimidin-2-yl)-piperidine-3-carboxylic acid (S)-{2-cyclohexyl-1-[2-(4-trifluoromethoxy-phenylamino)-ethylcarbamoyl]-ethyl}-amide; |
| xciv. | (S)-2-(3-Benzo[1,3] dioxol-5-yl-ureido)-N-[2-(4-methoxy-phenylamino)-ethyl]-3-phenyl-propionamide; |
| xcv. | 3-Cyclohexyl-2-(S)-[2-(2,5-difluorophenyl)-acetylamino]-N-[2-(4-fluoro-phenylamino)-ethyl]-propionamide; |
| xcvi. | (S)-2-[3-(3-Fluoro-benzyl)-ureido]-N-[2-(4-methoxy-phenylamino)-ethyl]-3-phenyl-propionamide; |
| xcvii. | (S)-N-[2-(4-Methoxy-phenylamino)-ethyl]-3-phenyl-2-(3-o-tolyl-ureido)-propionamide; |
| xcviii. | (S)-N-{2-[4-(3,4-Dichloro-phenoxy)-phenyl]-1-[2-(4-methoxy-phenylamino)-ethylcarbamoyl]-ethyl}-3-methyl-benzamide; |
| xcix. | 3-Cyclohexyl-2-(S)-[2-(3,4-difluoro-phenyl)-acetylamino]-N-[2-(4-fluoro-phenylamino)-ethyl]-propionamide; |
| c. | 3-Cyclohexyl-2-(S)-[2-(2,4-difluoro-phenyl)-acetylamino]-N-[2-(4-fluoro-phenylamino)-ethyl]-propionamide; |
| ci. | (S)-N-[2-(4-Methoxy-phenylamino)-ethyl]-2-(3-naphthalen-1-yl-ureido)-3-phenyl-propionamide; |
| cii. | (S)-2-[3-(2-tert-Butyl-6-methyl-phenyl)-ureido]-N-[2-(4-methoxy-phenylamino)-ethyl]-3-phenyl-propionamide; |
| ciii. | (S)-2-[3-(4-Acetyl-phenyl)-ureido]-N-[2-(4-methoxy-phenylamino)-ethyl]-3-phenyl-propionamide; |
| civ. | (S)-N-[2-(4-Methoxy-phenylamino)-ethyl]-2-[3-(3-methoxy-phenyl)-ureido]-3-phenyl-propionamide; |

TABLE I-continued

| | |
|---|---|
| cv. | (S)-Biphenyl-4-carboxylic acid {2-cyclohexyl-1-[2-(4-methoxy-phenylamino)-ethylcarbamoyl]-ethyl}-amide; |
| cvi. | (S)-N-{2-Cyclohexyl-1-[2-(4-methoxy-phenylamino)-ethylcarbamoyl]-ethyl}-3-trifluoromethyl-benzamide; |
| cvii. | 2-(S)-[2-(2-Chloro-4-fluoro-phenyl)-acetylamino]-3-cyclohexyl-N-[2-(4-fluoro-phenylamino)-ethyl]-propionamide; |
| cviii. | (S)-2-Chloro-N-{2-cyclohexyl-1-[2-(4-methoxy-phenylamino)-ethylcarbamoyl]-ethyl}-3-methyl-benzamide; |
| cix. | (S)-4-Benzyloxy-N-{2-cyclohexyl-1-[2-(4-methoxy-phenylamino)-ethylcarbamoyl]-ethyl}-benzamide; |
| cx. | (S)-4-Benzyloxy-N-{2-cyclohexyl-1-[2-(4-methoxy-phenylamino)-ethylcarbamoyl]-ethyl}-3,5-dimethyl-benzamide; |
| cxi. | (S)-N-{2-Cyclohexyl-1-[2-(4-methoxy-phenylamino)-ethylcarbamoyl]-ethyl}-4-methoxy-3,5-dimethyl-benzamide; |
| cxii. | (S)-3-Bromo-N-{2-cyclohexyl-1-[2-(4-methoxy-phenylamino)-ethylcarbamoyl]-ethyl}-4-methyl-benzamide; |
| cxiii. | (S)-5-Fluoro-1H-indole-2-carboxylic acid {2-cyclohexyl-1-[2-(4-methoxy-phenylamino)-ethylcarbamoyl]-ethyl}-amide; |
| cxiv. | (S)-2-Amino-4-methyl-thiazole-5-carboxylic acid {2-cyclohexyl-1-[2-(4-methoxy-phenylamino)-ethylcarbamoyl]-ethyl}-amide; |
| cxv. | (S)-1-Phenyl-5-trifluoromethyl-1H-pyrazole-4-carboxylic acid {2-cyclohexyl-1-[2-(4-methoxy-phenylamino)-ethylcarbamoyl]-ethyl}-amide; |
| cxvi. | (S)-1-(4-Chloro-phenyl)-5-trifluoromethyl-1H-pyrazole-4-carboxylic acid {2-cyclohexyl-1-[2-(4-methoxy-phenylamino)-ethylcarbamoyl]-ethyl}-amide; |
| cxvii. | (S)-5-(3-Trifluoromethyl-phenyl)-furan-2-carboxylic acid {2-cyclohexyl-1-[2-(4-methoxy-phenylamino)-ethylcarbamoyl]-ethyl}-amide; |
| cxviii. | (S)-3-Chloro-N-{2-cyclohexyl-1-[2-(4-methoxy-phenylamino)-ethylcarbamoyl]-ethyl}-benzamide; |
| cxix. | (S)-N-{2-Cyclohexyl-1-[2-(4-methoxy-phenylamino)-ethylcarbamoyl]-ethyl}-3-dimethylamino-benzamide; |
| cxx. | (S)-3-Cyano-N-{2-cyclohexyl-1-[2-(4-methoxy-phenylamino)-ethylcarbamoyl]-ethyl}-benzamide; |
| cxxi. | (S)-4-Cyano-N-{2-cyclohexyl-1-[2-(4-methoxy-phenylamino)-ethylcarbamoyl]-ethyl}-benzamide; |
| cxxii. | N-{2-cyclohexyl-1-(S)-[2-(4-trifluoromethoxy-phenylamino)-ethylcarbamoyl]-ethyl}-2-(R)-phenyl-propionamide; |
| cxxiii. | (S)-N-{2-Cyclohexyl-1-[2-(4-methoxy-phenylamino)-ethylcarbamoyl]-ethyl}-3-(2-methyl-thiazol-4-yl)-benzamide; |
| cxxiv. | (S)-N-{2-Cyclohexyl-1-[2-(4-methoxy-phenylamino)-ethylcarbamoyl]-ethyl}-4-[1,2,4]triazol-1-yl-benzamide; |
| cxxv. | 3-Cyclohexyl-2-(S)-[2-(3,5-difluoro-phenyl)-acetylamino]-N-[2-(4-fluoro-phenylamino)-ethyl]-propionamide; |
| cxxvi. | (S)-N-{3-Cyclohexyl-1-[2-(4-methoxy-phenylamino)-ethylcarbamoyl]-propyl}-3-trifluoromethyl-benzamide; |
| cxxvii. | (S)-N-{3-Cyclohexyl-1-[2-(4-methoxy-phenylamino)-ethylcarbamoyl]-propyl}-4-morpholin-4-yl-benzamide; |
| cxxviii. | (4-Cyclohexyl-N-[2-(4-methoxy-phenylamino)-ethyl]-2-(S)-(2-(S)-phenyl-propionylamino)-butyramide; |
| cxxix. | (S)-4-Benzyloxy-N-{3-cyclohexyl-1-[2-(4-methoxy-phenylamino)-ethylcarbamoyl]-propyl}-benzamide; |
| cxxx. | (S)-Biphenyl-4-carboxylic acid {3-cyclohexyl-1-[2-(4-methoxy-phenylamino)-ethylcarbamoyl]-propyl}-amide; |
| cxxxi. | (S)-5-Chloro-1H-indole-2-carboxylic acid {3-cyclohexyl-1-[2-(4-methoxy-phenylamino)-ethylcarbamoyl]-propyl}-amide; |
| cxxxii. | (S)-5-Fluoro-1H-indole-2-carboxylic acid {3-cyclohexyl-1-[2-(4-methoxy-phenylamino)-ethylcarbamoyl]-propyl}-amide; |
| cxxxiii. | (S)-2-Amino-4-methyl-thiazole-5-carboxylic acid {3-cyclohexyl-1-[2-(4-methoxy-phenylamino)-ethylcarbamoyl]-propyl}-amide; |
| cxxxiv. | (S)-5-Chloro-benzofuran-2-carboxylic acid {3-cyclohexyl-1-[2-(4-methoxy-phenylamino)-ethylcarbamoyl]-propyl}-amide; |
| cxxxv. | N-{2-cyclohexyl-1-(S)-[2-(4-trifluoromethoxy-phenylamino)-ethylcarbamoyl]-ethyl}-2-(R)-phenyl-butyramide; |
| cxxxvi. | (S)-5-(3-Trifluoromethyl-phenyl)-furan-2-carboxylic acid {3-cyclohexyl-1-[2-(4-methoxy-phenylamino)-ethylcarbamoyl]-propyl}-amide; |
| cxxxvii. | (S)-Benzothiazole-6-carboxylic acid {3-cyclohexyl-1-[2-(4-methoxy-phenylamino)-ethylcarbamoyl]-propyl}-amide; |
| cxxxviii. | (S)-N-{3-Cyclohexyl-1-[2-(4-methoxy-phenylamino)-ethylcarbamoyl]-propyl}-3-trifluoromethoxy-benzamide; |
| cxxxix. | (S)-3-Cyano-N-{3-cyclohexyl-1-[2-(4-methoxy-phenylamino)-ethylcarbamoyl]-propyl}-benzamide; |
| cxl. | (S)-4-Cyano-N-{3-cyclohexyl-1-[2-(4-methoxy-phenylamino)-ethylcarbamoyl]-propyl}-benzamide; |
| cxli. | N-{2-cyclohexyl-1-(S)-[2-(4-trifluoromethoxy-phenylamino)-ethylcarbamoyl]-ethyl}-4-phenoxy-benzamide; |
| cxlii. | (S)-N-{3-Cyclohexyl-1-[2-(4-methoxy-phenylamino)-ethylcarbamoyl]-propyl}-3-(2-methyl-thiazol-4-yl)-benzamide; |
| cxliii. | (S)-N-{3-Cyclohexyl-1-[2-(4-methoxy-phenylamino)-ethylcarbamoyl]-propyl}-4-[1,2,4]triazol-1-yl-benzamide; |
| cxliv. | (S)-Biphenyl-3-carboxylic acid {3-cyclohexyl-1-[2-(4-methoxy-phenylamino)-ethylcarbamoyl]-propyl}-amide; |
| cxlv. | (S)-N-{2-Cyclohexyl-1-[2-(4-methoxy-phenylamino)-ethylcarbamoyl]-ethyl}-2-fluoro-benzamide; |
| cxlvi. | (S)-N-{2-Cyclohexyl-1-[2-(4-methoxy-phenylamino)-ethylcarbamoyl]-ethyl}-3,4-difluoro-benzamide; |
| cxlvii. | (S)-N-{2-Cyclohexyl-1-[2-(4-methoxy-phenylamino)-ethylcarbamoyl]-ethyl}-3-fluoro-2-methyl-benzamide; |
| cxlviii. | (S)-2-Chloro-N-{2-cyclohexyl-1-[2-(4-methoxy-phenylamino)-ethylcarbamoyl]-ethyl}-5-methyl-benzamide; |
| cxlix. | (S)-N-{2-Cyclohexyl-1-[2-(4-methoxy-phenylamino)-ethylcarbamoyl]-ethyl}-4-fluoro-3-trifluoromethyl-benzamide; |
| cl. | (S)-5-Methyl-1-phenyl-1H-pyrazole-4-carboxylic acid {2-cyclohexyl-1-[2-(4-methoxy-phenylamino)-ethylcarbamoyl]-ethyl}-amide; |
| cli. | (S)-N-{2-Cyclohexyl-1-[2-(4-methoxy-phenylamino)-ethylcarbamoyl]-ethyl}-4-propyl-benzamide; |
| clii. | 3-Cyclohexyl-2-(S)-[2-(4-fluoro-phenyl)-acetylamino]-N-[2-(4-fluoro-phenylamino)-ethyl]-propionamide; |
| cliii. | (S)-N-{2-Cyclohexyl-1-[2-(4-methoxy-phenylamino)-ethylcarbamoyl]-ethyl}-4-methoxy-benzamide; |
| cliv. | (S)-N-{2-Cyclohexyl-1-[2-(4-methoxy-phenylamino)-ethylcarbamoyl]-ethyl}-2-fluoro-5-trifluoromethyl-benzamide; |
| clv. | (S)-3-Chloro-N-{2-cyclohexyl-1-[2-(4-methoxy-phenylamino)-ethylcarbamoyl]-ethyl}-2-fluoro-benzamide; |
| clvi. | (S)-5-Chloro-N-{2-cyclohexyl-1-[2-(4-methoxy-phenylamino)-ethylcarbamoyl]-ethyl}-2-fluoro-benzamide; |
| clvii. | (S)-N-{2-Cyclohexyl-1-[2-(4-methoxy-phenylamino)-ethylcarbamoyl]-ethyl}-5-fluoro-2-methyl-benzamide; |
| clviii. | (S)-1-Phenyl-cyclopropanecarboxylic acid {2-cyclohexyl-1-[2-(4-methoxy-phenylamino)-ethylcarbamoyl]-ethyl}-amide; |
| clix. | (S)-3-Cyclohexyl-N-[2-(4-methoxy-phenylamino)-ethyl]-2-(2-phenylamino-acetylamino)-propionamide; |
| clx. | 3-Cyclohexyl-2-(S)-(2-(R)-hydroxy-2-phenyl-acetylamino)-N-[2-(4-methoxy-phenylamino)-ethyl]-propionamide; |
| clxi. | (S)-1-(4-Fluoro-phenyl)-5-methyl-1H-pyrazole-4-carboxylic acid {2-cyclohexyl-1-[2-(4-methoxy-phenylamino)-ethylcarbamoyl]-ethyl}-amide; |
| clxii. | (S)-1-(4-Methoxy-phenyl)-5-methyl-1H-pyrazole-4-carboxylic acid {2-cyclohexyl-1-[2-(4-methoxy-phenylamino)-ethylcarbamoyl]-ethyl}-amide; |
| clxiii. | (S)-1-(4-Chloro-phenyl)-5-methyl-1H-pyrazole-4-carboxylic acid {2-cyclohexyl-1-[2-(4-methoxy-phenylamino)-ethylcarbamoyl]-ethyl}-amide; |
| clxiv. | N-{2-Cyclohexyl-1-(S)-[2-(4-methoxy-phenylamino)-ethylcarbamoyl]-ethyl}-2-(S)-phenyl-butyramide; |
| clxv. | (S)-N-{2-Cyclohexyl-1-[2-(4-methoxy-phenylamino)-ethylcarbamoyl]-ethyl}-3-fluoro-5-trifluoromethyl-benzamide; |
| clxvi. | (S)-N-{2-Cyclohexyl-1-[2-(4-methoxy-phenylamino)-ethylcarbamoyl]-ethyl}-2-fluoro-3-trifluoromethyl-benzamide; |
| clxvii. | (S)-N-{2-Cyclohexyl-1-[2-(4-methoxy-phenylamino)-ethylcarbamoyl]-ethyl}-4-fluoro-3-methyl-benzamide; |
| clxviii. | (S)-5-(4-Chloro-phenyl)-furan-2-carboxylic acid {2-cyclohexyl-1-[2-(4-methoxy-phenylamino)-ethylcarbamoyl]-ethyl}-amide; |
| clxix. | (S)-N-{2-Cyclohexyl-1-[2-(4-methoxy-phenylamino)-ethylcarbamoyl]-ethyl}-2-fluoro-4-trifluoromethyl-benzamide; |
| clxx. | (S)-4'-Chloro-biphenyl-4-carboxylic acid {2-cyclohexyl-1-[2-(4-methoxy-phenylamino)-ethylcarbamoyl]-ethyl}-amide; |
| clxxi. | (S)-3',5'-Dichloro-biphenyl-4-carboxylic acid {2-cyclohexyl-1-[2-(4-methoxy-phenylamino)-ethylcarbamoyl]-ethyl}-amide; |
| clxxii. | (S)-3'-Methoxy-biphenyl-4-carboxylic acid {2-cyclohexyl-1-[2-(4-methoxy-phenylamino)-ethylcarbamoyl]-ethyl}-amide; |
| clxxiii. | (S)-3'-Chloro-biphenyl-4-carboxylic acid {2-cyclohexyl-1-[2-(4-methoxy-phenylamino)-ethylcarbamoyl]-ethyl}-amide; |
| clxxiv. | (S)-2'-Methoxy-biphenyl-4-carboxylic acid {2-cyclohexyl-1-[2-(4-methoxy-phenylamino)-ethylcarbamoyl]-ethyl}-amide; |
| clxxv. | (S)-4'-Chloro-biphenyl-3-carboxylic acid {2-cyclohexyl-1-[2-(4-methoxy-phenylamino)-ethylcarbamoyl]-ethyl}-amide; |
| clxxvi. | (S)-4-Benzo[1,3]dioxol-5-yl-N-{2-cyclohexyl-1-[2-(4-methoxy-phenylamino)-ethylcarbamoyl]-ethyl}-benzamide; |
| clxxvii. | (S)-5-Bromo-furan-2-carboxylic acid {2-cyclohexyl-1-[2-(4-methoxy-phenylamino)-ethylcarbamoyl]-ethyl}-amide; |

TABLE I-continued

| | |
|---|---|
| clxxviii. | (S)-3,5-Dibromo-N-{2-cyclohexyl-1-[2-(4-methoxy-phenylamino-ethylcarbamoyl]-ethyl}-benzamide; |
| clxxix. | (S)-3,5-Dichloro-N-{2-cyclohexyl-1-[2-(4-methoxy-phenylamino)-ethylcarbamoyl]-ethyl}-benzamide; |
| clxxx. | (S)-N-{2-Cyclohexyl-1-[2-(4-methoxy-phenylamino)-ethylcarbamoyl]-ethyl}-3,5-dimethoxy-benzamide; |
| clxxxi. | (S)-Biphenyl-3-carboxylic acid {2-cyclohexyl-1-[2-(4-methoxy-phenylamino)-ethylcarbamoyl]-ethyl}-amide; |
| clxxxii. | (S)-5-Bromo-thiophene-2-carboxylic acid {2-cyclohexyl-1-[2-(4-methoxy-phenylamino)-ethylcarbamoyl]-ethyl}-amide; |
| clxxxiii. | (S)-N-{2-Cyclohexyl-1-[2-(4-methoxy-phenylamino)-ethylcarbamoyl]-ethyl}-4-phenoxy-benzamide; |
| clxxxiv. | (S)-N-{2-Cyclohexyl-1-[2-(4-methoxy-phenylamino)-ethylcarbamoyl]-ethyl}-3-phenoxy-benzamide; |
| clxxxv. | (S)-1H-Indole-3-carboxylic acid {2-cyclohexyl-1-[2-(4-methoxy-phenylamino)-ethylcarbamoyl]-ethyl}-amide; |
| clxxxvi. | (S)-Benzothiazole-6-carboxylic acid {2-cyclohexyl-1-[2-(4-methoxy-phenylamino)-ethylcarbamoyl]-ethyl}-amide; |
| clxxxvii. | (S)-2-Amino-benzothiazole-6-carboxylic acid {2-cyclohexyl-1-[2-(4-methoxy-phenylamino)-ethylcarbamoyl]-ethyl}-amide; |
| clxxxviii. | (S)-4-Methyl-2-(4-trifluoromethyl-phenyl)-thiazole-5-carboxylic acid {2-cyclohexyl-1-[2-(4-methoxy-phenylamino)-ethylcarbamoyl]-ethyl}-amide; |
| clxxxix. | (S)-4-(4-Chloro-phenyl)-thiophene-2-carboxylic acid {2-cyclohexyl-1-[2-(4-methoxy-phenylamino)-ethylcarbamoyl]-ethyl}-amide; |
| cxc. | (S)-2-Methyl-5-trifluoromethyl-oxazole-4-carboxylic acid {2-cyclohexyl-1-[2-(4-methoxy-phenylamino)-ethylcarbamoyl]-ethyl}-amide; |
| cxci. | (S)-4-(4-Methoxy-phenyl)-thiophene-2-carboxylic acid {2-cyclohexyl-1-[2-(4-methoxy-phenylamino)-ethylcarbamoyl]-ethyl}-amide; |
| cxcii. | N-{2-Cyclohexyl-1-(S)-[2-(4-methoxy-phenylamino)-ethylcarbamoyl]-ethyl}-2-(S)-phenyl-propionamide; |
| cxciii. | (S)-5-(2-Chloro-5-trifluoromethyl-phenyl)-furan-2-carboxylic acid {2-cyclohexyl-1-[2-(4-methoxy-phenylamino)-ethylcarbamoyl]-ethyl}-amide; |
| cxciv. | (S)-2'-Chloro-biphenyl-4-carboxylic acid {2-cyclohexyl-1-[2-(4-trifluoromethoxy-phenylamino)-ethylcarbamoyl]-ethyl}-amide; |
| cxcv. | (S)-1-(5-Bromo-pyrimidin-2-yl)-piperidine-4-carboxylic acid {2-cyclohexyl-1-[2-(4-methoxy-phenylamino)-ethylcarbamoyl]-ethyl}-amide; |
| cxcvi. | (S)-N-{2-Cyclohexyl-1-[2-(4-methoxy-phenylamino)-ethylcarbamoyl]-ethyl}-4-(4,6-dimethyl-pyrimidin-2-ylamino)-benzamide; |
| cxcvii. | (S)-1-(5-Bromo-pyrimidin-2-yl)-piperidine-3-carboxylic acid {2-cyclohexyl-1-[2-(4-methoxy-phenylamino)-ethylcarbamoyl]-ethyl}-amide; |
| cxcviii. | (S)-3'-Fluoro-biphenyl-4-carboxylic acid {2-cyclohexyl-1-[2-(4-trifluoromethoxy-phenylamino)-ethylcarbamoyl]-ethyl}-amide; |
| cxcix. | (S)-3-Aminomethyl-N-{2-cyclohexyl-1-[2-(4-methoxy-phenylamino)-ethylcarbamoyl]-ethyl}-benzamide; |
| cc. | (S)-N-{2-Cyclohexyl-1-[2-(4-trifluoromethoxy-phenylamino)-ethylcarbamoyl]-ethyl}-3-morpholin-4-ylmethyl-benzamide; |
| cci. | (S)-5-(2-Fluoro-phenyl)-thiophene-2-carboxylic acid {2-cyclohexyl-1-[2-(4-trifluoromethoxy-phenylamino)-ethylcarbamoyl]-ethyl}-amide; |
| ccii. | (S)-N-{3-Cyclohexyl-1-[2-(4-methoxy-phenylamino)-ethylcarbamoyl]-propyl}-3-methyl-benzamide; |
| cciii. | (S)-N-{4-Cyclohexyl-1-[2-(4-methoxy-phenylamino)-ethylcarbamoyl]-butyl}-3-methyl-benzamide; |
| cciv. | (S)-N-{[2-(4-Methoxy-phenylamino)-ethylcarbamoyl]-phenyl-methyl}-3-methyl-benzamide; |
| ccv. | (S)-5-(4-Trifluoromethyl-phenyl)-thiophene-2-carboxylic acid {2-cyclohexyl-1-[2-(4-trifluoromethoxy-phenylamino)-ethylcarbamoyl]-ethyl}-amide; |
| ccvi. | (S)-N-{1-[2-(4-Methoxy-phenylamino)-ethylcarbamoyl]-3-phenyl-propyl}-3-methyl-benzamide; |
| ccvii. | (S)-5-(4-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccviii. | (S)-N-{1-[2-(4-Methoxy-phenylamino)-ethylcarbamoyl]-4-phenyl-but-3-enyl}-3-methyl-benzamide; |
| ccix. | (S)-5-(3-Trifluoromethoxy-phenyl)-thiophene-2-carboxylic acid {2-cyclohexyl-1-[2-(4-trifluoromethoxy-phenylamino)-ethylcarbamoyl]-ethyl}-amide; |
| ccx. | (S)-5-(2-Methoxy-phenyl)-furan-2-carboxylic acid {2-cyclohexyl-1-[2-(4-trifluoromethoxy-phenylamino)-ethylcarbamoyl]-ethyl}-amide; |
| ccxi. | N-{(4-Methoxy-phenyl)-[2-(4-methoxy-phenylamino)-ethylcarbamoyl]-methyl}-3-methyl-benzamide; |
| ccxii. | (S)-5-(2-Fluoro-phenyl)-furan-2-carboxylic acid {2-cyclohexyl-1-[2-(4-trifluoromethoxy-phenylamino)-ethylcarbamoyl]-ethyl}-amide; |
| ccxiii. | (S)-5-(4-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxiv. | N-{(2-Benzyloxy-phenyl)-[2-(4-methoxy-phenylamino)-ethylcarbamoyl]-methyl}-3-methyl-benzamide; |
| ccxv. | (S)-5-(4-Trifluoromethoxy-phenyl)-furan-2-carboxylic acid {2-cyclohexyl-1-[2-(4-trifluoromethoxy-phenylamino)-ethylcarbamoyl]-ethyl}-amide; |
| ccxvi. | N-{(2-Chloro-phenyl)-[2-(4-methoxy-phenylamino)-ethylcarbamoyl]-methyl}-3-methyl-benzamide; |
| ccxvii. | N-{(4-Benzyloxy-phenyl)-[2-(4-methoxy-phenylamino)-ethylcarbamoyl]-methyl}-3-methyl-benzamide; |
| ccxviii. | N-{[2-(4-Methoxy-phenylamino)-ethylcarbamoyl]-naphthalen-1-yl-methyl}-3-methyl-benzamide; |
| ccxix. | (S)-5-(2-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxx. | N-{[2-(4-Methoxy-phenylamino)-ethylcarbamoyl]-o-tolyl-methyl}-3-methyl-benzamide; |
| ccxxi. | (S)-N-{2-Cyclohexyl-1-[2-(4-methoxy-phenylamino)-ethylcarbamoyl]-ethyl}-4-[1,2,4]triazol-1-yl-benzamide; |
| ccxxii. | N-{(2,4-Dichloro-phenyl)-[2-(4-methoxy-phenylamino)-ethylcarbamoyl]-methyl}-3-methyl-benzamide; |
| ccxxiii. | N-{(2,3-Dichloro-phenyl)-[2-(4-methoxy-phenylamino)-ethylcarbamoyl]-methyl}-3-methyl-benzamide; |
| ccxxiv. | N-{(2,4-Dimethyl-phenyl)-[2-(4-methoxy-phenylamino)-ethylcarbamoyl]-methyl}-3-methyl-benzamide; |
| ccxxv. | N-{(2,4-Dimethoxy-phenyl)-[2-(4-methoxy-phenylamino)-ethylcarbamoyl]-methyl}-3-methyl-benzamide; |
| ccxxvi. | N-{[2-(4-Methoxy-phenylamino)-ethylcarbamoyl]-thiophen-2-yl-methyl}-3-methyl-benzamide; |
| ccxxvii. | N-{(4-Fluoro-phenyl)-[2-(4-methoxy-phenylamino)-ethylcarbamoyl]-methyl}-3-methyl-benzamide; |
| ccxxviii. | (S)-N-{2-(4-Hydroxy-phenyl)-1-[2-(4-methoxy-phenylamino)-ethylcarbamoyl]-ethyl}-3-methyl-benzamide; |
| ccxxix. | (S)-N-{2-(2,4-Dichloro-phenyl)-1-[2-(4-methoxy-phenylamino)-ethylcarbamoyl]-ethyl}-3-methyl-benzamide; |
| ccxxx. | (S)-N-{2-(3,5-Difluoro-phenyl)-1-[2-(4-methoxy-phenylamino)-ethylcarbamoyl]-ethyl}-3-methyl-benzamide; |
| ccxxxi. | (S)-N-{2-(3,4-Dichloro-phenyl)-1-[2-(4-methoxy-phenylamino)-ethylcarbamoyl]-ethyl}-3-methyl-benzamide; |
| ccxxxii. | (S)-4-Benzyloxy-N-{2-cyclohexyl-1-[2-(4-trifluoromethoxy-phenylamino)-ethylcarbamoyl]-ethyl}-benzamide; |
| ccxxxiii. | (S)-N-{2-(4-Acetylamino-phenyl)-1-[2-(4-methoxy-phenylamino)-ethylcarbamoyl]-ethyl}-3-methyl-benzamide; |
| ccxxxiv. | (S)-Biphenyl-4-carboxylic acid {2-cyclohexyl-1-[2-(4-trifluoromethoxy-phenylamino)-ethylcarbamoyl]-ethyl}-amide; |
| ccxxxv. | (S)-N-{1-[2-(4-Methoxy-phenylamino)-ethylcarbamoyl]-2-p-tolyl-ethyl}-3-methyl-benzamide; |
| ccxxxvi. | (S)-N-{2-(3-Fluoro-phenyl)-1-[2-(4-methoxy-phenylamino)-ethylcarbamoyl]-ethyl}-3-methyl-benzamide; |
| ccxxxvii. | (S)-N-{2-(3,4-Difluoro-phenyl)-1-[2-(4-methoxy-phenylamino)-ethylcarbamoyl]-ethyl}-3-methyl-benzamide; |
| ccxxxviii. | (S)-N-{1-[2-(4-Methoxy-phenylamino)-ethylcarbamoyl]-2-m-tolyl-ethyl}-3-methyl-benzamide; |
| ccxxxix. | (S)-N-{1-[2-(4-Methoxy-phenylamino)-ethylcarbamoyl]-2-(2-trifluoromethyl-phenyl)-ethyl}-3-methyl-benzamide; |
| ccxl. | (S)-N-{2-(4-Cyano-phenyl)-1-[2-(4-methoxy-phenylamino)-ethylcarbamoyl]-ethyl}-3-methyl-benzamide; |
| ccxli. | (S)-N-{2-(4-Bromo-phenyl)-1-[2-(4-methoxy-phenylamino)-ethylcarbamoyl]-ethyl}-3-methyl-benzamide; |
| ccxlii. | (S)-N-{2-(4-Iodo-phenyl)-1-[2-(4-methoxy-phenylamino)-ethylcarbamoyl]-ethyl}-3-methyl-benzamide; |
| ccxliii. | (S)-N-{2-(4-Chloro-phenyl)-1-[2-(4-methoxy-phenylamino)-ethylcarbamoyl]-ethyl}-3-methyl-benzamide; |
| ccxliv. | (S)-N-{1-[2-(4-Methoxy-phenylamino)-ethylcarbamoyl]-2-(4-nitro-phenyl)-ethyl}-3-methyl-benzamide; |
| ccxlv. | (S)-N-{2-(4-Fluoro-phenyl)-1-[2-(4-methoxy-phenylamino)-ethylcarbamoyl]-ethyl}-3-methyl-benzamide; |

TABLE I-continued

| | |
|---|---|
| ccxlvi. | (S)-5-(3-Trifluoromethyl-phenyl)-furan-2-carboxylic acid {2-cyclohexyl-1-[2-(4-trifluoromethoxy-phenylamino)-ethylcarbamoyl]-ethyl}-amide; |
| ccxlvii. | (S)-N-{2-(4-Benzyloxy-phenyl)-1-[2-(4-methoxy-phenylamino)-ethylcarbamoyl]-ethyl}-3-methyl-benzamide; |
| ccxlviii. | (S)-N-{2-[4-(2,6-Dichloro-benzyloxy)-phenyl]-1-[2-(4-methoxy-phenylamino)-ethylcarbamoyl]-ethyl}-3-methyl-benzamide; |
| ccxlix. | (S)-N-{2-(4-Methoxy-phenyl)-1-[2-(4-methoxy-phenylamino)-ethylcarbamoyl]-ethyl}-3-methyl-benzamide; |
| ccl. | 2-Amino-4-methyl-thiazole-5-carboxylic acid (S)-{2-cyclohexyl-1-[2-(4-trifluoromethoxy-phenylamino)-ethylcarbamoyl]-ethyl}-amide; |
| ccli. | (S)-5-(2-Chloro-5-trifluoromethyl-phenyl)-furan-2-carboxylic acid {2-cyclohexyl-1-[2-(4-trifluoromethoxy-phenylamino)-ethylcarbamoyl]-ethyl}-amide; |
| cclii. | (S)-N-{1-[2-(4-Methoxy-phenylamino)-ethylcarbamoyl]-2-(3-trifluoromethyl-phenyl)-ethyl}-3-methyl-benzamide; |
| ccliii. | (S)-N-{1-[2-(4-Methoxy-phenylamino)-ethylcarbamoyl]-2-(4-trifluoromethyl-phenyl)-ethyl}-3-methyl-benzamide; |
| ccliv. | (S)-N-{2-Benzyloxy-1-[2-(4-methoxy-phenylamino)-ethylcarbamoyl]-ethyl}-3-methyl-benzamide; |
| cclv. | (S)-N-{2-(4-tert-Butyl-phenyl)-1-[2-(4-methoxy-phenylamino)-ethylcarbamoyl]-ethyl}-3-methyl-benzamide; |
| cclvi. | Cyclohexyl-N-[2-(4-methoxy-phenylamino)-ethyl]-2-(S)-(2-(S)-phenyl-propionylamino)-butyramide; |
| cclvii. | (S)-N-{2-(1H-Indol-3-yl)-1-[2-(4-methoxy-phenylamino)-ethylcarbamoyl]-ethyl}-3-methyl-benzamide; |
| cclviii. | (S)-N-{1-[2-(4-Methoxy-phenylamino)-ethylcarbamoyl]-2-naphthalen-1-yl-ethyl}-3-methyl-benzamide; |
| cclix. | (S)-N-{2-Benzyloxy-1-[2-(4-methoxy-phenylamino)-ethylcarbamoyl]-propyl}-3-methyl-benzamide; |
| cclx. | 3-Cyclohexyl-2-(S)-[2-(3-fluoro-phenyl)-acetylamino]-N-[2-(4-fluoro-phenylamino)-ethyl]-propionamide; |
| cclxi. | (S)-N-{1-[2-(4-Methoxy-phenylamino)-ethylcarbamoyl]-2-naphthalen-2-yl-ethyl}-3-methyl-benzamide; |
| cclxii. | (S)-N-{1-[2-(4-Methoxy-phenylamino)-ethylcarbamoyl]-2-pyridin-3-yl-ethyl}-3-methyl-benzamide; |
| cclxiii. | (S)-N-{1-[2-(4-Methoxy-phenylamino)-ethylcarbamoyl]-2-pyridin-4-yl-ethyl}-3-methyl-benzamide; |
| cclxiv. | Furan-2-carboxylic acid (S)-{2-cyclohexyl-1-[2-(4-fluoro-phenylamino)-ethylcarbamoyl]-ethyl}-amide; |
| cclxv. | 3-Cyclohexyl-N-[2-(4-fluoro-phenylamino)-ethyl]-2-(S)-(2-tetrazol-1-yl-acetylamino)-propionamide; |
| cclxvi. | N-[1-[2-(4-Methoxy-phenylamino)-ethylcarbamoyl]-2-(4-nitro-phenyl)-propyl]-3-methyl-benzamide; |
| cclxvii. | (S)-N-[1-[2-(4-Methoxy-phenylamino)-ethylcarbamoyl]-2-(4-m-tolyloxy-phenyl)-ethyl]-3-methyl-benzamide; |
| cclxviii. | threo-N-{1-[2-(4-Methoxy-phenylamino)-ethylcarbamoyl]-2-phenyl-propyl}-3-methyl-benzamide; |
| cclxix. | erythro-N-{1-[2-(4-Methoxy-phenylamino)-ethylcarbamoyl]-2-phenyl-propyl}-3-methyl-benzamide; |
| cclxx. | (S)-N-{2-Biphenyl-4-yl-1-[2-(4-methoxy-phenylamino)-ethylcarbamoyl]-ethyl}-3-methyl-benzamide; |
| cclxxi. | (S)-N-[1-[2-(4-Methoxy-phenylamino)-ethylcarbamoyl]-2-(3'-nitro-biphenyl-4-yl)-ethyl]-3-methyl-benzamide; |
| cclxxii. | Furan-3-carboxylic acid (S)-{2-cyclohexyl-1-[2-(4-fluoro-phenylamino)-ethylcarbamoyl]-ethyl}-amide; |
| cclxxiii. | (S)-N-[1-[2-(4-Methoxy-phenylamino)-ethylcarbamoyl]-2-(2'-nitro-biphenyl-4-yl)-ethyl]-3-methyl-benzamide; |
| cclxxiv. | (S)-N-[1-[2-(4-Methoxy-phenylamino)-ethylcarbamoyl]-2-(4-pyridin-3-yl-phenyl)-ethyl]-3-methyl-benzamide; |
| cclxxv. | (S)-N-[1-[2-(4-Methoxy-phenylamino)-ethylcarbamoyl]-2-(4-thiophen-3-yl-phenyl)-ethyl]-3-methyl-benzamide; |
| cclxxvi. | (S)-N-{2-(4'-Cyano-biphenyl-4-yl)-1-[2-(4-methoxy-phenylamino)-ethylcarbamoyl]-ethyl}-3-methyl-benzamide; |
| cclxxvii. | (S)-N-[1-[2-(4-Methoxy-phenylamino)-ethylcarbamoyl]-2-(4-pyridin-4-yl-phenyl)-ethyl]-3-methyl-benzamide; |
| cclxxviii. | (S)-N-{2-(4'-Chloro-biphenyl-4-yl)-1-[2-(4-methoxy-phenylamino)-ethylcarbamoyl]-ethyl}-3-methyl-benzamide; |
| cclxxix. | (S)-N-{2-(2',3'-Dimethoxy-biphenyl-4-yl)-1-[2-(4-methoxy-phenylamino)-ethylcarbamoyl]-ethyl}-3-methyl-benzamide; |
| cclxxx. | (S)-N-{2-(3'-Amino-biphenyl-4-yl)-1-[2-(4-methoxy-phenylamino)-ethylcarbamoyl]-ethyl}-3-methyl-benzamide; |
| cclxxxi. | (S)-N-{2-(3',4'-Dimethoxy-biphenyl-4-yl)-1-[2-(4-methoxy-phenylamino)-ethylcarbamoyl]-ethyl}-3-methyl-benzamide; |
| cclxxxii. | (S)-N-{2-(4'-Hydroxymethyl-biphenyl-4-yl)-1-[2-(4-methoxy-phenylamino)-ethylcarbamoyl]-ethyl}-3-methyl-benzamide; |
| cclxxxiii. | (S)-N-{2-(5'-Fluoro-2'-methoxy-biphenyl-4-yl)-1-[2-(4-methoxy-phenylamino)-ethylcarbamoyl]-ethyl}-3-methyl-benzamide; |
| cclxxxiv. | (S)-N-{2-(3'-Hydroxymethyl-biphenyl-4-yl)-1-[2-(4-methoxy-phenylamino)-ethylcarbamoyl]-ethyl}-3-methyl-benzamide; |
| cclxxxv. | (S)-N-{2-(2',5'-Dimethoxy-biphenyl-4-yl)-1-[2-(4-methoxy-phenylamino)-ethylcarbamoyl]-ethyl}-3-methyl-benzamide; |
| cclxxxvi. | (S)-N-{2-(2',5'-Dichloro-biphenyl-4-yl)-1-[2-(4-methoxy-phenylamino)-ethylcarbamoyl]-ethyl}-3-methyl-benzamide; |
| cclxxxvii. | (S)-N-{2-(4'-Dimethylamino-biphenyl-4-yl)-1-[2-(4-methoxy-phenylamino)-ethylcarbamoyl]-ethyl}-3-methyl-benzamide; |
| cclxxxviii. | (S)-N-{2-(2'-Acetyl-biphenyl-4-yl)-1-[2-(4-methoxy-phenylamino)-ethylcarbamoyl]-ethyl}-3-methyl-benzamide; |
| cclxxxix. | (S)-N-{2-(4'-Hydroxy-biphenyl-4-yl)-1-[2-(4-methoxy-phenylamino)-ethylcarbamoyl]-ethyl}-3-methyl-benzamide; |
| ccxc. | (S)-N-{2-(3'-Acetyl-biphenyl-4-yl)-1-[2-(4-methoxy-phenylamino)-ethylcarbamoyl]-ethyl}-3-methyl-benzamide; |
| ccxci. | (S)-N-{2-[4-(2,4-Dimethoxy-pyrimidin-5-yl)-phenyl]-1-[2-(4-methoxy-phenylamino)-ethylcarbamoyl]-ethyl}-3-methyl-benzamide; |
| ccxcii. | (S)-N-{1-[2-(4-Methoxy-phenylamino)-ethylcarbamoyl]-2-[4-(6-methoxy-pyridin-3-yl)-phenyl]-ethyl}-3-methyl-benzamide; |
| ccxciii. | Methanesulfonyl-thiophene-2-carboxylic acid (S)-{2-cyclohexyl-1-[2-(4-fluoro-phenylamino)-ethylcarbamoyl]-ethyl}-amide; |
| ccxciv. | N-(S)-{2-cyclohexyl-1-[2-(4-fluoro-phenylamino)-ethylcarbamoyl]-ethyl}-2-(S)-phenyl-propionamide; |
| ccxcv. | Pyridazine-4-carboxylic acid (S)-{2-cyclohexyl-1-[2-(4-fluoro-phenylamino)-ethylcarbamoyl]-ethyl}-amide; |
| ccxcvi. | N-(S)-{2-cyclohexyl-1-[2-(4-fluoro-phenylamino)-ethylcarbamoyl]-ethyl}-3-methanesulfonyl-benzamide; |
| ccxcvii. | 3-Cyclohexyl-N-[2-(4-fluoro-phenylamino)-ethyl]-2-(S)-(2-1H-tetrazol-5-yl-acetylamino)-propionamide; |
| ccxcviii. | Cyclopropanecarboxylic acid (S)-{2-cyclohexyl-1-[2-(4-fluoro-phenylamino)-ethylcarbamoyl]-ethyl}-amide; |
| ccxcix. | N-(S)-{2-cyclohexyl-1-[2-(4-fluoro-phenylamino)-ethylcarbamoyl]-ethyl}-4-methanesulfonylamino-benzamide; |
| ccc. | (S)-N-{2-[4-(4-Chloro-phenoxy)-phenyl]-1-[2-(4-methoxy-phenylamino)-ethylcarbamoyl]-ethyl}-3-methyl-benzamide; |
| ccci. | 3-Cyclohexyl-N-[2-(4-fluoro-phenylamino)-ethyl]-2-(S)-[2-(4-methoxy-phenyl)-acetylamino]-propionamide; |
| cccii. | 2-(S)-[2-(3-Chloro-phenyl)-acetylamino]-3-cyclohexyl-N-[2-(4-fluoro-phenylamino)-ethyl]-propionamide; |
| ccciii. | 3-Cyclohexyl-N-[2-(4-fluoro-phenylamino)-ethyl]-2-(S)-phenylacetylamino-propionamide; |
| ccciv. | 3-Cyclohexyl-N-[2-(4-fluoro-phenylamino)-ethyl]-2-(S)-(2-o-tolyl-acetylamino)-propionamide; |
| cccv. | 2-(S)-[2-(4-Chloro-phenyl)-acetylamino]-3-cyclohexyl-N-[2-(4-fluoro-phenylamino)-ethyl]-propionamide; |
| cccvi. | 3-Cyclohexyl-2-(S)-[2-(2-fluoro-phenyl)-acetylamino]-N-[2-(4-fluoro-phenylamino)-ethyl]-propionamide; |
| cccvii. | 3-Cyclohexyl-2-(S)-diphenylacetylamino-N-[2-(4-fluoro-phenylamino)-ethyl]-propionamide; |
| cccviii. | N-(S)-{2-cyclohexyl-1-[2-(4-fluoro-phenylamino)-ethylcarbamoyl]-ethyl}-2-(2-fluoro-biphenyl-4-yl)-propionamide; |
| cccix. | N-{2-cyclohexyl-1-(S)-[2-(4-fluoro-phenylamino)-ethylcarbamoyl]-ethyl}-2-p-tolyl-propionamide; |
| cccx. | N-{2-cyclohexyl-1-(S)-[2-(4-fluoro-phenylamino)-ethylcarbamoyl]-ethyl}-2-(4-fluoro-phenyl)-propionamide; |
| cccxi. | N-{2-cyclohexyl-1-(S)-[2-(4-fluoro-phenylamino)-ethylcarbamoyl]-ethyl}-2-(4-hydroxy-phenyl)-propionamide; |
| cccxii. | 2-(4-Chloro-phenyl)-N-{2-cyclohexyl-1-(S)-[2-(4-fluoro-phenylamino)-ethylcarbamoyl]-ethyl}-propionamide; |
| cccxiii. | N-(S)-{2-cyclohexyl-1-[2-(4-fluoro-phenylamino)-ethylcarbamoyl]-ethyl}-4-methanesulfonyl-benzamide; |
| cccxiv. | Thiazole-4-carboxylic acid (S)-{2-cyclohexyl-1-[2-(4-fluoro-phenylamino)-ethylcarbamoyl]-ethyl}-amide; |
| cccxv. | N-{2-cyclohexyl-1-(S)-[2-(4-fluoro-phenylamino)-ethylcarbamoyl]-ethyl}-2-(R)-phenyl-propionamide; |
| cccxvi. | 4-Cyano-N-(S)-{2-cyclohexyl-1-[2-(4-fluoro-phenylamino)-ethylcarbamoyl]-ethyl}-benzamide; |
| cccxvii. | 3-Cyclohexyl-N-[2-(4-fluoro-phenylamino)-ethyl]-2-(S)-(2-(R)-hydroxy-2-phenyl-acetylamino)-propionamide; |
| cccxviii. | N-{2-cyclohexyl-1-(S)-[2-(4-fluoro-phenylamino)-ethylcarbamoyl]-ethyl}-2-(R)-phenyl-butyramide; |
| cccxix. | Phenyl-cyclopropanecarboxylic acid (S)-{2-cyclohexyl-1-[2-(4-fluoro-phenylamino)-ethylcarbamoyl]-ethyl}-amide; |

TABLE I-continued

| | |
|---|---|
| cccxx. | N-(S)-{2-cyclohexyl-1-[2-(4-fluoro-phenylamino)-ethylcarbamoyl]-ethyl}-2-(R,S)-(4-fluoro-phenyl)-propionamide; |
| cccxxi. | Cyano-N-(S)-{2-cyclohexyl-1-[2-(4-fluoro-phenylamino)-ethylcarbamoyl]-ethyl}-benzamide; |
| cccxxii. | 5-(4-Fluoro-phenyl)-furan-2-carboxylic acid (S)-{2-cyclohexyl-1-[2-(4-fluoro-phenylamino)-ethylcarbamoyl]-ethyl}-amide; |
| cccxxiii. | Cyclohexyl-N-[2-(4-fluoro-phenylamino)-ethyl]-2-(S)-[2-(3-trifluoromethyl-phenyl)-acetylamino]-propionamide; |
| cccxxiv. | Cyano-N-(S)-{2-cyclohexyl-1-[2-(4-fluoro-phenylamino)-ethylcarbamoyl]-ethyl}-benzamide; |
| cccxxv. | 3-Cyclohexyl-N-[2-(4-fluoro-phenylamino)-ethyl]-2-(S)-[2-(4-trifluoromethyl-phenyl)-acetylamino]-propionamide; |
| cccxxvi. | 3-Cyclohexyl-N-[2-(4-fluoro-phenylamino)-ethyl]-2-(S)-[2-(4-methanesulfonyl-phenyl)-acetylamino]-propionamide; |
| cccxxvii. | (S)-N-[1-[2-(4-Methoxy-phenylamino)-ethylcarbamoyl]-2-(4-phenoxy-phenyl)-ethyl]-3-methyl-benzamide; |
| cccxxviii. | (S)-N-{2-[4-(4-Methoxy-phenoxy)-phenyl]-1-[2-(4-methoxy-phenylamino)-ethylcarbamoyl]-ethyl}-3-methyl-benzamide; |
| cccxxix. | (S)-N-{2-[4-(3-Chloro-phenoxy)-phenyl]-1-[2-(4-methoxy-phenylamino)-ethylcarbamoyl]-ethyl}-3-methyl-benzamide; |
| cccxxx. | (S)-N-{2-[4-(3,5-Dimethyl-phenoxy)-phenyl]-1-[2-(4-methoxy-phenylamino)-ethylcarbamoyl]-ethyl}-3-methyl-benzamide. |

\* \* \* \* \*